(12) United States Patent
Djordjevic et al.

(10) Patent No.: US 10,428,336 B2
(45) Date of Patent: Oct. 1, 2019

(54) METHOD FOR MODULATING PLANT GROWTH

(71) Applicant: The Australian National University, Acton (AU)

(72) Inventors: Michael Djordjevic, Kingston (AU); Nijat Imin, Kaleen (AU); Christina Delay, Braddon (AU)

(73) Assignee: The Australian National University, Acton (AU)

( * ) Notice: Subject to any disclaimer, the term of this patent is extended or adjusted under 35 U.S.C. 154(b) by 0 days.

(21) Appl. No.: 15/029,244

(22) PCT Filed: Oct. 16, 2014

(86) PCT No.: PCT/AU2014/000975
§ 371 (c)(1),
(2) Date: Apr. 13, 2016

(87) PCT Pub. No.: WO2015/054728
PCT Pub. Date: Apr. 23, 2015

(65) Prior Publication Data
US 2016/0374338 A1    Dec. 29, 2016

(30) Foreign Application Priority Data
Oct. 16, 2013  (AU) ................................ 2013903988

(51) Int. Cl.
*C12N 15/82* (2006.01)
*A01N 37/46* (2006.01)
*A01N 65/00* (2009.01)

(52) U.S. Cl.
CPC ......... *C12N 15/8216* (2013.01); *A01N 37/46* (2013.01); *A01N 65/00* (2013.01)

(58) Field of Classification Search
None
See application file for complete search history.

(56) References Cited

U.S. PATENT DOCUMENTS

| 5,780,296 | A  | 7/1998 | Holloman et al. |
| 6,255,113 | B1 | 7/2001 | Zarling et al.  |
| 6,686,515 | B1 | 2/2004 | Lassner et al.  |
| 2011/0296556 | A1 | 12/2011 | Sammons et al. |

FOREIGN PATENT DOCUMENTS

| WO | 1992/006205 A1 | 4/1992 |
| WO | 1997/048814 A2 | 12/1997 |
| WO | 1998/026082 A1 | 6/1998 |
| WO | 1999/025821 A1 | 5/1999 |
| WO | 1999/025840 A1 | 5/1999 |
| WO | 1999/025854 A1 | 5/1999 |
| WO | 1999/025855 A1 | 5/1999 |
| WO | 1999/032619 A1 | 7/1999 |
| WO | 1999/049029 A1 | 9/1999 |
| WO | 1999/053050 A1 | 10/1999 |
| WO | 2013/104026 A1 | 7/2013 |

OTHER PUBLICATIONS

Delay et al., "CEP Genes Regulate Root and Shoot Development in Response to Environmental Cues and are Specific to Seed Plants", Journal of Experimental Botany, vol. 64, No. 17, 2013, pp. 5383-5394.
Huault et al., "Local and Systemic Regulation of Plant Root System Architecture and Symbiotic Nodulation by a Receptor-Like Kinase", PLOS Genetics, vol. 10, Issue. 12, Dec. 2014, pp. 1-11.
International Preliminary Report on Patentability received for PCT Patent Application No. PCT/AU2014/000975, dated Feb. 10, 2016, 8 pages.
International Search Report and Written Opinion received for PCT Patent Application No. PCT/AU2014/000975, dated Dec. 8, 2014, 15 pages.
Ohyama et al., "Identification of a Biologically Active, Small, Secreted Peptide in Arabidopsis by in Silico Gene Screening, followed by LC-MS-based Structure Analysis", The Plant Journal, vol. 55, 2008, pp. 152-160.
Shinya et al., "Characterization of Receptor Proteins using Affinity Cross-Linking with Biotinylated Ligands", Plant and Cell Physiology, vol. 51, No. 2, 2010, pp. 262-270.
Stes et al., "Phosphoproteomics-Based Peptide Ligand-Receptor Kinase Pairing. Commentary on:" A Peptide Hormone and its Receptor Protein Kinase Regulate Plant Cell Expansion, Frontiers in Plant Science, vol. 6, No. 224, Apr. 2015, pp. 1-3.
Tabata et al., "Perception of Root-Derived Peptides by Shoot LRR-RKs Mediates Systemic N-Demand Signaling", Science, vol. 346, No. 6207, Oct. 17, 2014, pp. 343-346.
Radzman et al., "Different pathways act downstream of the peptide receptor CRA2 to regulate lateral root and nodule development", Plant Physiology Preview, published Jun. 24, 2016 as DOI:10.1104/pp.16.00113, pp. 1-49.

*Primary Examiner* — Elizabeth F McElwain
(74) *Attorney, Agent, or Firm* — Morrison & Foerster LLP

(57) ABSTRACT

The present invention provides a method for modulating non-root plant growth of a plant employing plant regulatory peptides, nucleotides encoding same, receptors therefor, binding agents thereof or agonists or antagonists thereof. Such methods encompass methods for increasing shoot growth or accelerating shoot development of plants, whereby said plants: yield a greater amount of above-ground plant matter than an untreated or wild-type plant grown under the same conditions; grows faster than an untreated or wild-type plant grown under tire same conditions; develops faster than an untreated or wild-type plant grown under the same conditions. The methods find particular application, wherein the conditions comprise stress conditions, and in particular abiotic stress conditions, which may be selected from increased salinity, drought, nitrogen limitation and pH stress.

17 Claims, 19 Drawing Sheets
Specification includes a Sequence Listing.

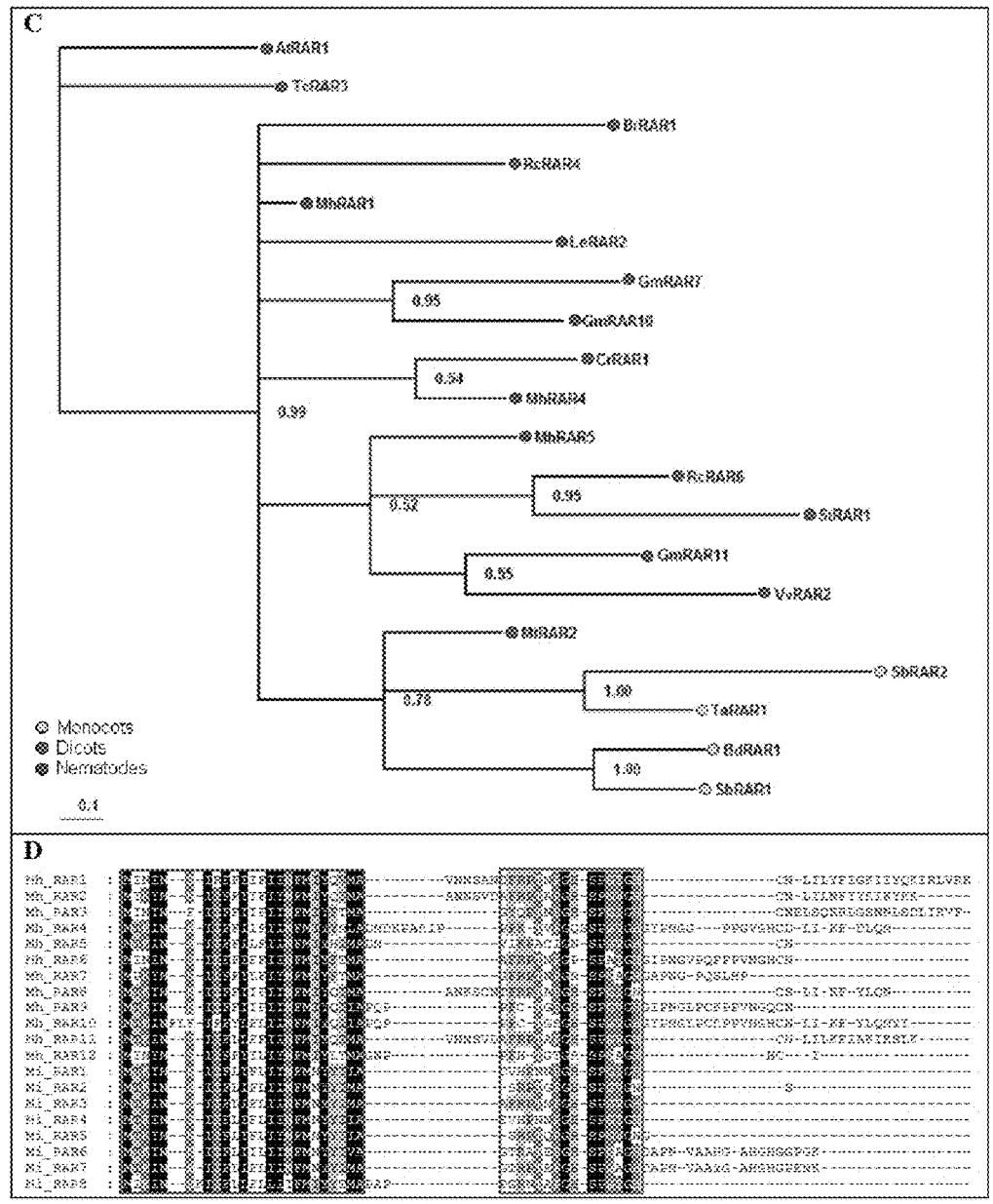
Figure 2 (Cont<sup>d</sup>)

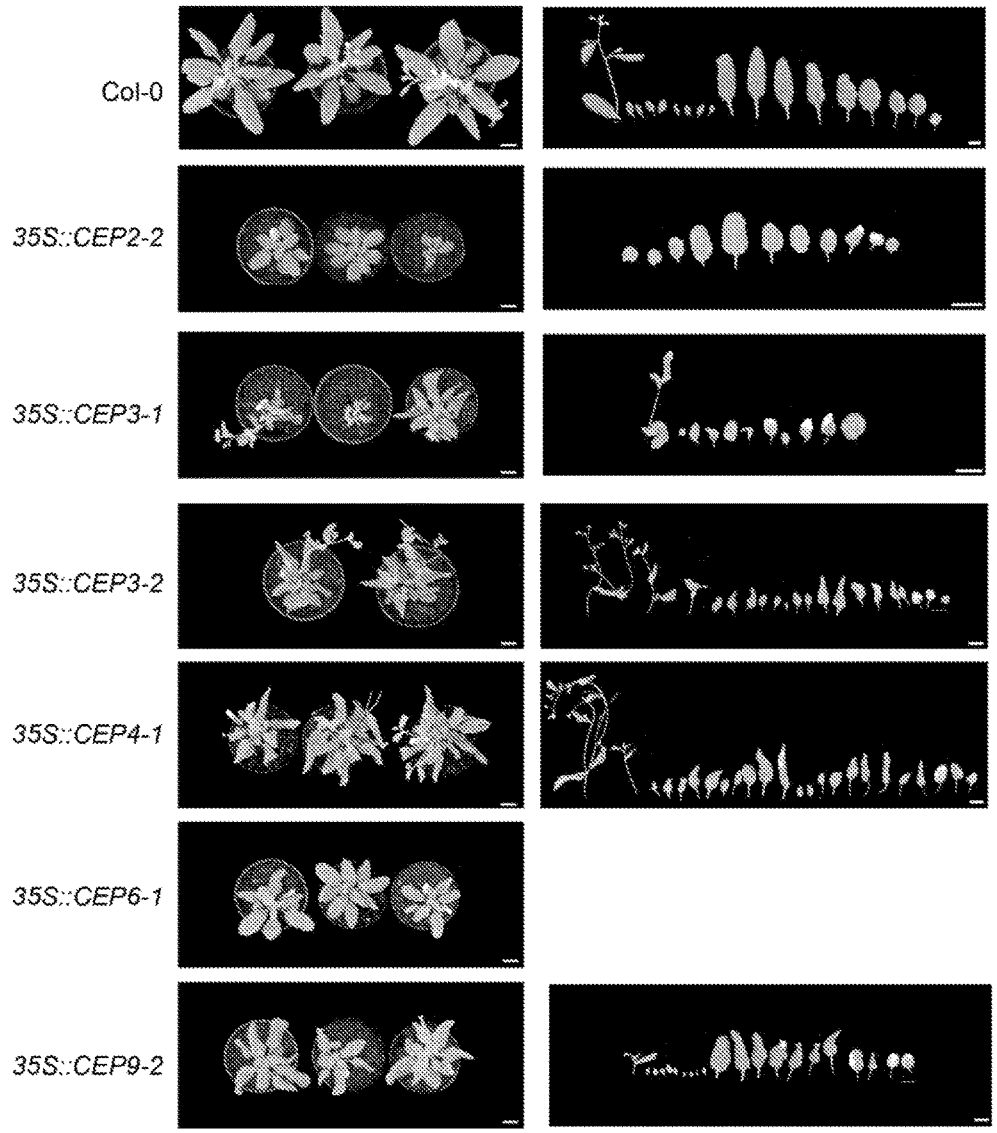
Figure 10 (Cont'd))

SEQUENCE LISTING

<160> NUMBER OF SEQ ID NOS: 508

<210> SEQ ID NO 1
<211> LENGTH: 619
<212> TYPE: DNA
<213> ORGANISM: Arabidopsis thaliana

<400> SEQUENCE: 1

```
acaccttatg ttctccaatc caacacatat attttcttcc acaaaaaaag acatatttta      60
ccttgttttg ttttacatat tcttatattt tatcgatttg tctttgtccc cggctcatgg     120
gaatgtcgaa taggtcagtt tctacatcca ttttttttcct tgcattggtg gttttgcatg   180
gaattcagga cacagaagag agacatttga aaactacttc gttagagatt gagggaattt    240
ataaaaaaac tgaggccgag catcctagca ttgtggtcac atatacacgg cgtggtgtcc    300
ttcagaagga ggtcattgcc caccccacag actttaggcc aacaaatccc ggaaacagcc    360
caggcgttgg acactctaac gggcgacatt gattcgatca tcatacgt cataatctta      420
tatcatatag aaaattacat gtattttcat tcagacttgt cttctaatgc taaaggggtg    480
tttggacatc actttatcat ttcaatgttt tgacagtact atgatcatta tgtctttgtc    540
gtgggtttgt tacactgtca cgtattgtaa gattatataa tgaatgaatt gcttttaaaa    600
attaatatat acattaatg                                                  619
```

<210> SEQ ID NO 2
<211> LENGTH: 91
<212> TYPE: PRT
<213> ORGANISM: Arabidopsis thaliana

<400> SEQUENCE: 2

```
Met Gly Met Ser Asn Arg Ser Val Ser Thr Ser Ile Phe Phe Leu Ala
1               5                   10                  15

Leu Val Val Leu His Gly Ile Gln Asp Thr Glu Glu Arg His Leu Lys
            20                  25                  30

Thr Thr Ser Leu Glu Ile Glu Gly Ile Tyr Lys Lys Thr Glu Ala Glu
        35                  40                  45

His Pro Ser Ile Val Val Thr Tyr Thr Arg Arg Gly Val Leu Gln Lys
    50                  55                  60

Glu Val Ile Ala His Pro Thr Asp Phe Arg Pro Thr Asn Pro Gly Asn
65                  70                  75                  80

Ser Pro Gly Val Gly His Ser Asn Gly Arg His
            85                  90
```

<210> SEQ ID NO 3
<211> LENGTH: 381
<212> TYPE: DNA
<213> ORGANISM: Arabidopsis thaliana

<400> SEQUENCE: 3

```
atgaagctat tcattatcac cgtggtgacc attttgacca tctcaagggt atttgacaaa      60
acaccagcca ccactgaagc aagaaagtcg aaaaagatgg tcggtcatga gcatttcaat    120
gaatatttgg atcctacttt tgcagggcat acatttggag tagttaaaga agattttctc    180
gaagtaaaaa agctaaagaa aattggtgat gaaataatc taaaaaacag atttataaat     240
gagtttgcgc ctactaatcc agaagatagt ctcggtattg ggcatccaag agttctaaac   300
aacaaattta caaatgattt tgcgcctact aatccaggag atagtcccgg tatcaggcat   360
ccaggagttg tgaatgttta a                                              381
```

<210> SEQ ID NO 4
<211> LENGTH: 126
<212> TYPE: PRT
<213> ORGANISM: Arabidopsis thaliana

<400> SEQUENCE: 4

Met Lys Leu Phe Ile Ile Thr Val Val Thr Ile Leu Thr Ile Ser Arg
1               5                   10                  15

Val Phe Asp Lys Thr Pro Ala Thr Thr Glu Ala Arg Lys Ser Lys Lys
            20                  25                  30

Met Val Gly His Glu His Phe Asn Glu Tyr Leu Asp Pro Thr Phe Ala
        35                  40                  45

Gly His Thr Phe Gly Val Val Lys Glu Asp Phe Leu Glu Val Lys Lys
    50                  55                  60

Leu Lys Lys Ile Gly Asp Glu Asn Asn Leu Lys Asn Arg Phe Ile Asn
65                  70                  75                  80

Glu Phe Ala Pro Thr Asn Pro Glu Asp Ser Leu Gly Ile Gly His Pro
                85                  90                  95

Arg Val Leu Asn Asn Lys Phe Thr Asn Asp Phe Ala Pro Thr Asn Pro
            100                 105                 110

Gly Asp Ser Pro Gly Ile Arg His Pro Gly Val Val Asn Val
        115                 120                 125

<210> SEQ ID NO 5
<211> LENGTH: 415
<212> TYPE: DNA
<213> ORGANISM: Arabidopsis thaliana

<400> SEQUENCE: 5
aatacatttt cgccttcgac taaatattat aatttagctt cttttttttt ctaattctcg      60
tctcggtttt tctagtaatg gcgacgatta atgtttacgt ttttgcattt atctttcttt     120
tgactattag tgttggttca attgaaggcc gaaaactcac caaattcacc gtaacgacgt     180
ctgaggaaat cagagctggt ggctctgtat tgtcgtcgtc acctccgact gagccacttg     240
agtcgccgcc gagccacggg gttgatacct tcagacctac ggaacctggt catagccccg     300
gtattggaca ttccgtacat aattaacgga gaggaacaat agcatcgtct atgtgattac     360
atgttgaaaa tatgattggc ctggtgactt ttttttttctg aatatgtatt tacgt        415

<210> SEQ ID NO 6
<211> LENGTH: 82
<212> TYPE: PRT
<213> ORGANISM: Arabidopsis thaliana

<400> SEQUENCE: 6

Met Ala Thr Ile Asn Val Tyr Val Phe Ala Phe Ile Phe Leu Leu Thr
1               5                   10                  15

Ile Ser Val Gly Ser Ile Glu Gly Arg Lys Leu Thr Lys Phe Thr Val
            20                  25                  30

Thr Thr Ser Glu Glu Ile Arg Ala Gly Gly Ser Val Leu Ser Ser Ser
        35                  40                  45

Pro Pro Thr Glu Pro Leu Glu Ser Pro Ser His Gly Val Asp Thr
    50                  55                  60

Phe Arg Pro Thr Glu Pro Gly His Ser Pro Gly Ile Gly His Ser Val
65                  70                  75                  80

His Asn

<210> SEQ ID NO 7
<211> LENGTH: 261
<212> TYPE: DNA
<213> ORGANISM: Arabidopsis thaliana

<400> SEQUENCE: 7

```
atggtgtctc gcggttgttc aatcacagtt ttgtttcgct ttcttatagt tcttttggtg     60
atacaagtac actttgagaa tacaaaagca gctcgacatg caccagttgt ttcgtggtca    120
ccacctgagc cgcctaagga tgattttgtg tggtaccaca agatcaaccg cttcaaaaac    180
atagaacaag atgcattccg accaacccac caaggtccta gtcaaggtat tggacacaaa    240
aaccctccag gtgctcctta a                                              261
```

<210> SEQ ID NO 8
<211> LENGTH: 86
<212> TYPE: PRT
<213> ORGANISM: Arabidopsis thaliana

<400> SEQUENCE: 8

```
Met Val Ser Arg Gly Cys Ser Ile Thr Val Leu Phe Arg Phe Leu Ile
1               5                   10                  15

Val Leu Leu Val Ile Gln Val His Phe Glu Asn Thr Lys Ala Ala Arg
            20                  25                  30

His Ala Pro Val Val Ser Trp Ser Pro Pro Glu Pro Pro Lys Asp Asp
        35                  40                  45

Phe Val Trp Tyr His Lys Ile Asn Arg Phe Lys Asn Ile Glu Gln Asp
    50                  55                  60

Ala Phe Arg Pro Thr His Gln Gly Pro Ser Gln Gly Ile Gly His Lys
65                  70                  75                  80

Asn Pro Pro Gly Ala Pro
                85
```

<210> SEQ ID NO 9
<211> LENGTH: 690
<212> TYPE: DNA
<213> ORGANISM: Arabidopsis thaliana

<400> SEQUENCE: 9

```
atggtatttt accaaacacc aatcaccact gaagcaagaa gcttgaggaa acaaacgac      60 caagatcatt ttaaagctgg atttacagat gatttcgtgc ccacttctcc aggaaacagt   120
cctggtgtgg acacaaaaa aggtaatgtg aatgttgaag ggtttcaaga tgacttcaag   180
cccacggaag aagaaagtt gctgaaaact aacgttcaag atcatttcaa aaccggatct   240
acagatgatt ttgcacctac ttcccctgga cacagtcccg ggtgggaca caagaaagga   300 aatgtcaatg ttgaaagttc cgaagatgac ttcaaacaca aggaaggaag aaagcttcaa   360
caaacaaacg gtcaaaatca tttcaaaacc ggatctacgg acgattttgc acctacttct   420
ccgggaaaca gtcctgggat aggtcacaag aaagggcatg caaatgttaa agggtttaaa   480
gatgacttcg cacccacgga agaaatacga ttgcagaaaa tgaacggtca agatcatttc   540
aaaaccggat ctaccgatga tttcgcacct acaactccag aaacagtcc cggtatgggc    600 cataagaaag gagatgactt caaacccacg acaccaggac atagccccgg ggttggtcat   660
gctgtcaaga acgatgaacc taaagcttaa                                     690
```

<210> SEQ ID NO 10

```
<211> LENGTH: 243
<212> TYPE: PRT
<213> ORGANISM: Arabidopsis thaliana

<400> SEQUENCE: 10

Met Lys Leu Leu Ser Ile Thr Leu Thr Ser Ile Val Ile Ser Met Val
1               5                   10                  15

Phe Tyr Gln Thr Pro Ile Thr Thr Glu Ala Arg Ser Leu Arg Lys Thr
            20                  25                  30

Asn Asp Gln Asp His Phe Lys Ala Gly Phe Thr Asp Asp Phe Val Pro
        35                  40                  45

Thr Ser Pro Gly Asn Ser Pro Gly Val Gly His Lys Lys Gly Asn Val
50                  55                  60

Asn Val Glu Gly Phe Gln Asp Asp Phe Lys Pro Thr Glu Gly Arg Lys
65                  70                  75                  80

Leu Leu Lys Thr Asn Val Gln Asp His Phe Lys Thr Gly Ser Thr Asp
                85                  90                  95

Asp Phe Ala Pro Thr Ser Pro Gly His Ser Pro Gly Val Gly His Lys
            100                 105                 110

Lys Gly Asn Val Asn Val Glu Ser Ser Glu Asp Asp Phe Lys His Lys
        115                 120                 125

Glu Gly Arg Lys Leu Gln Gln Thr Asn Gly Gln Asn His Phe Lys Thr
    130                 135                 140

Gly Ser Thr Asp Asp Phe Ala Pro Thr Ser Pro Gly Asn Ser Pro Gly
145                 150                 155                 160

Ile Gly His Lys Lys Gly His Ala Asn Val Lys Gly Phe Lys Asp Asp
                165                 170                 175

Phe Ala Pro Thr Glu Glu Ile Arg Leu Gln Lys Met Asn Gly Gln Asp
            180                 185                 190

His Phe Lys Thr Gly Ser Thr Asp Asp Phe Ala Pro Thr Thr Pro Gly
        195                 200                 205

Asn Ser Pro Gly Met Gly His Lys Lys Gly Asp Asp Phe Lys Pro Thr
    210                 215                 220

Thr Pro Gly His Ser Pro Gly Val Gly His Ala Val Lys Asn Asp Glu
225                 230                 235                 240

Pro Lys Ala

<210> SEQ ID NO 11
<211> LENGTH: 501
<212> TYPE: DNA
<213> ORGANISM: Arabidopsis thaliana

<400> SEQUENCE: 11
acttcacatc accactctca aatattctca agagtcctta caacgatat ttagttttttt      60 cccttttttc tgttttcttt ttatctccca ttttttcttcc aatataatgg aatcgtttat    120
gggtcaaaag aaaacattgt acgcgtgtta tttttaatg ttggtgtttt tttagggtt      180 caattgtgtc catggacgaa ccctaaaagt tgatgataag attaatggtg gtcattatga    240
tagcaagacg atgatggcat tggcaaagca caatgatatg atggttgatg acaaggcaat    300
gcagttctcg ccgccaccac caccaccacc gccgtcacaa tcgggaggta agatgctga    360 agatttcagg cctacaacgc ctggccacag ccctggcatt ggccatagtt tatcccataa    420
ttgatcattt tcatgcaatt tcacatatgt atatatgtgt tgtgaactta tgattaaata    480
ttgttcgttt taattttttct t                                            501
```

<210> SEQ ID NO 12
<211> LENGTH: 105
<212> TYPE: PRT
<213> ORGANISM: Arabidopsis thaliana

<400> SEQUENCE: 12

Met Glu Ser Phe Met Gly Gln Lys Lys Thr Leu Tyr Ala Cys Tyr Phe
1               5                   10                  15

Leu Met Leu Val Phe Phe Leu Gly Phe Asn Cys Val His Gly Arg Thr
            20                  25                  30

Leu Lys Val Asp Asp Lys Ile Asn Gly Gly His Tyr Asp Ser Lys Thr
        35                  40                  45

Met Met Ala Leu Ala Lys His Asn Asp Met Met Val Asp Asp Lys Ala
    50                  55                  60

Met Gln Phe Ser Pro Pro Pro Pro Pro Pro Ser Gln Ser Gly
65                  70                  75                  80

Gly Lys Asp Ala Glu Asp Phe Arg Pro Thr Thr Pro Gly His Ser Pro
                85                  90                  95

Gly Ile Gly His Ser Leu Ser His Asn
            100                 105

<210> SEQ ID NO 13
<211> LENGTH: 306
<212> TYPE: DNA
<213> ORGANISM: Arabidopsis thaliana

<400> SEQUENCE: 13
atgaaactct cagtttatat cattcttagt attctcttca tttcgacggt attttatgaa      60
attcagttta cggaggcgag acagttgcga aaaccgacg atcaagatca tgatgatcat     120
catttcacag tcgggtacac tgatgatttt gggcctactt ctcctggtaa cagcccgggc     180
attggtcata agatgaagga gaatgaagaa aatgctggag gtataaaga tgacttcgaa      240 cctacgacgc caggacatag tcccggcgtt ggacatgctg tcaagaacaa tgagcctaat     300
gcttaa                                                                306

<210> SEQ ID NO 14
<211> LENGTH: 101
<212> TYPE: PRT
<213> ORGANISM: Arabidopsis thaliana

<400> SEQUENCE: 14

Met Lys Leu Ser Val Tyr Ile Ile Leu Ser Ile Leu Phe Ile Ser Thr
1               5                   10                  15

Val Phe Tyr Glu Ile Gln Phe Thr Glu Ala Arg Gln Leu Arg Lys Thr
            20                  25                  30

Asp Asp Gln Asp His Asp His His Phe Thr Val Gly Tyr Thr Asp
        35                  40                  45

Asp Phe Gly Pro Thr Ser Pro Gly Asn Ser Pro Gly Ile Gly His Lys
    50                  55                  60

Met Lys Glu Asn Glu Glu Asn Ala Gly Gly Tyr Lys Asp Asp Phe Glu
65                  70                  75                  80

Pro Thr Thr Pro Gly His Ser Pro Gly Val Gly His Ala Val Lys Asn
                85                  90                  95

Asn Glu Pro Asn Ala
            100

```
<210> SEQ ID NO 15
<211> LENGTH: 589
<212> TYPE: DNA
<213> ORGANISM: Medicago truncatula

<400> SEQUENCE: 15
atgaaatatt tcgctctttt tcttgcccta attgcatgca actattccct tcaatctcat    60
gcaaggctca ttaaaccatc gaaccatcac aatgttccaa tttcaacatc agagaagaaa   120
gttgagtcaa caataaaatc aaacaatgaa gtagctagtt attttggaga ttcaagtgaa   180
gctcacacaa atgcattcca accaacaaca ccaggaaata gtcctggtgt tggtcataga   240
tattttaccg atgaagatat cgacgtgaat tcgaaaaaga cggtagctca gagcaaagat   300
gataataaat atgtgactga ggatactaca aatgagttcc aaaaaacaaa ccctggtcac   360
agtcctggtg ttggtcattc ttaccaaaac aaaattggaa attgatgtaa atatgcaatt   420
aataatttat tttattagtt aggtgtatgc tgtataatta atcaatcaat taattattaa   480
gtgttctcca tagtttcatt ctgcattaca gattgtgaaa tcttgcata tcccaaacca    540 tgagcttggg tttaattaat tattggctat tgattgtatc attcaattc               589

<210> SEQ ID NO 16
<211> LENGTH: 142
<212> TYPE: PRT
<213> ORGANISM: Medicago truncatula

<400> SEQUENCE: 16

Met Ala Tyr Lys Phe Gln Tyr Thr Met Lys Tyr Phe Ala Leu Phe Leu
1               5                   10                  15

Ala Leu Ile Ala Cys Asn Tyr Ser Leu Gln Ser His Ala Arg Leu Ile
            20                  25                  30

Lys Pro Ser Asn His His Asn Val Pro Ile Ser Thr Ser Glu Lys Lys
        35                  40                  45

Val Glu Ser Thr Ile Lys Ser Asn Asn Glu Val Ala Ser Tyr Phe Gly
    50                  55                  60

Asp Ser Ser Glu Ala His Thr Asn Ala Phe Gln Pro Thr Thr Pro Gly
65                  70                  75                  80

Asn Ser Pro Gly Val Gly His Arg Tyr Phe Thr Asp Glu Asp Ile Asp
                85                  90                  95

Val Asn Ser Lys Lys Thr Val Ala Gln Ser Lys Asp Asp Asn Lys Tyr
            100                 105                 110

Val Thr Glu Asp Thr Thr Asn Glu Phe Gln Lys Thr Asn Pro Gly His
        115                 120                 125

Ser Pro Gly Val Gly His Ser Tyr Gln Asn Lys Ile Gly Asn
    130                 135                 140

<210> SEQ ID NO 17
<211> LENGTH: 249
<212> TYPE: DNA
<213> ORGANISM: Medicago truncatula

<400> SEQUENCE: 17
atggcacatt tagctcgcat tgcttgttc tatgtactat tgttttttgtc tcatgaacta    60 ctactcacta caactgaggg taggagtttg agacaaagca ttcagccacc aaacatagcc   120
tctaccaaaa tgatgagcac aagccaattg taccaccgta gcaatagaag tttggaggga   180
gatgttgaag cttttaggcc cacaactcct ggacacagtc tggcattgg tcattccatt    240 aataattaa                                                          249
```

<210> SEQ ID NO 18
<211> LENGTH: 82
<212> TYPE: PRT
<213> ORGANISM: Medicago truncatula

<400> SEQUENCE: 18

Met Ala His Leu Ala Arg Ile Cys Leu Phe Tyr Val Leu Leu Phe Leu
1               5                   10                  15

Ser His Glu Leu Leu Thr Thr Thr Glu Gly Arg Ser Leu Arg Gln
            20                  25                  30

Ser Ile Gln Pro Pro Asn Ile Ala Ser Thr Lys Met Met Ser Thr Ser
        35                  40                  45

Gln Leu Tyr His Arg Ser Asn Arg Ser Leu Glu Gly Asp Val Glu Ala
    50                  55                  60

Phe Arg Pro Thr Thr Pro Gly His Ser Pro Gly Ile Gly His Ser Ile
65                  70                  75                  80

Asn Asn

<210> SEQ ID NO 19
<211> LENGTH: 640
<212> TYPE: DNA
<213> ORGANISM: Medicago truncatula

<400> SEQUENCE: 19
ttttaaagta tattggtaca tgtgtaacac gacccaaaat aattttttcta aaaggaaat      60 gaaaaaaga gaaatgaac atccaaaaca atcaacgttg agctccacca ttttgcagca     120
gtttatttaa attagtaacc tggctcggca gatcaatcat taataggagg tggagcgctc    180
atgcgacatt ctacttcttg tgtccagcac ctggactatt tcctggtgtt gtgggacgaa    240
aatcattcgt ctcaagattc ttgtaacgtt tcaatttgtg agaatggata tcggattgat    300
cgggagcaaa agtgtgaata tctggaagat gactagcagc tttgtcttga ttaacactaa    360
cggataatgc aacatgcttg tgatactcac acaccgaaat tatgtctgtc ggggaaatct    420
tggctttaac taataacgcc ttagtgccgt gacatgacat cagatccctt agagctcgat    480
tatatgacat taatatagct ttttccgaga ctacagatgg actcaaggat atgaaagcca    540
atatggccaa caacccagcc aaacaatatt ttggaccata actcatgttt tctagcgcaa    600
tgcttattaa gtgataatgc aagcactttt atatttttt                           640

<210> SEQ ID NO 20
<211> LENGTH: 131
<212> TYPE: PRT
<213> ORGANISM: Medicago truncatula

<400> SEQUENCE: 20

Met Ser Tyr Gly Pro Lys Tyr Cys Leu Ala Gly Leu Leu Ala Ile Leu
1               5                   10                  15

Ala Phe Ile Ser Leu Ser Pro Ser Val Val Ser Glu Lys Ala Ile Leu
            20                  25                  30

Met Ser Tyr Asn Arg Ala Leu Arg Asp Leu Met Ser Cys His Gly Thr
        35                  40                  45

Lys Ala Leu Leu Val Lys Ala Lys Ile Ser Pro Thr Asp Ile Ile Ser
    50                  55                  60

Val Cys Glu Tyr His Lys His Val Ala Leu Ser Val Ser Val Asn Gln
65                  70                  75                  80

-continued

Asp Lys Ala Ala Ser His Leu Pro Asp Ile His Thr Phe Ala Pro Asp
            85                  90                  95

Gln Ser Asp Ile His Ser His Lys Leu Lys Arg Tyr Lys Asn Leu Glu
        100                 105                 110

Thr Asn Asp Phe Arg Pro Thr Thr Pro Gly Asn Ser Pro Gly Ala Gly
    115                 120                 125

His Lys Lys
    130

<210> SEQ ID NO 21
<211> LENGTH: 243
<212> TYPE: DNA
<213> ORGANISM: Medicago truncatula

<400> SEQUENCE: 21
atgggtgaga aaaccatgtt attaacattt ttacttctta ttattatgca acaaaacatt      60
ggttcaattg aagcatcaag gttgctaaat attaatccac caccaactat tcctaaaagt     120
ccacaagctc cttcacatga ttattggtat tcgataaacg atgataaggg tggtgacgat     180 gctttttcgcc ctacaagtcc aggacatagc cctggggtag gacatcaaac accacctcca    240
tga                                                                   243

<210> SEQ ID NO 22
<211> LENGTH: 80
<212> TYPE: PRT
<213> ORGANISM: Medicago truncatula

<400> SEQUENCE: 22

Met Gly Glu Lys Thr Met Leu Leu Thr Phe Leu Leu Leu Ile Ile Met
1               5                   10                  15

Gln Gln Asn Ile Gly Ser Ile Glu Ala Ser Arg Leu Leu Asn Ile Asn
            20                  25                  30

Pro Pro Pro Thr Ile Pro Lys Ser Pro Gln Ala Pro Ser His Asp Tyr
        35                  40                  45

Trp Tyr Ser Ile Asn Asp Asp Lys Gly Gly Asp Asp Ala Phe Arg Pro
    50                  55                  60

Thr Ser Pro Gly His Ser Pro Gly Val Gly His Gln Thr Pro Pro Pro
65                  70                  75                  80

<210> SEQ ID NO 23
<211> LENGTH: 249
<212> TYPE: DNA
<213> ORGANISM: Medicago truncatula

<400> SEQUENCE: 23
atggaaaata ctaaaaggct tcaaattatt tgtgttctta ttttgttttt ggttttgcaa      60
caagaagttg tgattgttca agggaggcat ttgaggtcta aattgtgtag agattgcaca     120
aagcctcata aaagatccat tgctcatcat ggagggaagt cttcaagacg tgtagggtat     180
gaagttgatg attttaggcc tacatctcca gggcatagtc caggtgttgg tcattccatc     240
cataattaa                                                             249

<210> SEQ ID NO 24
<211> LENGTH: 85
<212> TYPE: PRT
<213> ORGANISM: Medicago truncatula

<400> SEQUENCE: 24

Met Ala His Phe Thr Arg Ser Cys Leu Ile Phe Val Leu Leu Ile
1               5                   10                  15

Ser Cys Glu Leu Leu Ser Ile Glu Gly Arg Ser Leu Arg Lys Ser Ile
            20                  25                  30

Gly Ser Pro Lys Ala Ala Ser Val Glu Thr Met Thr Arg Ser Val Val
                35                  40                  45

Leu Ser Pro Arg Gln Leu Gln Asn Asn Gly Arg Asn Leu Glu Gly Ser
        50                  55                  60

Val Glu Ala Phe Arg Pro Thr Thr Pro Gly His Ser Pro Gly Val Gly
65                  70                  75                  80

His Ser Leu Lys Asn
                85

<210> SEQ ID NO 25
<211> LENGTH: 249
<212> TYPE: DNA
<213> ORGANISM: Medicago truncatula

<400> SEQUENCE: 25
atggaaaata ctaaaaggct tcaaattatt tgtgttctta ttttgttttt ggttttgcaa      60
caagaagttg tgattgttca agggaggcat ttgaggtcta aattgtgtag agattgcaca    120
aagcctcata aagatccat tgctcatcat ggagggaagt cttcaagacg tgtagggtat    180
gaagttgatg attttaggcc tacatctcca gggcatagtc caggtgttgg tcattccatc    240
cataattaa                                                            249

<210> SEQ ID NO 26
<211> LENGTH: 82
<212> TYPE: PRT
<213> ORGANISM: Medicago truncatula

<400> SEQUENCE: 26

Met Glu Asn Thr Lys Arg Leu Gln Ile Ile Cys Val Leu Ile Leu Phe
1               5                   10                  15

Leu Val Leu Gln Gln Glu Val Val Ile Val Gln Gly Arg His Leu Arg
            20                  25                  30

Ser Lys Leu Cys Arg Asp Cys Thr Lys Pro His Lys Arg Ser Ile Ala
        35                  40                  45

His His Gly Gly Lys Ser Ser Arg Arg Val Gly Tyr Glu Val Asp Asp
    50                  55                  60

Phe Arg Pro Thr Ser Pro Gly His Ser Pro Gly Val Gly His Ser Ile
65                  70                  75                  80

His Asn

<210> SEQ ID NO 27
<211> LENGTH: 375
<212> TYPE: DNA
<213> ORGANISM: Medicago truncatula

<400> SEQUENCE: 27
atgggtttgt ttcaagtcac aacaaaatat tgatcgtta ttctagcact aagtattgta      60
tacaattcct ttcaaataac tcaagccagg ccaattaaac cattgaatca acaatcttca    120
ttaaacacac aagactcggg tgcaatccac actaactctt tcggccgac aacaccagga    180 agtagtcctg gtgttggcca ccgaaatttt gttgtaggag ataagaacac gagaacaatg    240
gtggttgttc agagcccgga tgttgaggtt tttgtgacga taagagatc cgatgatggt    300

```
ttcaaaccta caaatcctag tcatagtcct ggagttggcc atggttacca taccaaaatt    360
agacatttaa attag                                                     375
```

<210> SEQ ID NO 28
<211> LENGTH: 124
<212> TYPE: PRT
<213> ORGANISM: Medicago truncatula

<400> SEQUENCE: 28

```
Met Gly Leu Phe Gln Val Thr Thr Lys Tyr Leu Ile Val Ile Leu Ala
1               5                   10                  15

Leu Ser Ile Val Tyr Asn Ser Phe Gln Ile Thr Gln Ala Arg Pro Ile
            20                  25                  30

Lys Pro Leu Asn Gln Gln Ser Ser Leu Asn Thr Gln Asp Ser Gly Ala
        35                  40                  45

Ile His Thr Asn Ser Phe Arg Pro Thr Thr Pro Gly Ser Ser Pro Gly
    50                  55                  60

Val Gly His Arg Asn Phe Val Val Gly Asp Lys Asn Thr Arg Thr Met
65                  70                  75                  80

Val Val Val Gln Ser Pro Asp Val Glu Val Phe Val Thr Asn Lys Arg
                85                  90                  95

Ser Asp Asp Gly Phe Lys Pro Thr Asn Pro Ser His Ser Pro Gly Val
            100                 105                 110

Gly His Gly Tyr His Thr Lys Ile Arg His Leu Asn
        115                 120
```

<210> SEQ ID NO 29
<211> LENGTH: 309
<212> TYPE: DNA
<213> ORGANISM: Medicago truncatula

<400> SEQUENCE: 29

```
atggcacaaa acaagaccat agttttctct gttatttccc tagcattgat cattttctgc     60
atgcagtcga tcgagggggcg ccttgtaaaa tacatcgatg aaagtaaccct cctgaagaat   120 gttaaacatg atggaatttc agatgcaaat gaagctactc ttgttaacgt gactccaaca    180
atattgccac caagtgctgt ggtaggttca aatggggttg cagcacctcc tccaagtcat    240
gatgtgggtg cttttagacc cacaacccct gggaacagtc ctggtgtagg tcactctatt    300
cactactag                                                            309
```

<210> SEQ ID NO 30
<211> LENGTH: 102
<212> TYPE: PRT
<213> ORGANISM: Medicago truncatula

<400> SEQUENCE: 30

```
Met Ala Gln Asn Lys Thr Ile Val Phe Ser Val Ile Ser Leu Ala Leu
1               5                   10                  15

Ile Ile Phe Cys Met Gln Ser Ile Glu Gly Arg Leu Val Lys Tyr Ile
            20                  25                  30

Asp Glu Ser Asn Leu Leu Lys Asn Val Lys His Asp Gly Ile Ser Asp
        35                  40                  45

Ala Asn Glu Ala Thr Leu Val Asn Val Thr Pro Thr Ile Leu Pro Pro
    50                  55                  60

Ser Ala Val Val Gly Ser Asn Gly Val Ala Ala Pro Pro Pro Ser His
65                  70                  75                  80
```

Asp Val Gly Ala Phe Arg Pro Thr Thr Pro Gly Asn Ser Pro Gly Val
             85                  90                  95

Gly His Ser Ile His Tyr
            100

<210> SEQ ID NO 31
<211> LENGTH: 456
<212> TYPE: DNA
<213> ORGANISM: Medicago truncatula

<400> SEQUENCE: 31
atgggtgaat tcaggccat gcaaaaatat tttgccattt ttcttgtatt agttgcctac    60
catatttttcc ttccaactca agctaggaag ataaaaccat tgattgaaga taatcccaaa   120
cctaccttca catcccttaa aactgctgta aatattcctt ctccaacatt tgagaagaaa   180
gttaaccttc ccatgatgcc aaatcatggt gtcgcaagta taggagattc aagcggagat   240
acaaatgctt tccgacccac aacaccagga agcagtcctg gtgttggtca tcggaagttt   300
gtaggagagg ttaaagatag tacagttgtt cggagtccga atgttaaagt ttttgtgact   360
tctgagagat caaaagatgc ttttaaacct acttacccaa atcatagccc aggtgttgga   420
catgttaacc aaagcacaaa aggacaacta aattag                              456

<210> SEQ ID NO 32
<211> LENGTH: 151
<212> TYPE: PRT
<213> ORGANISM: Medicago truncatula

<400> SEQUENCE: 32

Met Gly Glu Phe Gln Ala Met Gln Lys Tyr Phe Ala Ile Phe Leu Val
1               5                   10                  15

Leu Val Ala Tyr His Ile Phe Leu Pro Thr Gln Ala Arg Lys Ile Lys
            20                  25                  30

Pro Leu Ile Glu Asp Asn Pro Lys Pro Thr Phe Thr Ser Leu Lys Thr
        35                  40                  45

Ala Val Asn Ile Pro Ser Pro Thr Phe Glu Lys Lys Val Asn Leu Pro
    50                  55                  60

Met Met Pro Asn His Gly Val Ala Ser Ile Gly Asp Ser Ser Gly Asp
65                  70                  75                  80

Thr Asn Ala Phe Arg Pro Thr Thr Pro Gly Ser Ser Pro Gly Val Gly
                85                  90                  95

His Arg Lys Phe Val Gly Glu Val Lys Asp Ser Thr Val Val Arg Ser
            100                 105                 110

Pro Asn Val Lys Val Phe Val Thr Ser Glu Arg Ser Lys Asp Ala Phe
        115                 120                 125

Lys Pro Thr Tyr Pro Asn His Ser Pro Gly Val Gly His Val Asn Gln
    130                 135                 140

Ser Thr Lys Gly Gln Leu Asn
145                 150

<210> SEQ ID NO 33
<211> LENGTH: 573
<212> TYPE: DNA
<213> ORGANISM: Medicago truncatula

<400> SEQUENCE: 33
atggctgaga aaatcatgtt tgtaacctat ttacttatcc ttattattat gcaacaatac    60
cttggatcaa tggaagcatc aaggtttata aatgataata ataaggatgg tgatgatgct   120

-continued

```
ttccgtccaa ctccttcagg tcatagtctt ggggtgggac atatattacc accaccatca    180
agtattatcc ctaaagtctt attgaaaagt caacaacctc cttcatctga ttatttgtat    240
accataaagg atgataataa ggacggtgat gatcctccat cacatgatta ttggtattcc    300
ataaatgatg ataataaaga tggtgatgat gctttccgtc caaatcctcc aggtcatagt    360
cctggagggg gacatacgtt accaccatca ccaccaagtg ttatccctac agtcttattg    420
gaaaatccac aacctatttc atctgattat ttctataaca taaaggatga ataataaggat    480 ggtgatgatg cttttcgccc aactcctcct ggtcatagcc ctggaggggg acatacatta    540
ccaccatcac caccaattgt ttttatgaac taa                                  573
```

<210> SEQ ID NO 34
<211> LENGTH: 223
<212> TYPE: PRT
<213> ORGANISM: Medicago truncatula

<400> SEQUENCE: 34

```
Met Ala Glu Lys Ile Met Phe Val Thr Tyr Leu Leu Ile Leu Ile Ile
1               5                   10                  15

Met Gln Gln Tyr Leu Gly Ser Met Glu Ala Ser Arg Phe Ile Asn Asp
            20                  25                  30

Asn Asn Lys Asp Gly Asp Asp Ala Phe Arg Pro Thr Pro Ser Gly His
        35                  40                  45

Ser Leu Gly Val Gly His Ile Leu Pro Pro Ser Ser Ile Ile Pro
    50                  55                  60

Lys Val Leu Leu Lys Ser Gln Gln Pro Pro Ser Ser Asp Tyr Leu Tyr
65                  70                  75                  80

Thr Ile Lys Asp Asp Asn Lys Asp Gly Asp Asp Ala Phe Arg Pro Thr
                85                  90                  95

Pro Pro Gly His Ser Pro Gly Gly Gly His Thr Leu Pro Pro Ser Pro
            100                 105                 110

Pro Ser Ile Val Pro Ile Ile Ser Leu Lys Ser Leu Gln Pro Pro Ser
        115                 120                 125

His Asp Tyr Trp Tyr Ser Ile Asn Asp Asp Asn Lys Asp Gly Asp Asp
    130                 135                 140

Ala Phe Arg Pro Asn Pro Pro Gly His Ser Pro Gly Gly Gly His Thr
145                 150                 155                 160

Leu Pro Pro Ser Pro Pro Ser Val Ile Pro Thr Val Leu Leu Glu Asn
                165                 170                 175

Pro Gln Pro Ile Ser Ser Asp Tyr Phe Tyr Asn Ile Lys Asp Asp Asn
            180                 185                 190

Lys Asp Gly Asp Asp Ala Phe Arg Pro Thr Pro Pro Gly His Ser Pro
        195                 200                 205

Gly Gly Gly His Thr Leu Pro Pro Ser Pro Pro Ile Val Phe Met
    210                 215                 220
```

<210> SEQ ID NO 35
<211> LENGTH: 258
<212> TYPE: DNA
<213> ORGANISM: Medicago truncatula

<400> SEQUENCE: 35

```
atggcaaaga aaaccattat gttaagcttt cttgttttc tcattcttgt gcaaattt      60 ggtttgatgg aagtgctagg gaagaatgtt gaagcaccac caacaattcc aagagttttg    120
```

```
ttgaggagtc cacaagctcc ttccattggc ttttatacca aaaatgatga caaggatagt    180
caaggtgatg cttttcgtcc aactagtcct ggtcatagtc ctggtgtggg ccatgattcg    240
ccaccaaatt ttccttaa                                                  258
```

<210> SEQ ID NO 36
<211> LENGTH: 85
<212> TYPE: PRT
<213> ORGANISM: Medicago truncatula

<400> SEQUENCE: 36

```
Met Ala Lys Lys Thr Ile Met Leu Ser Phe Leu Val Phe Leu Ile Leu
1               5                   10                  15

Val Gln Asn Phe Gly Leu Met Glu Val Leu Gly Lys Asn Val Glu Ala
            20                  25                  30

Pro Pro Thr Ile Pro Arg Val Leu Leu Arg Ser Pro Gln Ala Pro Ser
        35                  40                  45

Ile Gly Phe Tyr Thr Lys Asn Asp Asp Lys Asp Ser Gln Gly Asp Ala
    50                  55                  60

Phe Arg Pro Thr Ser Pro Gly His Ser Pro Gly Val Gly His Asp Ser
65                  70                  75                  80

Pro Pro Asn Phe Pro
                85
```

<210> SEQ ID NO 37
<211> LENGTH: 105
<212> TYPE: PRT
<213> ORGANISM: Arabidopsis lyrata

<400> SEQUENCE: 37

```
Met Glu Ser Ser Met Gly Gln Lys Lys Thr Leu Tyr Ala Cys Ile Phe
1               5                   10                  15

Leu Met Met Val Phe Phe Leu Gly Phe Asn Cys Gly His Gly Arg Thr
            20                  25                  30

Leu Lys Val Asp Asp Lys Ile Asp Gly Gly His Asp Asp Ser Lys Thr
        35                  40                  45

Met Met Ala Leu Ala Lys His Asn Val Met Met Val Asp Asp Lys Thr
    50                  55                  60

Val Gln Phe Ser Pro Pro Pro Pro Ser Pro Ser Gln Ser Gly
65                  70                  75                  80

Gly Lys Glu Ala Glu Asp Phe Arg Pro Thr Thr Pro Gly His Ser Pro
                85                  90                  95

Gly Ile Gly His Ser Leu Ser His Asn
            100                 105
```

<210> SEQ ID NO 38
<211> LENGTH: 231
<212> TYPE: PRT
<213> ORGANISM: Arabidopsis lyrata

<400> SEQUENCE: 38

```
Met Lys Leu Leu Ser Ile Thr Val Met Thr Ile Val Ile Ser Met Val
1               5                   10                  15

Phe Asp Gln Thr Pro Ile Thr Thr Glu Ala Arg Arg Leu Arg Asn Thr
            20                  25                  30

Asn Asp Gln Asp His Phe Lys Ala Gly Ser Thr Asp Asp Phe Ala Pro
        35                  40                  45

Thr Ser Pro Gly Asn Ser Pro Gly Val Gly His Arg Lys Gly Lys Val
```

```
                 50                  55                  60
Asn Val Glu Gly Phe Gln Asp Asp Phe Lys Pro Thr Glu Arg Lys
 65                  70                  75                  80

Leu Leu Lys Thr Asn Gly Gln Asp His Phe Lys Thr Gly Ser Thr Asp
                 85                  90                  95

Asp Phe Ala Pro Thr Ser Pro Gly His Ser Pro Gly Val Gly His Arg
                100                 105                 110

Lys Asp Thr Ala Asn Val Glu Arg Phe Gln Gln Thr Asn Gly Gln Asn
                115                 120                 125

His Phe Lys Thr Gly Ser Thr Asp Glu Phe Ala Pro Thr Ser Pro Gly
                130                 135                 140

Asn Ser Pro Gly Ile Gly His Lys Lys Gly Asn Ala Asn Val Lys Gly
145                 150                 155                 160

Phe Lys Asp Asp Phe Ala Pro Thr Glu Glu Ile Arg Leu Lys Lys Met
                165                 170                 175

Asn Gly Lys Asp His Phe Lys Ser Gly Ser Thr Asp Asp Phe Ala Pro
                180                 185                 190

Thr Thr Pro Gly Asn Ser Pro Gly Met Gly Lys Lys Gly Asp Asp
                195                 200                 205

Phe Lys Pro Thr Thr Pro Gly His Ser Pro Gly Val Gly His Ala Val
                210                 215                 220

Asn Asn Asn Glu Pro Lys Ala
225                 230
```

<210> SEQ ID NO 39
<211> LENGTH: 90
<212> TYPE: PRT
<213> ORGANISM: Arabidopsis lyrata

<400> SEQUENCE: 39

```
Met Gly Met Ser Asn Arg Ser Val Ser Thr Ser Leu Phe Phe Leu Ala
  1               5                  10                  15

Leu Val Val Leu His Gly Ile Gln Asp Thr Glu Glu Arg His Leu Lys
                 20                  25                  30

Thr Thr Ser Leu Glu Val Glu Gly Ile Tyr Lys Lys Thr Glu Ala Glu
                 35                  40                  45

Asn Pro Ser Ile Val Val Thr Tyr Thr Arg Arg Ser Val Leu Gln Lys
 50                  55                  60

Ala Val Ile Ala His Pro Thr Asp Phe Arg Pro Thr Asn Pro Gly Asn
 65                  70                  75                  80

Ser Pro Gly Val Gly His Ser His Gly Arg
                 85                  90
```

<210> SEQ ID NO 40
<211> LENGTH: 92
<212> TYPE: PRT
<213> ORGANISM: Solanum lycopersicum

<400> SEQUENCE: 40

```
Met Ala Gln Pro Lys Ile Met Tyr Thr Cys Ala Phe Phe Leu Ala Leu
  1               5                  10                  15

Ile Phe Phe Ser Tyr Gly Ile Leu Leu Ser Glu Gly Arg Val Leu Phe
                 20                  25                  30

Lys Lys Glu Lys Asn Asn Asn Thr Ile Phe Ser His His Glu Glu Asn
                 35                  40                  45

Ser His Thr Lys Val Val Lys Asn Asn Tyr Phe Asn Asn Ile Asp His
```

```
                50                  55                  60
Asn Asn Met His Asp Asn Ile Asn Ile Ser Glu Glu Gly Gly Pro Gly
 65                  70                  75                  80
His Ser Pro Gly Val Gly His Gly Gly Pro Pro
                 85                  90

<210> SEQ ID NO 41
<211> LENGTH: 81
<212> TYPE: PRT
<213> ORGANISM: Solanum lycopersicum

<400> SEQUENCE: 41

Met Ala Ser Ser Tyr Gln Lys Ser Ile Tyr Met Val Ile Phe Tyr Val
 1               5                  10                  15
Phe Leu Phe Leu Phe Leu His Gln Cys Glu Leu Ile Val Ala Ser Arg
                20                  25                  30
Val Val Val Met Lys Phe His Gln Pro Met Met Pro Pro Ser Thr Asn
                35                  40                  45
Ile Leu Ser Phe Asn Arg Tyr Lys Lys Ser Glu Ile Val Lys Asp Tyr
            50                  55                  60
Ser Gly Pro Gly His Ser Pro Gly Met Gly His Asn Asp Pro Pro Gly
 65                  70                  75                  80
Ala

<210> SEQ ID NO 42
<211> LENGTH: 74
<212> TYPE: PRT
<213> ORGANISM: Solanum lycopersicum

<400> SEQUENCE: 42

Met Ala Ser Ser Tyr Lys Lys Ser Ile Tyr Met Val Leu Phe Tyr Val
 1               5                  10                  15
Phe Val Phe Leu Leu Leu Gln Gln Cys Glu Leu Ile Val Ala Ser Arg
                20                  25                  30
Val Val Val Met Lys Phe His Gln Pro Lys Pro Pro Ser Thr Asn Ile
                35                  40                  45
Phe Ser Phe Asn Arg Tyr Lys Lys Ser Glu Val Val Lys Asp Tyr Ser
            50                  55                  60
Gly Pro Gly His Ser Pro Gly Met Gly His
 65                  70

<210> SEQ ID NO 43
<211> LENGTH: 82
<212> TYPE: PRT
<213> ORGANISM: Lycopersicum esculentum

<400> SEQUENCE: 43

Met Ala Ser Ser Tyr Gln Lys Ser Ile Tyr Met Val Ile Phe Tyr Val
 1               5                  10                  15
Phe Leu Phe Leu Phe Leu His Gln Cys Glu Leu Ile Val Ala Ser Arg
                20                  25                  30
Val Val Val Met Lys Phe His Gln Pro Met Met Pro Pro Ser Thr Asn
                35                  40                  45
Ile Leu Ser Phe Asn Arg Tyr Lys Lys Ser Glu Ile Val Lys Asp Tyr
            50                  55                  60
Ser Gly Pro Gly His Ser Pro Gly Met Gly His Asn Asp Pro Pro Gly
 65                  70                  75                  80
```

Ala Pro

<210> SEQ ID NO 44
<211> LENGTH: 120
<212> TYPE: PRT
<213> ORGANISM: Lycopersicum esculentum

<400> SEQUENCE: 44

Met Val Ile Val Thr Asn Thr Lys Ile Gln Phe Ala Phe Ile
1               5                   10                  15

Leu Val Leu Ile Leu Phe Ser His Glu Ile Leu Cys Val Glu Ala Ile
            20                  25                  30

Arg His Leu Lys Ser Glu Lys Met Glu Val Val Ser Val Glu Ile Ser
        35                  40                  45

Val Ser Ser Thr Gln Ile Val Val Thr Ser Glu Thr Phe Asn Lys Ile
    50                  55                  60

Gly Lys Ile Gln Lys Ser Leu Thr Trp Leu Pro Ser Lys Asp Asp Ile
65                  70                  75                  80

His Lys Ser Ile Asn Asp Pro Thr Glu Ala Thr Lys Ser Val Lys Val
                85                  90                  95

Val Glu Lys Met Asp Asp Phe Gly Pro Thr Gly Pro Gly His Ser Pro
            100                 105                 110

Gly Ile Gly His Ser Ile His Ser
        115                 120

<210> SEQ ID NO 45
<211> LENGTH: 93
<212> TYPE: PRT
<213> ORGANISM: Gossypium hirsutum

<400> SEQUENCE: 45

Leu Phe Leu Phe Gln Pro Leu Lys Trp Pro Lys Pro Thr Ser Leu Tyr
1               5                   10                  15

Pro Leu Pro Phe Ser Pro Ser Phe Cys Leu Leu Thr Gly Ser Gln Phe
            20                  25                  30

Ser Lys Glu Ala Arg Val Leu Lys Ala Asp His Lys Thr His His His
        35                  40                  45

Ser Ser Leu Asn Val Asn Val Lys Gly Asp Val Leu Pro Asp Gly Ser
    50                  55                  60

Ala Thr Val Asn Asn Val Gln Lys Ala Ala Tyr Arg Thr Asp Ala Phe
65                  70                  75                  80

Arg Ser Thr Thr Pro Gly His Ser Pro Gly Ala Gly His
                85                  90

<210> SEQ ID NO 46
<211> LENGTH: 103
<212> TYPE: PRT
<213> ORGANISM: Lactuca sativa

<400> SEQUENCE: 46

Met Val His Phe Gln Ile Tyr Pro Cys Val Phe Phe Leu Leu Ile Ile
1               5                   10                  15

Ser Phe His Gly Leu Ile Pro Leu Phe Glu Gly Arg Lys Leu Lys Asp
            20                  25                  30

Val Thr Ala Phe Arg Pro Thr Thr Pro Gly Asn Ser Pro Gly Ala Gly
        35                  40                  45

His Ser Phe Thr Glu Asn Arg Pro Tyr Phe Arg Ser Lys Glu Val Glu
    50                  55                  60

```
Ser Lys Asp Ser Gly Ile His His Pro Asn Ser Glu Ser Ala Thr Gly
 65                  70                  75                  80

Phe Arg Pro Thr Lys Pro Gly Asn Ser Pro Gly Ala Gly His Ser Ile
                 85                  90                  95

His Asn Gln Thr Ala Met Pro
            100
```

```
<210> SEQ ID NO 47
<211> LENGTH: 210
<212> TYPE: PRT
<213> ORGANISM: Euphorbia esula

<400> SEQUENCE: 47

Met Ala Glu Ile Gln Lys Phe Val Ile Phe Leu Leu Ala Ile Val Phe
  1               5                  10                  15

Tyr Leu Gln Ser Gln Ser Thr Ser Ala Arg Pro Val Lys Phe Val Asn
                 20                  25                  30

Lys Lys Gly Leu Ala Leu Lys Lys Asn Ser Asp Ser Phe Lys Leu His
             35                  40                  45

Gln Thr Met Lys Lys Glu Gln Met Pro Pro Val Asp Lys Thr Gly
 50                  55                  60

Phe Phe Gly Asp Phe Ser Asp Lys Ser Thr Asp Asp Phe Arg Pro Thr
 65                  70                  75                  80

Ser Pro Gly Tyr Ser Pro Gly Val Gly His Pro Lys Ala Val Phe Ala
                 85                  90                  95

Asn Ser Gln Ser Asp Arg Ile Asp His Ser Thr Ala Arg Lys Glu Glu
            100                 105                 110

Glu Ser Thr Thr Asp Asp Phe Arg Pro Thr Glu Pro Gly Tyr Ser Pro
            115                 120                 125

Gly Val Gly His Pro Met Glu Ala Ser Thr Ser Asp Lys Asp Asp
130                 135                 140

Tyr Arg Pro Thr Glu Pro Gly His Ser Pro Gly Ala Gly His Pro Lys
145                 150                 155                 160

Glu Glu Ser Thr Asp Asp Phe Arg Pro Thr Ala Pro Gly Phe Ser Pro
                165                 170                 175

Gly Val Gly His Arg Lys Glu Val Val Thr Val Pro Glu Ala Glu Asn
            180                 185                 190

Asp Phe Ser Gly Thr Lys Asp Asp Tyr Arg Pro Thr Gln Pro Gly His
                195                 200                 205

Ser Pro
    210
```

```
<210> SEQ ID NO 48
<211> LENGTH: 232
<212> TYPE: PRT
<213> ORGANISM: Euphorbia esula
<220> FEATURE:
<221> NAME/KEY: SITE
<222> LOCATION: (212)..(215)
<223> OTHER INFORMATION: Xaa can be any naturally occurring amino acid
<220> FEATURE:
<221> NAME/KEY: SITE
<222> LOCATION: (218)..(219)
<223> OTHER INFORMATION: Xaa can be any naturally occurring amino acid

<400> SEQUENCE: 48

Ile Ser Lys Ser Pro Asn Ala Ile Tyr Pro Pro Ala Thr Ser Ile Ser
  1               5                  10                  15
```

```
Phe Asp Asp Glu Glu Glu Pro Gln Glu Ala His Val Tyr Ala Phe
             20                  25                  30

Arg Pro Thr Ala Pro Gly His Ser Pro Gly Val Gly His Lys Glu Glu
         35                  40                  45

Leu Glu Asp Ala His Leu Tyr Ala Phe Arg Pro Thr Ala Pro Gly His
 50                      55                  60

Ser Pro Gly Val Gly His Lys Glu Glu Pro Glu Asp Ser Met Asn Ser
 65                  70                  75                  80

His Val Ile Ile Ser Lys Ser Pro Asn Ala Ile Tyr Pro Pro Thr Thr
                 85                  90                  95

Ser Ile Ser Phe Asp Glu Glu Glu Pro Gln Glu Ala His Leu Tyr
             100                 105                 110

Ala Phe Arg Pro Thr Ala Pro Gly His Ser Pro Gly Val Gly His Lys
         115                 120                 125

Glu Glu Leu Glu Asp Ala His Leu Tyr Ala Phe Arg Pro Thr Ala Pro
     130                 135                 140

Gly His Ser Pro Gly Val Gly Tyr Lys Glu Glu Pro Glu Asp Ser Met
145                 150                 155                 160

Asn Ser His Val Arg Ile Ser Lys Tyr Pro Asn Ala Ile Tyr Pro Pro
                 165                 170                 175

Thr Thr Ser Ile Ser Phe Asp Glu Glu Glu Glu Pro Gln Glu Ala
             180                 185                 190

His Leu Tyr Ala Phe Arg Pro Thr Ala Pro Gly His Ser Pro Gly Val
     195                 200                 205

Gly His Lys Xaa Xaa Xaa Asp Ala Xaa Xaa Tyr Ala Ala Ile Ala
210                 215                 220

Lys Gly Leu Ala Thr Pro Ser Ser
225                 230

<210> SEQ ID NO 49
<211> LENGTH: 158
<212> TYPE: PRT
<213> ORGANISM: Glycine max

<400> SEQUENCE: 49

Met Ala Lys Phe Gln Val Leu His Glu Tyr Phe Phe Ile Phe Leu Ala
 1               5                  10                  15

Leu Val Val Cys Asp Gly Ser Leu Leu Thr His Gly Arg Lys Ile Asn
             20                  25                  30

Ile Lys Pro Leu Asn Gln Leu His Ser Ser Leu Asn Thr Lys Thr Val
         35                  40                  45

Ala Asn His Pro Asn Pro Thr Ser Leu Pro Ser Leu Lys Thr Lys Val
 50                  55                  60

Glu Ser Pro Gln His His Glu Glu Ser Ser Lys Leu Glu Asp Ser Gly
 65                  70                  75                  80

Ala Asp Asn Thr Asn Ala Phe Arg Pro Thr Thr Pro Gly Gly Ser Pro
                 85                  90                  95

Gly Val Gly His Lys Met Ile Thr Ser Ser Ser Glu Asp Asn Lys Val
             100                 105                 110

Lys Thr Met Val Val Val His Ser Pro Asp Val Glu Val Phe Lys Thr
         115                 120                 125

Glu Gly Ser Lys Asp Asp Phe Lys Pro Thr Asp Pro Gly His Ser Pro
     130                 135                 140

Gly Val Gly His Ala Tyr Lys Asn Lys Ile Gly Asp Glu Asn
145                 150                 155
```

<210> SEQ ID NO 50
<211> LENGTH: 87
<212> TYPE: PRT
<213> ORGANISM: Glycine max

<400> SEQUENCE: 50

Met Ala His Phe Thr Arg Thr Cys Leu Leu Val Leu Leu Phe Leu
1               5                   10                  15

Ser Cys Glu Leu Leu Cys Ile Glu Gly Arg Gly Leu Lys Ala Thr Thr
            20                  25                  30

Lys Ser Pro Lys Ser Val Ser Val Arg Ala Met Ser Thr Thr Lys Gly
        35                  40                  45

Ala Val Ala Lys Pro Ser Gln Leu Glu Thr Ile Ala Lys Ser Leu Asn
    50                  55                  60

Gly Phe Val Glu Ala Phe Arg Pro Thr Thr Pro Gly His Ser Pro Gly
65                  70                  75                  80

Val Gly His Ser Val Asn Asn
                85

<210> SEQ ID NO 51
<211> LENGTH: 144
<212> TYPE: PRT
<213> ORGANISM: Glycine max

<400> SEQUENCE: 51

Met His Lys Tyr Phe Thr Ile Phe Val Ala Leu Phe Ala Cys His Gly
1               5                   10                  15

Ser Leu Phe Ala His Gly Arg Gln Ile Lys Pro Leu Asn Gln His Ser
            20                  25                  30

Ser Leu Asn Thr Asn Pro Ile Leu Ala Pro Leu Ser Arg Thr Ser Ile
        35                  40                  45

Lys Val Ile Glu Ala Pro Ile Val Pro Lys Phe Lys Phe Ser Asp Val
    50                  55                  60

Asp Ser Gly Asp Ser Gly Ala Asp His Ala Asn Ala Phe Arg Pro Thr
65                  70                  75                  80

Thr Pro Gly Asn Ser Pro Gly Val Gly His Lys Lys Phe Glu Glu Asp
            85                  90                  95

Lys Val Met Lys Val Met Gly Ala Leu Val His Ser Pro Asp Val Lys
            100                 105                 110

Thr Ser Val Ala Glu Gly Ser Phe Glu Asn Asp Phe Lys Pro Thr Asp
        115                 120                 125

Pro Gly His Ser Pro Gly Val Gly His Pro Arg Gln Asn Lys Arg Asn
    130                 135                 140

<210> SEQ ID NO 52
<211> LENGTH: 94
<212> TYPE: PRT
<213> ORGANISM: Glycine max

<400> SEQUENCE: 52

Met Ala Gln His Lys Phe Leu Leu Cys Leu Ile Leu Leu Ala Leu Ile
1               5                   10                  15

Ile Phe Cys Gln Gly Leu His Ser Ile Glu Gly Arg Tyr Leu Lys Ser
            20                  25                  30

Asp His Glu Ile Ile Lys His Gln Tyr Gln Met His Ser Gly Ile Ser
        35                  40                  45

```
Thr Thr Asn Val Ala Ala Leu Val Ala Asp Val Ser Pro Pro Thr Pro
    50                  55                  60

Pro Ser Ala Ala Val Pro Gly Arg Asp Asn Asp Asn Phe Arg Pro Thr
65                  70                  75                  80

Ala Pro Gly His Ser Pro Gly Val Gly His Ala Ala His Asn
                85                  90
```

<210> SEQ ID NO 53
<211> LENGTH: 141
<212> TYPE: PRT
<213> ORGANISM: Glycine max

<400> SEQUENCE: 53

```
Met Ala Ala Gln Val Leu His Lys Tyr Phe Ile Phe Leu Ala Leu
1               5                   10                  15

Val Val Cys His Gly Ser Leu Val Ala His Gly Arg Lys Ile Asn Val
                20                  25                  30

Lys Pro Leu Asn Gln Gln His Tyr Ser Leu Asn Thr Lys Thr Val Ala
            35                  40                  45

Asn Asn Asn Pro Tyr Pro Ser Leu Pro Ser Leu Lys Thr Lys Val Glu
    50                  55                  60

Ser Pro Gln Tyr Glu Glu Ala Asn Lys Leu Gly Asp Ser Gly Ser Thr
65                  70                  75                  80

Gly Val Gly His Lys Ile Ile Thr Ser Ser Gly Asp Asn Lys Met Lys
                85                  90                  95

Thr Met Val Val Val Gln Ser Pro Asp Val Glu Val Phe Val Thr Lys
                100                 105                 110

Gly Ser Lys Asp Asp Phe Lys Pro Thr Asp Pro Gly His Ser Pro Gly
            115                 120                 125

Val Gly His Val Tyr Gln Asn Lys Ile Gly Gln Ala Asn
        130                 135                 140
```

<210> SEQ ID NO 54
<211> LENGTH: 86
<212> TYPE: PRT
<213> ORGANISM: Glycine max

<400> SEQUENCE: 54

```
Met Glu Asn Ser Ser Leu Arg Asn Ile Ala Phe Val Leu Phe Leu Phe
1               5                   10                  15

Leu Ile Leu His His Gln Val Leu Phe Val Gln Gly Arg Asn Leu Lys
                20                  25                  30

Cys Pro Leu Cys Lys Glu Cys Ser Lys Ser Gln Lys Asn Thr Met Ser
            35                  40                  45

Val Ala Ser Tyr Glu Val His Gln Glu Gly Leu Arg Arg Val Glu Tyr
    50                  55                  60

Glu Val Asp Asp Phe Arg Pro Thr Thr Pro Gly His Ser Pro Gly Val
65                  70                  75                  80

Gly His Ser Ile Asn Asn
                85
```

<210> SEQ ID NO 55
<211> LENGTH: 109
<212> TYPE: PRT
<213> ORGANISM: Glycine max

<400> SEQUENCE: 55

```
Met Ala Asn Ser Lys Leu Gly Phe Asn Phe Met Val Ser Ala Ile Phe
```

-continued

```
                1               5                  10                  15
Leu Ser Leu Met Thr Phe His Gly Thr Phe Ser Val Gln Gly Arg Pro
                20                  25                  30

Leu Lys Met Glu Ile Lys Glu Gln Val Thr Thr His Glu Asn Ile Ile
                35                  40                  45

Asp Glu Ile Ala Lys Ala Ala Glu Tyr Thr Ala Thr Trp His Arg His
        50                  55                  60

Thr Leu Glu Phe Glu Asp Thr Lys Asn Pro Gln Tyr Asp Gly Val Thr
65                  70                  75                  80

Asn Asp Phe Gln Pro Thr Asp Pro Gly His Ser Pro Gly Ala Gly His
                85                  90                  95

Ser Ser Pro His Ala Asn Ile Val Ser Ile Ser Lys Pro
                100                 105
```

<210> SEQ ID NO 56
<211> LENGTH: 75
<212> TYPE: PRT
<213> ORGANISM: Glycine max
<220> FEATURE:
<221> NAME/KEY: SITE
<222> LOCATION: (75)..(75)
<223> OTHER INFORMATION: Xaa can be any naturally occurring amino acid

<400> SEQUENCE: 56

```
Ile Lys Leu Ile Asp Ala Pro Ile Val Pro Lys Phe Lys Phe Ala Asp
1               5                   10                  15

Val Asp Ser Gly Asp Ser Gly Ala Asp His Ala Asn Ala Phe Arg Pro
                20                  25                  30

Thr Thr Pro Gly Asn Ser Pro Gly Val Gly His Lys Lys Phe Glu Gly
                35                  40                  45

Glu Asp Lys Asp Ala Gly Ser Phe Glu Asn Asp Phe Arg Pro Thr Asp
        50                  55                  60

Pro Gly His Ser Pro Gly Val Gly His Pro Xaa
65                  70                  75
```

<210> SEQ ID NO 57
<211> LENGTH: 87
<212> TYPE: PRT
<213> ORGANISM: Glycine max

<400> SEQUENCE: 57

```
Met Ala Gln Asn Lys Phe Leu Leu Ser Leu Val Leu Ala Leu Ile
1               5                   10                  15

Ile Phe Cys Gln Gly Phe His Ser Ile Glu Gly Arg Tyr Leu Lys Ser
                20                  25                  30

Gly Glu Thr Ile Lys His Gln Met His Ser Gly Ile Ser Thr Thr Asn
                35                  40                  45

Val Ala Asp Val Ser Pro Pro Thr Pro Pro Ser Ala Ala Val Pro Gly
        50                  55                  60

Arg Asp Val Asp Asn Phe Arg Pro Thr Ala Pro Gly His Ser Pro Gly
65                  70                  75                  80

Val Gly His Thr Val His Asn
                85
```

<210> SEQ ID NO 58
<211> LENGTH: 108
<212> TYPE: PRT
<213> ORGANISM: Glycine max

<400> SEQUENCE: 58

Met Ala Asn Leu Lys Leu Val Phe Thr Met Ser Ser Ile Leu Leu Val
1               5                   10                  15

Leu Val Phe Phe Asn Gly Ile Leu Pro Ala Met Gly Arg Pro Leu Lys
            20                  25                  30

Lys Glu His Ile Thr Thr Thr Tyr Glu Asn Ser Val Lys Glu Met Gly
        35                  40                  45

Thr Val Glu Asp Asn Asn Ile Leu Leu Trp Arg Arg Ser Ile Ile Glu
    50                  55                  60

Asn Asn Ala Ala Asn Asp Gly Gly Val Asp Lys Trp Ile Asp Asp Phe
65                  70                  75                  80

Arg Pro Met Asp Pro Gly His Ser Pro Gly Ala Gly His Ser Ser Pro
                85                  90                  95

Thr Pro Lys Asp Ala Thr Asn Gly Ala Pro Arg Pro
            100                 105

<210> SEQ ID NO 59
<211> LENGTH: 81
<212> TYPE: PRT
<213> ORGANISM: Glycine max

<400> SEQUENCE: 59

Met Ala Gln Lys Ile Ile Trp Leu Thr Phe Leu Val Phe Leu Ile Leu
1               5                   10                  15

Gln His Asn Phe Gly Thr Met Glu Ala Ser Arg Lys Leu Ile His Thr
            20                  25                  30

His Pro Pro Pro Ala Ile Pro Arg Ser Pro Gln Ala Pro Ala Leu Trp
        35                  40                  45

Tyr Thr Pro Asn Asp Glu Asp Gly Gly His Asp Ala Phe Arg Pro Thr
    50                  55                  60

Cys Arg Gly His Ser Pro Gly Ala Gly His Asp Asn Pro Pro Thr Lys
65                  70                  75                  80

Pro

<210> SEQ ID NO 60
<211> LENGTH: 81
<212> TYPE: PRT
<213> ORGANISM: Glycine max

<400> SEQUENCE: 60

Met Ala Arg Leu Thr His Phe Val Leu Leu Phe Val Leu Leu Phe Leu
1               5                   10                  15

Ser His Glu Leu Leu Gly Ser Glu Gly Arg Asn Leu Arg Gln Ile Thr
            20                  25                  30

Ile Gln Ser Pro Asp Ala Thr Lys Ala Met Ser Ile Ala Thr Lys Ser
        35                  40                  45

Ala Asn Ala Ile Pro Ser Tyr Arg Ser Ile Arg Ser Leu Ser Gly Asp
    50                  55                  60

Val Glu Ala Phe Arg Pro Thr Thr Pro Gly His Ser Pro Gly Val Gly
65                  70                  75                  80

His

<210> SEQ ID NO 61
<211> LENGTH: 87
<212> TYPE: PRT
<213> ORGANISM: Glycine max

```
<400> SEQUENCE: 61

Met Ala His Phe Thr Arg Thr Cys Leu Leu Leu Val Leu Leu Phe Leu
1               5                   10                  15

Ser Cys Glu Leu Leu Cys Ile Glu Gly Arg Gly Leu Lys Ala Thr Thr
            20                  25                  30

Lys Ser Pro Lys Ser Val Ser Val Arg Ala Met Ser Thr Thr Lys Gly
        35                  40                  45

Ala Val Ala Lys Pro Ser Gln Leu Glu Thr Ile Ala Lys Ser Leu Asn
50                  55                  60

Gly Phe Val Glu Ala Phe Arg Pro Thr Thr Pro Gly His Ser Pro Gly
65                  70                  75                  80

Val Gly His Ser Val Asn Asn
                85

<210> SEQ ID NO 62
<211> LENGTH: 163
<212> TYPE: PRT
<213> ORGANISM: Glycine max

<400> SEQUENCE: 62

Met Ala Ile Phe Gln Tyr Ala Thr Arg Lys Cys Leu Val Ile Phe Leu
1               5                   10                  15

Leu Leu Val Ala Phe Asn Gly Ser Leu Leu Thr His Gly Arg Gln Ile
            20                  25                  30

Lys Pro Leu Asn Gln Gln His Ser Ser Leu Asn Asn Asp Thr Val Val
        35                  40                  45

Lys His Ser Val Asn Asn Val Pro Thr His Pro Ser Gly Lys Lys
50                  55                  60

Lys Val Val Asp Ser Ser Ser Val Val Pro Lys Tyr Gly Val Glu Ser
65                  70                  75                  80

Phe Gly Asp Ser Met Ser Ser Asp Thr Asn Ala Phe Arg Pro Thr Thr
                85                  90                  95

Pro Gly Asn Ser Pro Gly Val Gly His Arg Lys Phe Ala Pro Glu Asp
            100                 105                 110

Lys Asp Val Glu Ala Met Val Ala Ser Val Gln Ser Pro Asp His Val
        115                 120                 125

Lys Val Tyr Val Thr Glu Gly Thr Gln Asn Gln Asp Gly Phe Lys Pro
    130                 135                 140

Thr Asn Pro Gly His Ser Pro Gly Val Gly His Ala Gln Gln Asn Lys
145                 150                 155                 160

Ile Gly Gln

<210> SEQ ID NO 63
<211> LENGTH: 76
<212> TYPE: PRT
<213> ORGANISM: Glycine max

<400> SEQUENCE: 63

Glu Ser Pro Gln His His Glu Glu Ser Ser Lys Leu Glu Asp Ser Gly
1               5                   10                  15

Ala Asp Asn Thr Asn Ala Phe Arg Pro Thr Thr Pro Gly Gly Ser Pro
            20                  25                  30

Gly Val Gly His Lys Met Ile Thr Ser Ser Glu Asp Asn Lys Gly
        35                  40                  45

Ser Lys Asp Asp Phe Lys Pro Thr Asp Pro Gly His Ser Pro Gly Val
    50                  55                  60
```

Gly His Ala Tyr Lys Asn Lys Ile Gly Asp Gly Asn
65                  70                  75

<210> SEQ ID NO 64
<211> LENGTH: 108
<212> TYPE: PRT
<213> ORGANISM: Glycine max

<400> SEQUENCE: 64

Met Thr Asn Leu Lys Leu Val Phe Thr Ile Ser Ser Ile Leu Leu Ala
1               5                   10                  15

Leu Val Phe Ile Asn Gly Ile Ser Ser Val Met Gly Arg Pro Leu Lys
            20                  25                  30

Lys Glu His Ile Ile Thr Thr Thr Tyr Glu Asn Ser Val Lys Glu Met
        35                  40                  45

Gly Thr Val Glu Asp Asn Asn Ile Leu Leu Trp Arg Arg Ser Ile Ile
    50                  55                  60

Glu Asn Ala Ala Asn Asp Gly Gly Val Asp Lys Trp Ile Asp Asp Phe
65                  70                  75                  80

Arg Pro Thr Asp Pro Gly His Ser Pro Gly Ala Gly His Ser Ser Pro
                85                  90                  95

Thr Pro Lys Asp Ala Ser Asn Gly Ala Pro Arg Pro
            100                 105

<210> SEQ ID NO 65
<211> LENGTH: 95
<212> TYPE: PRT
<213> ORGANISM: Lotus japonicus

<400> SEQUENCE: 65

Met Thr Asn Ser Lys Lys Leu Val Phe Thr Ile Ser Ser Ile Leu Leu
1               5                   10                  15

Leu Thr Leu Met Phe Ser Asn Phe Ile Phe Ser Ala His Gly Arg Pro
            20                  25                  30

Leu Lys Thr Glu Asn Lys Glu His Val Thr Thr Tyr Glu Asn Asn Ser
        35                  40                  45

Val Lys Glu Met Ala Thr Gly Glu Asn Asp His Lys Val Gly Lys Leu
    50                  55                  60

Ile Asn Asp Phe Lys Pro Thr Asp Pro Gly His Ser Pro Gly Val Gly
65                  70                  75                  80

His Ser Ser Pro Ile Pro Met Asp Ala Asn Glu Pro Pro Arg Ser
                85                  90                  95

<210> SEQ ID NO 66
<211> LENGTH: 89
<212> TYPE: PRT
<213> ORGANISM: Lotus japonicus

<400> SEQUENCE: 66

Met Ala Gln Asn Lys Pro Ile Phe Ser Leu Ile Leu Ala Leu Ile
1               5                   10                  15

Ile Phe Cys His Gly Phe Gln Ser Ile Glu Gly Arg Tyr Phe Lys Ile
            20                  25                  30

Gly Glu Gly Thr Gln His Leu Met Lys His Gly Asp Phe Ser Thr Thr
        35                  40                  45

Asn Gly Val Val Ser Gly Ala Ser Glu Ala Pro Ser Leu Thr Pro Ser
    50                  55                  60

```
Arg Asp Val Ser Gly Phe Lys Gln Pro Thr Thr Gly Pro Gly His Ser
 65                  70                  75                  80

Pro Gly Val Gly His Ser Ile His Asn
                 85
```

<210> SEQ ID NO 67
<211> LENGTH: 99
<212> TYPE: PRT
<213> ORGANISM: Lotus japonicus

<400> SEQUENCE: 67

```
Met Ala Lys Thr Asn Leu Lys Phe Val Cys Val Phe Leu Leu Leu
 1               5                  10                  15

Ile Leu His His Gln His Val Cys Val Gln Gly Arg His Leu Arg Ser
                 20                  25                  30

Cys Leu Cys Arg Gly Cys Pro Lys Thr Cys Val Lys Ile Lys Ser Gly
                 35                  40                  45

Val Ala His Gly Val Gly Asp Arg Gly Asn Arg Ala Thr Thr His Asp
             50                  55                  60

Tyr Asp Thr His Gln Gly Arg Lys Arg Leu Val Glu Tyr Glu Val Glu
 65                  70                  75                  80

Ala Phe Arg Pro Thr Ser Pro Gly His Ser Pro Gly Val Gly His Ser
                 85                  90                  95

Ile Asn Asn
```

<210> SEQ ID NO 68
<211> LENGTH: 86
<212> TYPE: PRT
<213> ORGANISM: Lotus japonicus

<400> SEQUENCE: 68

```
Met Glu Glu Lys Thr Val Met Leu Thr Leu Leu Val Ile Leu Ile Leu
 1               5                  10                  15

Gln His Asn Tyr Gly Ser Met Ala Leu Ser Gly Asn Asn Ile His Pro
                 20                  25                  30

Pro Pro Ala Ile Pro Arg Ala Leu Leu Arg Ser Pro Gln Pro Pro Ser
                 35                  40                  45

Pro Gly Trp Tyr Thr Ile Asn Asp Asp Lys Val Gly Glu Gly Asp Ala
             50                  55                  60

Phe Arg Pro Thr Thr Pro Gly His Ser Pro Gly Val Gly His Asp Ser
 65                  70                  75                  80

Pro Pro Asn Phe His Ala
                 85
```

<210> SEQ ID NO 69
<211> LENGTH: 91
<212> TYPE: PRT
<213> ORGANISM: Lotus japonicus

<400> SEQUENCE: 69

```
Met Ala His Phe Ala Arg Thr Cys Leu Leu Phe Val Leu Leu Phe Val
 1               5                  10                  15

Ser Cys Glu Leu Leu Cys Ile Glu Gly Arg Thr Leu Ser Lys Asn Val
                 20                  25                  30

Leu Asp His Ser Leu Lys Ser Ser Val Lys Ala Met Ser Ile Ala
             35                  40                  45

Thr Val Lys Thr Glu Asn Gly Val Val Ala Ser Pro Ser Gln Leu Arg
 50                  55                  60
```

```
Arg Ser Met Glu Gly Tyr Val Glu Ala Phe Arg Pro Thr Thr Pro Gly
 65                  70                  75                  80

His Ser Pro Gly Val Gly His Ser Val His Asn
                 85                  90
```

<210> SEQ ID NO 70
<211> LENGTH: 125
<212> TYPE: PRT
<213> ORGANISM: Lotus japonicus

<400> SEQUENCE: 70

```
Met Gly Glu Phe Gln Ala Arg Thr Ile Tyr Phe Leu Val Phe Leu Ala
  1               5                  10                  15

Leu Phe Ala Cys Asn Cys Ser Leu Leu Cys His Gly Arg Pro Leu Lys
                 20                  25                  30

Pro Val Asn Ser Pro Ile Met Pro Asn Gln Asp Val Ala Thr Ser Gly
             35                  40                  45

Asp Ala Gly Ala Ser Tyr Thr Asn Ala Phe Glu Pro Thr Thr Pro
         50                  55                  60

Gly Asn Ser Pro Gly Val Gly His Arg Ser Phe Ala Gly Glu Asp Asn
 65                  70                  75                  80

Lys Met Val Ala Ala Gln Ser Pro Asp Val Gly Val Ser Val Thr Gln
                 85                  90                  95

Gly Ser Glu Ser Asp Phe Lys Pro Thr Asp Pro Gly His Ser Pro Gly
                100                 105                 110

Val Gly His Ala Tyr Gln Glu Lys Ile Gly His Leu Asn
            115                 120                 125
```

<210> SEQ ID NO 71
<211> LENGTH: 210
<212> TYPE: PRT
<213> ORGANISM: Populus trichocarpa

<400> SEQUENCE: 71

```
Met Pro His Pro Ala Val Pro Ser Phe Gly Asn Ser Ala Ala Val Tyr
  1               5                  10                  15

Lys Asp Asp Phe Arg Pro Thr Thr Pro Gly Val Ser Pro Gly Val Gly
                 20                  25                  30

His Pro Lys Thr Ile Gly Thr Asn Ser Asn Glu His Ser Leu Thr
             35                  40                  45

Asp Phe Lys Asp Phe Gln Pro Thr Pro Gly His Ser Pro Gly
         50                  55                  60

Ala Gly His Ala Leu Ala Asn Asp Asp Asn Glu Glu Val Ser Pro
 65                  70                  75                  80

Lys Ala Pro Gly Pro Ser Ile Glu Arg Ser Gly Thr Ala Phe Lys Pro
                 85                  90                  95

Thr Thr Pro Gly His Ser Pro Gly Ala Gly His Ala Leu Ala Asn Asp
                100                 105                 110

Asp Asp Asn Glu Glu Val Ser Pro Lys Ala Pro Gly Ser Ser Ile Glu
            115                 120                 125

Arg Ser Gly Thr Ala Phe Lys Pro Thr Thr Pro Gly His Ser Pro Gly
            130                 135                 140

Ile Gly His Leu Phe Ser Glu Asn Asp Thr Asp Lys Asn Glu Ile Thr
145                 150                 155                 160

Ala Ser Lys Ala Ser Ser Ile Glu His Ser Val Thr Gly Val Thr Asp
                165                 170                 175
```

```
Asp Phe Arg Pro Thr Val Pro Gly His Ser Pro Gly Ile Gly His Ala
                180                 185                 190

Phe Arg Pro Pro Thr Pro Gly His Ser Pro Gly Val Gly His Ser Ile
        195                 200                 205

His Asn
    210

<210> SEQ ID NO 72
<211> LENGTH: 370
<212> TYPE: PRT
<213> ORGANISM: Populus trichocarpa

<400> SEQUENCE: 72

Met Ala Glu Thr Cys Lys Cys Ala Phe Leu Ile Leu Ala Phe Val Thr
1               5                   10                  15

Cys Phe Gln Ile Leu Phe Ile Glu Gly Arg Ser Ile Lys Gln Thr Asn
                20                  25                  30

Lys Gln Glu His Val Thr Asn Glu Ile Glu Pro Leu Lys Glu Met Ala
            35                  40                  45

Asn Gln Ser Thr Asn Thr Asn Leu His His Asn Thr Ala Asn Asn Gln
        50                  55                  60

Lys Val Ser Leu Pro Ser Pro Val His Ile Pro Thr Val His His
65                  70                  75                  80

Ser Lys Ala Gly Arg Lys Glu Met Thr Pro Pro Met Val Pro Ser Phe
                85                  90                  95

Ser Gly Ser Pro Gly Val Arg His Pro Lys Thr Pro Gly Ala Asn Ser
            100                 105                 110

Val Thr Thr Val Lys Asp Asp Phe Lys Pro Ile Thr Ser Gly Gln Ser
        115                 120                 125

Pro Gly Val Gly His Asn Asn Asp Asn Ser Val Thr Ala Phe Lys Asp
    130                 135                 140

Asp Phe Gln Pro Thr Thr Pro Gly Asn Ser Pro Gly Val Gly His Ile
145                 150                 155                 160

Leu Val Asp Glu Asp Asp Ser Glu Asp Asp Pro Lys Ala Pro Gly
                165                 170                 175

Thr Ser Ser Ser Asn Glu Arg Ser Gly Ala Ala Phe Lys Pro Thr Thr
                180                 185                 190

Pro Gly His Ser Pro Gly Val Gly His Met Ser Ser Val Asp Gln Ser
            195                 200                 205

Asp Lys Thr Asp Leu Lys Ala Ser Lys Thr Glu Leu Ser Val Thr Thr
        210                 215                 220

Pro Ala Phe Lys Pro Thr Thr Pro Gly His Ser Pro Gly Val Gly His
225                 230                 235                 240

Met Ser Ser Val Asp Gln Ser Asp Lys Ile Asp Ser Lys Ala Ser Glu
                245                 250                 255

Ile Glu His Phe Asn Thr Glu His Ser Val Thr Thr Pro Gly His Ser
            260                 265                 270

Pro Ala Val Gly His Ile Leu Ser Asp Glu Asp Glu Asp Asn Glu
        275                 280                 285

Asp Val Asp Pro Lys Ala Pro Gly Thr Gly Ser Ser Ile Lys Arg Ser
    290                 295                 300

Gly Ala Ala Phe Lys Pro Thr Thr Pro Gly His Ser Pro Gly Ile Gly
305                 310                 315                 320

His Met Ser Ser Val Asp Gln Ser Asp Lys Thr Asp Arg Lys Ala Thr
```

```
                    325                 330                 335
Asn Ile Glu His Ser Val Ala Arg Val Pro Asp Gly Phe Arg Pro Ala
                340                 345                 350
Val Pro Ile Gln Gly Pro Gly Val Gly His Val Phe Gln Ala Gln Thr
            355                 360                 365
Lys Asn
    370

<210> SEQ ID NO 73
<211> LENGTH: 158
<212> TYPE: PRT
<213> ORGANISM: Populus trichocarpa

<400> SEQUENCE: 73

Met Ile Gln Arg His Pro Val Leu Ala Pro Val Met Lys Arg Ser Gly
1               5                   10                  15
Ala Ala Phe Lys Pro Thr Thr Pro Gly His Ser Pro Gly Ile Gly His
                20                  25                  30
Met Ser Ser Val Asp Gln Thr Phe Lys Pro Thr Thr Pro Gly His Ser
            35                  40                  45
Pro Gly Ile Gly His Met Ser Ser Val Asp Gln Ser Asp Lys Thr Asp
        50                  55                  60
Ser Lys Ala Ser Glu Ile Lys His Ser Val Thr Thr Pro Gly His Ser
65                  70                  75                  80
Ser Arg Val Gly His Ile Leu Ser Asp Glu Asp Ala Asp Asp Thr Phe
                85                  90                  95
Lys Pro Thr Thr Pro Gly His Ser Pro Gly Ile Gly His Met Ser Ser
                100                 105                 110
Val Asp Gln Ser Asp Lys Thr Asp Arg Lys Ala Thr Asn Ile Glu His
            115                 120                 125
Ser Val Ala Arg Val Pro Asp Gly Phe Arg Pro Ala Val Pro Ile Gln
        130                 135                 140
Gly Pro Gly Val Gly His Val Phe Gln Ala Gln Thr Lys Asn
145                 150                 155

<210> SEQ ID NO 74
<211> LENGTH: 90
<212> TYPE: PRT
<213> ORGANISM: Populus trichocarpa

<400> SEQUENCE: 74

Met Ala Asp Lys Thr Arg Ser Phe Met Leu Thr Phe Phe Thr Val Val
1               5                   10                  15
Leu Leu Leu Leu His Gln His Phe Asp Leu Thr Ala Ala Ser Arg Pro
                20                  25                  30
Leu Asp Ile His Ser Pro Ala Ile Pro Arg Ser Gly Ser Glu Pro Pro
            35                  40                  45
Pro Thr Asp Val His Asp Arg Trp Tyr Arg Ile Asn Arg Tyr Lys Asn
        50                  55                  60
Leu Glu Ser Asp Ala Phe Arg Pro Thr Thr Pro Gly His Ser Pro Gly
65                  70                  75                  80
Val Gly His Glu Asn Pro Pro Ala Ala Pro
                85                  90

<210> SEQ ID NO 75
<211> LENGTH: 88
<212> TYPE: PRT
```

<213> ORGANISM: Populus trichocarpa

<400> SEQUENCE: 75

Met Ala Lys Gly Lys Leu Ile Phe Thr Ser Thr Leu Ile Ile Val Leu
1               5                   10                  15

Val Leu Cys Tyr Gly Ile Thr Ser Ser Val Gly Arg Leu Leu Lys Thr
            20                  25                  30

Gly Glu Asn Thr Ser Ser Phe Ser Leu His Arg Asp Leu Leu Val Ser
        35                  40                  45

Glu Ala Arg Ser Glu Pro Val Thr Pro Gly Pro Asp His Ala Asp Ala
    50                  55                  60

Asp Ser Asp Asp Phe Lys Pro Thr Thr Pro Gly His Ser Pro Gly Ala
65                  70                  75                  80

Gly His Ser Thr Pro Gly His Asn
                85

<210> SEQ ID NO 76
<211> LENGTH: 70
<212> TYPE: PRT
<213> ORGANISM: Populus trichocarpa

<400> SEQUENCE: 76

Met Ala Gln Ser Asn Leu Leu Ser Ala Phe Val Phe Leu Val Leu Ile
1               5                   10                  15

Phe Ser His Glu Leu Gln Phe Ile Glu Gly Arg Tyr Leu Asn Leu Lys
            20                  25                  30

Thr Pro Asn Lys Phe Leu Gln Lys Glu Ile Arg Arg Leu Val Glu Ser
        35                  40                  45

Asn Ser Lys Leu His Val Asn Asp Asn Leu Asp Lys Pro Val Asn Ala
    50                  55                  60

Thr Lys Val Ala Pro Pro
65                  70

<210> SEQ ID NO 77
<211> LENGTH: 244
<212> TYPE: PRT
<213> ORGANISM: Vitis vinifera

<400> SEQUENCE: 77

Met Ala Ile Ile Gln Val Ile His Ala Cys Ser Leu Leu Leu Ala Val
1               5                   10                  15

Ile Thr Tyr His Asp Ile Leu Tyr Thr Glu Gly Arg Pro Ile Asn Ser
            20                  25                  30

Val Thr Lys Gln Glu Phe Ser Ser Thr Asp Phe Glu Pro Gly Asn Glu
        35                  40                  45

Thr Gly Ser Gln Gly Thr Glu His Lys Glu Asp His Trp Tyr Thr Pro
    50                  55                  60

Pro Pro Pro Glu Pro Asn Pro Ser Val Lys Asn Ser Val Val Gly Lys
65                  70                  75                  80

Asp Ile Leu Pro Pro Ile Thr Pro Asn Tyr Ser Ile Gly Phe Gly Asp
                85                  90                  95

Ser Thr Ala Val Tyr Lys Asp Gly Phe Arg Pro Thr Thr Pro Gly Ser
            100                 105                 110

Ser Pro Gly Ile Gly His Gln Phe Val Pro Thr Lys Glu Asp Ile Gln
        115                 120                 125

Pro Lys Ala Leu Gly Asn Ser Pro Ser Val Arg His Ser Val Thr Ala
    130                 135                 140

Tyr Lys Asp Asp Tyr Arg Pro Thr Met Pro Gly His Ser Pro Gly Glu
145                 150                 155                 160

Pro Asn Pro Gly Val Lys Asn Ser Val Ala Gly Lys Lys Glu Leu Pro
                165                 170                 175

Pro Pro Met Leu Pro Asn Tyr Ser Val Gly Phe Gly Asp Ser Thr Ala
            180                 185                 190

Val Ser Lys Asp Asp Phe Arg Pro Thr Thr Pro Gly Ser Ser Pro Gly
        195                 200                 205

Val Gly His His Ser Asp Asp Tyr Arg Pro Thr Lys Pro Gly His Ser
    210                 215                 220

Pro Gly Val Gly His Ser Leu Gln Lys Thr Asn Ala Glu Pro Asn Ala
225                 230                 235                 240

Glu Pro Asn Ala

<210> SEQ ID NO 78
<211> LENGTH: 140
<212> TYPE: PRT
<213> ORGANISM: Vitis vinifera

<400> SEQUENCE: 78

Met Ala Lys Ile Arg Phe Ile His Ala Tyr Ser Leu Leu Ala Val
1               5                   10                  15

Ile Thr Tyr His His Ile Leu Cys Thr Glu Ala Arg Pro Ile Lys Ser
                20                  25                  30

Pro Ser Ser Ile Asp Tyr Glu Pro Gly Lys Glu Thr Gly Ser Gln Gly
            35                  40                  45

Thr Glu His Lys Asp Val Trp Ser Gly Pro Pro Pro Glu Pro Asn
50                  55                  60

Pro Ile Val Lys Asn Ser Val Ala Gly Lys Glu Ile Leu Pro Pro
65                  70                  75                  80

Met Ile Pro Asn Tyr Ser Val Gly Phe Gly Asp Ser Ala Ala Val His
                85                  90                  95

Thr Asp Gly Phe Arg Pro Thr Thr Pro Gly Ser Ser Pro Gly Ile Gly
            100                 105                 110

His Ser Ala Pro Thr Lys Glu Asp Ile Glu Pro Lys Ala Pro Gly
                115                 120                 125

Asn Ser Pro Lys Thr Phe Arg Gln Gly Lys Gln Gly
            130                 135                 140

<210> SEQ ID NO 79
<211> LENGTH: 140
<212> TYPE: PRT
<213> ORGANISM: Vitis vinifera

<400> SEQUENCE: 79

Met Ala Lys Val His Ile Ile His Ala Cys Ser Leu Leu Ala Val
1               5                   10                  15

Ile Thr Asn His Asp Ile Leu Tyr Thr Glu Gly Arg Pro Met Lys Ser
                20                  25                  30

Leu Ser Lys His Glu Phe Ser Ser Ile Asp Ser Gly Pro Gly Thr Glu
            35                  40                  45

Thr Gly Ser Glu Gly Ile Glu His Lys Asp Asp His Arg Ser Ala Pro
50                  55                  60

Pro Pro Pro Glu Pro Asn Pro Gly Val Lys Asn Ser Val Ala Gly Lys
65                  70                  75                  80

Lys Glu Leu Pro Pro Met Met Pro Asn Tyr Thr Thr Gly Leu Ala
                85              90                  95

Asp Ser Thr Ala Val Tyr Glu Asp Asp Phe Arg Pro Thr Pro Pro Gly
            100                 105                 110

Ser Ser Pro Gly Ile Gly His His Phe Asp Phe Arg Pro Thr Thr Pro
            115                 120                 125

Gly His Ser Pro Gly Val Gly His Ser Leu Gln Asn
            130                 135             140

<210> SEQ ID NO 80
<211> LENGTH: 110
<212> TYPE: PRT
<213> ORGANISM: Vitis vinifera

<400> SEQUENCE: 80

Met Ala Lys Val Lys Leu Ile Met Ser Ile Tyr Val Phe Ile Leu Ala
1               5                   10                  15

Leu Val Leu Ile Tyr Gly Gly Leu Met Ser Glu Gly Arg Lys Leu Asp
                20                  25                  30

Ile Glu Lys Asn Ser Lys Cys Glu Met Cys Val Ser Ile Asp Glu Lys
            35                  40                  45

Ile Ser Val Leu Gly Asn Leu His Arg Ser Ser Lys Ala Asn Ala Arg
50                  55                  60

Pro His Ala Pro Ala Arg Gln Ser Pro Gly Ala Asp Arg Leu Phe Thr
65                  70                  75                  80

Asp Asp Gly Val Asp Val Gln Ser Thr Thr Pro Gly His Ser Pro Gly
                85                  90                  95

Val Gly His Ser Val Gly Pro Ala Ser Asn Asp Pro Asn Pro
            100                 105                 110

<210> SEQ ID NO 81
<211> LENGTH: 166
<212> TYPE: PRT
<213> ORGANISM: Vitis vinifera

<400> SEQUENCE: 81

Met Asp Arg Gln Asp Ala Ile Leu Asp Ile Gln Trp Leu Lys Lys Ile
1               5                   10                  15

Leu Val Arg His Arg Val Ile Thr Asn His Asp Ile Leu Tyr Thr Glu
                20                  25                  30

Gly Arg Pro Met Lys Ser Leu Ser Lys His Glu Phe Ser Ser Ile Asp
            35                  40                  45

Ser Gly Pro Gly Thr Glu Thr Gly Ser Glu Gly Ile Glu His Lys Asp
50                  55                  60

Asp His Arg Ser Ala Pro Pro Pro Glu Pro Asn Pro Gly Val Lys
65                  70                  75                  80

Asn Ser Val Ala Gly Lys Lys Glu Leu Pro Pro Met Met Pro Asn
                85                  90                  95

Tyr Thr Thr Gly Leu Ala Asp Ser Thr Ala Val Tyr Glu Asp Asp Phe
            100                 105                 110

Arg Pro Thr Pro Pro Gly Ser Ser Pro Gly Ile Gly His His Phe Val
            115                 120                 125

Pro Thr Lys Gly Asp Ile Gln Pro Lys Ala Gln Gly Asn Ser Pro Gly
            130                 135                 140

Val Gly Gln Ser Val Thr Ala Tyr Lys Asp Asp Tyr Pro Pro Thr Lys
145                 150                 155                 160

Pro Ala Arg Ser Gln Pro
              165

<210> SEQ ID NO 82
<211> LENGTH: 173
<212> TYPE: PRT
<213> ORGANISM: Vitis vinifera

<400> SEQUENCE: 82

Met Ala Lys Ile Gln Val Ile His Ala Cys Ser Leu Val Leu Ala Val
1             5                10               15

Ile Thr Tyr His Asp Ile Leu Tyr Thr Glu Gly Arg Pro Ile Lys Ser
            20               25               30

Leu Asp Lys His Glu Phe Ser Ser Ile Asp Ser Glu Pro Gly Thr Glu
            35               40               45

Thr Gly Ser Gln Gly Ile Glu His Lys Asp Asp His Trp Ala Ala Pro
    50               55               60

Pro Gln Glu Pro Asn Pro Gly Val Lys Asn Ser Val Ala Gly Lys Lys
65             70               75              80

Glu Leu Pro Pro Pro Met Leu Pro Asn Tyr Ser Val Gly Phe Gly Asp
            85               90               95

Ser Thr Ala Val Ser Lys Asp Asp Phe Arg Pro Thr Thr Pro Gly Ser
           100              105             110

Ser Pro Gly Val Gly His His Ser Val Pro Thr Lys Asp Asp Thr Gln
           115              120             125

Pro Lys Ala Leu Arg Asn Ser Pro Ser Val Arg Gln Ser Val Thr Ala
    130              135             140

Tyr Lys Asp Asp Tyr Arg Pro Thr Lys Pro Gly His Ser Pro Gly Val
145           150              155            160

Gly His Ser Leu Gln Lys Thr Asn Ala Glu Pro Asn Ala
           165              170

<210> SEQ ID NO 83
<211> LENGTH: 89
<212> TYPE: PRT
<213> ORGANISM: Vitis vinifera

<400> SEQUENCE: 83

Met Ala Asn Thr Arg Phe Leu Gly Ala Cys Ala Val Leu Leu Val Leu
1             5                10               15

Leu Leu Cys His Glu Phe Ser Cys Val Lys Gly Arg His Leu Arg Ser
            20               25               30

Ala Met Cys Lys Lys Cys Ser Arg His Arg Gln Thr Ser Leu Arg Ala
            35               40               45

Thr Glu Ala Gly Glu Ala Pro Ser Gly Leu Pro Gln Met Ser Thr Ser
    50               55               60

Lys Met Glu His Ile Glu Asp Phe Arg Pro Thr Ser Pro Gly His Ser
65             70               75              80

Pro Gly Val Gly His Ser Ile His Asn
           85

<210> SEQ ID NO 84
<211> LENGTH: 267
<212> TYPE: PRT
<213> ORGANISM: Ricinus communis

<400> SEQUENCE: 84

Met Arg Lys Gln Leu Glu Ala Phe Gln Lys Glu Leu Ala Lys Arg Gly

```
            1               5                  10                 15
Val Ser Asn Thr Ile Asn Leu His Gln Ser Lys Leu Ala Gly Gln Asp
                    20                  25                 30
His Gln Glu Gln Thr His Thr Gly Phe Ser Asp Phe Ala Ala Ser
                35                  40                  45
Val Asp Ala Phe Arg Pro Thr Pro Pro Gly Asn Ser Pro Gly Val Gly
        50                  55                  60
His Pro Lys Ala Val Val Thr Ser Ser Thr Thr Asp Gln His Ser
 65                  70                  75                  80
Leu Thr Gly Leu Arg His Asp Tyr Ser Asn Leu His Lys Ser Ser His
                    85                  90                  95
Asn Ile Pro Gly Asn Val Gln Gln Ser Met Ser Gly Lys Glu Glu Thr
                100                 105                 110
Ser Pro Thr Ser Leu Asp Val Phe Ala Ala Ser Thr Asp Asp Phe
                115                 120                 125
Arg Pro Thr Ser Pro Gly Tyr Ser Pro Gly Val Gly His Pro Lys Ala
                130                 135                 140
Val Val Thr Ser Ser Thr Ala Asp Gln His Ser Phe Thr Gly Val
145                 150                 155                 160
Lys Asp Tyr Tyr Asn Asn Val His Lys Ser Asn His Ile Gly Val Ala
                    165                 170                 175
Asp Asn Val Lys Lys Pro Val Ser Gly Lys Gly Glu Met Leu Pro Thr
                180                 185                 190
Val Thr Thr Thr Ser Phe Asp Ala Ser Ala Ala Ser Thr Lys Asp Asp
                    195                 200                 205
Phe Arg Pro Thr Ala Pro Gly Phe Ser Pro Gly Val Gly His Pro Lys
        210                 215                 220
Lys Val Val Thr Ser Ser Ser Thr Lys His Ser Ile Thr Gly Phe Lys
225                 230                 235                 240
Asp Asp Tyr Arg Pro Thr Gln Pro Gly His Ser Pro Gly Val Gly His
                    245                 250                 255
Ser Tyr Gln Lys Asn Asn Ala Gly Gln Asp Pro
                260                 265

<210> SEQ ID NO 85
<211> LENGTH: 101
<212> TYPE: PRT
<213> ORGANISM: Ricinus communis

<400> SEQUENCE: 85

Met Ala Ile Ala Ala Ser Ala Ala Ala Thr Asn Leu Met Gly Thr Cys
 1               5                  10                  15
Thr Cys Leu Leu Val Leu Ile Leu Cys His Glu Ala Ile Tyr Val Val
                20                  25                  30
Glu Gly Arg His Leu Lys Pro Lys Leu Cys Lys Lys Cys Ser Arg Arg
                35                  40                  45
Ser Glu Ser Ser Leu Asp Val Ser Lys Asp Gly His His Asn Thr Thr
        50                  55                  60
Thr His Leu Leu Asn Gly Asp Gln Glu Lys Ile Ser Lys Met Asp Phe
 65                  70                  75                  80
Val Asp Asp Phe Arg Pro Thr Ala Pro Gly His Ser Pro Gly Val Gly
                    85                  90                  95
His Ser Ile Gln Asn
                100
```

<210> SEQ ID NO 86
<211> LENGTH: 95
<212> TYPE: PRT
<213> ORGANISM: Ricinus communis

<400> SEQUENCE: 86

Met Ala Asn Val Cys Tyr Thr Cys Leu Phe Phe Leu Val Met Leu Leu
1               5                   10                  15

Ser Tyr Asp Leu Val Cys Ile Glu Ala Arg Gln Leu Lys Leu Arg Glu
            20                  25                  30

Asn Met Lys Cys Val Lys Cys Leu Ser Ala Pro Asp Ser Lys Glu Ser
        35                  40                  45

Ile Thr Arg Asn Pro Arg Gly Asp Asn Ala Met Ser Ser Ser Gln Asp
    50                  55                  60

Gly Ile Glu Pro Lys Asp Gly Ser Asn Asn Phe Asp Ala Phe Arg Pro
65                  70                  75                  80

Thr Asn Pro Gly His Ser Pro Gly Val Gly His Ser Ile Gln His
                85                  90                  95

<210> SEQ ID NO 87
<211> LENGTH: 86
<212> TYPE: PRT
<213> ORGANISM: Ricinus communis

<400> SEQUENCE: 87

Met Ala Arg Val Lys Leu Asn Phe Ser Ile Val Leu Val Ile Ala Leu
1               5                   10                  15

Val Val Ser Tyr Gly Ile Thr Ser Thr Glu Arg Gln Leu Arg Met
            20                  25                  30

Gln Val Arg Ala Ala Gly Met Glu Lys Gly Thr Gly Asn Leu Tyr Phe
        35                  40                  45

Gly Arg Ser Leu Leu Val Asp Asn Asp Gly Asp Ser Asp Asp Phe Arg
    50                  55                  60

Pro Thr Asn Pro Gly His Ser Pro Gly Ala Gly His Ser Thr Gly Pro
65                  70                  75                  80

Ser Ser Lys Asn Ala His
                85

<210> SEQ ID NO 88
<211> LENGTH: 123
<212> TYPE: PRT
<213> ORGANISM: Ricinus communis

<400> SEQUENCE: 88

Met Ala Gln Thr Asn Leu Leu Phe Gly Cys Ile Phe Ile Met Leu Ile
1               5                   10                  15

Phe Phe Gln Glu Leu Gln Ser Ile Ser Gly Arg His Leu Asn Leu Glu
            20                  25                  30

Thr Asn His Lys Phe Ser Lys Ile Gln Val Ser Tyr Ile Asn Phe Glu
        35                  40                  45

Arg Gln His Arg Gln Phe Ile Gly His Asn Val Asp Ile Glu His Asn
    50                  55                  60

Asp Leu Asn Lys Asp Val Phe Ala Ala Asn Lys Met Ser Pro Ala Ala
65                  70                  75                  80

Pro Val Ala Ala Ala Gly Gly Ile Gly Glu Ala Glu Ser Pro Pro
                85                  90                  95

Pro Pro Ala Ser Gly His Val Asp Asp Phe Arg Pro Thr Ala Pro Gly 100                 105                 110
His Ser Pro Gly Val Gly His Ser Ile Gln Asn
            115                 120

<210> SEQ ID NO 89
<211> LENGTH: 89
<212> TYPE: PRT
<213> ORGANISM: Ricinus communis

<400> SEQUENCE: 89

Met Ala Asn Arg Ala Phe Leu Leu Thr Leu Phe Ala Ile Ser Phe Leu
1               5                   10                  15

Leu Leu His Gln His Leu Asp Ser Ala Val Ala Ser Arg Pro Leu His
            20                  25                  30

Met His Pro Pro Ala Ile Ile Ser Gln Gly Ser Leu Lys Arg Pro Leu
        35                  40                  45

Pro Pro Ser Thr Ala Leu Leu Tyr Ser Ile Asn Arg His Lys Phe Thr
    50                  55                  60

Glu Thr Glu Ala Phe Arg Pro Thr Ala Pro Gly His Ser Ser Gly Val
65                  70                  75                  80

Gly His Gly Asn Pro Ala Ala Pro
            85

<210> SEQ ID NO 90
<211> LENGTH: 267
<212> TYPE: PRT
<213> ORGANISM: Ricinus communis

<400> SEQUENCE: 90

Met Arg Lys G

```
            210                 215                 220
Lys Val Val Thr Ser Ser Thr Lys His Ser Ile Thr Gly Phe Lys
225                 230                 235                 240

Asp Asp Tyr Arg Pro Thr Gln Pro Gly His Ser Pro Gly Val Gly His
                245                 250                 255

Ser Tyr Gln Lys Asn Asn Ala Gly Gln Asp Pro
            260                 265
```

<210> SEQ ID NO 91
<211> LENGTH: 61
<212> TYPE: PRT
<213> ORGANISM: Ricinus communis

<400> SEQUENCE: 91

```
Met Lys Cys Val Lys Cys Leu Ser Ala Pro Asp Ser Lys Glu Ser Ile
1               5                   10                  15

Thr Arg Asn Pro Arg Gly Asp Asn Ala Met Ser Ser Gln Asp Gly
            20                  25                  30

Ile Glu Pro Lys Asp Gly Ser Asn Asn Phe Asp Ala Phe Arg Pro Thr
                35                  40                  45

Asn Pro Gly His Ser Pro Gly Gly His Ser Ile Gln His
        50                  55                  60
```

<210> SEQ ID NO 92
<211> LENGTH: 70
<212> TYPE: PRT
<213> ORGANISM: Ricinus communis

<400> SEQUENCE: 92

```
Met Ala Gln Ser Asn Leu Leu Ser Ala Phe Val Phe Leu Val Leu Ile
1               5                   10                  15

Phe Ser His Glu Leu Gln Phe Ile Glu Gly Arg Tyr Leu Asn Leu Lys
            20                  25                  30

Thr Pro Asn Lys Phe Leu Gln Lys Glu Ile Arg Arg Leu Val Glu Ser
            35                  40                  45

Asn Ser Lys Leu His Val Asn Asp Asn Leu Asp Lys Pro Val Asn Ala
        50                  55                  60

Thr Lys Val Ala Pro Pro
65                  70
```

<210> SEQ ID NO 93
<211> LENGTH: 84
<212> TYPE: PRT
<213> ORGANISM: Casuarina glauca

<400> SEQUENCE: 93

```
Met Ala His Arg Thr Leu Met Leu Thr Leu Ser Leu Val Ile Leu Leu
1               5                   10                  15

Leu Gln Gln Thr Ile Val Ser Val Thr Ala Ser Arg Pro Val Ser Ile
            20                  25                  30

His Pro Pro Asp Val Leu Arg Gly Ser Leu Ser Ile Pro Lys Pro Pro
        35                  40                  45

Ser Thr Glu Trp Phe Thr Val Asn Arg Tyr Lys Lys Leu Glu Asp Ala
        50                  55                  60

Phe Arg Pro Thr Ser Pro Gly His Ser Pro Gly Val Gly His Gly Thr
65                  70                  75                  80

Pro Pro Ala Ala
```

<210> SEQ ID NO 94
<211> LENGTH: 124
<212> TYPE: PRT
<213> ORGANISM: Gossypium hirsutum

<400> SEQUENCE: 94

Met Glu Phe Arg Arg Met His Thr Phe Ala Val Phe Leu Leu Ile Ala
1               5                   10                  15

Cys Tyr Leu Val Leu Ser Val Glu Gly Arg Phe Leu Lys Ser Leu Ser
            20                  25                  30

Lys Asn Asn Ser Lys Gln Val Leu Pro Pro Thr Pro Thr Lys Ala
        35                  40                  45

Ser Asp Phe Gly Asp Ser Ile Glu Gly Tyr Lys Glu Asp Phe Arg Pro
    50                  55                  60

Thr Thr Pro Gly Asn Ser Pro Gly Val Gly His Ser Phe Ala Asp Val
65                  70                  75                  80

Val Glu Asp Ile Val Glu Gln Asn Pro Ala Ser Ile Ser Val Gln Gly
                85                  90                  95

Asn Gly Lys Arg Ser Ile Ala Val His Ser Pro Gly Val Gly His Ser
            100                 105                 110

Phe Ala Asp Val Val Glu Asp Ile Val Glu Gln Asn
            115                 120

<210> SEQ ID NO 95
<211> LENGTH: 360
<212> TYPE: PRT
<213> ORGANISM: Jatropha curcas

<400> SEQUENCE: 95

Met Ala Glu Thr Leu Val Ser Tyr Lys Trp Thr Leu Phe Leu Leu Ala
1               5                   10                  15

Leu Ile Ser Trp Leu Gln Ile Leu Phe Ser Gln Ala Arg Pro Ile Lys
            20                  25                  30

Ser Thr Asp Ile His Gln Ser Ser Asn Asp Asn Phe Leu Pro Lys Ala
        35                  40                  45

Pro Ala Gly Phe Thr Ser Pro Lys Gly Ala Asn Pro Val Thr Ser Ser
    50                  55                  60

Ser Ala Asp Asp Phe Arg Pro Thr Thr Gly Gly His Ser Pro Gly Ala
65                  70                  75                  80

Gly His Pro Lys Lys Met Val Thr Ser Ser Asp Val Glu His Ser Val
                85                  90                  95

Thr Lys Pro Glu Ala Asp Gly Arg Thr Val Lys Leu His Gln Asn Lys
            100                 105                 110

Leu Thr Gly Thr Thr Thr Ala Ser Thr Ala Asn Asp Phe Arg Pro Thr
        115                 120                 125

Lys Pro Gly Tyr Ser Pro Gly Val Gly His Pro Lys Gln Ile Val Thr
    130                 135                 140

Ser Ser Asn Ile Glu His Ser Ile Thr Gly Phe Lys Ala Thr Lys Pro
145                 150                 155                 160

Val Leu Gly Ser Asp Thr Tyr Asn Leu His Gln Asn Lys Leu Thr Gly
                165                 170                 175

Thr Thr Met Ala Ser Thr Thr Asn Asp Phe Arg Pro Thr Ser Pro Gly
            180                 185                 190

Tyr Ser Pro Gly Val Gly His Pro Lys Lys Ile Asp Ala Ser Ser Asn
        195                 200                 205

```
Val Glu His Ser Val Thr Gly Phe Lys Ala Asn Ile Ala Val Gly Gly
    210                 215                 220

Thr Asp Asn Leu His Gln Asn Lys Leu Thr Gly Thr Thr Ile Ala Ser
225                 230                 235                 240

Thr Thr Asn Asp Phe Arg Pro Thr Ser Pro Gly Tyr Ser Pro Gly Val
                245                 250                 255

Gly His Pro Lys Lys Val Asp Ala Ser Ser Asn Val Glu His Ser Val
                260                 265                 270

Thr Gly Phe Lys Ala Asn Ile Ala Val Gly Gly Thr Asp Asn Leu His
            275                 280                 285

Gln Asn Lys Leu Thr Gly Thr Ala Thr Ala Ser Thr Thr Asn Asp Phe
    290                 295                 300

Arg Pro Thr Ala Pro Gly Tyr Ser Pro Gly Val Gly His Pro Lys Ala
305                 310                 315                 320

Val Leu Val Pro Ser Ser Thr Asn Ser Asn Val Asp Asp Tyr Arg Pro
                325                 330                 335

Thr Gln Pro Gly His Ser Pro Gly Val Gly His Lys Ser Ser Asp
                340                 345                 350

Leu Val Pro Asn Pro Glu Thr Gly
            355                 360

<210> SEQ ID NO 96
<211> LENGTH: 107
<212> TYPE: PRT
<213> ORGANISM: Theobroma cacao

<400> SEQUENCE: 96

Met Ala Lys Thr Asn Leu Ile Val Leu Ala Gly Ala Leu Leu Leu Val
1               5                   10                  15

Leu Leu Phe Ser Tyr Gly Ile Thr Phe Thr Glu Arg Val Leu Lys
            20                  25                  30

Thr Asp Lys Asp Val Lys Pro Ala Gly Asn Tyr Val Thr Asn Val Met
        35                  40                  45

Thr Ser Ser His Lys Thr Asn Leu Asn Arg Asp Ile Leu Glu Asp Gly
    50                  55                  60

Thr Val Asp Val Pro Thr Ser Ser Gly Asn Gly Thr Ala Phe Asp
65                  70                  75                  80

Ala Asp Asp Phe Arg Pro Thr Thr Pro Gly His Ser Pro Gly Ala Gly
                85                  90                  95

His Ser Thr Gly Pro Ala Ser Asn Asp Lys Asn
            100                 105

<210> SEQ ID NO 97
<211> LENGTH: 107
<212> TYPE: PRT
<213> ORGANISM: Theobroma cacao

<400> SEQUENCE: 97

Met Ala Lys Thr Asn Leu Val Val Leu Ala Gly Ala Leu Leu Leu Val
1               5                   10                  15

Leu Leu Phe Ser Tyr Gly Ile Thr Phe Thr Glu Glu Arg Val Leu Lys
            20                  25                  30

Thr Asp Lys Asp Val Lys Pro Ala Gly Asn Ser Val Thr Asn Val Met
        35                  40                  45

Thr Ser Ser Arg Lys Thr Asn Leu Asn Arg Asp Asn Leu Glu Asp Gly
    50                  55                  60
```

-continued

```
Thr Asp Asp Val Pro Thr Ala Ser Ser Gly Asn Asp Thr Ala Phe Asp
 65                  70                  75                  80

Ala Asp Asp Phe Arg Pro Thr Pro Gly His Ser Pro Gly Ala Gly
                 85                  90                  95

His Ser Thr Gly Pro Ala Ser Ser Asp Lys Asn
            100                 105

<210> SEQ ID NO 98
<211> LENGTH: 107
<212> TYPE: PRT
<213> ORGANISM: Theobroma cacao

<400> SEQUENCE: 98

Met Ala Lys Thr Asn Leu Ile Val Leu Ala Gly Ala Leu Leu Val
 1               5                  10                  15

Leu Leu Phe Ser Tyr Gly Ile Thr Phe Thr Glu Glu Arg Val Leu Lys
                 20                  25                  30

Thr Asp Lys Asp Val Lys Pro Ala Gly Asn Tyr Val Thr Asn Val Met
             35                  40                  45

Thr Ser Ser His Lys Thr Asn Leu Asn Arg Asp Ile Leu Glu Asp Gly
         50                  55                  60

Thr Val Asp Val Pro Thr Ser Ser Ser Gly Asn Gly Thr Ala Phe Asp
 65                  70                  75                  80

Ala Asn Asp Phe Arg Pro Thr Thr Pro Gly His Ser Pro Gly Ala Gly
                 85                  90                  95

His Ser Thr Gly Pro Ala Ser Asn Asp Lys Asn
            100                 105

<210> SEQ ID NO 99
<211> LENGTH: 121
<212> TYPE: PRT
<213> ORGANISM: Theobroma cacao

<400> SEQUENCE: 99

Ala Glu Gly Val Leu Gly Thr Ala Lys Asp Val Asn Pro Gly Gly Lys
 1               5                  10                  15

Phe Val Thr Asn Val Ala Ala Gly Arg His Lys Thr Asn Leu Ile Arg
                 20                  25                  30

Ala Phe Leu Glu Asp Gly Thr Val Asp Val Pro Thr Ser Ser Ser Gly
             35                  40                  45

Asn Gly Thr Ala Phe Gly Ala Asn Asp Phe Arg Pro Pro Thr Pro Gly
         50                  55                  60

His Gly Pro Gly Ala Gly His Ser Thr Gly Pro Ala Ser Asn Asp Lys
 65                  70                  75                  80

Asn Trp Ile Pro Leu Pro Ala Arg Thr Ile Ile Phe Pro Leu Pro Trp
                 85                  90                  95

Val Ala Thr Phe Thr Gln Ser Leu Val Gly Tyr Ile Ser Tyr Asp Phe
            100                 105                 110

Val Leu Ala Leu Pro Lys Ala Leu Lys
            115                 120

<210> SEQ ID NO 100
<211> LENGTH: 96
<212> TYPE: PRT
<213> ORGANISM: Malus domestica

<400> SEQUENCE: 100

Met Ala Asn Gly Lys Leu Ser Phe Leu Leu Leu Val Leu Ile Ser Ser
```

```
               1               5                  10                  15
Tyr Gly Ile Ile Ser Thr Glu Glu Arg Phe Leu Lys Thr Asp His Thr
                20                  25                  30

Asn Gly Gly Ser Thr Ser Met Ile Ser His Asp Asn Tyr Leu Asn Ser
                35                  40                  45

Arg Arg Asn Val Phe Glu Asn Glu Leu Ser Asp Ser Val Pro Pro Val
        50                  55                  60

Pro Gly Tyr His Ser Ala Ser Asp Tyr Arg Pro Thr Thr Pro Gly His
65                  70                  75                  80

Ser Pro Gly Ala Gly His Ser Val Gly Pro Gln Val Glu Pro Asn Gln
                85                  90                  95
```

<210> SEQ ID NO 101
<211> LENGTH: 153
<212> TYPE: PRT
<213> ORGANISM: Carica Papaya

<400> SEQUENCE: 101

```
               1               5                  10                  15
Met Glu Tyr Gln Thr Ile Val Arg Cys Gly Ile Leu Leu Ala Leu Leu
1               5                  10                  15

Phe Ala Ser Leu Met Ile Thr Glu Ala Arg Lys Ile Arg Glu Leu Ile
                20                  25                  30

Thr Gly Asn Asn Gly Asp Phe Asp Asp Ser Phe Ala Ala His Asp Thr
                35                  40                  45

Ala Gly Phe Arg Pro Thr Thr Pro Gly Ile Ser Pro Gly Val Gly His
        50                  55                  60

Ser Phe Gln Asn Gly Asn Lys Asp Met Ser Gly Ser Lys Ala Ala His
65                  70                  75                  80

Phe Lys Pro Pro Ser Ser Asp Tyr Gln Lys Glu Thr Ser Pro Pro Arg
                85                  90                  95

Ala Pro Lys Ala Pro Gly Asn Ser Pro Gly Gly Ile Gly Asp Ser Phe
                100                 105                 110

Ala Asp Val Asn Ser Gln Gly Trp Ser Asn Lys Asp Asp Phe Gln Val
        115                 120                 125

Thr Val Gln Ala Thr Ser Pro Gly His Ser Gly Gly Val Gly His Gly
        130                 135                 140

Asp Asn Asp Asp Glu Pro Asn Ala Arg
145                 150
```

<210> SEQ ID NO 102
<211> LENGTH: 70
<212> TYPE: PRT
<213> ORGANISM: Carica papaya

<400> SEQUENCE: 102

```
               1               5                  10                  15
Met Ala Asn Val Ala Cys Ser Cys Leu Phe Leu Val Val Met Ile Leu
1               5                  10                  15

Cys Ser His Cys Leu His Gly Thr Gln Gly Arg Asn Leu Lys Asn Thr
                20                  25                  30

Pro Ser Ser Ser Lys Asn Met Asn Phe Pro Lys Pro Ser Ser Val Lys
                35                  40                  45

Ser Thr Glu Ala Ile Val Glu Ala Phe Arg Pro Thr Thr Pro Gly His
        50                  55                  60

Ser Pro Gly Val Gly His
65                  70
```

```
<210> SEQ ID NO 103
<211> LENGTH: 114
<212> TYPE: PRT
<213> ORGANISM: Carica papaya

<400> SEQUENCE: 103

Met Ala Arg Thr Gly Leu Met Gly Val Cys Val Leu Phe Leu Val Leu
1               5                   10                  15

Leu Val Cys Gln Glu Ile Val Phe Val Asn Ala Arg His Leu Arg Asp
            20                  25                  30

Arg Ile Leu Cys Glu Lys Cys Ser Thr Thr His His His Arg His His
        35                  40                  45

His His His His His His His His Leu Asp Lys Ile Arg Leu Ser
    50                  55                  60

Val Ala Pro Ala Asn Gly Ala Gly Pro Val His Val Asn Asp Gly Ala
65                  70                  75                  80

Gly Ser Glu Gln Gln Arg Trp Ser Thr Lys Asp Glu Tyr Val Asp Asp
                85                  90                  95

Phe Arg Pro Thr Thr Pro Gly His Ser Pro Gly Val Gly His Ser Ile
            100                 105                 110

Gly Asn

<210> SEQ ID NO 104
<211> LENGTH: 151
<212> TYPE: PRT
<213> ORGANISM: Fragaria vesca

<400> SEQUENCE: 104

Met Glu Ala Lys Cys Ala Val Val Phe Ala Leu Ile Ala Cys Leu Asp
1               5                   10                  15

Ile Ala Ser Val Glu Gly Ile Arg Pro Phe Trp Ser Glu Thr Lys Ser
            20                  25                  30

Thr Glu Thr Ile Leu Ile Asp Ser Ile Glu Ala Asn Tyr Lys Arg Glu
        35                  40                  45

Leu Gly Glu Gln Ser Gly Gln His Asn Asn Leu Lys Gly Glu Phe Lys
    50                  55                  60

Ser Ala Val Val Lys Asn Gln Gly His Phe Ala Lys Leu Gly Ala Pro
65                  70                  75                  80

Ala Tyr Asn Asp Glu Glu Asp Phe Arg Pro Thr Thr Pro Gly Asn Ser
                85                  90                  95

Pro Gly Ala Gly His Lys Ser Leu Gln Val Ser Glu Pro Lys Thr Val
            100                 105                 110

Val Val Ala Gly Arg Asn Tyr Phe Thr Ala Gly Thr Lys Glu Asp Tyr
        115                 120                 125

Arg Pro Thr Gln Pro Gly His Ser Pro Gly Val Gly His Ala Leu Gln
    130                 135                 140

Glu Asn Val Lys Pro Met Pro
145                 150

<210> SEQ ID NO 105
<211> LENGTH: 101
<212> TYPE: PRT
<213> ORGANISM: Fragaria vesca

<400> SEQUENCE: 105

Met Ala Asn Ala Thr Tyr Thr Cys Leu Phe Phe Leu Leu Val Ile Phe
1               5                   10                  15
```

```
Ser His Glu Leu Ile Ser Cys Thr Glu Gly Arg Asn Leu Lys Val Thr
            20                  25                  30

Ser Lys Lys Leu Lys Cys Gly Lys Cys Leu Ser Pro Asp Ile Asp Ala
        35                  40                  45

Lys Ser Ile Ala Gly Asp Gln Gly Ser Gly Gly Ser Ser Ser Ser Asn
65              55                  60

Gln Ile Gln Ser Pro Pro Val Val Pro Leu Pro Ala Ser Pro Gly Arg
65              70                  75                  80

Val Glu Ala Phe Arg Pro Thr Thr Pro Gly His Ser Pro Gly Val Gly
                85                  90                  95

His Ser Val His Asn
            100
```

<210> SEQ ID NO 106
<211> LENGTH: 103
<212> TYPE: PRT
<213> ORGANISM: Fragaria vesca

<400> SEQUENCE: 106

```
Met Ala Lys Arg Arg Gln Thr Arg Leu Ile Ala Thr Thr Thr Thr Cys
1               5                   10                  15

Thr Leu Leu Ile Val Leu Ile Cys Cys His Glu Ile Thr Leu Val Asp
            20                  25                  30

Gly Arg His Leu Lys Pro Gly Asp Cys Lys Lys Cys Ser Arg Arg His
        35                  40                  45

Arg Glu Leu Asn Thr Leu Ser Ala Ala Lys Val Gly Asp His Asn Arg
50                  55                  60

Ser Ala Arg Leu Val Arg Ala Ala Glu Thr Lys Thr Ser Lys Ala Glu
65              70                  75                  80

His Val Thr Asp Asp Phe Arg Pro Thr Thr Pro Gly His Ser Pro Gly
                85                  90                  95

Val Gly His Ser Ile Asn Asn
            100
```

<210> SEQ ID NO 107
<211> LENGTH: 87
<212> TYPE: PRT
<213> ORGANISM: Prunus persica

<400> SEQUENCE: 107

```
Met Val Ser Phe Phe Met Val Ala Leu Leu Leu Gly Gln Asn Ser Asp
1               5                   10                  15

Leu Val Ala Ala Ser Arg Pro Leu His Leu His Thr His Pro Pro Ala
            20                  25                  30

Ile His Ile Gly Ser Leu Asn Lys Pro Ile Pro Pro Ser Ile Gly Arg
        35                  40                  45

Phe Thr Ile Asn Arg Tyr Lys Met Thr Glu Ser Ser Ser Gly Ala Asp
50                  55                  60

Ala Phe Arg Pro Thr Ser Pro Gly His Ser Pro Gly Val Gly His Gln
65              70                  75                  80

Asp Pro Pro Gly Ala Leu Leu
            85
```

<210> SEQ ID NO 108
<211> LENGTH: 91
<212> TYPE: PRT
<213> ORGANISM: Cucumis sativus

<400> SEQUENCE: 108

Met Ala His Arg Ser Leu His Leu Asn Ser Phe Phe Pro Leu Val Ala
1               5                   10                  15

Leu Leu Leu Leu Leu Leu Leu Leu His Ser Leu Phe Val Thr Ser Ser
            20                  25                  30

Arg Pro Leu His Gly Ile His Pro His Asn Pro His Ala Ile Thr Pro
        35                  40                  45

Pro Ala Pro Val Ser Leu Glu Thr Ser Phe Ser Ile Asn Arg Tyr Lys
50                  55                  60

Tyr Val Glu Thr Asp Ala Phe Arg Pro Thr Ser Pro Gly His Ser Pro
65                  70                  75                  80

Gly Val Gly His Asn Glu Pro Pro Gly Lys Pro
                85                  90

<210> SEQ ID NO 109
<211> LENGTH: 155
<212> TYPE: PRT
<213> ORGANISM: Manihot esculenta

<400> SEQUENCE: 109

Leu His Cys Phe Cys Cys Arg Cys Phe Arg Pro Thr Asp Pro Gly Asn
1               5                   10                  15

Ser Pro Gly Val Gly His His Leu Ser Gln Glu Glu Ser Asp Glu Glu
            20                  25                  30

Thr Asp Pro Lys Pro Pro Arg Lys Asp Tyr Gly Pro Lys Pro Gly His
        35                  40                  45

Ser Gln Pro Val Gly Arg Asp Ile Ile Phe Ser Asn Pro Ser Asn Thr
50                  55                  60

Lys Gly Ser Gln Pro Ala Ser Ser Ser His Asn Pro Val Asn Ala Val
65                  70                  75                  80

Pro Leu Thr Pro Thr Ala Phe Asp Ala Ser Ala Ser Ser Met Glu
                85                  90                  95

Gly Phe Arg Pro Thr Thr Pro Gly Tyr Ser Pro Gly Val Gly His Pro
            100                 105                 110

Asn Ala Glu Ile Ser Ser Ser Asn Val Glu Thr Ser Val Thr Arg Phe
        115                 120                 125

Glu Asp Asp His Arg Pro Thr Gln Pro Gly His Ser Pro Gly Val Gly
    130                 135                 140

His Ala Tyr Leu Glu Asn Asn Ala Glu Pro Asn
145                 150                 155

<210> SEQ ID NO 110
<211> LENGTH: 80
<212> TYPE: PRT
<213> ORGANISM: Citrus sinensis

<400> SEQUENCE: 110

Met Leu Thr Leu Leu Val Leu Leu Leu Ser Lys Ser Phe Asp Leu
1               5                   10                  15

Ile Ser Ala Ser Arg Pro Pro His Ile His Pro Pro Thr Ile Pro Arg
            20                  25                  30

Gly Ser Leu Leu Asn Lys Val Lys Pro Pro Ser Phe His Ala Tyr Thr
        35                  40                  45

Ala Asn Arg Tyr Lys Leu Thr Glu Ser Glu Ala Phe Arg Pro Thr Ser
50                  55                  60

Pro Gly His Ser Pro Gly Val Gly His Lys Gly Pro Pro Gly Ser Asp 65                  70                  75                  80

<210> SEQ ID NO 111
<211> LENGTH: 80
<212> TYPE: PRT
<213> ORGANISM: Citrus clementina

<400> SEQUENCE: 111

Met Leu Thr Leu Leu Val Val Leu Leu Leu Ser Lys Ser Phe Asp Leu
1               5                   10                  15

Ile Ser Ala Ser Arg Pro Pro His Ile His Pro Thr Ile Pro Arg
                20                  25                  30

Gly Ser Leu Leu Asn Lys Val Lys Pro Pro Ser Phe His Ala Tyr Thr
            35                  40                  45

Ala Asn Arg Tyr Lys Leu Thr Glu Ser Glu Ala Phe Arg Pro Thr Ser
        50                  55                  60

Pro Gly His Ser Pro Gly Val Gly His Lys Gly Pro Pro Gly Ser Asp
65                  70                  75                  80

<210> SEQ ID NO 112
<211> LENGTH: 81
<212> TYPE: PRT
<213> ORGANISM: Catharanthus roseus

<400> SEQUENCE: 112

Met Ala Asn Ile Ser Cys Lys Cys Leu Phe Met Ile Phe Leu Leu Ile
1               5                   10                  15

Leu Val Ser Ile Glu Gln Val Pro Ile Ser Val Glu Gly Arg Asn Leu
                20                  25                  30

Arg Gly Glu Lys Val Lys Val Arg Ile Leu Gly Gln Glu Thr Arg Asn
            35                  40                  45

Arg Ala Glu Lys Ser Arg Arg Val Leu Gln Gly Glu Val Asp Ser Phe
        50                  55                  60

Arg Pro Thr Asn Pro Gly Arg Ser Pro Gly Ile Gly His Ser Thr His
65                  70                  75                  80

Asp

<210> SEQ ID NO 113
<211> LENGTH: 81
<212> TYPE: PRT
<213> ORGANISM: Solanum tuberosum

<400> SEQUENCE: 113

Met Ala Ser Ser Tyr Lys Lys Ser Ile Tyr Met Val Leu Phe Tyr Val
1               5                   10                  15

Phe Val Phe Leu Leu Leu Gln Gln Cys Glu Leu Ile Val Ala Ser Arg
                20                  25                  30

Val Val Val Met Lys Phe His Gln Pro Lys Pro Pro Ser Thr Asn Ile
            35                  40                  45

Phe Ser Phe Asn Arg Tyr Lys Lys Ser Glu Val Val Lys Asp Tyr Ser
        50                  55                  60

Gly Pro Gly His Ser Pro Gly Met Gly His Asp Asn Pro Pro Gly Ala
65                  70                  75                  80

Ser

<210> SEQ ID NO 114
<211> LENGTH: 94
<212> TYPE: PRT

<213> ORGANISM: Solanum tuberosum

<400> SEQUENCE: 114

Met Ala Ile Leu Ser Tyr His Lys Val Ile Cys Met Phe Ile Leu Tyr
1               5                   10                  15

Ile Phe Ile Ile Ser Ile Ala Leu Gln Gln Phe Val Leu Val Asp Ala
                20                  25                  30

Ser Arg Ser Phe Ser Arg Tyr Pro Pro Pro Pro Pro Val Glu Ile
            35                  40                  45

Thr His Gly Glu Val Lys Ser Leu Ser Ser Asp Asn Phe Ser Phe Asn
    50                  55                  60

Gly Ser Lys Ser Lys Tyr Glu Lys Asp Ile Pro Tyr Val Thr Pro
65                  70                  75                  80

Gly His Ser Pro Gly Met Gly His Asp Thr Pro Pro Ser Ser
                85                  90

<210> SEQ ID NO 115
<211> LENGTH: 99
<212> TYPE: PRT
<213> ORGANISM: Brassica napus

<400> SEQUENCE: 115

Met Gly Gln Lys Lys Thr Leu Phe Val Cys Val Phe Val Met Val
1               5                   10                  15

Leu Phe Asn Gly Phe Asn Cys Val His Gly Arg Thr Leu Arg Asn Met
                20                  25                  30

Lys Val Asp Asp Lys Met Asn Val Gly His Asp Ser Lys Thr Met
            35                  40                  45

Lys Ala Met Asn Asn Asp Leu Ile Val Asp Glu Lys Ala Val Gln Leu
    50                  55                  60

Ser Gln Pro Pro Pro Ser Pro Pro Glu Ser Lys Asp Ala Glu Asp
65                  70                  75                  80

Phe Arg Pro Thr Thr Pro Gly His Ser Pro Gly Ile Gly His Ser Leu
                85                  90                  95

Ser His Asn

<210> SEQ ID NO 116
<211> LENGTH: 56
<212> TYPE: PRT
<213> ORGANISM: Brassica napus

<400> SEQUENCE: 116

Asn Val Asp Gly His Lys Glu Gly Ile Glu Val Phe Gln Ala Lys Ile
1               5                   10                  15

Leu Lys Asn Ile Tyr Ala Tyr Ala Pro Thr Asp Pro Gly Asn Ser Pro
                20                  25                  30

Gly Ile Gly His His Lys Met Asp Val His Val Ser Asn Asp Phe Lys
            35                  40                  45

Val Val Arg Lys Leu Lys Lys Asn
    50                  55

<210> SEQ ID NO 117
<211> LENGTH: 188
<212> TYPE: PRT
<213> ORGANISM: Brassica napus

<400> SEQUENCE: 117

Met Met Thr Ile Met Ala Ile Ser Ile Val Phe Val Gln Val Pro Ser

-continued

```
              1               5                  10                 15
            Thr Thr Glu Ala Arg Pro Leu Glu Ile Thr Glu Asn Lys Asn His Phe
                           20                 25                 30
            Lys Val Thr Ser Leu Asn Asn Phe Val Ser Thr Ile Pro Val Gly His
                           35                 40                 45
            Asn Val Asp Gly His Lys Glu Gly Ile Glu Leu Phe Gln Glu Lys Ile
                50                 55                 60
            Leu Lys Asn Ile Tyr Ala Tyr Ala Pro Thr Asp Pro Gly Asn Ser Pro
             65                 70                 75                 80
            Gly Ile Gly His His Lys Met Asp Val His Ala Pro Glu Leu Ser Asn
                           85                 90                 95
            Asp Phe Lys Val Val Arg Pro Leu Glu Ile Thr Glu Asn Lys Asn His
                          100                105                110
            Phe Lys Val Met Ser Leu Asn Asn Phe Val Ser Thr Val Pro Glu Gly
                          115                120                125
            His Asn Val Asp Gly His Lys Glu Gly Ile Glu Val Phe Gln Ala Lys
                          130                135                140
            Ile Leu Lys Asn Ile Tyr Ala Tyr Ala Pro Thr Asp Pro Gly Asn Ser
            145                150                155                160
            Pro Gly Ile Gly His His Lys Met Asp Val His Ala Pro Ala Arg Ser
                          165                170                175
            Asn Asp Phe Lys Val Val Arg Lys Leu Lys Lys Asn
                          180                185

<210> SEQ ID NO 118
<211> LENGTH: 154
<212> TYPE: PRT
<213> ORGANISM: Eucalyptus grandis

<400> SEQUENCE: 118

Met Leu Ser Arg His Leu Leu Ser Arg Val Leu Ser Leu Ser Leu Ser
            1               5                  10                 15
            Leu Ser Leu Ser Pro Pro Pro Leu Pro Pro Thr Val Pro Ala Met Ala
                           20                 25                 30
            Pro Asn Lys Val Leu Tyr Ala Phe Ala Phe Leu Leu Ala Leu Ser
                           35                 40                 45
            Leu Glu Leu Gln Ser Thr Gln Ala Arg Gln Leu Lys Leu Thr Met Gln
                50                 55                 60
            Lys Gln Lys Ser Phe Pro Asn Lys Leu Pro Asn Val His Lys Leu Leu
             65                 70                 75                 80
            Glu Lys Glu Leu Arg Lys Thr Ile Ala Glu Gln Ser Arg Asn Leu His
                           85                 90                 95
            Gly Glu Ile Leu Asn Lys Ala Thr Asn Ala Ala Val Ser Thr Thr Pro
                          100                105                110
            Ala Pro Pro Pro Ser Ser Thr Ile Val Ala Ala Thr Thr Pro Pro Pro
                          115                120                125
            Ser Pro Gly Arg Ser Leu Asp Asp Phe Arg Pro Thr Gln Pro Gly His
                          130                135                140
            Ser Pro Gly Val Gly His Ser Leu Gln Asn
            145                150

<210> SEQ ID NO 119
<211> LENGTH: 83
<212> TYPE: PRT
<213> ORGANISM: Mimulus guttatus
```

```
<400> SEQUENCE: 119

Met Ala Ala Lys Val Phe Ala Cys Leu Val Phe Ile Phe Ala Ile Leu
1               5                   10                  15

Ser Asn Gln Val Phe His Met Glu Gly Arg Asn Leu Val Val Arg Glu
            20                  25                  30

Asn Ala Ser Asn Ala Glu Ala Arg Gly Glu Asn Ile Lys Ser Pro Asn
        35                  40                  45

Lys Glu Ile Gly Ser His Arg Phe Arg Phe Asp Glu Gly Tyr Met Asp
50                  55                  60

Ser Tyr Arg Pro Thr Thr Pro Gly His Ser Pro Gly Ile Gly His Ser
65                  70                  75                  80

Lys His Asp

<210> SEQ ID NO 120
<211> LENGTH: 92
<212> TYPE: PRT
<213> ORGANISM: Aquilegia coerulea

<400> SEQUENCE: 120

Met Ala Lys Asn Lys Leu Ile Cys Thr Cys Thr Leu Leu Val Leu
1               5                   10                  15

Val Leu Ser His Glu Met Ile His Thr Glu Gly Arg His Leu Lys Ile
            20                  25                  30

Lys Lys Arg Thr Ala Cys Val Lys Cys Ser Ser Ser Asn Thr Val Arg
        35                  40                  45

Gly Lys Lys Glu Ser Asp Gly Gln Lys Thr Ser Asp Val His His Lys
50                  55                  60

Ile Thr Pro Met Ala Gly Phe Val Glu Ala Phe Arg Pro Thr Thr Pro
65                  70                  75                  80

Gly His Ser Pro Gly Ile Gly His Ser Ile Gln His
            85                  90

<210> SEQ ID NO 121
<211> LENGTH: 190
<212> TYPE: PRT
<213> ORGANISM: Oryza sativa

<400> SEQUENCE: 121

Met Lys Gly Lys Arg Thr Phe Leu Ser Ser Leu Asn Lys Glu His Ile
1               5                   10                  15

Lys Lys Phe Tyr Val Leu Glu Arg Val Val Ala Gln Phe Tyr Leu Phe
            20                  25                  30

Ser Ser Gln Gly Arg Pro Leu Pro Asp Asp Asp Gly Ile Thr Ser Glu
        35                  40                  45

Met Gln Ile Arg Arg Tyr Leu Leu Ser His Gly Asn Gly Val Val Glu
50                  55                  60

Gly Ala Val Ser Pro Ser Ser Glu Ile Gly Gly Pro Met Val Gly Ala
65                  70                  75                  80

Ser Gly Gly Val Arg Pro Thr Asn Pro Gly His Ser Pro Gly Ile Gly
            85                  90                  95

His His Val Ala Ile Asn Gly Asp Val Asp Asp Val Arg Pro
                100                 105                 110

Thr Asn Pro Gly His Ser Pro Gly Ile Gly His His Ala Ile Val Asn
        115                 120                 125

Gly Ala Asp Asp Ala Asp Asp Val Arg Pro Thr Asn Pro Gly His Ser
130                 135                 140
```

Pro Gly Ile Gly His Ala Val Val Asn Ser Ala Asp Asp Ala Asp
145                 150                 155                 160

Asp Val Arg Pro Thr Asn Pro Gly His Ser Pro Gly Ile Gly His Ala
                165                 170                 175

Phe Val Asn Lys Ile Asp Gly Pro Ala Gly Lys Lys Lys Leu
            180                 185                 190

<210> SEQ ID NO 122
<211> LENGTH: 176
<212> TYPE: PRT
<213> ORGANISM: Oryza sativa

<400> SEQUENCE: 122

Met Ala Asn Ile Cys Thr Met Leu Ala Ile Leu Val Phe Ser Leu Gln
1               5                   10                  15

Leu Phe Ser Ser Gln Gly Arg Pro Leu Pro Asp Asp Asp Gly Ile Thr
                20                  25                  30

Ser Glu Met Gln Ile Arg Arg Tyr Leu Leu Ser His Gly Asn Gly Val
            35                  40                  45

Val Glu Gly Ala Val Ser Pro Ser Ser Glu Ile Gly Gly Pro Met Val
        50                  55                  60

Gly Ala Ser Gly Gly Val Arg Pro Thr Asn Pro Gly His Ser Pro Gly
65                  70                  75                  80

Ile Gly His His Val Ile Asn Gly Asp Val Asp Asp Asp Val
                85                  90                  95

Arg Pro Thr Asn Pro Gly His Ser Pro Gly Ile Gly His His Ala Ile
            100                 105                 110

Val Asn Gly Ala Asp Asp Ala Asp Val Arg Pro Thr Asn Pro Gly
        115                 120                 125

His Ser Pro Gly Ile Gly His Ala Val Val Asn Gly Ala Asp Asp Asn
    130                 135                 140

Ala Asp Asp Val Arg Pro Thr Asn Pro Gly His Ser Pro Gly Ile Gly
145                 150                 155                 160

His Ala Phe Val Asn Lys Ile Asp Gly Pro Ala Gly Lys Lys Lys Leu
                165                 170                 175

<210> SEQ ID NO 123
<211> LENGTH: 102
<212> TYPE: PRT
<213> ORGANISM: Oryza sativa

<400> SEQUENCE: 123

Met Ala Leu Asn Lys Ser Ser Asn Ser Ile Ser Lys Ala Phe Phe Leu
1               5                   10                  15

Val Leu Ile Ile Leu Ala Ser Gln Val Met Leu Ser His Gly Ile Pro
                20                  25                  30

Leu Glu Met His Arg Arg Tyr Leu Leu Ser His Ala Ala Asp Ala Thr
            35                  40                  45

Lys Gly Val Met Glu Gly Thr Ile Thr Pro Thr Glu Gly Glu Gly Phe
        50                  55                  60

Ala Gly Ala Asn Asp Asp Val Arg Pro Thr Asn Pro Gly His Ser Pro
65                  70                  75                  80

Gly Ile Gly His Ala Phe Thr Asn Asn Lys Ile Gly Arg Lys Leu Leu
                85                  90                  95

Leu Ala Ala Asp Asp Val
            100

<210> SEQ ID NO 124
<211> LENGTH: 137
<212> TYPE: PRT
<213> ORGANISM: Oryza sativa

<400> SEQUENCE: 124

Met Ser Ser Ser Lys Leu Asn Leu Ile Phe Val Leu Gly Ile Ile Phe
1               5                   10                  15

Phe Leu Ser Ser Asp Met Ile Ile Val Cys Ser Gln Gly Arg Pro Leu
            20                  25                  30

Ile Ala Glu Ala Ala Ala Ala Ala Ala Gln Gln Gln Arg His Leu
        35                  40                  45

Leu Ser Ser Ser Ser Ala Pro Arg Ser Gly Gly Asp Val Glu Glu
50                  55                  60

Ala Ala Ala Gly Gly Gly Lys Gly Thr Thr Thr Ala Met Thr Gln Gly
65                  70                  75                  80

Thr Leu Ser Pro Asp Ala Ala Glu Ser Gly Gly Gly Gly Gly Gly
                85                  90                  95

Val Gly Ile Val Glu Asp Ala Arg Pro Thr Ala Pro Gly His Ser Pro
            100                 105                 110

Gly Ala Gly His Ala Phe Thr Asn Lys Asn Gly Val Gly Arg Arg Leu
            115                 120                 125

Leu Val Val Thr Ile Ser Thr Leu Ile
            130                 135

<210> SEQ ID NO 125
<211> LENGTH: 96
<212> TYPE: PRT
<213> ORGANISM: Oryza sativa

<400> SEQUENCE: 125

Met Ala Gly Leu Lys Leu Ser Ser Cys Val Leu Val Ala Leu Leu Phe
1               5                   10                  15

Val Ser Ser His Val Val Arg His Gly Glu Ala Arg Arg Leu Thr Ala
            20                  25                  30

Gly Val Ala Ala Pro Ala Ser Lys Gly Gly Glu Glu Glu Ala Pro Gln
        35                  40                  45

Tyr Ala Ser Ala Arg Gly Gly Gln Pro Ala Ala Ala Gly Gly Gly
        50                  55                  60

Val Thr Ala Ala Ser Lys Met Ala Ser Thr Asp Gly Arg Pro Thr Ser
65                  70                  75                  80

Pro Gly His Ser Pro Gly Ile Gly Asn Lys Ala Thr Gly Asn Val Arg
                85                  90                  95

<210> SEQ ID NO 126
<211> LENGTH: 182
<212> TYPE: PRT
<213> ORGANISM: Oryza barthii

<400> SEQUENCE: 126

Met Ala Leu Asn Lys Asn Val Ser Asn Ile Cys Thr Met Leu Ala Ile
1               5                   10                  15

Leu Val Phe Ser Leu Gln Leu Phe Ser Ser Gln Gly Arg Pro Leu Pro
            20                  25                  30

Asp Asp Asp Gly Ile Thr Ser Glu Met Gln Ile Arg Arg Tyr Leu Leu
        35                  40                  45

```
Ser His Gly Asn Arg Val Val Glu Gly Ala Val Ser Pro Ser Ser Glu
    50                  55                  60

Ile Gly Gly Pro Met Val Gly Ala Ser Gly Gly Val Arg Pro Thr Asn
 65                  70                  75                  80

Pro Gly His Ser Pro Gly Ile Gly His His Val Val Ile Asn Gly Asp
                 85                  90                  95

Ile Asp Asp Asp Val Arg Pro Thr Asn Pro Gly His Ser Pro Gly
             100                 105                 110

Ile Gly His His Ala Ile Val Asn Gly Ala Asp Asp Ala Asp Asp Val
            115                 120                 125

Arg Pro Thr Asn Pro Gly His Ser Pro Gly Ile Gly His Ala Val Val
    130                 135                 140

Asn Gly Ala Asp Asp Asp Ala Asp Asp Val Arg Pro Thr Asn Pro Gly
145                 150                 155                 160

His Ser Pro Gly Ile Gly His Ala Phe Val Asn Lys Ile Asp Gly Pro
                165                 170                 175

Ala Gly Lys Lys Lys Leu
            180

<210> SEQ ID NO 127
<211> LENGTH: 113
<212> TYPE: PRT
<213> ORGANISM: Sorghum bicolor

<400> SEQUENCE: 127

Met Ala Leu Asn Lys Lys Asn Thr Asn Thr Cys Thr Ser Val Leu
 1               5                  10                  15

Leu Leu Leu Ser Leu Val Ile Phe Ser Gln Phe Leu Ala Ser His Gly
                20                  25                  30

Arg Pro Leu Pro Thr Gly Ser Tyr Ile Thr Thr Ala Ala Ala Val His
             35                  40                  45

Gly Arg Asn Leu Leu Ser His Gly Ser Gly Ser Val Pro Lys Gly Met
 50                  55                  60

Leu Glu Gly Thr Val Ser Pro Ser Ser Glu Ile His Gly Asp Asn Gly
 65                  70                  75                  80

Ser Met Val Gly Ala Asp Asp Val Arg Pro Ser Asn Pro Gly His Ser
                 85                  90                  95

Pro Gly Ile Gly His Ala Phe Ile Asn Glu Lys Gly Thr Gly Arg Lys
            100                 105                 110

Leu

<210> SEQ ID NO 128
<211> LENGTH: 96
<212> TYPE: PRT
<213> ORGANISM: Sorghum bicolor

<400> SEQUENCE: 128

Met Ala Ser Ser Lys Val Val Cys Ala Cys Ile Leu Ile Ile Leu Val
 1               5                  10                  15

Ile Ser Ser Gln Ala Asp Ala Arg Arg Leu Val Thr Ala Thr Cys Asn
                20                  25                  30

Gly Lys Glu Gly Ala Cys Lys Gly Val Val Val Glu Gly Tyr
             35                  40                  45

Gly Gly Phe Ser Ala Lys Gln Lys Met Ala Thr Ala Thr Ser Ser Glu
 50                  55                  60

Gln Val Gly Glu Gly Met Pro Ala Thr Thr Thr Asp Ser Arg Pro Thr
```

```
                65                  70                  75                  80
Ala Pro Gly Asn Ser Pro Gly Ile Gly Asn Arg Gly Lys Thr Asn Asn
                85                  90                  95

<210> SEQ ID NO 129
<211> LENGTH: 93
<212> TYPE: PRT
<213> ORGANISM: Triticum aestivum

<400> SEQUENCE: 129

Met Ala Gly Ser Lys His Ala Ser Ser Cys Thr Cys Ile Leu Ile Ile
1               5                   10                  15

Leu Val Val Ser Ser His Leu Ala Pro Cys Glu Ala Arg Arg Leu Met
                20                  25                  30

Val Ala Ser Ala Lys Ile Thr Gly Asp Glu Ala Cys Lys Ser Ser Gly
            35                  40                  45

Cys Arg Ala Val Gln Gly Thr Ala Ser Gly Ala Ala Ala Thr Ser Lys
        50                  55                  60

Met Ala Thr Thr Asp Gly Arg Gly Thr Gly Pro Gly His Ser Pro Gly
65                  70                  75                  80

Ile Gly Asn Lys Leu His Ala Ala Gly Asn Asp Arg Arg
                85                  90

<210> SEQ ID NO 130
<211> LENGTH: 99
<212> TYPE: PRT
<213> ORGANISM: Triticum aestivum

<400> SEQUENCE: 130

Met Ala Gly Ser Lys His Val Ser Ser Cys Thr Cys Ile Leu Ile Met
1               5                   10                  15

Leu Val Val Ser Ser His Leu Ala Ser Cys Pro Cys Glu Ala Arg Arg
                20                  25                  30

Leu Met Ala Ala Ser Ala Lys Ile Asn Gly Asp Glu Ala Cys Met Ser
            35                  40                  45

Ala Gly Cys Arg Ala Val Gln Gly Thr Ala Ser Gly Thr Ala Glu Ala
        50                  55                  60

Thr Trp Lys Met Ala Thr Thr Asp Ser Arg Gly Thr Ala Pro Gly His
65                  70                  75                  80

Ser Pro Gly Ile Gly Asn Lys Leu His Ala Gly Thr Val Thr Val
                85                  90                  95

Lys Arg Asn

<210> SEQ ID NO 131
<211> LENGTH: 99
<212> TYPE: PRT
<213> ORGANISM: Triticum aestivum

<400> SEQUENCE: 131

Met Ala Arg Ser Lys Val Leu Cys Thr Cys Ile Leu Ile Ile Ile Leu
1               5                   10                  15

Ser Ser Ile Gln Ala Glu Ala Arg Arg Leu Thr Thr Ala Thr Ala Val
                20                  25                  30

Thr Val Ala Ser Lys Gly Lys Glu Pro Trp Cys Ala Leu Glu Ser Asn
            35                  40                  45

Ser Arg Ser Leu Arg Ala Thr Ser Ser Glu Thr Ser Ile Ala Gly Ala
        50                  55                  60
```

```
Gln Gly Leu Asn Gly Gly Ala Met Ser Thr Ala Thr Thr Val Glu Ser
 65                  70                  75                  80

Arg Gly Thr Ala Pro Gly Asn Ser Pro Gly Ile Gly Asn Lys Gly Lys
                 85                  90                  95

Ile Asn Asn

<210> SEQ ID NO 132
<211> LENGTH: 88
<212> TYPE: PRT
<213> ORGANISM: Hordeum vulgare

<400> SEQUENCE: 132

Phe Arg Pro Gly Ala Pro Ala Thr Gly Gly Arg Arg Arg Arg Arg Arg
  1               5                  10                  15

Trp Ser Gly Gly Ser Ser Arg Arg Thr Ser Thr Arg Trp Ala Ala Ala
                 20                  25                  30

Trp Cys Cys Ala Arg Arg Thr Ser Arg Gly Arg Arg Cys Ser Trp Arg
                 35                  40                  45

Pro Thr Thr Pro Gly Thr Ser Pro Gly Ile Thr Ser Trp Trp Thr Ala
 50                  55                  60

Gly Ser Pro Trp Arg Ser Arg Ser Thr Cys Arg Arg Ala Glu Asp Gly
 65                  70                  75                  80

Gly Glu Gln Pro Glu Glu Asn Glu
                 85

<210> SEQ ID NO 133
<211> LENGTH: 71
<212> TYPE: PRT
<213> ORGANISM: Hordeum vulgare

<400> SEQUENCE: 133

Arg His Glu Ala Ser Arg Arg Thr Ser Thr Arg Trp Ala Ala Ala Trp
  1               5                  10                  15

Cys Cys Ala Arg Arg Thr Ser Arg Gly Arg Arg Cys Ser Trp Arg Pro
                 20                  25                  30

Thr Thr Pro Gly Thr Ser Pro Gly Ile Thr Ser Trp Trp Thr Ala Gly
                 35                  40                  45

Ser Pro Trp Arg Ser Arg Ser Thr Cys Arg Arg Ala Glu Asp Gly Gly
 50                  55                  60

Glu Gln Pro Glu Glu Asn Glu
 65                  70

<210> SEQ ID NO 134
<211> LENGTH: 75
<212> TYPE: PRT
<213> ORGANISM: Hordeum vulgare

<400> SEQUENCE: 134

Met Ala Ile Ser Ser Lys Ile Ala Val Val Phe Met Leu Leu Leu Ser
  1               5                  10                  15

Thr Thr Phe Met Gln Leu Pro Val Pro Ala Asp Ala Arg Arg Leu Glu
                 20                  25                  30

Val Lys Ala Pro Ile Leu Asn Val His Arg Pro Cys Thr Gly Arg Ser
                 35                  40                  45

Thr Leu Glu Thr Pro Pro Glu Gln Val Glu Ser Thr Thr Pro Gly His
 50                  55                  60

Ser Pro Ser Ile Gly His Asn Ser Pro Pro Asn
 65                  70                  75
```

<210> SEQ ID NO 135
<211> LENGTH: 96
<212> TYPE: PRT
<213> ORGANISM: Saccharum officinarum

<400> SEQUENCE: 135

Met Ala Ser Ser Lys Val Val Cys Ala Cys Ile Leu Ile Ile Leu Val
1               5                   10                  15

Ile Ser Ser Arg Ala Asp Ala Arg Arg Leu Val Ala Ala Thr Cys Asn
                20                  25                  30

Gly Lys Glu Gly Ala Cys Lys Gly Gly Ile Ile Val Val Glu Gly Tyr
            35                  40                  45

Gly Gly Phe Ser Ala Lys Gln Lys Met Ala Thr Ala Arg Ser Thr Glu
        50                  55                  60

Glu Val Ser Glu Gly Met Pro Ala Thr Thr Met Asp Ser Arg Pro Thr
65              70                  75                  80

Tyr Pro Gly Asn Ser Pro Gly Ile Gly Asn Lys Gly Gln Ile Asn Asn
                85                  90                  95

<210> SEQ ID NO 136
<211> LENGTH: 34
<212> TYPE: PRT
<213> ORGANISM: Saccharum officinarum

<400> SEQUENCE: 136

Thr Met Asp Ser Arg Pro Thr Tyr Pro Gly Asn Ser Pro Gly Ile Gly
1               5                   10                  15

Asn Lys Gly Glu Asn Gln Gln Leu Ala Gly Arg Val Leu Ile Cys Val
                20                  25                  30

Leu Ile

<210> SEQ ID NO 137
<211> LENGTH: 60
<212> TYPE: PRT
<213> ORGANISM: Zea mays

<400> SEQUENCE: 137

Ser Ser His Ala Asp Ala Arg Arg Leu Val Ala Thr Thr Cys Asn Gly
1               5                   10                  15

Thr Glu Gly Gly Ala Cys Lys Gly Gly Ile Phe Val Gln Gly Tyr Ala
                20                  25                  30

Gly Leu Ser Ala Arg Gln Lys Met Ala Ala Thr Ala Thr Ser Thr Glu
            35                  40                  45

Gln Val Val Gly Gly Gly Glu Gly Met Pro Ala
        50                  55                  60

<210> SEQ ID NO 138
<211> LENGTH: 112
<212> TYPE: PRT
<213> ORGANISM: Zea mays

<400> SEQUENCE: 138

Met Gln Gln Pro Tyr Glu His Ser Gly Ser Gly Ser Ser Pro Ala
1               5                   10                  15

Cys Arg Ser Arg Gln Ile Ala Pro Ala His Cys Thr Ala Pro Thr Thr
                20                  25                  30

Val Ala Ser Thr Pro Arg Ser Arg Tyr Leu Leu Val Val Gln Ser Ser
            35                  40                  45

```
Ser Ala Thr Thr Ala Thr Ala Tyr Ser Thr Lys Ala Gly Met Ile
    50                  55                  60

Glu Gly Thr Val Thr Pro Ser Glu Gly Gly Ala Pro Gly Ala Thr Glu
65                  70                  75                  80

Asp Val Arg Pro Thr Asn Pro Ser His Ser Pro Gly Ile Gly His Ala
                85                  90                  95

Phe Thr His Asn Lys Ile Gly Arg Lys Leu Leu Ala Ala Ile Ser Gln
            100                 105                 110
```

<210> SEQ ID NO 139
<211> LENGTH: 90
<212> TYPE: PRT
<213> ORGANISM: Zea mays

<400> SEQUENCE: 139

```
Ala Ala Gly Leu Val Val Lys Pro Ser Trp Ala Cys Ile Val Ile Ile
1               5                   10                  15

Val Leu Ile Val Thr Leu Ser Ser Gly Ala Ala Ser Gly Glu Ala Arg
                20                  25                  30

Arg Leu Leu Met Ala Glu Lys His Ala Ala Glu Gly Ala Cys Ala Gly
            35                  40                  45

Gly Cys Ser Pro Pro Val Gln Gly Leu Thr Ala Thr Thr Thr Ser Lys
    50                  55                  60

Met Ala Thr Thr Asp Gly Arg Pro Thr Ala Pro Gly His Ser Pro Gly
65                  70                  75                  80

Ile Gly Asn Lys Ile Ala Gly Asn Thr Arg
                85                  90
```

<210> SEQ ID NO 140
<211> LENGTH: 92
<212> TYPE: PRT
<213> ORGANISM: Zea mays

<400> SEQUENCE: 140

```
Met His Ser His Arg Ser Arg His Leu Lys Pro Arg Gln Arg Glu Ala
1               5                   10                  15

Ala Gly Gly Val Phe Phe Asn Gly Gly Thr Glu Gly Gly Ala Cys Lys
                20                  25                  30

Gly Gly Ile Phe Val Gln Gly Tyr Ala Gly Leu Ser Ala Arg Gln Lys
            35                  40                  45

Met Ala Ala Thr Ala Thr Ser Thr Glu Gln Val Val Val Val Gly Glu
    50                  55                  60

Gly Met Pro Ala Thr Thr Thr Asp Ser Arg Pro Thr Ala Pro Gly Asn
65                  70                  75                  80

Ser Pro Gly Ile Gly Asn Lys Gly Lys Ile Asn Asn
                85                  90
```

<210> SEQ ID NO 141
<211> LENGTH: 113
<212> TYPE: PRT
<213> ORGANISM: Brachypodium distachyon

<400> SEQUENCE: 141

```
Met Ala Pro Ser Ile Ser Lys Asn Thr Asn Thr Cys Thr Cys Ala Leu
1               5                   10                  15

Leu Leu Ile Phe Val Val Leu Phe Ser Gln Leu Val Glu Ser Gln Ser
                20                  25                  30
```

```
Arg Ser Leu Pro His Gly Ser Leu Ile Ser Thr Met His Arg Arg Tyr
         35                  40                  45

Leu Leu Ser His Val Asn Gly Ala Ser Pro Asn Gly Leu Ala Glu Gly
 50                  55                  60

Ala Val Ser Pro Pro Ser Glu Ile His Gly Gly Asp Gly Pro Leu Val
 65                  70                  75                  80

Asp Val Arg Asp Gly Val Arg Pro Ser Asn Pro Gly His Ser Pro Gly
                 85                  90                  95

Ile Gly His Ser Phe Val Asn Arg Asn Gly Pro Ala Gly Asn Asn Lys
                100                 105                 110

Leu

<210> SEQ ID NO 142
<211> LENGTH: 109
<212> TYPE: PRT
<213> ORGANISM: Setaria italica

<400> SEQUENCE: 142

Met Ala Leu Asn Lys Asn Pro Ser Thr Cys Thr Ser Ala Leu Leu Leu
 1               5                  10                  15

Leu Ala Leu Leu Val Thr Phe Ser Gln Leu Ala Ser Gln Gly Arg
                 20                  25                  30

Pro Phe Pro Thr Val Ser Tyr Ile Thr Thr Met His Gly Arg Thr Leu
                 35                  40                  45

Leu Ser His Gly Ser Asp Ser Val Pro Lys Gly Met Val Glu Gly Thr
 50                  55                  60

Val Ser Pro Ser Ser Glu Ile His Gly Asp Lys Gly Ser Met Val Asp
 65                  70                  75                  80

Ala Asp Asp Val Arg Pro Ser Thr Pro Arg His Ser Pro Gly Ile Gly
                 85                  90                  95

His Ala Phe Ile Asn Lys Asn Gly Leu Gly Arg Lys Leu
                100                 105

<210> SEQ ID NO 143
<211> LENGTH: 135
<212> TYPE: PRT
<213> ORGANISM: Phoenix dactylifera

<400> SEQUENCE: 143

Met Ala Gly Lys Lys Gln Phe Tyr Ser Cys Ile Leu Val Ile Val Leu
 1               5                  10                  15

Ile Leu Ala Asn Asp Tyr Leu Ser Ser Glu Gly Arg His Leu Lys Glu
                 20                  25                  30

Glu Lys Phe Lys Ser Arg Gly Cys Arg Glu Cys Pro Glu Arg Gly Asp
                 35                  40                  45

Ser Lys Ile Glu Arg Arg Thr Ser Ser Met Val Ser Asn Thr Ile Glu
 50                  55                  60

Gly His Asp Asn Arg Val Leu Met Val Ala Met Asp Ala Arg Pro Thr
 65                  70                  75                  80

Ala Gly Asp Ser Asn Ile Glu Arg Gly Thr Ser Ser Met Thr Ser Lys
                 85                  90                  95

Thr Ile Glu Gly His Asp Ala Arg Val Leu Thr Ala Ala Ile Asp Ser
                100                 105                 110

Arg Pro Thr Ala Pro Gly His Ser Pro Gly Val Gly His Ser Ile Asn
                115                 120                 125

Ser Arg Gly Gly Asp Lys Asn
```

130             135

<210> SEQ ID NO 144
<211> LENGTH: 92
<212> TYPE: PRT
<213> ORGANISM: Phoenix dactylifera

<400> SEQUENCE: 144

Met Val Gly Ile Lys Pro Val His Ile Ser Ala Leu Phe Val Leu
1               5                   10                  15

Ile Leu Ala Arg Lys Phe Ala Leu Thr Glu Glu Arg His Phe Ile Leu
            20                  25                  30

Val Lys Thr Lys Ile Ser Glu Lys Cys Pro Lys Gln Gly Asp Thr Arg
        35                  40                  45

Ile Gly Arg Met Asn Arg Gly Ile Asn His Gly Asp Ala Val Leu Ala
    50                  55                  60

Phe Ala Asp Gly Asp Arg Pro Ser Val Pro Gly His Ser Pro Gly Val
65                  70                  75                  80

Gly His Ser His Glu Ser Lys Asp Gly Gly Lys Asn
                85                  90

<210> SEQ ID NO 145
<211> LENGTH: 115
<212> TYPE: PRT
<213> ORGANISM: Phoenix dactylifera

<400> SEQUENCE: 145

Met Pro Asn Leu Pro Leu Ser Leu Ser Leu Ser Leu Met Ala
1               5                   10                  15

Gly Lys Lys His Phe Tyr Ala Cys Ala Leu Val Ile Val Leu Ile Leu
            20                  25                  30

Val Asn Glu Cys Leu Ser Ser Glu Gly Arg His Leu Met Ala Gly Lys
        35                  40                  45

Phe Lys Ala Lys Gly Cys Glu Glu Cys Leu Ala Arg Gly Gly Asn Asn
    50                  55                  60

Ile Glu Gly Thr Thr Ser Ser Leu Val Ser His Thr Ile Glu Gly His
65                  70                  75                  80

Asp Asp Arg Val Leu Ile Val Thr Thr Glu Asp Ala Arg Pro Thr Thr
                85                  90                  95

Pro Gly His Ser Pro Gly Val Gly His Gly Ile Lys Ser Gly Gly
                100                 105                 110

Asp Lys Asn
        115

<210> SEQ ID NO 146
<211> LENGTH: 99
<212> TYPE: PRT
<213> ORGANISM: Phoenix dactylifera

<400> SEQUENCE: 146

Met Ala Ala Asn Lys Arg Phe Tyr Pro Cys Ala Leu Leu Ile Ile Met
1               5                   10                  15

Val Leu Ala Ser Glu Thr Phe Ser Glu Gly Arg Thr Leu Met Glu
            20                  25                  30

Asp Lys Ala Arg Val Cys Arg Arg Cys Leu Val Glu Asn Thr Ser Phe
        35                  40                  45

Lys Gly Leu Val Glu Gly Pro Thr Val Pro Pro Ala Val Asp Gly Asp
    50                  55                  60

```
Asn Ala Leu Met Ala Asp Thr Glu Asp Ala Arg Pro Thr Thr Pro Gly
 65                  70                  75                  80

His Ser Pro Gly Val Gly His Ser Phe Asn Gly Lys Asp Val Ile Asn
                 85                  90                  95

Lys Asp Val

<210> SEQ ID NO 147
<211> LENGTH: 100
<212> TYPE: PRT
<213> ORGANISM: Phoenix dactylifera

<400> SEQUENCE: 147

Met Ala Ala Asn Lys Pro Phe Tyr Thr Tyr Ala Leu Leu Ile Leu Met
  1               5                  10                  15

Ile Leu Ala Phe Glu Thr Phe Thr Ser Val Gly Arg Thr Leu Val Glu
                 20                  25                  30

Asp Lys Thr Lys Val Cys Arg Arg Cys Leu Val Gln Asp Ala Gly Ala
             35                  40                  45

Lys Gly Met Val Glu Gly Pro Ile Ser Pro Ala Ile His Gly Asp
 50                  55                  60

Asp Ala Leu Met Val Gly Ile Ser Asp Ala Arg Pro Thr Thr Pro Gly
 65                  70                  75                  80

His Ser Pro Gly Val Gly His Ser Phe Asn Tyr Lys Asn Val Val Ile
                 85                  90                  95

Asn Lys Asn Val
            100

<210> SEQ ID NO 148
<211> LENGTH: 15
<212> TYPE: PRT
<213> ORGANISM: Arabidopsis thaliana

<400> SEQUENCE: 148

Asp Phe Arg Pro Thr Asn Pro Gly Asn Ser Pro Gly Val Gly His
  1               5                  10                  15

<210> SEQ ID NO 149
<211> LENGTH: 15
<212> TYPE: PRT
<213> ORGANISM: Arabidopsis thaliana

<400> SEQUENCE: 149

Asp Phe Ala Pro Thr Asn Pro Gly Asp Ser Pro Gly Ile Arg His
  1               5                  10                  15

<210> SEQ ID NO 150
<211> LENGTH: 15
<212> TYPE: PRT
<213> ORGANISM: Arabidopsis thaliana

<400> SEQUENCE: 150

Thr Phe Arg Pro Thr Glu Pro Gly His Ser Pro Gly Ile Gly His
  1               5                  10                  15

<210> SEQ ID NO 151
<211> LENGTH: 15
<212> TYPE: PRT
<213> ORGANISM: Arabidopsis thaliana

<400> SEQUENCE: 151
```

```
Ala Phe Arg Pro Thr His Gln Gly Pro Ser Gln Gly Ile Gly His
1               5                   10                  15

<210> SEQ ID NO 152
<211> LENGTH: 15
<212> TYPE: PRT
<213> ORGANISM: Arabidopsis thaliana

<400> SEQUENCE: 152

Asp Phe Val Pro Thr Ser Pro Gly Asn Ser Pro Gly Val Gly His
1               5                   10                  15

<210> SEQ ID NO 153
<211> LENGTH: 15
<212> TYPE: PRT
<213> ORGANISM: Arabidopsis thaliana

<400> SEQUENCE: 153

Asp Phe Ala Pro Thr Ser Pro Gly His Ser Pro Gly Val Gly His
1               5                   10                  15

<210> SEQ ID NO 154
<211> LENGTH: 15
<212> TYPE: PRT
<213> ORGANISM: Arabidopsis thaliana

<400> SEQUENCE: 154

Asp Phe Ala Pro Thr Ser Pro Gly Asn Ser Pro Gly Ile Gly His
1               5                   10                  15

<210> SEQ ID NO 155
<211> LENGTH: 15
<212> TYPE: PRT
<213> ORGANISM: Arabidopsis thaliana

<400> SEQUENCE: 155

Asp Phe Lys Pro Thr Thr Pro Gly His Ser Pro Gly Val Gly His
1               5                   10                  15

<210> SEQ ID NO 156
<211> LENGTH: 15
<212> TYPE: PRT
<213> ORGANISM: Arabidopsis thaliana
<220> FEATURE:
<221> NAME/KEY: MOD_RES
<222> LOCATION: (4)..(4)
<223> OTHER INFORMATION: hydroxyproline
<220> FEATURE:
<221> NAME/KEY: MOD_RES
<222> LOCATION: (11)..(11)
<223> OTHER INFORMATION: hydroxyproline

<400> SEQUENCE: 156

Asp Phe Arg Pro Thr Thr Pro Gly His Ser Pro Gly Ile Gly His
1               5                   10                  15

<210> SEQ ID NO 157
<211> LENGTH: 15
<212> TYPE: PRT
<213> ORGANISM: Arabidopsis thaliana

<400> SEQUENCE: 157

Asp Phe Gly Pro Thr Ser Pro Gly Asn Ser Pro Gly Ile Gly His
1               5                   10                  15

<210> SEQ ID NO 158
```

```
<211> LENGTH: 15
<212> TYPE: PRT
<213> ORGANISM: Arabidopsis thaliana

<400> SEQUENCE: 158

Asp Phe Glu Pro Thr Thr Pro Gly His Ser Pro Gly Val Gly His
1               5                   10                  15

<210> SEQ ID NO 159
<211> LENGTH: 15
<212> TYPE: PRT
<213> ORGANISM: Arabidopsis lyrata

<400> SEQUENCE: 159

Asp Phe Arg Pro Thr Thr Pro Gly His Ser Pro Gly Ile Gly His
1               5                   10                  15

<210> SEQ ID NO 160
<211> LENGTH: 15
<212> TYPE: PRT
<213> ORGANISM: Arabidopsis lyrata

<400> SEQUENCE: 160

Thr Phe Arg Pro Thr Ala Pro Gly His Ser Pro Gly Ile Gly His
1               5                   10                  15

<210> SEQ ID NO 161
<211> LENGTH: 15
<212> TYPE: PRT
<213> ORGANISM: Arabidopsis lyrata

<400> SEQUENCE: 161

Asp Phe Ala Pro Thr Ser Pro Gly Asn Ser Pro Gly Val Gly His
1               5                   10                  15

<210> SEQ ID NO 162
<211> LENGTH: 15
<212> TYPE: PRT
<213> ORGANISM: Arabidopsis lyrata

<400> SEQUENCE: 162

Asp Phe Ala Pro Thr Ser Pro Gly His Ser Pro Gly Val Gly His
1               5                   10                  15

<210> SEQ ID NO 163
<211> LENGTH: 15
<212> TYPE: PRT
<213> ORGANISM: Arabidopsis lyrata

<400> SEQUENCE: 163

Glu Phe Ala Pro Thr Ser Pro Gly Asn Ser Pro Gly Ile Gly His
1               5                   10                  15

<210> SEQ ID NO 164
<211> LENGTH: 15
<212> TYPE: PRT
<213> ORGANISM: Arabidopsis lyrata

<400> SEQUENCE: 164

Asp Phe Ala Pro Thr Thr Pro Gly Asn Ser Pro Gly Met Gly His
1               5                   10                  15

<210> SEQ ID NO 165
<211> LENGTH: 15
<212> TYPE: PRT
```

<213> ORGANISM: Arabidopsis lyrata

<400> SEQUENCE: 165

Asp Phe Lys Pro Thr Thr Pro Gly His Ser Pro Gly Val Gly His
1               5                   10                  15

<210> SEQ ID NO 166
<211> LENGTH: 15
<212> TYPE: PRT
<213> ORGANISM: Medicago truncatula

<400> SEQUENCE: 166

Ala Phe Gln Pro Thr Thr Pro Gly Asn Ser Pro Gly Val Gly His
1               5                   10                  15

<210> SEQ ID NO 167
<211> LENGTH: 15
<212> TYPE: PRT
<213> ORGANISM: Medicago truncatula

<400> SEQUENCE: 167

Glu Phe Gln Lys Thr Asn Pro Gly His Ser Pro Gly Val Gly His
1               5                   10                  15

<210> SEQ ID NO 168
<211> LENGTH: 15
<212> TYPE: PRT
<213> ORGANISM: Medicago truncatula

<400> SEQUENCE: 168

Ala Phe Arg Pro Thr Thr Pro Gly His Ser Pro Gly Ile Gly His
1               5                   10                  15

<210> SEQ ID NO 169
<211> LENGTH: 15
<212> TYPE: PRT
<213> ORGANISM: Medicago truncatula

<400> SEQUENCE: 169

Asp Phe Arg Pro Thr Thr Pro Gly Asn Ser Pro Gly Ala Gly His
1               5                   10                  15

<210> SEQ ID NO 170
<211> LENGTH: 15
<212> TYPE: PRT
<213> ORGANISM: Medicago truncatula

<400> SEQUENCE: 170

Ala Phe Arg Pro Thr Ser Pro Gly His Ser Pro Gly Val Gly His
1               5                   10                  15

<210> SEQ ID NO 171
<211> LENGTH: 15
<212> TYPE: PRT
<213> ORGANISM: Medicago truncatula

<400> SEQUENCE: 171

Ala Phe Arg Pro Thr Thr Pro Gly His Ser Pro Gly Val Gly His
1               5                   10                  15

<210> SEQ ID NO 172
<211> LENGTH: 15
<212> TYPE: PRT
<213> ORGANISM: Medicago truncatula

```
<400> SEQUENCE: 172

Asp Phe Arg Pro Thr Ser Pro Gly His Ser Pro Gly Val Gly His
1               5                   10                  15

<210> SEQ ID NO 173
<211> LENGTH: 15
<212> TYPE: PRT
<213> ORGANISM: Medicago truncatula

<400> SEQUENCE: 173

Ser Phe Arg Pro Thr Thr Pro Gly Ser Ser Pro Gly Val Gly His
1               5                   10                  15

<210> SEQ ID NO 174
<211> LENGTH: 15
<212> TYPE: PRT
<213> ORGANISM: Medicago truncatula

<400> SEQUENCE: 174

Gly Phe Lys Pro Thr Asn Pro Ser His Ser Pro Gly Val Gly His
1               5                   10                  15

<210> SEQ ID NO 175
<211> LENGTH: 15
<212> TYPE: PRT
<213> ORGANISM: Medicago truncatula

<400> SEQUENCE: 175

Ala Phe Arg Pro Thr Thr Pro Gly Asn Ser Pro Gly Val Gly His
1               5                   10                  15

<210> SEQ ID NO 176
<211> LENGTH: 15
<212> TYPE: PRT
<213> ORGANISM: Medicago truncatula

<400> SEQUENCE: 176

Ala Phe Arg Pro Thr Thr Pro Gly Ser Ser Pro Gly Val Gly His
1               5                   10                  15

<210> SEQ ID NO 177
<211> LENGTH: 15
<212> TYPE: PRT
<213> ORGANISM: Medicago truncatula

<400> SEQUENCE: 177

Ala Phe Lys Pro Thr Tyr Pro Asn His Ser Pro Gly Val Gly His
1               5                   10                  15

<210> SEQ ID NO 178
<211> LENGTH: 15
<212> TYPE: PRT
<213> ORGANISM: Medicago truncatula

<400> SEQUENCE: 178

Ala Phe Arg Pro Thr Pro Ser Gly His Ser Leu Gly Val Gly His
1               5                   10                  15

<210> SEQ ID NO 179
<211> LENGTH: 15
<212> TYPE: PRT
<213> ORGANISM: Medicago truncatula

<400> SEQUENCE: 179
```

-continued

```
Ala Phe Arg Pro Thr Pro Pro Gly His Ser Pro Gly Gly Gly His
1               5                   10                  15

<210> SEQ ID NO 180
<211> LENGTH: 15
<212> TYPE: PRT
<213> ORGANISM: Medicago truncatula

<400> SEQUENCE: 180

Ala Phe Arg Pro Asn Pro Pro Gly His Ser Pro Gly Gly Gly His
1               5                   10                  15

<210> SEQ ID NO 181
<211> LENGTH: 15
<212> TYPE: PRT
<213> ORGANISM: Medicago truncatula

<400> SEQUENCE: 181

Ala Phe Arg Pro Thr Pro Pro Gly His Ser Pro Gly Gly Gly His
1               5                   10                  15

<210> SEQ ID NO 182
<211> LENGTH: 15
<212> TYPE: PRT
<213> ORGANISM: Medicago truncatula

<400> SEQUENCE: 182

Ala Phe Arg Pro Thr Ser Pro Gly His Ser Pro Gly Val Gly His
1               5                   10                  15

<210> SEQ ID NO 183
<211> LENGTH: 15
<212> TYPE: PRT
<213> ORGANISM: Solanum lycopersicum

<400> SEQUENCE: 183

Ile Ser Glu Glu Gly Gly Pro Gly His Ser Pro Gly Val Gly His
1               5                   10                  15

<210> SEQ ID NO 184
<211> LENGTH: 15
<212> TYPE: PRT
<213> ORGANISM: Solanum lycopersicum

<400> SEQUENCE: 184

Val Lys Asp Tyr Ser Gly Pro Gly His Ser Pro Gly Met Gly His
1               5                   10                  15

<210> SEQ ID NO 185
<211> LENGTH: 15
<212> TYPE: PRT
<213> ORGANISM: Solanum lycopersicum

<400> SEQUENCE: 185

Val Lys Asp Tyr Ser Gly Pro Gly His Ser Pro Gly Met Gly His
1               5                   10                  15

<210> SEQ ID NO 186
<211> LENGTH: 15
<212> TYPE: PRT
<213> ORGANISM: Solanum lycopersicum

<400> SEQUENCE: 186

Asp Phe Gly Pro Thr Gly Pro Gly His Ser Pro Gly Ile Gly His
1               5                   10                  15
```

```
<210> SEQ ID NO 187
<211> LENGTH: 15
<212> TYPE: PRT
<213> ORGANISM: Gossypium hirsutum

<400> SEQUENCE: 187

Ala Phe Arg Ser Thr Thr Pro Gly His Ser Pro Gly Ala Gly His
1               5                   10                  15

<210> SEQ ID NO 188
<211> LENGTH: 15
<212> TYPE: PRT
<213> ORGANISM: Lactuca sativa

<400> SEQUENCE: 188

Ala Phe Arg Pro Thr Thr Pro Gly Asn Ser Pro Gly Ala Gly His
1               5                   10                  15

<210> SEQ ID NO 189
<211> LENGTH: 15
<212> TYPE: PRT
<213> ORGANISM: Lactuca sativa

<400> SEQUENCE: 189

Gly Phe Arg Pro Thr Lys Pro Gly Asn Ser Pro Gly Ala Gly His
1               5                   10                  15

<210> SEQ ID NO 190
<211> LENGTH: 15
<212> TYPE: PRT
<213> ORGANISM: Euphorbia esula

<400> SEQUENCE: 190

Asp Phe Arg Pro Thr Ser Pro Gly Tyr Ser Pro Gly Val Gly His
1               5                   10                  15

<210> SEQ ID NO 191
<211> LENGTH: 15
<212> TYPE: PRT
<213> ORGANISM: Euphorbia esula

<400> SEQUENCE: 191

Asp Phe Arg Pro Thr Glu Pro Gly Tyr Ser Pro Gly Val Gly His
1               5                   10                  15

<210> SEQ ID NO 192
<211> LENGTH: 15
<212> TYPE: PRT
<213> ORGANISM: Euphorbia esula

<400> SEQUENCE: 192

Asp Tyr Arg Pro Thr Glu Pro Gly His Ser Pro Gly Ala Gly His
1               5                   10                  15

<210> SEQ ID NO 193
<211> LENGTH: 15
<212> TYPE: PRT
<213> ORGANISM: Euphorbia esula

<400> SEQUENCE: 193

Asp Phe Arg Pro Thr Ala Pro Gly Phe Ser Pro Gly Val Gly His
1               5                   10                  15
```

```
<210> SEQ ID NO 194
<211> LENGTH: 15
<212> TYPE: PRT
<213> ORGANISM: Euphorbia esula

<400> SEQUENCE: 194

Ala Phe Arg Pro Thr Ala Pro Gly His Ser Pro Gly Val Gly His
1               5                   10                  15

<210> SEQ ID NO 195
<211> LENGTH: 15
<212> TYPE: PRT
<213> ORGANISM: Euphorbia esula

<400> SEQUENCE: 195

Ala Phe Arg Pro Thr Ala Pro Gly His Ser Pro Gly Val Gly His
1               5                   10                  15

<210> SEQ ID NO 196
<211> LENGTH: 15
<212> TYPE: PRT
<213> ORGANISM: Euphorbia esula

<400> SEQUENCE: 196

Ala Phe Arg Pro Thr Ala Pro Gly His Ser Pro Gly Val Gly His
1               5                   10                  15

<210> SEQ ID NO 197
<211> LENGTH: 15
<212> TYPE: PRT
<213> ORGANISM: Euphorbia esula

<400> SEQUENCE: 197

Ala Phe Arg Pro Thr Ala Pro Gly His Ser Pro Gly Val Gly Tyr
1               5                   10                  15

<210> SEQ ID NO 198
<211> LENGTH: 15
<212> TYPE: PRT
<213> ORGANISM: Euphorbia esula

<400> SEQUENCE: 198

Ala Phe Arg Pro Thr Ala Pro Gly His Ser Pro Gly Val Gly His
1               5                   10                  15

<210> SEQ ID NO 199
<211> LENGTH: 15
<212> TYPE: PRT
<213> ORGANISM: Glycine max

<400> SEQUENCE: 199

Ala Phe Arg Pro Thr Thr Pro Gly Gly Ser Pro Gly Val Gly His
1               5                   10                  15

<210> SEQ ID NO 200
<211> LENGTH: 15
<212> TYPE: PRT
<213> ORGANISM: Glycine max

<400> SEQUENCE: 200

Asp Phe Lys Pro Thr Asp Pro Gly His Ser Pro Gly Val Gly His
1               5                   10                  15

<210> SEQ ID NO 201
<211> LENGTH: 15
```

<212> TYPE: PRT
<213> ORGANISM: Glycine max

<400> SEQUENCE: 201

Ala Phe Arg Pro Thr Thr Pro Gly His Ser Pro Gly Val Gly His
1               5                   10                  15

<210> SEQ ID NO 202
<211> LENGTH: 15
<212> TYPE: PRT
<213> ORGANISM: Glycine max

<400> SEQUENCE: 202

Ala Phe Arg Pro Thr Thr Pro Gly Asn Ser Pro Gly Val Gly His
1               5                   10                  15

<210> SEQ ID NO 203
<211> LENGTH: 15
<212> TYPE: PRT
<213> ORGANISM: Glycine max

<400> SEQUENCE: 203

Asn Phe Arg Pro Thr Ala Pro Gly His Ser Pro Gly Val Gly His
1               5                   10                  15

<210> SEQ ID NO 204
<211> LENGTH: 15
<212> TYPE: PRT
<213> ORGANISM: Glycine max

<400> SEQUENCE: 204

Asp Phe Lys Pro Thr Asp Pro Gly His Ser Pro Gly Val Gly His
1               5                   10                  15

<210> SEQ ID NO 205
<211> LENGTH: 15
<212> TYPE: PRT
<213> ORGANISM: Glycine max

<400> SEQUENCE: 205

Asp Phe Arg Pro Thr Thr Pro Gly His Ser Pro Gly Val Gly His
1               5                   10                  15

<210> SEQ ID NO 206
<211> LENGTH: 15
<212> TYPE: PRT
<213> ORGANISM: Glycine max

<400> SEQUENCE: 206

Asp Phe Gln Pro Thr Asp Pro Gly His Ser Pro Gly Ala Gly His
1               5                   10                  15

<210> SEQ ID NO 207
<211> LENGTH: 15
<212> TYPE: PRT
<213> ORGANISM: Glycine max

<400> SEQUENCE: 207

Ala Phe Arg Pro Thr Thr Pro Gly Asn Ser Pro Gly Val Gly His
1               5                   10                  15

<210> SEQ ID NO 208
<211> LENGTH: 15
<212> TYPE: PRT
<213> ORGANISM: Glycine max

<400> SEQUENCE: 208

Asp Phe Arg Pro Thr Asp Pro Gly His Ser Pro Gly Val Gly His
1               5                   10                  15

<210> SEQ ID NO 209
<211> LENGTH: 15
<212> TYPE: PRT
<213> ORGANISM: Glycine max

<400> SEQUENCE: 209

Asn Phe Arg Pro Thr Ala Pro Gly His Ser Pro Gly Val Gly His
1               5                   10                  15

<210> SEQ ID NO 210
<211> LENGTH: 15
<212> TYPE: PRT
<213> ORGANISM: Glycine max

<400> SEQUENCE: 210

Asp Phe Arg Pro Met Asp Pro Gly His Ser Pro Gly Ala Gly His
1               5                   10                  15

<210> SEQ ID NO 211
<211> LENGTH: 15
<212> TYPE: PRT
<213> ORGANISM: Glycine max

<400> SEQUENCE: 211

Ala Phe Arg Pro Thr Cys Arg Gly His Ser Pro Gly Ala Gly His
1               5                   10                  15

<210> SEQ ID NO 212
<211> LENGTH: 15
<212> TYPE: PRT
<213> ORGANISM: Glycine max

<400> SEQUENCE: 212

Ala Phe Arg Pro Thr Thr Pro Gly His Ser Pro Gly Val Gly His
1               5                   10                  15

<210> SEQ ID NO 213
<211> LENGTH: 15
<212> TYPE: PRT
<213> ORGANISM: Glycine max

<400> SEQUENCE: 213

Gly Phe Lys Pro Thr Asn Pro Gly His Ser Pro Gly Val Gly His
1               5                   10                  15

<210> SEQ ID NO 214
<211> LENGTH: 15
<212> TYPE: PRT
<213> ORGANISM: Glycine max

<400> SEQUENCE: 214

Ala Phe Arg Pro Thr Thr Pro Gly Asn Ser Pro Gly Val Gly His
1               5                   10                  15

<210> SEQ ID NO 215
<211> LENGTH: 15
<212> TYPE: PRT
<213> ORGANISM: Glycine max

<400> SEQUENCE: 215

Ala Phe Arg Pro Thr Thr Pro Gly Gly Ser Pro Gly Val Gly His
1               5                   10                  15

<210> SEQ ID NO 216
<211> LENGTH: 15
<212> TYPE: PRT
<213> ORGANISM: Glycine max

<400> SEQUENCE: 216

Asp Phe Lys Pro Thr Asp Pro Gly His Ser Pro Gly Val Gly His
1               5                   10                  15

<210> SEQ ID NO 217
<211> LENGTH: 15
<212> TYPE: PRT
<213> ORGANISM: Glycine max

<400> SEQUENCE: 217

Asp Phe Arg Pro Thr Asp Pro Gly His Ser Pro Gly Ala Gly His
1               5                   10                  15

<210> SEQ ID NO 218
<211> LENGTH: 15
<212> TYPE: PRT
<213> ORGANISM: Lotus japonicus

<400> SEQUENCE: 218

Asp Phe Lys Pro Thr Asp Pro Gly His Ser Pro Gly Val Gly His
1               5                   10                  15

<210> SEQ ID NO 219
<211> LENGTH: 15
<212> TYPE: PRT
<213> ORGANISM: Lotus japonicus

<400> SEQUENCE: 219

Lys Gln Pro Thr Thr Gly Pro Gly His Ser Pro Gly Val Gly His
1               5                   10                  15

<210> SEQ ID NO 220
<211> LENGTH: 15
<212> TYPE: PRT
<213> ORGANISM: Lotus japonicus

<400> SEQUENCE: 220

Ala Phe Arg Pro Thr Ser Pro Gly His Ser Pro Gly Val Gly His
1               5                   10                  15

<210> SEQ ID NO 221
<211> LENGTH: 15
<212> TYPE: PRT
<213> ORGANISM: Lotus japonicus

<400> SEQUENCE: 221

Ala Phe Arg Pro Thr Thr Pro Gly His Ser Pro Gly Val Gly His
1               5                   10                  15

<210> SEQ ID NO 222
<211> LENGTH: 15
<212> TYPE: PRT
<213> ORGANISM: Lotus japonicus

<400> SEQUENCE: 222

Ala Phe Arg Pro Thr Thr Pro Gly His Ser Pro Gly Val Gly His

<210> SEQ ID NO 223
<211> LENGTH: 15
<212> TYPE: PRT
<213> ORGANISM: Lotus japonicus

<400> SEQUENCE: 223

Ala Phe Glu Pro Thr Thr Pro Gly Asn Ser Pro Gly Val Gly His
1               5                   10                  15

<210> SEQ ID NO 224
<211> LENGTH: 15
<212> TYPE: PRT
<213> ORGANISM: Lotus japonicus

<400> SEQUENCE: 224

Asp Phe Lys Pro Thr Asp Pro Gly His Ser Pro Gly Val Gly His
1               5                   10                  15

<210> SEQ ID NO 225
<211> LENGTH: 15
<212> TYPE: PRT
<213> ORGANISM: Populus trichocarpa

<400> SEQUENCE: 225

Asp Phe Arg Pro Thr Thr Pro Gly Val Ser Pro Gly Val Gly His
1               5                   10                  15

<210> SEQ ID NO 226
<211> LENGTH: 15
<212> TYPE: PRT
<213> ORGANISM: Populus trichocarpa

<400> SEQUENCE: 226

Asp Phe Gln Pro Thr Thr Pro Gly His Ser Pro Gly Ala Gly His
1               5                   10                  15

<210> SEQ ID NO 227
<211> LENGTH: 15
<212> TYPE: PRT
<213> ORGANISM: Populus trichocarpa

<400> SEQUENCE: 227

Ala Phe Lys Pro Thr Thr Pro Gly His Ser Pro Gly Ala Gly His
1               5                   10                  15

<210> SEQ ID NO 228
<211> LENGTH: 15
<212> TYPE: PRT
<213> ORGANISM: Populus trichocarpa

<400> SEQUENCE: 228

Ala Phe Lys Pro Thr Thr Pro Gly His Ser Pro Gly Ile Gly His
1               5                   10                  15

<210> SEQ ID NO 229
<211> LENGTH: 15
<212> TYPE: PRT
<213> ORGANISM: Populus trichocarpa

<400> SEQUENCE: 229

Asp Phe Arg Pro Thr Val Pro Gly His Ser Pro Gly Ile Gly His
1               5                   10                  15

<210> SEQ ID NO 230
<211> LENGTH: 15
<212> TYPE: PRT
<213> ORGANISM: Populus trichocarpa

<400> SEQUENCE: 230

Ala Phe Arg Pro Pro Thr Pro Gly His Ser Pro Gly Val Gly His
1               5                   10                  15

<210> SEQ ID NO 231
<211> LENGTH: 15
<212> TYPE: PRT
<213> ORGANISM: Populus trichocarpa

<400> SEQUENCE: 231

Asp Phe Lys Pro Ile Thr Ser Gly Gln Ser Pro Gly Val Gly His
1               5                   10                  15

<210> SEQ ID NO 232
<211> LENGTH: 15
<212> TYPE: PRT
<213> ORGANISM: Populus trichocarpa

<400> SEQUENCE: 232

Asp Phe Gln Pro Thr Thr Pro Gly Asn Ser Pro Gly Val Gly His
1               5                   10                  15

<210> SEQ ID NO 233
<211> LENGTH: 15
<212> TYPE: PRT
<213> ORGANISM: Populus trichocarpa

<400> SEQUENCE: 233

Ala Phe Lys Pro Thr Thr Pro Gly His Ser Pro Gly Val Gly His
1               5                   10                  15

<210> SEQ ID NO 234
<211> LENGTH: 15
<212> TYPE: PRT
<213> ORGANISM: Populus trichocarpa

<400> SEQUENCE: 234

Ala Phe Lys Pro Thr Thr Pro Gly His Ser Pro Gly Val Gly His
1               5                   10                  15

<210> SEQ ID NO 235
<211> LENGTH: 15
<212> TYPE: PRT
<213> ORGANISM: Populus trichocarpa

<400> SEQUENCE: 235

Glu His Ser Val Thr Thr Pro Gly His Ser Pro Ala Val Gly His
1               5                   10                  15

<210> SEQ ID NO 236
<211> LENGTH: 15
<212> TYPE: PRT
<213> ORGANISM: Populus trichocarpa

<400> SEQUENCE: 236

Ala Phe Lys Pro Thr Thr Pro Gly His Ser Pro Gly Ile Gly His
1               5                   10                  15

<210> SEQ ID NO 237

```
<211> LENGTH: 15
<212> TYPE: PRT
<213> ORGANISM: Populus trichocarpa

<400> SEQUENCE: 237

Gly Phe Arg Pro Ala Val Pro Ile Gln Gly Pro Gly Val Gly His
1               5                   10                  15

<210> SEQ ID NO 238
<211> LENGTH: 15
<212> TYPE: PRT
<213> ORGANISM: Populus trichocarpa

<400> SEQUENCE: 238

Ala Phe Lys Pro Thr Thr Pro Gly His Ser Pro Gly Ile Gly His
1               5                   10                  15

<210> SEQ ID NO 239
<211> LENGTH: 15
<212> TYPE: PRT
<213> ORGANISM: Populus trichocarpa

<400> SEQUENCE: 239

Thr Phe Lys Pro Thr Thr Pro Gly His Ser Pro Gly Ile Gly His
1               5                   10                  15

<210> SEQ ID NO 240
<211> LENGTH: 15
<212> TYPE: PRT
<213> ORGANISM: Populus trichocarpa

<400> SEQUENCE: 240

Lys His Ser Val Thr Thr Pro Gly His Ser Ser Arg Val Gly His
1               5                   10                  15

<210> SEQ ID NO 241
<211> LENGTH: 15
<212> TYPE: PRT
<213> ORGANISM: Populus trichocarpa

<400> SEQUENCE: 241

Thr Phe Lys Pro Thr Thr Pro Gly His Ser Pro Gly Ile Gly His
1               5                   10                  15

<210> SEQ ID NO 242
<211> LENGTH: 15
<212> TYPE: PRT
<213> ORGANISM: Populus trichocarpa

<400> SEQUENCE: 242

Ala Phe Arg Pro Thr Thr Pro Gly His Ser Pro Gly Val Gly His
1               5                   10                  15

<210> SEQ ID NO 243
<211> LENGTH: 15
<212> TYPE: PRT
<213> ORGANISM: Populus trichocarpa

<400> SEQUENCE: 243

Asp Phe Lys Pro Thr Thr Pro Gly His Ser Pro Gly Ala Gly His
1               5                   10                  15

<210> SEQ ID NO 244
<211> LENGTH: 15
<212> TYPE: PRT
```

<210> SEQ ID NO 244 (continued)
<213> ORGANISM: Populus trichocarpa

<400> SEQUENCE: 244

Asp Phe Arg Pro Thr Ala Pro Gly His Ser Pro Gly Val Gly His
1               5                   10                  15

<210> SEQ ID NO 245
<211> LENGTH: 15
<212> TYPE: PRT
<213> ORGANISM: Vitis vinifera

<400> SEQUENCE: 245

Gly Phe Arg Pro Thr Thr Pro Gly Ser Ser Pro Gly Ile Gly His
1               5                   10                  15

<210> SEQ ID NO 246
<211> LENGTH: 15
<212> TYPE: PRT
<213> ORGANISM: Vitis vinifera

<400> SEQUENCE: 246

Asp Phe Arg Pro Thr Thr Pro Gly Ser Ser Pro Gly Val Gly His
1               5                   10                  15

<210> SEQ ID NO 247
<211> LENGTH: 15
<212> TYPE: PRT
<213> ORGANISM: Vitis vinifera

<400> SEQUENCE: 247

Asp Tyr Arg Pro Thr Lys Pro Gly His Ser Pro Gly Val Gly His
1               5                   10                  15

<210> SEQ ID NO 248
<211> LENGTH: 15
<212> TYPE: PRT
<213> ORGANISM: Vitis vinifera

<400> SEQUENCE: 248

Gly Phe Arg Pro Thr Thr Pro Gly Ser Ser Pro Gly Ile Gly His
1               5                   10                  15

<210> SEQ ID NO 249
<211> LENGTH: 15
<212> TYPE: PRT
<213> ORGANISM: Vitis vinifera

<400> SEQUENCE: 249

Asp Phe Arg Pro Thr Pro Pro Gly Ser Ser Pro Gly Ile Gly His
1               5                   10                  15

<210> SEQ ID NO 250
<211> LENGTH: 15
<212> TYPE: PRT
<213> ORGANISM: Vitis vinifera

<400> SEQUENCE: 250

Asp Phe Arg Pro Thr Thr Pro Gly His Ser Pro Gly Val Gly His
1               5                   10                  15

<210> SEQ ID NO 251
<211> LENGTH: 15
<212> TYPE: PRT
<213> ORGANISM: Vitis vinifera

```
<400> SEQUENCE: 251

Asp Val Gln Ser Thr Thr Pro Gly His Ser Pro Gly Val Gly His
1               5                   10                  15

<210> SEQ ID NO 252
<211> LENGTH: 15
<212> TYPE: PRT
<213> ORGANISM: Vitis vinifera

<400> SEQUENCE: 252

Asp Phe Arg Pro Thr Pro Pro Gly Ser Ser Pro Gly Ile Gly His
1               5                   10                  15

<210> SEQ ID NO 253
<211> LENGTH: 15
<212> TYPE: PRT
<213> ORGANISM: Vitis vinifera

<400> SEQUENCE: 253

Asp Phe Arg Pro Thr Thr Pro Gly Ser Ser Pro Gly Val Gly His
1               5                   10                  15

<210> SEQ ID NO 254
<211> LENGTH: 15
<212> TYPE: PRT
<213> ORGANISM: Vitis vinifera

<400> SEQUENCE: 254

Asp Tyr Arg Pro Thr Lys Pro Gly His Ser Pro Gly Val Gly His
1               5                   10                  15

<210> SEQ ID NO 255
<211> LENGTH: 15
<212> TYPE: PRT
<213> ORGANISM: Vitis vinifera

<400> SEQUENCE: 255

Asp Phe Arg Pro Thr Ser Pro Gly His Ser Pro Gly Val Gly His
1               5                   10                  15

<210> SEQ ID NO 256
<211> LENGTH: 15
<212> TYPE: PRT
<213> ORGANISM: Ricinus communis

<400> SEQUENCE: 256

Ala Phe Arg Pro Thr Pro Pro Gly Asn Ser Pro Gly Val Gly His
1               5                   10                  15

<210> SEQ ID NO 257
<211> LENGTH: 15
<212> TYPE: PRT
<213> ORGANISM: Ricinus communis

<400> SEQUENCE: 257

Asp Phe Arg Pro Thr Ser Pro Gly Tyr Ser Pro Gly Val Gly His
1               5                   10                  15

<210> SEQ ID NO 258
<211> LENGTH: 15
<212> TYPE: PRT
<213> ORGANISM: Ricinus communis

<400> SEQUENCE: 258
```

Asp Phe Arg Pro Thr Ala Pro Gly Phe Ser Pro Gly Val Gly His
1               5                   10                  15

<210> SEQ ID NO 259
<211> LENGTH: 15
<212> TYPE: PRT
<213> ORGANISM: Ricinus communis

<400> SEQUENCE: 259

Asp Tyr Arg Pro Thr Gln Pro Gly His Ser Pro Gly Val Gly His
1               5                   10                  15

<210> SEQ ID NO 260
<211> LENGTH: 15
<212> TYPE: PRT
<213> ORGANISM: Ricinus communis

<400> SEQUENCE: 260

Asp Phe Arg Pro Thr Ala Pro Gly His Ser Pro Gly Val Gly His
1               5                   10                  15

<210> SEQ ID NO 261
<211> LENGTH: 15
<212> TYPE: PRT
<213> ORGANISM: Ricinus communis

<400> SEQUENCE: 261

Ala Phe Arg Pro Thr Asn Pro Gly His Ser Pro Gly Val Gly His
1               5                   10                  15

<210> SEQ ID NO 262
<211> LENGTH: 15
<212> TYPE: PRT
<213> ORGANISM: Ricinus communis

<400> SEQUENCE: 262

Asp Phe Arg Pro Thr Asn Pro Gly His Ser Pro Gly Ala Gly His
1               5                   10                  15

<210> SEQ ID NO 263
<211> LENGTH: 15
<212> TYPE: PRT
<213> ORGANISM: Ricinus communis

<400> SEQUENCE: 263

Asp Phe Arg Pro Thr Ala Pro Gly His Ser Pro Gly Val Gly His
1               5                   10                  15

<210> SEQ ID NO 264
<211> LENGTH: 15
<212> TYPE: PRT
<213> ORGANISM: Ricinus communis

<400> SEQUENCE: 264

Ala Phe Arg Pro Thr Ala Pro Gly His Ser Ser Gly Val Gly His
1               5                   10                  15

<210> SEQ ID NO 265
<211> LENGTH: 15
<212> TYPE: PRT
<213> ORGANISM: Ricinus communis

<400> SEQUENCE: 265

Ala Phe Arg Pro Thr Asn Pro Gly His Ser Pro Gly Val Gly His
1               5                   10                  15

```
<210> SEQ ID NO 266
<211> LENGTH: 15
<212> TYPE: PRT
<213> ORGANISM: Casuarina glauca

<400> SEQUENCE: 266

Ala Phe Arg Pro Thr Ser Pro Gly His Ser Pro Gly Val Gly His
1               5                   10                  15

<210> SEQ ID NO 267
<211> LENGTH: 15
<212> TYPE: PRT
<213> ORGANISM: Jatropha curcas

<400> SEQUENCE: 267

Ala Phe Arg Pro Thr Asn Pro Gly His Ser Pro Gly Val Gly His
1               5                   10                  15

<210> SEQ ID NO 268
<211> LENGTH: 15
<212> TYPE: PRT
<213> ORGANISM: Jatropha curcas

<400> SEQUENCE: 268

Asp Phe Arg Pro Thr Thr Gly Gly His Ser Pro Gly Ala Gly His
1               5                   10                  15

<210> SEQ ID NO 269
<211> LENGTH: 15
<212> TYPE: PRT
<213> ORGANISM: Jatropha curcas

<400> SEQUENCE: 269

Asp Phe Arg Pro Thr Lys Pro Gly Tyr Ser Pro Gly Val Gly His
1               5                   10                  15

<210> SEQ ID NO 270
<211> LENGTH: 15
<212> TYPE: PRT
<213> ORGANISM: Jatropha curcas

<400> SEQUENCE: 270

Asp Phe Arg Pro Thr Ser Pro Gly Tyr Ser Pro Gly Val Gly His
1               5                   10                  15

<210> SEQ ID NO 271
<211> LENGTH: 15
<212> TYPE: PRT
<213> ORGANISM: Jatropha curcas

<400> SEQUENCE: 271

Asp Phe Arg Pro Thr Ser Pro Gly Tyr Ser Pro Gly Val Gly His
1               5                   10                  15

<210> SEQ ID NO 272
<211> LENGTH: 15
<212> TYPE: PRT
<213> ORGANISM: Jatropha curcas

<400> SEQUENCE: 272

Asp Phe Arg Pro Thr Ala Pro Gly Tyr Ser Pro Gly Val Gly His
1               5                   10                  15
```

```
<210> SEQ ID NO 273
<211> LENGTH: 15
<212> TYPE: PRT
<213> ORGANISM: Theobroma cacao

<400> SEQUENCE: 273

Asp Phe Arg Pro Thr Thr Pro Gly His Ser Pro Gly Ala Gly His
1               5                   10                  15

<210> SEQ ID NO 274
<211> LENGTH: 15
<212> TYPE: PRT
<213> ORGANISM: Theobroma cacao

<400> SEQUENCE: 274

Asp Phe Arg Pro Thr Pro Pro Gly His Ser Pro Gly Ala Gly His
1               5                   10                  15

<210> SEQ ID NO 275
<211> LENGTH: 15
<212> TYPE: PRT
<213> ORGANISM: Theobroma cacao

<400> SEQUENCE: 275

Asp Phe Arg Pro Pro Thr Pro Gly His Gly Pro Gly Ala Gly His
1               5                   10                  15

<210> SEQ ID NO 276
<211> LENGTH: 15
<212> TYPE: PRT
<213> ORGANISM: Malus domestica

<400> SEQUENCE: 276

Asp Tyr Arg Pro Thr Thr Pro Gly His Ser Pro Gly Ala Gly His
1               5                   10                  15

<210> SEQ ID NO 277
<211> LENGTH: 15
<212> TYPE: PRT
<213> ORGANISM: Carica papaya

<400> SEQUENCE: 277

Gly Phe Arg Pro Thr Thr Pro Gly Ile Ser Pro Gly Val Gly His
1               5                   10                  15

<210> SEQ ID NO 278
<211> LENGTH: 15
<212> TYPE: PRT
<213> ORGANISM: Carica papaya

<400> SEQUENCE: 278

Ala Phe Arg Pro Thr Thr Pro Gly His Ser Pro Gly Val Gly His
1               5                   10                  15

<210> SEQ ID NO 279
<211> LENGTH: 15
<212> TYPE: PRT
<213> ORGANISM: Carica papaya

<400> SEQUENCE: 279

Asp Phe Arg Pro Thr Thr Pro Gly His Ser Pro Gly Val Gly His
1               5                   10                  15

<210> SEQ ID NO 280
<211> LENGTH: 15
```

```
<212> TYPE: PRT
<213> ORGANISM: Fragaria vesca

<400> SEQUENCE: 280

Asp Phe Arg Pro Thr Thr Pro Gly Asn Ser Pro Gly Ala Gly His
1               5                   10                  15

<210> SEQ ID NO 281
<211> LENGTH: 15
<212> TYPE: PRT
<213> ORGANISM: Fragaria vesca

<400> SEQUENCE: 281

Asp Tyr Arg Pro Thr Gln Pro Gly His Ser Pro Gly Val Gly His
1               5                   10                  15

<210> SEQ ID NO 282
<211> LENGTH: 15
<212> TYPE: PRT
<213> ORGANISM: Fragaria vesca

<400> SEQUENCE: 282

Ala Phe Arg Pro Thr Thr Pro Gly His Ser Pro Gly Val Gly His
1               5                   10                  15

<210> SEQ ID NO 283
<211> LENGTH: 15
<212> TYPE: PRT
<213> ORGANISM: Fragaria vesca

<400> SEQUENCE: 283

Asp Phe Arg Pro Thr Thr Pro Gly His Ser Pro Gly Val Gly His
1               5                   10                  15

<210> SEQ ID NO 284
<211> LENGTH: 15
<212> TYPE: PRT
<213> ORGANISM: Prunus persica

<400> SEQUENCE: 284

Ala Phe Arg Pro Thr Ser Pro Gly His Ser Pro Gly Val Gly His
1               5                   10                  15

<210> SEQ ID NO 285
<211> LENGTH: 15
<212> TYPE: PRT
<213> ORGANISM: Cucumis sativus

<400> SEQUENCE: 285

Ala Phe Arg Pro Thr Ser Pro Gly His Ser Pro Gly Val Gly His
1               5                   10                  15

<210> SEQ ID NO 286
<211> LENGTH: 15
<212> TYPE: PRT
<213> ORGANISM: Manihot esculenta

<400> SEQUENCE: 286

Cys Phe Arg Pro Thr Asp Pro Gly Asn Ser Pro Gly Val Gly His
1               5                   10                  15

<210> SEQ ID NO 287
<211> LENGTH: 15
<212> TYPE: PRT
<213> ORGANISM: Manihot esculenta
```

<400> SEQUENCE: 287

Gly Phe Arg Pro Thr Thr Pro Gly Tyr Ser Pro Gly Val Gly His
1               5                   10                  15

<210> SEQ ID NO 288
<211> LENGTH: 15
<212> TYPE: PRT
<213> ORGANISM: Manihot esculenta

<400> SEQUENCE: 288

Asp His Arg Pro Thr Gln Pro Gly His Ser Pro Gly Val Gly His
1               5                   10                  15

<210> SEQ ID NO 289
<211> LENGTH: 15
<212> TYPE: PRT
<213> ORGANISM: Citrus sinensis

<400> SEQUENCE: 289

Ala Phe Arg Pro Thr Ser Pro Gly His Ser Pro Gly Val Gly His
1               5                   10                  15

<210> SEQ ID NO 290
<211> LENGTH: 15
<212> TYPE: PRT
<213> ORGANISM: Citrus clementina

<400> SEQUENCE: 290

Ala Phe Arg Pro Thr Ser Pro Gly His Ser Pro Gly Val Gly His
1               5                   10                  15

<210> SEQ ID NO 291
<211> LENGTH: 15
<212> TYPE: PRT
<213> ORGANISM: Catharanthus roseus

<400> SEQUENCE: 291

Ser Phe Arg Pro Thr Asn Pro Gly Arg Ser Pro Gly Ile Gly His
1               5                   10                  15

<210> SEQ ID NO 292
<211> LENGTH: 15
<212> TYPE: PRT
<213> ORGANISM: Solanum tuberosum

<400> SEQUENCE: 292

Val Lys Asp Tyr Ser Gly Pro Gly His Ser Pro Gly Met Gly His
1               5                   10                  15

<210> SEQ ID NO 293
<211> LENGTH: 15
<212> TYPE: PRT
<213> ORGANISM: Solanum tuberosum

<400> SEQUENCE: 293

Asp Ile Pro Tyr Val Thr Pro Gly His Ser Pro Gly Met Gly His
1               5                   10                  15

<210> SEQ ID NO 294
<211> LENGTH: 15
<212> TYPE: PRT
<213> ORGANISM: Brassica napus

<400> SEQUENCE: 294

```
Asp Phe Arg Pro Thr Thr Pro Gly His Ser Pro Gly Ile Gly His
1               5                   10                  15

<210> SEQ ID NO 295
<211> LENGTH: 15
<212> TYPE: PRT
<213> ORGANISM: Brassica napus

<400> SEQUENCE: 295

Ala Tyr Ala Pro Thr Asp Pro Gly Asn Ser Pro Gly Ile Gly His
1               5                   10                  15

<210> SEQ ID NO 296
<211> LENGTH: 15
<212> TYPE: PRT
<213> ORGANISM: Brassica napus

<400> SEQUENCE: 296

Ala Tyr Ala Pro Thr Asp Pro Gly Asn Ser Pro Gly Ile Gly His
1               5                   10                  15

<210> SEQ ID NO 297
<211> LENGTH: 15
<212> TYPE: PRT
<213> ORGANISM: Brassica napus

<400> SEQUENCE: 297

Ala Tyr Ala Pro Thr Asp Pro Gly Asn Ser Pro Gly Ile Gly His
1               5                   10                  15

<210> SEQ ID NO 298
<211> LENGTH: 15
<212> TYPE: PRT
<213> ORGANISM: Eucalyptus grandis

<400> SEQUENCE: 298

Asp Phe Arg Pro Thr Gln Pro Gly His Ser Pro Gly Val Gly His
1               5                   10                  15

<210> SEQ ID NO 299
<211> LENGTH: 15
<212> TYPE: PRT
<213> ORGANISM: Eucalyptus grandis

<400> SEQUENCE: 299

Ser Tyr Arg Pro Thr Thr Pro Gly His Ser Pro Gly Ile Gly His
1               5                   10                  15

<210> SEQ ID NO 300
<211> LENGTH: 15
<212> TYPE: PRT
<213> ORGANISM: Aquilegia coerulea

<400> SEQUENCE: 300

Ala Phe Arg Pro Thr Thr Pro Gly His Ser Pro Gly Ile Gly His
1               5                   10                  15

<210> SEQ ID NO 301
<211> LENGTH: 15
<212> TYPE: PRT
<213> ORGANISM: Oryza sativa

<400> SEQUENCE: 301

Gly Val Arg Pro Thr Asn Pro Gly His Ser Pro Gly Ile Gly His
```

-continued

```
1               5                   10                  15

<210> SEQ ID NO 302
<211> LENGTH: 15
<212> TYPE: PRT
<213> ORGANISM: Oryza sativa

<400> SEQUENCE: 302

Asp Val Arg Pro Thr Asn Pro Gly His Ser Pro Gly Ile Gly His
1               5                   10                  15

<210> SEQ ID NO 303
<211> LENGTH: 15
<212> TYPE: PRT
<213> ORGANISM: Oryza sativa

<400> SEQUENCE: 303

Asp Val Arg Pro Thr Asn Pro Gly His Ser Pro Gly Ile Gly His
1               5                   10                  15

<210> SEQ ID NO 304
<211> LENGTH: 15
<212> TYPE: PRT
<213> ORGANISM: Oryza sativa

<400> SEQUENCE: 304

Asp Val Arg Pro Thr Asn Pro Gly His Ser Pro Gly Ile Gly His
1               5                   10                  15

<210> SEQ ID NO 305
<211> LENGTH: 15
<212> TYPE: PRT
<213> ORGANISM: Oryza sativa

<400> SEQUENCE: 305

Asp Val Arg Pro Thr Asn Pro Gly His Ser Pro Gly Ile Gly His
1               5                   10                  15

<210> SEQ ID NO 306
<211> LENGTH: 15
<212> TYPE: PRT
<213> ORGANISM: Oryza sativa

<400> SEQUENCE: 306

Asp Ala Arg Pro Thr Ala Pro Gly His Ser Pro Gly Ala Gly His
1               5                   10                  15

<210> SEQ ID NO 307
<211> LENGTH: 15
<212> TYPE: PRT
<213> ORGANISM: Oryza sativa

<400> SEQUENCE: 307

Asp Gly Arg Pro Thr Ser Pro Gly His Ser Pro Gly Ile Gly Asn
1               5                   10                  15

<210> SEQ ID NO 308
<211> LENGTH: 15
<212> TYPE: PRT
<213> ORGANISM: Oryza sativa

<400> SEQUENCE: 308

Asp Ser Arg Pro Thr Ala Pro Gly Asn Ser Pro Gly Ile Gly Asn
1               5                   10                  15
```

```
<210> SEQ ID NO 309
<211> LENGTH: 15
<212> TYPE: PRT
<213> ORGANISM: Oryza sativa

<400> SEQUENCE: 309

Gln Val Asp Ser Thr Thr Pro Gly His Ser Pro Ser Ile Gly His
1               5                   10                  15

<210> SEQ ID NO 310
<211> LENGTH: 15
<212> TYPE: PRT
<213> ORGANISM: Brachypodium distachyon
<220> FEATURE:
<221> NAME/KEY: MOD_RES
<222> LOCATION: (7)..(7)
<223> OTHER INFORMATION: hydroxyproline
<220> FEATURE:
<221> NAME/KEY: MOD_RES
<222> LOCATION: (11)..(11)
<223> OTHER INFORMATION: hydroxyproline

<400> SEQUENCE: 310

Leu Ala Asp Ser Thr Thr Pro Gly His Ser Pro Ser Ile Gly His
1               5                   10                  15

<210> SEQ ID NO 311
<211> LENGTH: 15
<212> TYPE: PRT
<213> ORGANISM: Brachypodium distachyon

<400> SEQUENCE: 311

Asp Ser Arg Pro Thr Gly Pro Gly His Ser Pro Gly Ala Gly His
1               5                   10                  15

<210> SEQ ID NO 312
<211> LENGTH: 15
<212> TYPE: PRT
<213> ORGANISM: Oryza barthii

<400> SEQUENCE: 312

Gly Val Arg Pro Thr Asn Pro Gly His Ser Pro Gly Ile Gly His
1               5                   10                  15

<210> SEQ ID NO 313
<211> LENGTH: 15
<212> TYPE: PRT
<213> ORGANISM: Oryza barthii

<400> SEQUENCE: 313

Asp Val Arg Pro Thr Asn Pro Gly His Ser Pro Gly Ile Gly His
1               5                   10                  15

<210> SEQ ID NO 314
<211> LENGTH: 15
<212> TYPE: PRT
<213> ORGANISM: Oryza barthii

<400> SEQUENCE: 314

Asp Val Arg Pro Thr Asn Pro Gly His Ser Pro Gly Ile Gly His
1               5                   10                  15

<210> SEQ ID NO 315
<211> LENGTH: 15
<212> TYPE: PRT
<213> ORGANISM: Sorghum bicolor
```

<400> SEQUENCE: 315

Asp Val Arg Pro Ser Asn Pro Gly His Ser Pro Gly Ile Gly His
1               5                   10                  15

<210> SEQ ID NO 316
<211> LENGTH: 15
<212> TYPE: PRT
<213> ORGANISM: Sorghum bicolor

<400> SEQUENCE: 316

Asp Ser Arg Pro Thr Ala Pro Gly Asn Ser Pro Gly Ile Gly Asn
1               5                   10                  15

<210> SEQ ID NO 317
<211> LENGTH: 15
<212> TYPE: PRT
<213> ORGANISM: Triticum aestivum

<400> SEQUENCE: 317

Asp Gly Arg Gly Thr Gly Pro Gly His Ser Pro Gly Ile Gly Asn
1               5                   10                  15

<210> SEQ ID NO 318
<211> LENGTH: 15
<212> TYPE: PRT
<213> ORGANISM: Triticum aestivum

<400> SEQUENCE: 318

Asp Ser Arg Gly Thr Ala Pro Gly His Ser Pro Gly Ile Gly Asn
1               5                   10                  15

<210> SEQ ID NO 319
<211> LENGTH: 15
<212> TYPE: PRT
<213> ORGANISM: Triticum aestivum

<400> SEQUENCE: 319

Asp Ser Arg Gly Thr Ala Pro Gly His Ser Pro Gly Ile Gly Asn
1               5                   10                  15

<210> SEQ ID NO 320
<211> LENGTH: 15
<212> TYPE: PRT
<213> ORGANISM: Triticum aestivum

<400> SEQUENCE: 320

Glu Ser Arg Gly Thr Ala Pro Gly Asn Ser Pro Gly Ile Gly Asn
1               5                   10                  15

<210> SEQ ID NO 321
<211> LENGTH: 15
<212> TYPE: PRT
<213> ORGANISM: Hordeum vulgare

<400> SEQUENCE: 321

Ser Trp Arg Pro Thr Thr Pro Gly Thr Ser Pro Gly Ile Thr Ser
1               5                   10                  15

<210> SEQ ID NO 322
<211> LENGTH: 15
<212> TYPE: PRT
<213> ORGANISM: Hordeum vulgare

<400> SEQUENCE: 322

-continued

Ser Trp Arg Pro Thr Thr Pro Gly Thr Ser Pro Gly Ile Thr Ser
1               5                   10                  15

<210> SEQ ID NO 323
<211> LENGTH: 15
<212> TYPE: PRT
<213> ORGANISM: Hordeum vulgare

<400> SEQUENCE: 323

Gln Val Glu Ser Thr Thr Pro Gly His Ser Pro Ser Ile Gly His
1               5                   10                  15

<210> SEQ ID NO 324
<211> LENGTH: 15
<212> TYPE: PRT
<213> ORGANISM: Saccharum officinarum

<400> SEQUENCE: 324

Asp Ser Arg Pro Thr Tyr Pro Gly Asn Ser Pro Gly Ile Gly Asn
1               5                   10                  15

<210> SEQ ID NO 325
<211> LENGTH: 15
<212> TYPE: PRT
<213> ORGANISM: Saccharum officinarum

<400> SEQUENCE: 325

Asp Ser Arg Pro Thr Tyr Pro Gly Asn Ser Pro Gly Ile Gly Asn
1               5                   10                  15

<210> SEQ ID NO 326
<211> LENGTH: 15
<212> TYPE: PRT
<213> ORGANISM: Zea mays

<400> SEQUENCE: 326

Asp Ser Arg Pro Thr Ala Pro Gly Asn Ser Pro Gly Ile Gly Asn
1               5                   10                  15

<210> SEQ ID NO 327
<211> LENGTH: 15
<212> TYPE: PRT
<213> ORGANISM: Zea mays

<400> SEQUENCE: 327

Asp Val Arg Pro Thr Asn Pro Ser His Ser Pro Gly Ile Gly His
1               5                   10                  15

<210> SEQ ID NO 328
<211> LENGTH: 15
<212> TYPE: PRT
<213> ORGANISM: Zea mays

<400> SEQUENCE: 328

Asp Gly Arg Pro Thr Ala Pro Gly His Ser Pro Gly Ile Gly Asn
1               5                   10                  15

<210> SEQ ID NO 329
<211> LENGTH: 15
<212> TYPE: PRT
<213> ORGANISM: Zea mays

<400> SEQUENCE: 329

Asp Ser Arg Pro Thr Ala Pro Gly Asn Ser Pro Gly Ile Gly Asn

```
1               5                  10                 15
```

<210> SEQ ID NO 330
<211> LENGTH: 15
<212> TYPE: PRT
<213> ORGANISM: Brachypodium distachyon

<400> SEQUENCE: 330

```
Gly Val Arg Pro Ser Asn Pro Gly His Ser Pro Gly Ile Gly His
1               5                  10                 15
```

<210> SEQ ID NO 331
<211> LENGTH: 15
<212> TYPE: PRT
<213> ORGANISM: Setaria italica

<400> SEQUENCE: 331

```
Asp Val Arg Pro Ser Thr Pro Arg His Ser Pro Gly Ile Gly His
1               5                  10                 15
```

<210> SEQ ID NO 332
<211> LENGTH: 15
<212> TYPE: PRT
<213> ORGANISM: Phoenix dactylifera

<400> SEQUENCE: 332

```
Asp Ser Arg Pro Thr Ala Pro Gly His Ser Pro Gly Val Gly His
1               5                  10                 15
```

<210> SEQ ID NO 333
<211> LENGTH: 15
<212> TYPE: PRT
<213> ORGANISM: Phoenix dactylifera

<400> SEQUENCE: 333

```
Gly Asp Arg Pro Ser Val Pro Gly His Ser Pro Gly Val Gly His
1               5                  10                 15
```

<210> SEQ ID NO 334
<211> LENGTH: 15
<212> TYPE: PRT
<213> ORGANISM: Phoenix dactylifera

<400> SEQUENCE: 334

```
Asp Ala Arg Pro Thr Thr Pro Gly His Ser Pro Gly Val Gly His
1               5                  10                 15
```

<210> SEQ ID NO 335
<211> LENGTH: 15
<212> TYPE: PRT
<213> ORGANISM: Phoenix dactylifera

<400> SEQUENCE: 335

```
Asp Ala Arg Pro Thr Thr Pro Gly His Ser Pro Gly Val Gly His
1               5                  10                 15
```

<210> SEQ ID NO 336
<211> LENGTH: 15
<212> TYPE: PRT
<213> ORGANISM: Phoenix dactylifera

<400> SEQUENCE: 336

```
Asp Ala Arg Pro Thr Thr Pro Gly His Ser Pro Gly Val Gly His
1               5                  10                 15
```

<210> SEQ ID NO 337
<211> LENGTH: 2187
<212> TYPE: DNA
<213> ORGANISM: Medicago truncatula

<400> SEQUENCE: 337

| | | | | | |
|---|---|---|---|---|---|
| cttcaactttt | gacgatttag | attcgatatt | ttgacacacc | aacaataaag | aatacaaaac | 60 |
| tatcatcata | gatataaaac | attagagcta | gtaatgatgc | attcaaaacc | caatcaaatt | 120 |
| gtttatacat | gcagtgtagt | acaaaatttt | gctacaagtc | aattcaatat | ttcaatttga | 180 |
| gagaagaaac | ttatacaatt | cattatttt | tcttcaactt | tgagcatgcg | gtgcacccaa | 240 |
| tttgataatt | agcctactat | aaagtttaaa | caagagagga | acccagaaaa | agctgccttt | 300 |
| cacttcaact | tgtccatcaa | aataaaatgc | tgaaattaaa | tagagaccat | aaactgctta | 360 |
| agtagtgctt | aattatacta | taatcaatga | aattaattaa | actataccac | tgttagtgga | 420 |
| agggaaggta | caagagaatc | tcatatatac | atatctttct | tcatcagggg | tccattctaa | 480 |
| attaatggtg | cgccagtcct | tcaactattc | tttattggtt | catcataact | tcaaatctta | 540 |
| ccagttttcc | aaaggaacaa | aattacaact | acatatctca | actacttgct | aaatgtccct | 600 |
| ttctcaacct | tcatattaac | ctataccaag | cacatatatt | aacctatact | catcggatta | 660 |
| gacgtgtctt | actgttggat | acatattgtg | tctgacatca | tcacatatgt | tttttaacg | 720 |
| gaaaattta | ttaaaaatca | agtccctaaa | gagagaccga | caagttagaa | acaacataat | 780 |
| aaattattat | tgacacatat | gattacatta | aattgtataa | attttcaaa | taattatcga | 840 |
| tgttgacgtt | ctgtattgtg | ttccgtgtcc | gtgtcttagt | ccatacttca | tacataataa | 900 |
| ctattacaat | gtatggccat | gcaaaattga | caaaaaataa | ttggccaact | acattggaga | 960 |
| ttcgtattga | ttgaacttaa | ttttgtatgg | aatagagata | cgattcacat | gtattatagg | 1020 |
| atgctgataa | taatcatgtt | ttggacataa | atagaatgga | atagagaaaa | caagagagca | 1080 |
| gaataaagca | aaacttccat | tagaggccac | aattattat | attaaaaaat | aataattaat | 1140 |
| tatgcttcaa | catacattgt | gatagattct | catcatttct | gaaaagaatt | ggaagatttc | 1200 |
| aacactaatt | ttgagagtat | atagtctaaa | aaatttatac | ggtttacgat | tcagttatgg | 1260 |
| ttaagtatta | tttaaaaaac | taacagaaat | atgttttttt | gtttaatttt | gttgaagata | 1320 |
| agtaaggata | gattaaaata | caactaatta | tttttgtttc | ttgtagtttt | tgaaatcact | 1380 |
| tttaaatgag | ttttgacaa | aactgtgaca | atgtaacaaa | atacataaaa | ataatggaaa | 1440 |
| aatcacaagt | ttccgaaaat | ttgcaaaaca | aacattaaag | ttcgatagaa | acatagaat | 1500 |
| actgaaccgt | aagcaattga | tccattgctc | ggcccataat | ctaaatatat | aaaataaatg | 1560 |
| tcaccatttt | aaaaaatgta | tatatttata | caccaaaaac | ttaagtaatt | tgagctcacc | 1620 |
| atttcttata | ttattgagca | tatctaagcg | taattgtgac | tgttccactt | aaaatcaaga | 1680 |
| tatttagatc | ttaaatcata | tataataagg | ttgatatgca | atgcaacata | agaagagagg | 1740 |
| tgaatatcaa | aagagacata | tatcatattc | ataataatgc | aaatgactaa | aaagagaaag | 1800 |
| attttatat | atgcaccccc | aaaagagcat | gttcgcccac | gtgagatagt | gatgtgaccc | 1860 |
| atagaattaa | aaaatatact | aatttgacat | ataaaattaa | aagctagcta | ttttgacac | 1920 |
| ataaacggtc | caaatttgca | gatcataaca | ctccacaaat | taagtcaaat | gaataatta | 1980 |
| gcactaagaa | tcttataaga | gagcactgtc | acactcacac | acattctaca | ttataaatac | 2040 |
| ccctcaagat | cccataacat | ttcatatcat | atatcttcta | atttgaacta | taacaagctt | 2100 |
| aaactttcaa | tacatatagt | tcattcattc | tctctactct | accttctcta | tttgttcgtg | 2160 | ttaatggctt ataaatttca atacaca 2187

<210> SEQ ID NO 338
<211> LENGTH: 140
<212> TYPE: PRT
<213> ORGANISM: Picea glauca

<400> SEQUENCE: 338

| Met | Lys | Gly | Tyr | Ala | Met | Ile | Val | Leu | Leu | Leu | Ala | Ser | Arg | Leu |
|---|---|---|---|---|---|---|---|---|---|---|---|---|---|---|
| 1 | | | | 5 | | | | | 10 | | | | | 15 |

| Gly | Glu | Ala | Ala | Arg | Ile | Phe | Gly | Phe | Lys | Pro | Phe | Tyr | Leu | Asn | Ser |
|---|---|---|---|---|---|---|---|---|---|---|---|---|---|---|---|
| | | | 20 | | | | | 25 | | | | | 30 | | |

| Asp | Ser | Gln | Val | Arg | Ala | Ala | Pro | Ala | Ser | Ser | Tyr | Pro | Ser | Val | Glu |
|---|---|---|---|---|---|---|---|---|---|---|---|---|---|---|---|
| | | | 35 | | | | | 40 | | | | | 45 | | |

| Glu | Lys | Thr | Pro | Glu | Lys | Ala | Val | Leu | Ala | Leu | Asn | Glu | Arg | Leu | Arg |
|---|---|---|---|---|---|---|---|---|---|---|---|---|---|---|---|
| | 50 | | | | | 55 | | | | | 60 | | | | |

| Arg | Arg | Ala | Ser | Val | Glu | Lys | His | Pro | Gly | Ser | Glu | Thr | Asn | Leu | Lys |
|---|---|---|---|---|---|---|---|---|---|---|---|---|---|---|---|
| 65 | | | | | 70 | | | | | 75 | | | | | 80 |

| Pro | Asn | Leu | Ser | Ala | Lys | Ser | Lys | Ala | Ser | Asn | Gln | Arg | Ser | Asn | Gly |
|---|---|---|---|---|---|---|---|---|---|---|---|---|---|---|---|
| | | | | 85 | | | | | 90 | | | | | 95 | |

| Leu | Leu | Arg | Thr | Thr | Phe | Pro | Ser | Val | Lys | Phe | Asp | Val | Val | Glu | Ala |
|---|---|---|---|---|---|---|---|---|---|---|---|---|---|---|---|
| | | | | 100 | | | | | 105 | | | | | 110 | |

| Asp | Met | Glu | Lys | Thr | Val | Ala | Tyr | Pro | Glu | Leu | Leu | Gly | Lys | Ser | Pro |
|---|---|---|---|---|---|---|---|---|---|---|---|---|---|---|---|
| | | | 115 | | | | | 120 | | | | | 125 | | |

| Gly | Val | Gly | His | Asp | Ile | Gln | Pro | Gly | Ser | Arg | His |
|---|---|---|---|---|---|---|---|---|---|---|---|
| | 130 | | | | | 135 | | | | | 140 |

<210> SEQ ID NO 339
<211> LENGTH: 140
<212> TYPE: PRT
<213> ORGANISM: Picea glauca

<400> SEQUENCE: 339

| Met | Lys | Gly | Tyr | Ala | Met | Ile | Val | Leu | Leu | Leu | Ala | Ser | Arg | Leu |
|---|---|---|---|---|---|---|---|---|---|---|---|---|---|---|
| 1 | | | | 5 | | | | | 10 | | | | | 15 |

| Gly | Glu | Ala | Ala | Arg | Ile | Phe | Gly | Phe | Lys | Pro | Phe | Tyr | Leu | Asn | Ser |
|---|---|---|---|---|---|---|---|---|---|---|---|---|---|---|---|
| | | | 20 | | | | | 25 | | | | | 30 | | |

| Asp | Ser | Gln | Val | Arg | Ala | Ala | Leu | Ala | Ser | Ser | Tyr | Pro | Ser | Val | Glu |
|---|---|---|---|---|---|---|---|---|---|---|---|---|---|---|---|
| | | | 35 | | | | | 40 | | | | | 45 | | |

| Glu | Lys | Thr | Pro | Glu | Lys | Ala | Val | Leu | Ala | Leu | Asn | Glu | Arg | Leu | Arg |
|---|---|---|---|---|---|---|---|---|---|---|---|---|---|---|---|
| | 50 | | | | | 55 | | | | | 60 | | | | |

| Arg | Arg | Ala | Ser | Val | Glu | Lys | His | Pro | Gly | Ser | Glu | Ser | Asn | Leu | Lys |
|---|---|---|---|---|---|---|---|---|---|---|---|---|---|---|---|
| 65 | | | | | 70 | | | | | 75 | | | | | 80 |

| Pro | Asn | Leu | Ser | Ala | Lys | Ser | Lys | Ala | Ser | Asn | Gln | Arg | Ser | Asn | Glu |
|---|---|---|---|---|---|---|---|---|---|---|---|---|---|---|---|
| | | | | 85 | | | | | 90 | | | | | 95 | |

| Leu | Leu | Arg | Thr | Ile | Leu | Pro | Ser | Val | Lys | Phe | Asp | Ala | Val | Glu | Pro |
|---|---|---|---|---|---|---|---|---|---|---|---|---|---|---|---|
| | | | | 100 | | | | | 105 | | | | | 110 | |

| Asp | Met | Glu | Lys | Thr | Val | Ala | Pro | Phe | Glu | Pro | Leu | Gly | His | Ser | Pro |
|---|---|---|---|---|---|---|---|---|---|---|---|---|---|---|---|
| | | | 115 | | | | | 120 | | | | | 125 | | |

| Gly | Ile | Gly | His | Asp | Asp | Pro | Pro | Arg | Ser | Arg | His |
|---|---|---|---|---|---|---|---|---|---|---|---|
| | 130 | | | | | 135 | | | | | 140 |

<210> SEQ ID NO 340
<211> LENGTH: 141
<212> TYPE: PRT
<213> ORGANISM: Picea glauca

<400> SEQUENCE: 340

Met Lys Gly Cys Ala Met Ile Val Leu Leu Phe Leu Ala Ala Pro Leu
1               5                   10                  15

Gly Glu Ala Ala Arg Ile Leu Cys Phe Lys Leu Phe Leu Met Asn Ser
            20                  25                  30

Asp Ser Gln Val Lys Ala Ala Pro Ala Arg Ser Tyr Ala Leu Val Gln
        35                  40                  45

Glu Arg Ala Pro Gly Lys Ala Val Leu Glu Leu Lys Glu Arg Leu Ser
50                  55                  60

Arg Lys Ala Ser Arg Glu Lys Tyr His Gly Ser Glu Ala Asn Met Asn
65                  70                  75                  80

Pro Asn Ile Ser Ala Asn Ser Thr Ala Ser His Gln His Ser Asn Gly
            85                  90                  95

Leu Leu Gln Lys Ile His Pro Ser Leu Lys Phe Asp Val Val Glu Pro
        100                 105                 110

Glu Arg Glu Lys Ser Phe Thr Pro Phe Leu Pro Leu Leu Gly His Ser
    115                 120                 125

Pro Gly Val Gly His Asn Asn Pro Pro Gly Phe Arg His
130                 135                 140

<210> SEQ ID NO 341
<211> LENGTH: 142
<212> TYPE: PRT
<213> ORGANISM: Picea glauca

<400> SEQUENCE: 341

Met Met Lys Gly Cys Ala Met Ile Val Leu Leu Phe Leu Ala Ala Pro
1               5                   10                  15

Leu Gly Glu Ala Ser Arg Ile Leu Cys Phe Lys Leu Phe Leu Met Asn
            20                  25                  30

Ser Asp Ser Gln Val Lys Ala Ala Pro Ala Arg Ser Tyr Ala Leu Val
        35                  40                  45

Gln Glu Arg Ala Pro Gly Lys Ala Val Leu Glu Leu Lys Glu Arg Leu
    50                  55                  60

Ser Arg Lys Ala Ser Arg Glu Lys Tyr His Gly Ser Glu Ala Asn Met
65                  70                  75                  80

Asn Pro Asn Ile Ser Ala Asn Ser Thr Ala Ser His Gln His Ser Asn
            85                  90                  95

Gly Leu Leu Gln Lys Ile His Pro Ser Leu Lys Phe Asp Val Val Glu
        100                 105                 110

Pro Glu Arg Glu Lys Ser Phe Thr Pro Phe Leu Pro Leu Leu Gly His
    115                 120                 125

Ser Pro Gly Val Gly His Asn Asn Pro Pro Gly Phe Arg His
130                 135                 140

<210> SEQ ID NO 342
<211> LENGTH: 142
<212> TYPE: PRT
<213> ORGANISM: Picea glauca

<400> SEQUENCE: 342

Met Met Lys Gly Cys Ala Met Ile Val Leu Leu Phe Leu Ala Ala Pro
1               5                   10                  15

Leu Gly Glu Ala Ser Arg Ile Leu Cys Phe Lys Leu Phe Leu Met Asn
            20                  25                  30

Ser Asp Ser Gln Val Lys Ala Ala Pro Ala Arg Ser Tyr Ala Leu Val
        35                  40                  45

```
            35                  40                  45
Gln Glu Arg Ala Pro Gly Lys Ala Val Leu Glu Leu Lys Glu Arg Leu
 50                  55                  60

Ser Arg Lys Ala Ser Arg Glu Lys Tyr His Gly Ser Glu Ala Asn Met
 65                  70                  75                  80

Asn Pro Asn Ile Ser Ala Asn Ser Thr Ala Ser His Gln His Ser Asn
                 85                  90                  95

Gly Leu Leu Gln Lys Ile His Pro Ser Leu Lys Phe Asp Val Val Glu
                100                 105                 110

Pro Glu Arg Glu Lys Ser Phe Thr Pro Phe Leu Pro Leu Leu Gly His
                115                 120                 125

Ser Pro Gly Ile Gly His Asn Asn Pro Pro Gly Phe Ser His
                130                 135                 140

<210> SEQ ID NO 343
<211> LENGTH: 142
<212> TYPE: PRT
<213> ORGANISM: Picea glauca

<400> SEQUENCE: 343

Met Met Lys Gly Cys Ala Met Ile Val Leu Leu Phe Leu Ala Ala Pro
  1               5                  10                  15

Leu Arg Glu Ala Ser Arg Ile Leu Cys Phe Lys Leu Phe Leu Met Asn
                 20                  25                  30

Ser Asp Ser Gln Val Lys Ala Ala Pro Ala Arg Ser Tyr Ala Leu Val
                 35                  40                  45

Gln Glu Arg Ala Pro Gly Lys Ala Val Leu Glu Leu Lys Glu Arg Leu
 50                  55                  60

Ser Arg Lys Ala Ser Arg Glu Lys Tyr His Gly Ser Glu Ala Asn Met
 65                  70                  75                  80

Asn Pro Asn Ile Ser Ala Asn Ser Thr Ala Ser His Gln His Ser Asn
                 85                  90                  95

Gly Leu Leu Gln Lys Ile His Pro Ser Leu Lys Phe Asp Val Val Glu
                100                 105                 110

Pro Glu Arg Glu Lys Ser Phe Thr Pro Phe Leu Pro Leu Leu Gly His
                115                 120                 125

Ser Pro Gly Val Gly His Asn Asn Pro Pro Gly Phe Arg His
                130                 135                 140

<210> SEQ ID NO 344
<211> LENGTH: 136
<212> TYPE: PRT
<213> ORGANISM: Picea glauca

<400> SEQUENCE: 344

Met Met Lys Ile Cys Ala Val Ile Ile Leu Leu Phe Ala Ala Pro
  1               5                  10                  15

Leu Gly Glu Ala Ser Arg Ile Phe Gly Phe Lys Pro Phe Ser Leu Lys
                 20                  25                  30

Asn Asp Ser Gln Val Lys Ala Thr Thr Ala Val Glu Glu Ser Thr Ala
                 35                  40                  45

Glu Lys Val Val Leu Glu Met Asn Glu Cys Phe Ser Lys Arg Ala Asn
 50                  55                  60

Leu Glu Lys His Pro Gly Ser Glu Ala Ser Leu Lys Pro Asn Val Ser
 65                  70                  75                  80

Ala Lys Ser Lys Ala Ser Asp Gln Arg Ser Asp Glu Leu Pro Gln Thr
```

```
                85                  90                  95

Ile Leu Leu Ser Leu Lys Phe Asn Ala Val Gln His Glu Glu Lys Lys
            100                 105                 110

Ser Val Pro Pro Phe Gln Pro Leu Gly His Ser Pro Gly Ile Gly His
            115                 120                 125

Glu Asn Pro Pro Gly Leu Arg Gln
            130                 135

<210> SEQ ID NO 345
<211> LENGTH: 155
<212> TYPE: PRT
<213> ORGANISM: Picea glauca

<400> SEQUENCE: 345

Met Lys Leu Gly Leu Trp Ser Val Trp Gly Ala Leu Met Leu Ser Cys
1               5                   10                  15

Val Leu Ser Tyr Ser Thr Ala Lys Ala Arg Leu Met Gly Phe Asn Pro
                20                  25                  30

Asn Ala Ile Gln Pro Pro Arg Pro Ala Leu Tyr Lys Ala Asn Glu
            35                  40                  45

Val Gly Asn Ile Phe Arg Asp Thr Pro Met Gly Arg Ser Ser Thr Ile
        50                  55                  60

Glu Lys Lys Gln Ile Ser Ile Ala Pro Ala Glu Thr Lys Leu Pro Ser
65                  70                  75                  80

Thr Leu Lys Val Thr Val Gln Gly Ser Leu Gly His Asn Asp Ala His
                85                  90                  95

Gly Ile Lys Glu Ala Glu Thr Val Ala Gly Gly Thr Gln Ile Phe Ser
            100                 105                 110

Lys Arg Pro Ser Glu Ser Asn Asn Asp Ser Ala Arg Met Lys Lys Val
            115                 120                 125

Asp Ala Val Met Ala Phe Arg Pro Ser Ser Ser Gly His Ser Pro Gly
            130                 135                 140

Ile Gly His Asp Asp Pro Pro Gly Pro Met Leu
145                 150                 155

<210> SEQ ID NO 346
<211> LENGTH: 73
<212> TYPE: PRT
<213> ORGANISM: Pinus contorta

<400> SEQUENCE: 346

Ala Asp Leu Glu Glu His Pro Gly Ser Asp Ala Asn Phe Lys Pro Ser
1               5                   10                  15

Val Phe Val Lys Ser Asn Ala Ser Asp Gln Arg Ser Asp Gly His Val
                20                  25                  30

Glu Glu Leu Val Pro Ser Leu Lys Phe Glu Val Val Gln His Asp Val
            35                  40                  45

Gln Lys Thr Ile Ser Pro Phe Pro Leu Gly His Ser Pro Gly Ile
        50                  55                  60

Gly His Asp Asp Pro Pro Gly Ser Lys
65                  70

<210> SEQ ID NO 347
<211> LENGTH: 74
<212> TYPE: PRT
<213> ORGANISM: Pinus contorta

<400> SEQUENCE: 347
```

Ala Asp Leu Glu Glu His Pro Gly Ser Asp Ala Asn Phe Lys Pro Ser
1               5                   10                  15

Val Phe Val Lys Ser Asn Ala Ser Asp Gln Arg Phe Asp Gly His Val
            20                  25                  30

Glu Glu Leu Val Pro Ser Leu Lys Phe Glu Val Val Gln His Asp Val
        35                  40                  45

Gln Lys Thr Ile Ser Pro Phe Lys Pro Leu Gly His Ser Pro Gly Ile
    50                  55                  60

Gly His Asp Asp Pro Pro Gly Ser Lys His
65              70

<210> SEQ ID NO 348
<211> LENGTH: 143
<212> TYPE: PRT
<213> ORGANISM: Pinus contorta

<400> SEQUENCE: 348

Met Lys Thr Ser Val Leu Ile Met Leu Met Phe Leu Ala Ala Pro Leu
1               5                   10                  15

Val Glu Ala Ala Arg Ile Ile Gly Phe Lys Pro Phe Ser Leu Asn Arg
            20                  25                  30

Asp Ser Gln Val Lys Ala Thr Pro Ala Thr Ser Tyr Pro Leu Val Glu
        35                  40                  45

Glu Arg Ala Pro Ala Lys Val Phe Val Glu Leu Lys Glu Pro Phe Gly
    50                  55                  60

Arg Arg Ala Asp Leu Thr Asp Leu Glu Glu His Pro Gly Ser Asp Ala
65                  70                  75                  80

Asn Phe Lys Pro Ser Val Phe Val Lys Ser Asn Ala Ser Asp Gln Arg
                85                  90                  95

Ser Asp Gly His Val Glu Glu Leu Val Pro Ser Leu Lys Phe Glu Val
            100                 105                 110

Val Gln His Asp Val Gln Lys Thr Ile Ser Pro Phe Lys Pro Leu Gly
        115                 120                 125

His Ser Pro Gly Ile Gly His Asp Asp Pro Pro Gly Ser Lys His
    130                 135                 140

<210> SEQ ID NO 349
<211> LENGTH: 137
<212> TYPE: PRT
<213> ORGANISM: Pinus contorta

<400> SEQUENCE: 349

Ile Met Leu Met Phe Leu Ala Ala Pro Leu Val Glu Ala Ala Arg Ile
1               5                   10                  15

Ile Gly Phe Lys Pro Phe Ser Leu Asn Arg Asp Ser Gln Val Lys Ala
            20                  25                  30

Thr Pro Ala Thr Ser Tyr Pro Leu Val Glu Glu Arg Ala Pro Ala Lys
        35                  40                  45

Val Phe Val Glu Leu Lys Glu Pro Phe Gly Arg Arg Ala Asp Leu Thr
    50                  55                  60

Asp Leu Glu Glu His Pro Gly Ser Asp Ala Asn Phe Lys Pro Ser Val
65                  70                  75                  80

Phe Val Lys Ser Asn Ala Ser Asp Gln Arg Phe Asp Gly His Val Glu
                85                  90                  95

Glu Leu Val Pro Ser Leu Lys Phe Glu Val Val Gln His Asp Val Gln
            100                 105                 110

```
Lys Thr Ile Ser Pro Phe Lys Pro Leu Gly His Ser Pro Gly Ile Gly
        115                 120                 125

His Asp Asp Pro Pro Gly Ser Lys His
    130                 135

<210> SEQ ID NO 350
<211> LENGTH: 112
<212> TYPE: PRT
<213> ORGANISM: Pinus engelmannii x

<400> SEQUENCE: 350

Met Asn Ser Asp Ser Gln Val Lys Ala Thr Pro Ala Arg Ser Tyr Ala
1               5                   10                  15

Leu Val Gln Glu Arg Ala Pro Gly Lys Ala Val Leu Glu Leu Lys Glu
            20                  25                  30

Arg Leu Ser Arg Lys Ala Ser Arg Glu Lys His His Gly Ser Glu Ala
        35                  40                  45

Asn Met Asn Pro Asn Ile Ser Ala Asn Ser Thr Ala Ser His Gln Arg
    50                  55                  60

Ser Asn Gly Ile Leu Gln Lys Ile His Ser Ser Leu Lys Phe Asp Val
65                  70                  75                  80

Val Glu Pro Glu Arg Glu Lys Ser Phe Thr Pro Phe Leu Pro Leu Leu
                85                  90                  95

Gly His Ser Pro Gly Val Gly His Asn Asn Pro Pro Gly Phe Lys His
            100                 105                 110

<210> SEQ ID NO 351
<211> LENGTH: 15
<212> TYPE: PRT
<213> ORGANISM: Picea glauca

<400> SEQUENCE: 351

Val Ala Tyr Pro Glu Leu Leu Gly Lys Ser Pro Gly Val Gly His
1               5                   10                  15

<210> SEQ ID NO 352
<211> LENGTH: 15
<212> TYPE: PRT
<213> ORGANISM: Picea glauca

<400> SEQUENCE: 352

Val Ala Pro Phe Glu Pro Leu Gly His Ser Pro Gly Ile Gly His
1               5                   10                  15

<210> SEQ ID NO 353
<211> LENGTH: 15
<212> TYPE: PRT
<213> ORGANISM: Picea glauca

<400> SEQUENCE: 353

Thr Pro Phe Leu Pro Leu Leu Gly His Ser Pro Gly Val Gly His
1               5                   10                  15

<210> SEQ ID NO 354
<211> LENGTH: 15
<212> TYPE: PRT
<213> ORGANISM: Picea glauca

<400> SEQUENCE: 354

Thr Pro Phe Leu Pro Leu Leu Gly His Ser Pro Gly Val Gly His
1               5                   10                  15
```

<210> SEQ ID NO 355
<211> LENGTH: 15
<212> TYPE: PRT
<213> ORGANISM: Picea glauca

<400> SEQUENCE: 355

Thr Pro Phe Leu Pro Leu Leu Gly His Ser Pro Gly Ile Gly His
1               5                   10                  15

<210> SEQ ID NO 356
<211> LENGTH: 15
<212> TYPE: PRT
<213> ORGANISM: Picea glauca

<400> SEQUENCE: 356

Thr Pro Phe Leu Pro Leu Leu Gly His Ser Pro Gly Val Gly His
1               5                   10                  15

<210> SEQ ID NO 357
<211> LENGTH: 15
<212> TYPE: PRT
<213> ORGANISM: Picea glauca

<400> SEQUENCE: 357

Val Pro Pro Phe Gln Pro Leu Gly His Ser Pro Gly Ile Gly His
1               5                   10                  15

<210> SEQ ID NO 358
<211> LENGTH: 15
<212> TYPE: PRT
<213> ORGANISM: Picea glauca

<400> SEQUENCE: 358

Ala Phe Arg Pro Ser Ser Ser Gly His Ser Pro Gly Ile Gly His
1               5                   10                  15

<210> SEQ ID NO 359
<211> LENGTH: 15
<212> TYPE: PRT
<213> ORGANISM: Pinus contorta

<400> SEQUENCE: 359

Ile Ser Pro Phe Lys Pro Leu Gly His Ser Pro Gly Ile Gly His
1               5                   10                  15

<210> SEQ ID NO 360
<211> LENGTH: 15
<212> TYPE: PRT
<213> ORGANISM: Pinus contorta

<400> SEQUENCE: 360

Ile Ser Pro Phe Lys Pro Leu Gly His Ser Pro Gly Ile Gly His
1               5                   10                  15

<210> SEQ ID NO 361
<211> LENGTH: 15
<212> TYPE: PRT
<213> ORGANISM: Pinus contorta

<400> SEQUENCE: 361

Ile Ser Pro Phe Lys Pro Leu Gly His Ser Pro Gly Ile Gly His
1               5                   10                  15

<210> SEQ ID NO 362
<211> LENGTH: 15
<212> TYPE: PRT
<213> ORGANISM: Pinus contorta

<400> SEQUENCE: 362

Ile Ser Pro Phe Lys Pro Leu Gly His Ser Pro Gly Ile Gly His
1               5                   10                  15

<210> SEQ ID NO 363
<211> LENGTH: 15
<212> TYPE: PRT
<213> ORGANISM: Pinus engelmannii x

<400> SEQUENCE: 363

Thr Pro Phe Leu Pro Leu Leu Gly His Ser Pro Gly Val Gly His
1               5                   10                  15

<210> SEQ ID NO 364
<211> LENGTH: 201
<212> TYPE: DNA
<213> ORGANISM: Meloidogyne hapla

<400> SEQUENCE: 364
atgattaata ttaattcaat tagatttttt attattttta taattaattt tatgatttat      60
caagtaatgg ctgttaataa ttcagctaat gacttccgac caacaaaccc aggccattca     120
ccaggaattg gacattgtaa tttaatttta tattttattg gcaaataat atatcaaaaa     180 ataagattag tcagaaaata a                                               201

<210> SEQ ID NO 365
<211> LENGTH: 66
<212> TYPE: PRT
<213> ORGANISM: Meloidogyne hapla

<400> SEQUENCE: 365

Met Ile Asn Ile Asn Ser Ile Arg Phe Phe Ile Ile Phe Ile Ile Asn
1               5                   10                  15

Phe Met Ile Tyr Gln Val Met Ala Val Asn Asn Ser Ala Asn Asp Phe
            20                  25                  30

Arg Pro Thr Asn Pro Gly His Ser Pro Gly Ile Gly His Cys Asn Leu
        35                  40                  45

Ile Leu Tyr Phe Ile Gly Lys Ile Ile Tyr Gln Lys Ile Arg Leu Val
    50                  55                  60

Arg Lys
65

<210> SEQ ID NO 366
<211> LENGTH: 183
<212> TYPE: DNA
<213> ORGANISM: Meloidogyne hapla

<400> SEQUENCE: 366
atgattaaaa ttaattctat tatattttt attattttta taattaattt tatgatttat       60
caaataatgg ctgctaataa ttcagttgat gccttccgac caacagcccc aggccattca     120
cccggagttg gacattgtaa tttaatttta aattttatat acaaaattaa atataaaaaa     180
taa                                                                   183

<210> SEQ ID NO 367
<211> LENGTH: 60

```
<212> TYPE: PRT
<213> ORGANISM: Meloidogyne hapla

<400> SEQUENCE: 367

Met Ile Lys Ile Asn Ser Ile Ile Phe Phe Ile Ile Phe Ile Ile Asn
1               5                   10                  15

Phe Met Ile Tyr Gln Ile Met Ala Ala Asn Asn Ser Val Asp Ala Phe
            20                  25                  30

Arg Pro Thr Ala Pro Gly His Ser Pro Gly Val Gly His Cys Asn Leu
        35                  40                  45

Ile Leu Asn Phe Ile Tyr Lys Ile Lys Tyr Lys Lys
    50                  55                  60

<210> SEQ ID NO 368
<211> LENGTH: 183
<212> TYPE: DNA
<213> ORGANISM: Meloidogyne hapla

<400> SEQUENCE: 368
atgattaata ttaatttat tatattttt attattttta ttattaattt tatgatttat      60
ttcacaatgg ctggttacca accaacaaac ccaggccatt cacccggaat tggccattgt    120
aatgaattat ctcaaaaaag attagggagt aataatttat cagatctgat tagggttttt    180
tag                                                                  183

<210> SEQ ID NO 369
<211> LENGTH: 60
<212> TYPE: PRT
<213> ORGANISM: Meloidogyne hapla

<400> SEQUENCE: 369

Met Ile Asn Ile Asn Phe Ile Ile Phe Phe Ile Ile Phe Ile Ile Asn
1               5                   10                  15

Phe Met Ile Tyr Phe Thr Met Ala Gly Tyr Gln Pro Thr Asn Pro Gly
            20                  25                  30

His Ser Pro Gly Ile Gly His Cys Asn Glu Leu Ser Gln Lys Arg Leu
        35                  40                  45

Gly Ser Asn Asn Leu Ser Asp Leu Ile Arg Val Phe
    50                  55                  60

<210> SEQ ID NO 370
<211> LENGTH: 213
<212> TYPE: DNA
<213> ORGANISM: Meloidogyne hapla

<400> SEQUENCE: 370
atgactaaaa ttaattctat tatattttt attattttta ttattaattt tatgatttat     60
tacaatttgg ctgataatga taaaccagcc aaaattccac ctttcaaaac agtcccaggc   120
cagagttcac ctggagtagg gcatggaatt ccaaatggag gtccacctgg agttggacat   180
tgtgatttaa ttaaatttga tttacaaaat taa                                213

<210> SEQ ID NO 371
<211> LENGTH: 70
<212> TYPE: PRT
<213> ORGANISM: Meloidogyne hapla

<400> SEQUENCE: 371

Met Thr Lys Ile Asn Ser Ile Ile Phe Phe Ile Ile Phe Ile Ile Asn
1               5                   10                  15
```

```
Phe Met Ile Tyr Tyr Asn Leu Ala Asp Asn Asp Lys Pro Ala Lys Ile
            20                  25                  30

Pro Pro Phe Lys Thr Val Pro Gly Gln Ser Ser Pro Gly Val Gly His
        35                  40                  45

Gly Ile Pro Asn Gly Gly Pro Gly Val Gly His Cys Asp Leu Ile
    50                  55                  60

Lys Phe Asp Leu Gln Asn
65                  70

<210> SEQ ID NO 372
<211> LENGTH: 133
<212> TYPE: DNA
<213> ORGANISM: Meloidogyne hapla

<400> SEQUENCE: 372
atgactaaaa ttaattctat tatatttttt attcttttta taattaattt tatgatttat     60
cacataatgg cagataatgt tattaaacca gcatgcattg gtaattcacc tggagttgga    120
cattgtaatt gaa                                                       133

<210> SEQ ID NO 373
<211> LENGTH: 43
<212> TYPE: PRT
<213> ORGANISM: Meloidogyne hapla

<400> SEQUENCE: 373

Met Thr Lys Ile Asn Ser Ile Ile Phe Phe Ile Leu Phe Ile Ile Asn
1               5                   10                  15

Phe Met Ile Tyr His Ile Met Ala Asp Asn Val Ile Lys Pro Ala Cys
            20                  25                  30

Ile Gly Asn Ser Pro Gly Val Gly His Cys Asn
        35                  40

<210> SEQ ID NO 374
<211> LENGTH: 171
<212> TYPE: DNA
<213> ORGANISM: Meloidogyne hapla

<400> SEQUENCE: 374
atgattaata ttaattctat tttatttttt attttttttta taattaattt tatgatttat     60
ttcactatgg ctgccttccg accaacaaat ccaggccctt cacccgcaat tggacatgga    120
attccaaatg gagttccaca acctccaccc gtaaatggac attgtaatta a             171

<210> SEQ ID NO 375
<211> LENGTH: 56
<212> TYPE: PRT
<213> ORGANISM: Meloidogyne hapla

<400> SEQUENCE: 375

Met Ile Asn Ile Asn Ser Ile Leu Phe Phe Ile Phe Phe Ile Ile Asn
1               5                   10                  15

Phe Met Ile Tyr Phe Thr Met Ala Ala Phe Arg Pro Thr Asn Pro Gly
            20                  25                  30

Pro Ser Pro Ala Ile Gly His Gly Ile Pro Asn Gly Val Pro Gln Pro
        35                  40                  45

Pro Pro Val Asn Gly His Cys Asn
    50                  55
```

<210> SEQ ID NO 376
<211> LENGTH: 153
<212> TYPE: DNA
<213> ORGANISM: Meloidogyne hapla

<400> SEQUENCE: 376

```
atgcctaaaa ttaattctat tttattttt attctttta ttattaattt tatgatttat      60
ttcacaatgg ctggattccg accaacaaat ccaggcaatt cacccggagc tggacatgga     120
gctccaaatg gaccccaaag tctccacccg taa                                  153
```

<210> SEQ ID NO 377
<211> LENGTH: 50
<212> TYPE: PRT
<213> ORGANISM: Meloidogyne hapla

<400> SEQUENCE: 377

```
Met Pro Lys Ile Asn Ser Ile Leu Phe Phe Ile Leu Phe Ile Ile Asn
1               5                   10                  15

Phe Met Ile Tyr Phe Thr Met Ala Gly Phe Arg Pro Thr Asn Pro Gly
            20                  25                  30

Asn Ser Pro Gly Ala Gly His Gly Ala Pro Asn Gly Pro Gln Ser Leu
        35                  40                  45

His Pro
    50
```

<210> SEQ ID NO 378
<211> LENGTH: 168
<212> TYPE: DNA
<213> ORGANISM: Meloidogyne hapla

<400> SEQUENCE: 378

```
atgactaaaa ttaattctat tatattttt attatttta taattaattt tatgatttat      60
caaataatgg ccgctaataa gtcatgtaat accttccgac ccacagctcc gggccattca    120
cccggaattg gaaattgtag tttaattaaa ttttatttac aaaattaa                  168
```

<210> SEQ ID NO 379
<211> LENGTH: 55
<212> TYPE: PRT
<213> ORGANISM: Meloidogyne hapla

<400> SEQUENCE: 379

```
Met Thr Lys Ile Asn Ser Ile Ile Phe Phe Ile Ile Phe Ile Ile Asn
1               5                   10                  15

Phe Met Ile Tyr Gln Ile Met Ala Ala Asn Lys Ser Cys Asn Thr Phe
            20                  25                  30

Arg Pro Thr Ala Pro Gly His Ser Pro Gly Ile Gly Asn Cys Ser Leu
        35                  40                  45

Ile Lys Phe Tyr Leu Gln Asn
    50                  55
```

<210> SEQ ID NO 380
<211> LENGTH: 177
<212> TYPE: DNA
<213> ORGANISM: Meloidogyne hapla

<400> SEQUENCE: 380

```
atgactaaaa ttaattctat tatattttt attatttta ttattaattt tatgatttat       60
caaataatag cacctcaacc tcctttctgc acaggaccag gccattcacc tggagttgga    120
```
catggaattc caaatggact tccatgtaag ccaccagtaa atggacaatg taattaa    177

<210> SEQ ID NO 381
<211> LENGTH: 58
<212> TYPE: PRT
<213> ORGANISM: Meloidogyne hapla

<400> SEQUENCE: 381

Met Thr Lys Ile Asn Ser Ile Ile Phe Phe Ile Ile Phe Ile Ile Asn
1               5                   10                  15

Phe Met Ile Tyr Gln Ile Ile Ala Pro Gln Pro Pro Phe Cys Thr Gly
            20                  25                  30

Pro Gly His Ser Pro Gly Val Gly His Gly Ile Pro Asn Gly Leu Pro
        35                  40                  45

Cys Lys Pro Pro Val Asn Gly Gln Cys Asn
    50                  55

<210> SEQ ID NO 382
<211> LENGTH: 212
<212> TYPE: DNA
<213> ORGANISM: Meloidogyne hapla

<400> SEQUENCE: 382
atgactaaaa ttaactttct atttatattt ttttatttat ttttgattat taattttatg    60
atttatcaaa taatagcacc tcaacctcct ttctgcacag gatcaggcca ttcacccgga   120
gttggacatg gaattccaaa tggacttcca tgtaagccac cagtaaatgg acattgtaat   180
ttaattaaat tttatttgca aaattatata at                                212

<210> SEQ ID NO 383
<211> LENGTH: 70
<212> TYPE: PRT
<213> ORGANISM: Meloidogyne hapla

<400> SEQUENCE: 383

Met Thr Lys Ile Asn Phe Leu Phe Ile Phe Phe Tyr Leu Phe Leu Ile
1               5                   10                  15

Ile Asn Phe Met Ile Tyr Gln Ile Ile Ala Pro Gln Pro Pro Phe Cys
            20                  25                  30

Thr Gly Ser Gly His Ser Pro Gly Val Gly His Gly Ile Pro Asn Gly
        35                  40                  45

Leu Pro Cys Lys Pro Pro Val Asn Gly His Cys Asn Leu Ile Lys Phe
    50                  55                  60

Tyr Leu Gln Asn Tyr Ile
65                  70

<210> SEQ ID NO 384
<211> LENGTH: 183
<212> TYPE: DNA
<213> ORGANISM: Meloidogyne hapla

<400> SEQUENCE: 384
atgactaaaa ttaattctat tatattttta ttatttttta taattaattt tatgattttat    60 caaataatgg ctgttaataa ttcagttgat gccttccgac aacagcccc aggccattca   120 cccggagttg gacattgtaa tttaatttta aaatttattg ccaaaattaa atctctcaaa   180
taa                                                                 183

<210> SEQ ID NO 385

```
<211> LENGTH: 60
<212> TYPE: PRT
<213> ORGANISM: Meloidogyne hapla

<400> SEQUENCE: 385

Met Thr Lys Ile Asn Ser Ile Ile Phe Leu Leu Phe Phe Ile Ile Asn
1               5                   10                  15

Phe Met Ile Tyr Gln Ile Met Ala Val Asn Asn Ser Val Asp Ala Phe
            20                  25                  30

Arg Pro Thr Ala Pro Gly His Ser Pro Gly Val Gly His Cys Asn Leu
        35                  40                  45

Ile Leu Lys Phe Ile Ala Lys Ile Lys Ser Leu Lys
    50                  55                  60

<210> SEQ ID NO 386
<211> LENGTH: 135
<212> TYPE: DNA
<213> ORGANISM: Meloidogyne hapla

<400> SEQUENCE: 386
atgattaata ttaattctat tatattttt attattttaa taattaattt tatgatttat      60
ttgacaatgg caggcaatcc acctttccat actggcactg gccgttcacc cggagctggc     120
catcattgta tttaa                                                       135

<210> SEQ ID NO 387
<211> LENGTH: 44
<212> TYPE: PRT
<213> ORGANISM: Meloidogyne hapla

<400> SEQUENCE: 387

Met Ile Asn Ile Asn Ser Ile Ile Phe Phe Ile Ile Leu Ile Ile Asn
1               5                   10                  15

Phe Met Ile Tyr Leu Thr Met Ala Gly Asn Pro Pro Phe His Thr Gly
            20                  25                  30

Thr Gly Arg Ser Pro Gly Ala Gly His His Cys Ile
        35                  40

<210> SEQ ID NO 388
<211> LENGTH: 39
<212> TYPE: PRT
<213> ORGANISM: Meloidogyne incognita

<400> SEQUENCE: 388

Met Thr Lys Ile Asn Ser Ile Ile Phe Leu Ile Phe Leu Ile Ile Asn
1               5                   10                  15

Phe Met Asn Tyr Tyr Ile Ile Ala Asp Val His Pro Asn Asn Pro Gly
            20                  25                  30

His Ser Pro Gly Ile Gly His
        35

<210> SEQ ID NO 389
<211> LENGTH: 39
<212> TYPE: PRT
<213> ORGANISM: Meloidogyne incognita

<400> SEQUENCE: 389

Met Thr Lys Ile Asn Ser Ile Ile Phe Leu Ile Phe Leu Ile Ile Asn
1               5                   10                  15

Phe Met Asn Tyr Tyr Ile Met Ala Ser Arg Pro Thr Gly Pro Gly His
            20                  25                  30
```

Ser Pro Gly Val Gly Asn Ser
        35

<210> SEQ ID NO 390
<211> LENGTH: 39
<212> TYPE: PRT
<213> ORGANISM: Meloidogyne incognita

<400> SEQUENCE: 390

Met Thr Lys Ile Asn Ser Ile Ile Phe Leu Ile Phe Leu Ile Ile Asn
1               5                   10                  15

Phe Met Asn Tyr Tyr Ile Met Ala Ala Phe Arg Pro Thr Asn Pro Gly
            20                  25                  30

His Ser Pro Gly Val Gly His
        35

<210> SEQ ID NO 391
<211> LENGTH: 39
<212> TYPE: PRT
<213> ORGANISM: Meloidogyne incognita

<400> SEQUENCE: 391

Met Thr Lys Ile Asn Ser Ile Ile Phe Leu Ile Phe Leu Ile Ile Asn
1               5                   10                  15

Phe Met Asn Tyr Tyr Ile Ile Ala Glu Val His Pro Asn Asn Pro Gly
            20                  25                  30

His Ser Pro Gly Ile Gly His
        35

<210> SEQ ID NO 392
<211> LENGTH: 39
<212> TYPE: PRT
<213> ORGANISM: Meloidogyne incognita

<400> SEQUENCE: 392

Met Thr Lys Ile Asn Ser Ile Ile Phe Leu Ile Phe Leu Ile Ile Asn
1               5                   10                  15

Phe Met Asn Tyr Tyr Ile Ile Ala Ser Arg Pro Thr Gln Pro Gly His
            20                  25                  30

Ser Pro Gly Val Gly Asn Gly
        35

<210> SEQ ID NO 393
<211> LENGTH: 57
<212> TYPE: PRT
<213> ORGANISM: Meloidogyne incognita

<400> SEQUENCE: 393

Met Thr Lys Ile Asn Ser Ile Ile Phe Leu Ile Ile Leu Ile Ile Asn
1               5                   10                  15

Phe Met Asn Tyr Tyr Ile Val Ala Gly Thr Arg Ala Thr Glu Pro Gly
            20                  25                  30

His Ser Pro Gly Ala Gly His Asp Ala Pro Asn Val Ala Ala His Gly
        35                  40                  45

Ala His Gly His Gly Gly Pro Gly Lys
        50                  55

<210> SEQ ID NO 394
<211> LENGTH: 57
<212> TYPE: PRT

<213> ORGANISM: Meloidogyne incognita

<400> SEQUENCE: 394

Met Thr Lys Ile Asn Ser

```
<210> SEQ ID NO 400
<211> LENGTH: 15
<212> TYPE: PRT
<213> ORGANISM: Meloidogyne hapla

<400> SEQUENCE: 400

Val Ile Lys Pro Ala Cys Ile Gly Asn Ser Pro Gly Val Gly His
1               5                   10                  15

<210> SEQ ID NO 401
<211> LENGTH: 15
<212> TYPE: PRT
<213> ORGANISM: Meloidogyne hapla

<400> SEQUENCE: 401

Ala Phe Arg Pro Thr Asn Pro Gly Pro Ser Pro Ala Ile Gly His
1               5                   10                  15

<210> SEQ ID NO 402
<211> LENGTH: 15
<212> TYPE: PRT
<213> ORGANISM: Meloidogyne hapla

<400> SEQUENCE: 402

Gly Phe Arg Pro Thr Asn Pro Gly Asn Ser Pro Gly Ala Gly His
1               5                   10                  15

<210> SEQ ID NO 403
<211> LENGTH: 15
<212> TYPE: PRT
<213> ORGANISM: Meloidogyne hapla

<400> SEQUENCE: 403

Thr Phe Arg Pro Thr Ala Pro Gly His Ser Pro Gly Ile Gly Asn
1               5                   10                  15

<210> SEQ ID NO 404
<211> LENGTH: 15
<212> TYPE: PRT
<213> ORGANISM: Meloidogyne hapla

<400> SEQUENCE: 404

Pro Pro Phe Cys Thr Gly Pro Gly His Ser Pro Gly Val Gly His
1               5                   10                  15

<210> SEQ ID NO 405
<211> LENGTH: 15
<212> TYPE: PRT
<213> ORGANISM: Meloidogyne hapla

<400> SEQUENCE: 405

Pro Pro Phe Cys Thr Gly Ser Gly His Ser Pro Gly Val Gly His
1               5                   10                  15

<210> SEQ ID NO 406
<211> LENGTH: 15
<212> TYPE: PRT
<213> ORGANISM: Meloidogyne hapla

<400> SEQUENCE: 406

Ala Phe Arg Pro Thr Ala Pro Gly His Ser Pro Gly Val Gly His
1               5                   10                  15

<210> SEQ ID NO 407
```

```
<211> LENGTH: 15
<212> TYPE: PRT
<213> ORGANISM: Meloidogyne hapla

<400> SEQUENCE: 407

Pro Pro Phe His Thr Gly Thr Gly Arg Ser Pro Gly Ala Gly His
1               5                   10                  15

<210> SEQ ID NO 408
<211> LENGTH: 15
<212> TYPE: PRT
<213> ORGANISM: Meloidogyne incognita

<400> SEQUENCE: 408

Asp Val His Pro Asn Asn Pro Gly His Ser Pro Gly Ile Gly His
1               5                   10                  15

<210> SEQ ID NO 409
<211> LENGTH: 15
<212> TYPE: PRT
<213> ORGANISM: Meloidogyne incognita

<400> SEQUENCE: 409

Ala Ser Arg Pro Thr Gly Pro Gly His Ser Pro Gly Val Gly Asn
1               5                   10                  15

<210> SEQ ID NO 410
<211> LENGTH: 15
<212> TYPE: PRT
<213> ORGANISM: Meloidogyne incognita

<400> SEQUENCE: 410

Ala Phe Arg Pro Thr Asn Pro Gly His Ser Pro Gly Val Gly His
1               5                   10                  15

<210> SEQ ID NO 411
<211> LENGTH: 15
<212> TYPE: PRT
<213> ORGANISM: Meloidogyne incognita

<400> SEQUENCE: 411

Glu Val His Pro Asn Asn Pro Gly His Ser Pro Gly Ile Gly His
1               5                   10                  15

<210> SEQ ID NO 412
<211> LENGTH: 15
<212> TYPE: PRT
<213> ORGANISM: Meloidogyne incognita

<400> SEQUENCE: 412

Ser Arg Pro Thr Gln Pro Gly His Ser Pro Gly Val Gly Asn Gly
1               5                   10                  15

<210> SEQ ID NO 413
<211> LENGTH: 15
<212> TYPE: PRT
<213> ORGANISM: Meloidogyne incognita

<400> SEQUENCE: 413

Gly Thr Arg Ala Thr Glu Pro Gly His Ser Pro Gly Ala Gly His
1               5                   10                  15

<210> SEQ ID NO 414
<211> LENGTH: 15
<212> TYPE: PRT
```

```
<213> ORGANISM: Meloidogyne incognita

<400> SEQUENCE: 414

Gly Thr Arg Pro Thr Glu Pro Gly His Ser Pro Gly Ala Gly His
1               5                   10                  15

<210> SEQ ID NO 415
<211> LENGTH: 15
<212> TYPE: PRT
<213> ORGANISM: Meloidogyne incognita

<400> SEQUENCE: 415

Pro Gly Arg Asn Thr Ala Pro Gly His Ser Pro Gly Ile Gly His
1               5                   10                  15

<210> SEQ ID NO 416
<211> LENGTH: 15
<212> TYPE: PRT
<213> ORGANISM: Artificial sequence
<220> FEATURE:
<223> OTHER INFORMATION: Nematode CEP searching sequence
<220> FEATURE:
<221> NAME/KEY: SITE
<222> LOCATION: (1)..(1)
<223> OTHER INFORMATION: Xaa can be any naturally occurring amino acid
<220> FEATURE:
<221> NAME/KEY: SITE
<222> LOCATION: (6)..(6)
<223> OTHER INFORMATION: Xaa can be any naturally occurring amino acid
<220> FEATURE:
<221> NAME/KEY: SITE
<222> LOCATION: (9)..(9)
<223> OTHER INFORMATION: Xaa can be any naturally occurring amino acid
<220> FEATURE:
<221> NAME/KEY: SITE
<222> LOCATION: (13)..(13)
<223> OTHER INFORMATION: Xaa can be any naturally occurring amino acid
<220> FEATURE:
<221> NAME/KEY: SITE
<222> LOCATION: (15)..(15)
<223> OTHER INFORMATION: Xaa can be any naturally occurring amino acid

<400> SEQUENCE: 416

Xaa Phe Arg Pro Thr Xaa Pro Gly Xaa Ser Pro Gly Xaa Gly Xaa
1               5                   10                  15

<210> SEQ ID NO 417
<211> LENGTH: 32
<212> TYPE: DNA
<213> ORGANISM: Artificial sequence
<220> FEATURE:
<223> OTHER INFORMATION: M. truncatula CEP1 forward primer

<400> SEQUENCE: 417
caccatggct tataaatttc aatacacaat ga                            32

<210> SEQ ID NO 418
<211> LENGTH: 23
<212> TYPE: DNA
<213> ORGANISM: Artificial sequence
<220> FEATURE:
<223> OTHER INFORMATION: M. truncatula CEP1 reverse primer

<400> SEQUENCE: 418
tcaatttcca attttgtttt ggt                                      23

<210> SEQ ID NO 419
<211> LENGTH: 22
<212> TYPE: DNA
```

```
<213> ORGANISM: Artificial sequence
<220> FEATURE:
<223> OTHER INFORMATION: M. truncatula CEP1 forward PCR primer

<400> SEQUENCE: 419
ccgatgaaga tatcgacgtg aa                                             22

<210> SEQ ID NO 420
<211> LENGTH: 29
<212> TYPE: DNA
<213> ORGANISM: Artificial sequence
<220> FEATURE:
<223> OTHER INFORMATION: M. truncatula CEP1 reverse PCR primer

<400> SEQUENCE: 420
gaactcattt gtagtatcct cagtcacat                                      29

<210> SEQ ID NO 421
<211> LENGTH: 20
<212> TYPE: DNA
<213> ORGANISM: Artificial sequence
<220> FEATURE:
<223> OTHER INFORMATION: M. truncatula CEP2 forward PCR primer

<400> SEQUENCE: 421
tagctcgcat ttgcttgttc                                                20

<210> SEQ ID NO 422
<211> LENGTH: 20
<212> TYPE: DNA
<213> ORGANISM: Artificial sequence
<220> FEATURE:
<223> OTHER INFORMATION: M. truncatula CEP2 reverse PCR primer

<400> SEQUENCE: 422
ggctgaatgc tttgtctcaa                                                20

<210> SEQ ID NO 423
<211> LENGTH: 20
<212> TYPE: DNA
<213> ORGANISM: Artificial sequence
<220> FEATURE:
<223> OTHER INFORMATION: M. truncatula CEP3 forward PCR primer

<400> SEQUENCE: 423
acgttgagct ccaccatttt                                                20

<210> SEQ ID NO 424
<211> LENGTH: 20
<212> TYPE: DNA
<213> ORGANISM: Artificial sequence
<220> FEATURE:
<223> OTHER INFORMATION: M. truncatula CEP3 reverse PCR primer

<400> SEQUENCE: 424
gagcgctcca cctcctatta                                                20

<210> SEQ ID NO 425
<211> LENGTH: 20
<212> TYPE: DNA
<213> ORGANISM: Artificial sequence
<220> FEATURE:
<223> OTHER INFORMATION: M. truncatula CEP4 forward PCR primer

<400> SEQUENCE: 425
catggaggtg gtgtttgatg                                                20
```

<210> SEQ ID NO 426
<211> LENGTH: 20
<212> TYPE: DNA
<213> ORGANISM: Artificial sequence
<220> FEATURE:
<223> OTHER INFORMATION: M. truncatula CEP4 reverse PCR primer

<400> SEQUENCE: 426
ttttcgccct acaagtccag                                          20

<210> SEQ ID NO 427
<211> LENGTH: 20
<212> TYPE: DNA
<213> ORGANISM: Artificial sequence
<220> FEATURE:
<223> OTHER INFORMATION: M. truncatula CEP5 forward PCR primer

<400> SEQUENCE: 427
gtgttgtttt gagcccaagg                                          20

<210> SEQ ID NO 428
<211> LENGTH: 20
<212> TYPE: DNA
<213> ORGANISM: Artificial sequence
<220> FEATURE:
<223> OTHER INFORMATION: M. truncatula CEP5 reverse PCR primer

<400> SEQUENCE: 428
tgttggtcga aaagcttcaa                                          20

<210> SEQ ID NO 429
<211> LENGTH: 20
<212> TYPE: DNA
<213> ORGANISM: Artificial sequence
<220> FEATURE:
<223> OTHER INFORMATION: M. truncatula CEP6 forward PCR primer

<400> SEQUENCE: 429
gctcatcatg gagggaagtc                                          20

<210> SEQ ID NO 430
<211> LENGTH: 20
<212> TYPE: DNA
<213> ORGANISM: Artificial sequence
<220> FEATURE:
<223> OTHER INFORMATION: M. truncatula CEP6 reverse PCR primer

<400> SEQUENCE: 430
tatgccctgg agatgtaggc                                          20

<210> SEQ ID NO 431
<211> LENGTH: 20
<212> TYPE: DNA
<213> ORGANISM: Artificial sequence
<220> FEATURE:
<223> OTHER INFORMATION: M. truncatula CEP7 forward PCR primer

<400> SEQUENCE: 431
ccggatgttg aggtttttgt                                          20

<210> SEQ ID NO 432
<211> LENGTH: 20
<212> TYPE: DNA
<213> ORGANISM: Artificial sequence
<220> FEATURE:

<223> OTHER INFORMATION: M. truncatula CEP7 reverse PCR primer

<400> SEQUENCE: 432
ggccaactcc aggactatga                                        20

<210> SEQ ID NO 433
<211> LENGTH: 20
<212> TYPE: DNA
<213> ORGANISM: Artificial sequence
<220> FEATURE:
<223> OTHER INFORMATION: M. truncatula CEP8 forward PCR primer

<400> SEQUENCE: 433
tccaacaata ttgccaccaa                                        20

<210> SEQ ID NO 434
<211> LENGTH: 20
<212> TYPE: DNA
<213> ORGANISM: Artificial sequence
<220> FEATURE:
<223> OTHER INFORMATION: M. truncatula CEP8 reverse PCR primer

<400> SEQUENCE: 434
gggttgtggg tctaaaagca                                        20

<210> SEQ ID NO 435
<211> LENGTH: 20
<212> TYPE: DNA
<213> ORGANISM: Artificial sequence
<220> FEATURE:
<223> OTHER INFORMATION: M. truncatula CEP9 forward PCR primer

<400> SEQUENCE: 435
tgatgccaaa tcatggtgtc                                        20

<210> SEQ ID NO 436
<211> LENGTH: 20
<212> TYPE: DNA
<213> ORGANISM: Artificial sequence
<220> FEATURE:
<223> OTHER INFORMATION: M. truncatula CEP9 reverse PCR primer

<400> SEQUENCE: 436
ggactgcttc ctggtgttgt                                        20

<210> SEQ ID NO 437
<211> LENGTH: 21
<212> TYPE: DNA
<213> ORGANISM: Artificial sequence
<220> FEATURE:
<223> OTHER INFORMATION: M. truncatula CEP10 forward PCR primer

<400> SEQUENCE: 437
tcaatggaag catcaaggtt t                                      21

<210> SEQ ID NO 438
<211> LENGTH: 20
<212> TYPE: DNA
<213> ORGANISM: Artificial sequence
<220> FEATURE:
<223> OTHER INFORMATION: M. truncatula CEP10 reverse PCR primer

<400> SEQUENCE: 438
tatatgtccc accccaagac                                        20

```
<210> SEQ ID NO 439
<211> LENGTH: 20
<212> TYPE: DNA
<213> ORGANISM: Artificial sequence
<220> FEATURE:
<223> OTHER INFORMATION: M. truncatula CEP11 forward PCR primer

<400> SEQUENCE: 439
agctccttcc attggctttt                                              20

<210> SEQ ID NO 440
<211> LENGTH: 19
<212> TYPE: DNA
<213> ORGANISM: Artificial sequence
<220> FEATURE:
<223> OTHER INFORMATION: M. truncatula CEP11 reverse PCR primer

<400> SEQUENCE: 440
ccccaccagg actatgacc                                               19

<210> SEQ ID NO 441
<211> LENGTH: 21
<212> TYPE: DNA
<213> ORGANISM: Artificial sequence
<220> FEATURE:
<223> OTHER INFORMATION: M. truncatula NRT2.5 forward PCR primer

<400> SEQUENCE: 441
ggagaaggag aaagggtctc a                                            21

<210> SEQ ID NO 442
<211> LENGTH: 21
<212> TYPE: DNA
<213> ORGANISM: Artificial sequence
<220> FEATURE:
<223> OTHER INFORMATION: M. truncatula NRT2.5 reverse PCR primer

<400> SEQUENCE: 442
tcagaaggcc tagttgaaat g                                            21

<210> SEQ ID NO 443
<211> LENGTH: 19
<212> TYPE: DNA
<213> ORGANISM: Artificial sequence
<220> FEATURE:
<223> OTHER INFORMATION: M. truncatula AGL1 forward PCR primer

<400> SEQUENCE: 443
gaaccgaagg gaagcataa                                               19

<210> SEQ ID NO 444
<211> LENGTH: 20
<212> TYPE: DNA
<213> ORGANISM: Artificial sequence
<220> FEATURE:
<223> OTHER INFORMATION: M. truncatula AGL1 reverse PCR primer

<400> SEQUENCE: 444
tgtcgtgcca tacaccttt                                               20

<210> SEQ ID NO 445
<211> LENGTH: 20
<212> TYPE: DNA
<213> ORGANISM: Artificial sequence
<220> FEATURE:
<223> OTHER INFORMATION: M. truncatula LBD38 forward PCR primer
```

<400> SEQUENCE: 445
gccacgctac tgttttcgta                                           20

<210> SEQ ID NO 446
<211> LENGTH: 20
<212> TYPE: DNA
<213> ORGANISM: Artificial sequence
<220> FEATURE:
<223> OTHER INFORMATION: M. truncatula LBD38 reverse PCR primer

<400> SEQUENCE: 446
gagctggtct ctgtggttca                                           20

<210> SEQ ID NO 447
<211> LENGTH: 22
<212> TYPE: DNA
<213> ORGANISM: Artificial sequence
<220> FEATURE:
<223> OTHER INFORMATION: M. hapla CEP10 forward PCR primer

<400> SEQUENCE: 447
gcacctcaac ctccttctg ca                                         22

<210> SEQ ID NO 448
<211> LENGTH: 26
<212> TYPE: DNA
<213> ORGANISM: Artificial sequence
<220> FEATURE:
<223> OTHER INFORMATION: M. hapla CEP10 reverse PCR primer

<400> SEQUENCE: 448
tgtccattta ctggtggctt acatgg                                    26

<210> SEQ ID NO 449
<211> LENGTH: 21
<212> TYPE: DNA
<213> ORGANISM: Artificial sequence
<220> FEATURE:
<223> OTHER INFORMATION: M. truncatula UBQ10 forward PCR primer

<400> SEQUENCE: 449
aacttgttgc atgggtcttg a                                         21

<210> SEQ ID NO 450
<211> LENGTH: 30
<212> TYPE: DNA
<213> ORGANISM: Artificial sequence
<220> FEATURE:
<223> OTHER INFORMATION: M. truncatula UBQ10 reverse PCR primer

<400> SEQUENCE: 450
cattaagttt gacaaagaga aagagacaga                                30

<210> SEQ ID NO 451
<211> LENGTH: 15
<212> TYPE: PRT
<213> ORGANISM: Medicago truncatula
<220> FEATURE:
<221> NAME/KEY: MOD_RES
<222> LOCATION: (4)..(4)
<223> OTHER INFORMATION: hydroxyproline
<220> FEATURE:
<221> NAME/KEY: MOD_RES
<222> LOCATION: (7)..(7)
<223> OTHER INFORMATION: hydroxyproline
<220> FEATURE:
<221> NAME/KEY: MOD_RES

```
<222> LOCATION: (11)..(11)
<223> OTHER INFORMATION: hydroxyproline, and may be mono-, di-, or
      tri-arabinosylated

<400> SEQUENCE: 451

Ala Phe Gln Pro Thr Thr Pro Gly Asn Ser Pro Gly Val Gly His
1               5                   10                  15

<210> SEQ ID NO 452
<211> LENGTH: 15
<212> TYPE: PRT
<213> ORGANISM: Medicago truncatula
<220> FEATURE:
<221> NAME/KEY: MOD_RES
<222> LOCATION: (11)..(11)
<223> OTHER INFORMATION: hydroxyproline

<400> SEQUENCE: 452

Glu Phe Gln Lys Thr Asn Pro Gly His Ser Pro Gly Val Gly His
1               5                   10                  15

<210> SEQ ID NO 453
<211> LENGTH: 19
<212> TYPE: PRT
<213> ORGANISM: Meloidogyne hapla
<220> FEATURE:
<221> NAME/KEY: MOD_RES
<222> LOCATION: (9)..(9)
<223> OTHER INFORMATION: hydroxyproline
<220> FEATURE:
<221> NAME/KEY: MOD_RES
<222> LOCATION: (15)..(15)
<223> OTHER INFORMATION: hydroxyproline

<400> SEQUENCE: 453

Ala Phe Arg His Tyr Pro Thr Ala Pro Gly His Ser His Tyr Pro Gly
1               5                   10                  15

Val Gly His

<210> SEQ ID NO 454
<211> LENGTH: 15
<212> TYPE: PRT
<213> ORGANISM: Artificial sequence
<220> FEATURE:
<223> OTHER INFORMATION: RKN and plant CEP peptide consensus sequence
<220> FEATURE:
<221> NAME/KEY: SITE
<222> LOCATION: (1)..(1)
<223> OTHER INFORMATION: N-terminal additional amino acid, Xaa may be
      no amino acid or D, A, P, G, S, V, E, P, T, Q, I, N, K, or C
<220> FEATURE:
<221> NAME/KEY: SITE
<222> LOCATION: (2)..(2)
<223> OTHER INFORMATION: Xaa is F, V, T, S, A, K, Y, R, G, I, Q, H, D,
      G, W
<220> FEATURE:
<221> NAME/KEY: SITE
<222> LOCATION: (3)..(3)
<223> OTHER INFORMATION: Xaa is R, A, Q, G, E, V, D, K, P, S, H, Q
<220> FEATURE:
<221> NAME/KEY: SITE
<222> LOCATION: (4)..(4)
<223> OTHER INFORMATION: Xaa is P, G, S, T, A, N, C, H, V, E, Y, K
<220> FEATURE:
<221> NAME/KEY: SITE
<222> LOCATION: (5)..(5)
<223> OTHER INFORMATION: Xaa is T, S, A, P, G, V, N, M, I
<220> FEATURE:
<221> NAME/KEY: SITE
<222> LOCATION: (6)..(6)
<223> OTHER INFORMATION: Xaa is T, N, A, G, P, D, K, S, V, Y, Q, E,
      C, H
```

```
<220> FEATURE:
<221> NAME/KEY: SITE
<222> LOCATION: (9)..(9)
<223> OTHER INFORMATION: Xaa is H, N, S, Y, P, R, T, G, V, F, Q, D
<220> FEATURE:
<221> NAME/KEY: SITE
<222> LOCATION: (13)..(13)
<223> OTHER INFORMATION: Xaa is I, V, A
<220> FEATURE:
<221> NAME/KEY: SITE
<222> LOCATION: (15)..(15)
<223> OTHER INFORMATION: Xaa is H, N

<400> SEQUENCE: 454

Xaa Xaa Xaa Xaa Xaa Xaa Pro Gly Xaa Ser Pro Gly Xaa Gly Xaa
1               5                   10                  15

<210> SEQ ID NO 455
<211> LENGTH: 15
<212> TYPE: PRT
<213> ORGANISM: Arapidopsis thaliana

<400> SEQUENCE: 455

Glu Phe Ala Pro Thr Asn Pro Glu Asp Ser Leu Gly Ile Gly His
1               5                   10                  15

<210> SEQ ID NO 456
<211> LENGTH: 15
<212> TYPE: PRT
<213> ORGANISM: Arapidopsis thaliana

<400> SEQUENCE: 456

Asp Phe Ala Pro Thr Thr Pro Gly Asn Ser Pro Gly Met Gly His
1               5                   10                  15

<210> SEQ ID NO 457
<211> LENGTH: 15
<212> TYPE: PRT
<213> ORGANISM: Arapidopsis thaliana

<400> SEQUENCE: 457

Ala Phe Arg Pro Thr Asn Pro Gly Asn Ser Pro Gly Ile Gly His
1               5                   10                  15

<210> SEQ ID NO 458
<211> LENGTH: 15
<212> TYPE: PRT
<213> ORGANISM: Arapidopsis thaliana

<400> SEQUENCE: 458

Glu Phe Arg Pro Thr Thr Pro Gly Asn Ser Pro Gly Ile Gly His
1               5                   10                  15

<210> SEQ ID NO 459
<211> LENGTH: 15
<212> TYPE: PRT
<213> ORGANISM: Arapidopsis thaliana

<400> SEQUENCE: 459

Asp Phe Ala Pro Thr Asn Pro Gly His Asn Pro Gly Ile Gly His
1               5                   10                  15

<210> SEQ ID NO 460
<211> LENGTH: 15
<212> TYPE: PRT
<213> ORGANISM: Arapidopsis thaliana
```

```
<400> SEQUENCE: 460

Asp Phe Ala Pro Thr Asn Pro Gly His Ser Pro Gly Ile Gly His
1               5                   10                  15

<210> SEQ ID NO 461
<211> LENGTH: 15
<212> TYPE: PRT
<213> ORGANISM: Arapidopsis thaliana

<400> SEQUENCE: 461

Asp Phe Ala Pro Thr Asn Pro Gly Asn Ser Pro Gly Ile Arg His
1               5                   10                  15

<210> SEQ ID NO 462
<211> LENGTH: 15
<212> TYPE: PRT
<213> ORGANISM: Arapidopsis thaliana

<400> SEQUENCE: 462

Ala Phe Arg Ser Thr Glu Pro Gly His Ser Pro Gly Val Gly His
1               5                   10                  15

<210> SEQ ID NO 463
<211> LENGTH: 15
<212> TYPE: PRT
<213> ORGANISM: Arapidopsis thaliana

<400> SEQUENCE: 463

Ala Phe Arg Pro Thr Gly Gln Gly Pro Ser Gln Gly Ile Gly His
1               5                   10                  15

<210> SEQ ID NO 464
<211> LENGTH: 15
<212> TYPE: PRT
<213> ORGANISM: Arapidopsis thaliana

<400> SEQUENCE: 464

Ile Tyr Arg Arg Leu Glu Ser Val Pro Ser Pro Gly Val Gly His
1               5                   10                  15

<210> SEQ ID NO 465
<211> LENGTH: 15
<212> TYPE: PRT
<213> ORGANISM: Arapidopsis thaliana

<400> SEQUENCE: 465

Val Asp Arg Tyr Leu Arg Ser Val Pro Ser Pro Gly Val Gly His
1               5                   10                  15

<210> SEQ ID NO 466
<211> LENGTH: 15
<212> TYPE: PRT
<213> ORGANISM: Arapidopsis thaliana

<400> SEQUENCE: 466

Ile Tyr Arg Arg Gln Gly Asp Val Pro Ser Pro Gly Ile Gly His
1               5                   10                  15

<210> SEQ ID NO 467
<211> LENGTH: 228
<212> TYPE: DNA
<213> ORGANISM: Arapidopsis thaliana

<400> SEQUENCE: 467
```

```
atggctaaat gcactttgac tagcttaata ctactactaa tagtgctggt tcttattcaa      60
gaatctcaca tcgttgaagg tcgacctttg aagtcatcgc gaatctctaa tgtctcgaag     120
aaattcgctg cgggcaactc gaatctgtcg agcaagttaa cgacagaaga tcattctttg     180
gatgcatttc ggcctaccaa ccctgggaac agtccaggaa ttggtcac                  228
```

<210> SEQ ID NO 468
<211> LENGTH: 76
<212> TYPE: PRT
<213> ORGANISM: Arabidopsis thaliana

<400> SEQUENCE: 468

```
Met Ala Lys Cys Thr Leu Thr Ser Leu Ile Leu Leu Ile Val Leu
1               5                   10                  15

Val Leu Ile Gln Glu Ser His Ile Val Glu Gly Arg Pro Leu Lys Ser
            20                  25                  30

Ser Arg Ile Ser Asn Val Ser Lys Lys Phe Ala Ala Gly Asn Ser Asn
        35                  40                  45

Leu Ser Ser Lys Leu Thr Thr Glu Asp His Ser Leu Asp Ala Phe Arg
    50                  55                  60

Pro Thr Asn Pro Gly Asn Ser Pro Gly Ile Gly His
65                  70                  75
```

<210> SEQ ID NO 469
<211> LENGTH: 261
<212> TYPE: DNA
<213> ORGANISM: Arabidopsis thaliana

<400> SEQUENCE: 469

```
atggcaaaag ctctgttctt caatttctgc atatctcttc ttattattgc catacttgtg      60
agccatgaaa tcataccaac agaggcaaga cacttgagga cccatagaaa gtcaatcaag     120
aacagtactc ttactgtaca cgaaggagcc ggtggcttga aaccggtgg tggctctgtg     180 aagactgaca ttagcaaaga gaacatggc gttgatgagt tccggccaac aactccggga     240
aacagccccg gcattggcca t                                               261
```

<210> SEQ ID NO 470
<211> LENGTH: 87
<212> TYPE: PRT
<213> ORGANISM: Arapidopsis thaliana

<400> SEQUENCE: 470

```
Met Ala Lys Ala Leu Phe Phe Asn Phe Cys Ile Ser Leu Leu Ile Ile
1               5                   10                  15

Ala Ile Leu Val Ser His Glu Ile Ile Pro Thr Glu Ala Arg His Leu
            20                  25                  30

Arg Thr His Arg Lys Ser Ile Lys Asn Ser Thr Leu Thr Val His Glu
        35                  40                  45

Gly Ala Gly Gly Leu Arg Thr Gly Gly Gly Ser Val Lys Thr Asp Ile
    50                  55                  60

Ser Lys Glu Glu His Gly Val Asp Glu Phe Arg Pro Thr Thr Pro Gly
65                  70                  75                  80

Asn Ser Pro Gly Ile Gly His
                85
```

<210> SEQ ID NO 471
<211> LENGTH: 196
<212> TYPE: DNA

<213> ORGANISM: Arapidopsis thaliana

<400> SEQUENCE: 471

```
atgaagctat ttattatcat tgtggtgacc agtttaacca tctcaaaggt atttgacaaa     60
acacttgtca ccattgaagc aagaaatttg aggaagatgg accgtcatga gcatttcaat    120
gctaatgaag atttcgtgga agcaaaaatg ttaaagaaaa ttgacaataa aaataatcta    180
aataatagat gtataa                                                    196
```

<210> SEQ ID NO 472
<211> LENGTH: 132
<212> TYPE: PRT
<213> ORGANISM: Arapidopsis thaliana

<400> SEQUENCE: 472

```
Met Lys Leu Phe Ile Ile Ile Val Val Thr Ser Leu Thr Ile Ser Lys
1               5                   10                  15

Val Phe Asp Lys Thr Leu Val Thr Ile Glu Ala Arg Asn Leu Arg Lys
            20                  25                  30

Met Asp Arg His Glu His Phe Asn Ala Asn Glu Asp Phe Val Glu Ala
        35                  40                  45

Lys Met Leu Lys Lys Ile Asp Asn Lys Asn Asn Leu Asn Asn Arg Cys
    50                  55                  60

Ile Asn Asp Phe Ala Pro Thr Asn Pro Gly His Asn Ser Gly Ile Gly
65                  70                  75                  80

His Pro Lys Val Ile Asn Asn Lys Phe Thr Lys Asp Phe Ala Pro Thr
                85                  90                  95

Asn Pro Gly His Ser Pro Gly Ile Gly His Leu Arg Val Val Asn Asn
            100                 105                 110

Lys Phe Thr Asn Asp Phe Ala Pro Thr Asn Pro Gly Asn Ser Pro Gly
        115                 120                 125

Ile Arg His Pro
    130
```

<210> SEQ ID NO 473
<211> LENGTH: 198
<212> TYPE: DNA
<213> ORGANISM: Arapidopsis thaliana

<400> SEQUENCE: 473

```
atggcaaaga cacgtcgtgt aatttaccct ttccttacta tagtactcct tttctgcgaa     60
ctcatcgacg aggcgcaagg tagccgtttt aggtgtcatc actcagaaga ttattcatgt    120
aagaaacgtt caagccatca ccatcatcat catcatcatc atcagcagca gcagcaccat    180
cacaaggaca ctccccca                                                 198
```

<210> SEQ ID NO 474
<211> LENGTH: 104
<212> TYPE: PRT
<213> ORGANISM: Arapidopsis thaliana

<400> SEQUENCE: 474

```
Met Ala Lys Thr Arg Arg Val Ile Tyr Leu Phe Leu Thr Ile Val Leu
1               5                   10                  15

Leu Phe Cys Glu Leu Ile Asp Glu Ala Gln Gly Ser Arg Phe Arg Cys
            20                  25                  30

His His Ser Glu Asp Tyr Ser Cys Lys Lys Arg Ser Ser His His His
        35                  40                  45
```

His His His His His Gln Gln Gln Gln His His Lys Asp Thr
          50                  55                  60

Pro Pro Glu Glu Leu Gln Gly Ser Ile Lys Thr Arg Arg Ser Lys Asp
65                  70                  75                  80

Ile Tyr Gly Leu Asn Ala Phe Arg Ser Thr Glu Pro Gly His Ser Pro
                85                  90                  95

Gly Val Gly His Leu Ile Lys Thr
            100

<210> SEQ ID NO 475
<211> LENGTH: 279
<212> TYPE: DNA
<213> ORGANISM: Arapidopsis thaliana

<400> SEQUENCE: 475
atggtgaacc gtgataattc tattgtggct ttatccttt  ttatgctctt cttgcttgtg    60
ttacatctgc attttgaaac tacaacagct gcgcgaaaac cagttagagt gtttggtccg   120
ccaagttcta tcgagtggtc accaccatca ccaccaaagg atgactttga atggttcgag   180
atcaatatat acaagaacat tgaacaaact gcattccgac ccactggtca aggtcctagc   240
caaggcatcg gacacaagga tccacctggt gctccataa                          279

<210> SEQ ID NO 476
<211> LENGTH: 92
<212> TYPE: PRT
<213> ORGANISM: Arapidopsis thaliana

<400> SEQUENCE: 476

Met Val Asn Arg Asp Asn Ser Ile Val Ala Leu Ser Phe Phe Met Leu
1               5                   10                  15

Phe Leu Leu Val Leu His Leu His Phe Glu Thr Thr Thr Ala Ala Arg
            20                  25                  30

Lys Pro Val Arg Val Phe Gly Pro Pro Ser Ser Ile Glu Trp Ser Pro
        35                  40                  45

Pro Ser Pro Pro Lys Asp Asp Phe Glu Trp Phe Glu Ile Asn Ile Tyr
50                  55                  60

Lys Asn Ile Glu Gln Thr Ala Phe Arg Pro Thr Gly Gln Gly Pro Ser
65                  70                  75                  80

Gln Gly Ile Gly His Lys Asp Pro Pro Gly Ala Pro
            85                  90

<210> SEQ ID NO 477
<211> LENGTH: 551
<212> TYPE: DNA
<213> ORGANISM: Arapidopsis thaliana

<400> SEQUENCE: 477
aaataaacta aaatttctt gcttcataac taattaatta atatctaaaa ttatacaaca     60
aaatcaatca ggtaatggct cgtccaagga tctccatttc gatgatttgc ttactcattt   120
tgattgttgg ttttgtcttg caatcttctc aagctagaaa agttctagtc ccttacggca   180
caagcaaggg tttgtttctt agtgccctac ccaagggcaa tgtaccacct tcgggtccaa   240
gcgacaaggg tcacacttct cctccggatg ataccgacca gcgtatggta ccagaaaact   300
cgccggagat ataccgtcga ctagaatcag tccctagccc cggcgtgggt cattaggcac   360
attaattgat tgtcgtcttt tcacttcata tatgttgaca tgttgtcgaa ttctattcac   420

```
aatgatatca tataccgttc gtaagtcttc tcaagaatgt ttgtgtatgt gtgtcttcat    480
atataattga tatagatatg tttgtgtgtg atccgatccg ttattgagta ataaaaaacc    540
actattctac a                                                         551
```

<210> SEQ ID NO 478
<211> LENGTH: 93
<212> TYPE: PRT
<213> ORGANISM: Arapidopsis thaliana

<400> SEQUENCE: 478

```
Met Ala Arg Pro Arg Ile Ser Ile Ser Met Ile Cys Leu Leu Ile Leu
1               5                   10                  15

Ile Val Gly Phe Val Leu Gln Ser Ser Gln Ala Arg Lys Val Leu Val
            20                  25                  30

Pro Tyr Gly Thr Ser Lys Gly Leu Phe Leu Ser Ala Leu Pro Lys Gly
        35                  40                  45

Asn Val Pro Pro Ser Gly Pro Ser Asp Lys Gly His Thr Ser Pro Pro
    50                  55                  60

Asp Asp Thr Asp Gln Arg Met Val Pro Glu Asn Ser Pro Glu Ile Tyr
65                  70                  75                  80

Arg Arg Leu Glu Ser Val Pro Ser Pro Gly Val Gly His
                85                  90
```

<210> SEQ ID NO 479
<211> LENGTH: 607
<212> TYPE: DNA
<213> ORGANISM: Arapidopsis thaliana

<400> SEQUENCE: 479

```
atagcaatct tgagtcttaa gaatttcatt gaatttatct ctctcgctct ctctctcttt     60
atttctcaac ccaaagatca aagctcttca tggccgttcg tctaattccg accatctggc    120
tcttcatagt ctttgccgtc atcgtgtcag ccttgccttc gctggtatct tcaagaaaac    180
tgttggaggt gaagaaacaa gaaaacttga cggtgagaga ggaagagaag agtcacatgc    240
ctcatgtgac caaaactagt acgttaagtg tctctaccaaa ggggaaaatt cccaactcga    300
caccgagcaa aagggtcac gcggccgtct tcgccggaaa gctccgatca cgacatctct    360
ccaccgttga tcggtatctc cgatccgttc ctagtcccgg tgttggccat tgatagtctc    420
ggctagattc atatatatat ttttttcttc catttagtac attctttatt ctaactatat    480
aatacgaaat ttcctacaag gtataccttt gttttagaa ttctttttt tttcaggtt      540 actacaactt ttgcatatgt aaattagtca aaagtttatt ttcttccata tcacacgagg    600
tttaata                                                              607
```

<210> SEQ ID NO 480
<211> LENGTH: 107
<212> TYPE: PRT
<213> ORGANISM: Arapidopsis thaliana

<400> SEQUENCE: 480

```
Met Ala Val Arg Leu Ile Pro Thr Ile Trp Leu Phe Ile Val Phe Ala
1               5                   10                  15

Val Ile Val Ser Ala Leu Pro Ser Leu Val Ser Ser Arg Lys Leu Leu
            20                  25                  30

Glu Val Lys Lys Gln Glu Asn Leu Thr Val Arg Glu Glu Glu Lys Ser
        35                  40                  45
```

His Met Pro His Val Thr Lys Thr Ser Thr Leu Ser Ala Leu Pro Lys
            50                  55                  60

Gly Lys Ile Pro Asn Ser Thr Pro Ser Lys Lys Gly His Ala Ala Val
 65                  70                  75                  80

Phe Ala Gly Lys Leu Arg Ser Arg His Leu Ser Thr Val Asp Arg Tyr
                 85                  90                  95

Leu Arg Ser Val Pro Ser Pro Gly Val Gly His
                100                 105

<210> SEQ ID NO 481
<211> LENGTH: 707
<212> TYPE: DNA
<213> ORGANISM: Arapidopsis thaliana

<400> SEQUENCE: 481
ataaccacaa cgctacaatc tcttcttgaa cctaaagaaa acaagaagaa agaaaaaatt    60
catataaatt ctcttatatt ttttcacctt tatattgaat ggatgcaacg aagattaagt   120
ttgacgttat attactctcc ttcttactaa ttatctccgg aattccttcg aatcttgggt   180
tgagtacaag tgtgagaggc actactagat cggagccgga agcctttcac ggcggtaaat   240
tcccggcaat gaagatgagg aagttgatgg caccaaacat ggaagttgat tattcgagtg   300
actattatga tggaggatca tcatcatcaa caacatcacc atcacctcca gtgcctgatt   360
atgatgatat ttatagaagg caaggtgatg tcccaagccc tggtattggc cactgatcca   420
tacatgtcat gcgtatatac acacacatat agacattttg tgttaaatat atttatacat   480
acatgttgtt tataatgttt ttgtccttgg aggtcgtctc cgtatgatca gttttatttt   540
gctcttttcc ttcattttttt tatatttga tcttatttca ttttgtcttt ttagttcata   600
aaatataatt gtgcccttcc tcttgaattg tctcatttcc tcgtgttgat gggagttcat   660
gtattcatgt atgtaataca actcataata aaaaaactgt atttgtc                707

<210> SEQ ID NO 482
<211> LENGTH: 105
<212> TYPE: PRT
<213> ORGANISM: Arapidopsis thaliana

<400> SEQUENCE: 482

Met Asp Ala Thr Lys Ile Lys Phe Asp Val Ile Leu Leu Ser Phe Leu
 1               5                  10                  15

Leu Ile Ile Ser Gly Ile Pro Ser Asn Leu Gly Leu Ser Thr Ser Val
                20                  25                  30

Arg Gly Thr Thr Arg Ser Glu Pro Glu Ala Phe His Gly Gly Lys Phe
                35                  40                  45

Pro Ala Met Lys Met Arg Lys Leu Met Ala Pro Asn Met Glu Val Asp
            50                  55                  60

Tyr Ser Ser Asp Tyr Tyr Asp Gly Gly Ser Ser Ser Thr Thr Ser
 65                  70                  75                  80

Pro Ser Pro Pro Val Pro Asp Tyr Asp Ile Tyr Arg Arg Gln Gly
                 85                  90                  95

Asp Val Pro Ser Pro Gly Ile Gly His
                100                 105

<210> SEQ ID NO 483
<211> LENGTH: 198
<212> TYPE: DNA
<213> ORGANISM: Brachypodium distachyon

<400> SEQUENCE: 483

```
atggccgttc cgttgaaagc tgttaccatt tcgtgttgc tgctgagcac taccttctgc      60
cagctccctg tgcctgtgca tgcaaggagg ctagaagtgc gagcgcctac cgtcgacatg     120
catcctccct gcactggaag gagcactctg gaggcatctg ctgtgctagc tgattcgacc     180
actccaggcc atagccct                                                    198
```

<210> SEQ ID NO 484
<211> LENGTH: 75
<212> TYPE: PRT
<213> ORGANISM: Brachypodium distachyon

<400> SEQUENCE: 484

Met Ala Val Pro Leu Lys Ala Val Thr Ile Phe Val Leu Leu Leu Ser
1               5                   10                  15

Thr Thr Phe Cys Gln Leu Pro Val Pro Val His Ala Arg Arg Leu Glu
            20                  25                  30

Val Arg Ala Pro Thr Val Asp Met His Pro Pro Cys Thr Gly Arg Ser
        35                  40                  45

Thr Leu Glu Ala Ser Ala Val Leu Ala Asp Ser Thr Thr Pro Gly His
    50                  55                  60

Ser Pro Ser Ile Gly His Asn Ser Pro Pro Asn
65                  70                  75

<210> SEQ ID NO 485
<211> LENGTH: 196
<212> TYPE: DNA
<213> ORGANISM: Brachypodium distachyon

<400> SEQUENCE: 485

```
ctgagcaaag cagccctcct gcttgcgctc ttgatccttt cctgtagcca catcatgtgc      60
tcccaaggca caagtactct catgacgacg atgcatggga gaaacttgct gcgccattcc    120
gaggaagcct cgaaggcgat gattagagcc accctctcgg ctgacggcta caatggaaaa    180
ggcggtggca gcggta                                                     196
```

<210> SEQ ID NO 486
<211> LENGTH: 101
<212> TYPE: PRT
<213> ORGANISM: Brachypodium distachyon

<400> SEQUENCE: 486

Leu Ser Lys Ala Ala Leu Leu Leu Ala Leu Ile Leu Ser Cys Ser
1               5                   10                  15

His Ile Met Cys Ser Gln Gly Thr Ser Thr Leu Met Thr Thr Met His
            20                  25                  30

Gly Arg Asn Leu Leu Arg His Ser Glu Glu Ala Ser Lys Ala Met Ile
        35                  40                  45

Arg Ala Thr Leu Ser Ala Asp Gly Tyr Asn Gly Lys Gly Gly Ser
    50                  55                  60

Gly Ile Gly Asn Val Glu Asp Ser Arg Pro Thr Gly Pro Gly His Ser
65                  70                  75                  80

Pro Gly Ala Gly His Ala Asp Thr Ser Asn Gly Val Gly Arg Lys Leu
                85                  90                  95

Leu Gly Leu Asn Gln
            100

```
<210> SEQ ID NO 487
<211> LENGTH: 197
<212> TYPE: DNA
<213> ORGANISM: Brachypodium distachyon

<400> SEQUENCE: 487
atggccctga tcagtatcag caaagttgct ctccttgctg tgttaatcct ttcctctcag    60
atcatgtttt ctcctctgac caacggcgcg atcactccgg cagaagacca aggcctggtg   120
gggacggcgg acgatgttcg cccctcgaac cctggccaca gcccgggtat aggccatgca   180
ttcaccaaca acaaggt                                                  197

<210> SEQ ID NO 488
<211> LENGTH: 77
<212> TYPE: PRT
<213> ORGANISM: Brachypodium distachyon

<400> SEQUENCE: 488

Met Ala Leu Ile Ser Ile Ser Lys Val Ala Leu Leu Ala Val Leu Ile
1               5                   10                  15

Leu Ser Ser Gln Ile Met Phe Ser Pro Leu Thr Asn Gly Ala Ile Thr
            20                  25                  30

Pro Ala Glu Asp Gln Gly Leu Val Gly Thr Ala Asp Asp Val Arg Pro
        35                  40                  45

Ser Asn Pro Gly His Ser Pro Gly Ile Gly His Ala Phe Thr Asn Asn
    50                  55                  60

Lys Val Gly Arg Arg Leu Leu Ile Thr Ser Ala Arg Glu
65                  70                  75

<210> SEQ ID NO 489
<211> LENGTH: 198
<212> TYPE: DNA
<213> ORGANISM: Brachypodium distachyon

<400> SEQUENCE: 489
atggcaccta gcataagcaa gaacactaac acttgcactt gtgcattact actaattttt    60
gtagttctgt ctcccagct cgtggaatct cagagcaggt ctctgcccca tggcagcttg    120
atctctacca tgcatcggag atacttgtta tcgcatgtaa acggagcatc gcccaatgga   180
ctggccgagg gcgccgta                                                 198

<210> SEQ ID NO 490
<211> LENGTH: 193
<212> TYPE: DNA
<213> ORGANISM: Brachypodium distachyon

<400> SEQUENCE: 490
atggctggtt caaaggcttt gtgcatttgc attctcatct tcatcgtcat ctcgagccag    60
caggcggagg cgaggcggct aacgaaggtg gcggccacga gcaagagcga gctaggcgcg   120
ttgaaagatg atgggcaaag cttcaaagca agggcagggc aagacggcaa agccatgccg   180
atggcgacca cgg                                                      193

<210> SEQ ID NO 491
<211> LENGTH: 87
<212> TYPE: PRT
<213> ORGANISM: Brachypodium distachyon

<400> SEQUENCE: 491

Met Ala Gly Ser Lys Ala Leu Cys Ile Cys Ile Leu Ile Phe Ile Val
```

```
                1               5                      10                     15
Ile Ser Ser Gln Gln Ala Glu Ala Arg Arg Leu Thr Lys Val Ala Ala
                    20                      25                     30

Thr Ser Lys Ser Glu Leu Gly Ala Leu Lys Asp Asp Gly Gln Ser Phe
                    35                      40                     45

Lys Ala Arg Ala Gly Gln Asp Gly Lys Ala Met Pro Met Ala Thr Thr
                    50                      55                     60

Val Asp Ser Arg Ser Thr Ser Pro Gly Asn Ser Pro Gly Ile Gly Asn
 65                         70                      75                 80

Lys Gly Lys Thr Thr Asn Asn
                    85
```

<210> SEQ ID NO 492
<211> LENGTH: 194
<212> TYPE: DNA
<213> ORGANISM: Brachypodium distachyon

<400> SEQUENCE: 492

```
atggcaggtt ccaaggtatc aataccacca tgcacatgca ttctgatcgt cttgatggtg      60
tcgagccact tggtgcccgg cgaggcaagg aggcttatgg cctcggcaac aggcaacggc     120
gaggacgaag cctgcaaatc agcagcaggg tgccgcgccg tgcaaggcag tgtaaccttc     180
gcggcggcgg cgac                                                       194
```

<210> SEQ ID NO 493
<211> LENGTH: 95
<212> TYPE: PRT
<213> ORGANISM: Brachypodium distachyon

<400> SEQUENCE: 493

```
Met Ala Gly Ser Lys Val Ser Ile Pro Pro Cys Thr Cys Ile Leu Ile
 1               5                      10                     15

Val Leu Met Val Ser Ser His Leu Val Pro Gly Glu Ala Arg Arg Leu
                    20                      25                     30

Met Ala Ser Ala Thr Gly Asn Gly Glu Asp Glu Ala Cys Lys Ser Ala
                    35                      40                     45

Ala Gly Cys Arg Ala Val Gln Gly Ser Val Thr Phe Ala Ala Ala Ala
                    50                      55                     60

Thr Ala Lys Met Ala Thr Thr Asp Gly Arg Ser Thr Ala Pro Gly His
 65                         70                      75                 80

Ser Pro Gly Ile Gly Asn Lys Leu His Ala Ala Gly Asn Asp Arg
                    85                      90                     95
```

<210> SEQ ID NO 494
<211> LENGTH: 198
<212> TYPE: DNA
<213> ORGANISM: Oryza sativa

<400> SEQUENCE: 494

```
atggccaaca tttgcactat gctagctata cttgtgtttt ccctgcagct attttcttct      60
cagggcaggc ctttgcctga cgacgatggc atcacctctg aaatgcagat caggagatac     120
ctgttatcgc atggcaatgg agtggtcgag ggcgccgtgt cccctcgtc ggagattggc     180
ggtcccatgg tcggcgcc                                                   198
```

<210> SEQ ID NO 495
<211> LENGTH: 197
<212> TYPE: DNA

<213> ORGANISM: Oryza sativa

<400> SEQUENCE: 495

```
ctaaacaagt cttccaacag tattagcaaa gcttttttcc ttgtgctaat tattcttgcc      60
tctcaagtaa tgctttctca tggcatacct cttgagatgc ataggaggta cttattatcg     120
catgcagccg atgcaacaaa agggtgatg  gagggaacaa tcaccctac agaaggtgaa      180
ggatttgctg gggcaaa                                                    197
```

<210> SEQ ID NO 496
<211> LENGTH: 196
<212> TYPE: DNA
<213> ORGANISM: Oryza sativa

<400> SEQUENCE: 496

```
ctgaatctca tcttcgtcct tgggatcatc ttcttccttt cttccgacat gatcatcgtg      60
tgctcacagg gaagacctct cattgcggag gcggcggcg  cggcggcggc gcagcagcag     120
agacacctgc tatcgtcgtc gtcgtcggca ccgcgttccg gcggcgacgt cgaagaagct     180
gccgccggcg gcggca                                                    196
```

<210> SEQ ID NO 497
<211> LENGTH: 194
<212> TYPE: DNA
<213> ORGANISM: Oryza sativa

<400> SEQUENCE: 497

```
atggcaggtc tcaagctctc atcatgcgtt ctggtcgctt tgctcttcgt gtcgagccac      60
gttgtgcgcc acggcgaggc gaggcggctg actgcggggg tggcggcgcc ggcgagcaag     120
ggcggcgagg aggaggcgcc gcagtacgca tccgctcgag gcggccagcc ggcggctgct     180
gccggtggcg gcgt                                                      194
```

<210> SEQ ID NO 498
<211> LENGTH: 195
<212> TYPE: DNA
<213> ORGANISM: Oryza sativa

<400> SEQUENCE: 498

```
atggctggac acaaggtggt attctgcact tgcattctga tcttcatcgt cgtcgtcatc      60
tcaggccagg ccgaagcacg gcggctggcg gcggtggcca acggcaatga ggatgccgtc     120
gccgtggaag gtgacgggag cttcagagca gtgcaagaaa ctgcttcttc tgcgtcgact     180
gatcatgcag ctgca                                                     195
```

<210> SEQ ID NO 499
<211> LENGTH: 106
<212> TYPE: PRT
<213> ORGANISM: Oryza sativa

<400> SEQUENCE: 499

```
Met Ala Gly His Lys Val Val Phe Cys Thr Cys Ile Leu Ile Phe Ile
1               5                   10                  15

Val Val Val Ile Ser Gly Gln Ala Glu Ala Arg Arg Leu Ala Ala Val
            20                  25                  30

Ala Asn Gly Asn Glu Asp Ala Val Ala Val Glu Gly Asp Gly Ser Phe
        35                  40                  45

Arg Ala Val Gln Glu Thr Ala Ser Ser Ala Ser Thr Asp His Ala Ala
    50                  55                  60
```

Ala Gly Arg Gly Gly Gly Ala Ala Ala Val Gln Gly Ser Met
65              70              75              80

Pro Met Thr Thr Thr Asp Ser Arg Pro Thr Ala Pro Gly Asn Ser Pro
                85              90              95

Gly Ile Gly Asn Lys Gly Lys Ile Asn Asn
        100             105

<210> SEQ ID NO 500
<211> LENGTH: 198
<212> TYPE: DNA
<213> ORGANISM: Oryza sativa

<400> SEQUENCE: 500
atggccattt cgtcgaaaaa tgttgctgtg ttcatgttgc ttctgagtgt catcttttc      60 atgcagcgct ctgtgccagt tcatgcaagg aagctggtag tgagggcacc tatgatctgc    120
atgcatcctc catgcacacg gaggaatgcc ctggaggtgc agctgaaca agttgattca     180 accactccag gccatagc                                                   198

<210> SEQ ID NO 501
<211> LENGTH: 76
<212> TYPE: PRT
<213> ORGANISM: Oryza sativa

<400> SEQUENCE: 501

Met Ala Ile Ser Ser Lys Asn Val Ala Val Phe Met Leu Leu Leu Ser
1               5                   10                  15

Val Ile Phe Phe Met Gln Arg Ser Val Pro Val His Ala Arg Lys Leu
                20                  25                  30

Val Val Arg Ala Pro Met Ile Cys Met His Pro Pro Cys Thr Arg Arg
            35                  40                  45

Asn Ala Leu Glu Val Pro Ala Glu Gln Val Asp Ser Thr Thr Pro Gly
        50                  55                  60

His Ser Pro Ser Ile Gly His Asn Thr Pro Pro Asn
65                  70                  75

<210> SEQ ID NO 502
<211> LENGTH: 15
<212> TYPE: PRT
<213> ORGANISM: Brachypodium distachyon

<400> SEQUENCE: 502

Asp Val Arg Pro Ser Asn Pro Gly His Ser Pro Gly Ile Gly His
1               5                   10                  15

<210> SEQ ID NO 503
<211> LENGTH: 15
<212> TYPE: PRT
<213> ORGANISM: Brachypodium distachyon

<400> SEQUENCE: 503

Asp Ser Arg Ser Thr Ser Pro Gly Asn Ser Pro Gly Ile Gly Asn
1               5                   10                  15

<210> SEQ ID NO 504
<211> LENGTH: 15
<212> TYPE: PRT
<213> ORGANISM: Brachypodium distachyon

<400> SEQUENCE: 504

```
Asp Gly Arg Ser Thr Ala Pro Gly His Ser Pro Gly Ile Gly Asn
1               5                   10                  15

<210> SEQ ID NO 505
<211> LENGTH: 15
<212> TYPE: PRT
<213> ORGANISM: Arabidopsis thaliana

<400> SEQUENCE: 505

Asp Phe Gly Pro Thr Ser Pro Gly Asn Ser Pro Gly Val Gly His
1               5                   10                  15

<210> SEQ ID NO 506
<211> LENGTH: 15
<212> TYPE: PRT
<213> ORGANISM: Mimulus guttatus

<400> SEQUENCE: 506

Ser Tyr Arg Pro Thr Thr Pro Gly His Ser Pro Gly Ile Gly His
1               5                   10                  15

<210> SEQ ID NO 507
<211> LENGTH: 15
<212> TYPE: PRT
<213> ORGANISM: Meloidogyne hapla

<400> SEQUENCE: 507

Asp Phe Arg Pro Thr Asn Pro Gly His Ser Pro Gly Ile Gly His
1               5                   10                  15

<210> SEQ ID NO 508
<211> LENGTH: 13
<212> TYPE: PRT
<213> ORGANISM: Brachypodium distachyon

<400> SEQUENCE: 508

Asp Ser Thr Thr Pro Gly His Ser Pro Ser Ile Gly His
1               5                   10
```

METHOD FOR MODULATING PLANT GROWTH

CROSS REFERENCE TO RELATED APPLICATIONS

This application is a U.S. National Phase of PCT/AU2014/000975, filed on Oct. 16, 2014, which claims priority to Australian Application No. 2013903988, filed on Oct. 16, 2013, the disclosures of which are hereby incorporated by reference in their entirety.

SUBMISSION OF SEQUENCE LISTING ON ASCII TEXT FILE

The content of the following submission on an ASCII text file is incorporated herein by reference in its entirety: a computer readable form (CRF) of the Sequence Listing (file name: 284502002700SUBSEQLIST2.txt, date recorded: Feb. 5, 2018, size: 262 KB).

FIELD OF THE INVENTION

The present invention relates to methods and materials for modulating plant growth, with particular reference to above-ground plant growth, and continued growth under stress conditions.

BACKGROUND TO THE INVENTION

An *Arabidopsis* gene, AtCEP1 (C-terminal encoded peptide), encoding a 14 or 15 amino acid secreted ligand has been previously described and reported to influence primary root growth (Ohyama K, Ogawa M, and Matsubayashi Y (2008), "Identification of a biologically active, small, secreted peptide in *Arabidopsis* by in silica gene screening, followed by LC-MS-based structure analysis", *The Plant Journal* 55(1):152-160). AtCEP1 corresponds to 1 CEP1 according to the nomenclature used herein.

In International patent publication no. WO 2013/104026, the entire disclosure of which is incorporated herein by cross-reference, we previously reported studies wherein a number of CEP peptides were identified across a broad range of plant families (angiosperms and gymnosperms), and some of these characterised. Phylogenetic and genetic tools were used to examine the distribution and function of this multigene family, and analyses indicated that this family of genes is unique to higher plants and, surprisingly, occur in root knot nematode (RKN) genomes. Generally, these genes encode secreted peptides that contain 14-15 amino acid long conserved domains. Over-expression studies were used to demonstrate that CEP peptides affect multiple aspects of root architecture and development including lateral root, nodule and root hair development, as well as shoot to root ratio.

SUMMARY OF THE INVENTION

The present investigations have surprisingly shown that CEP regulatory peptides not only affect the root architecture of plants, including nodule formation and competency thereof, but also significantly affect non-root plant growth, including increasing and/or accelerating non-root plant growth, development, or both, especially under sub-optimal conditions.

Thus, according to an aspect of the invention, there is provided a method for modulating non-root plant growth, said method comprising:

(a) contacting the leaves, shoots, stems or any combination thereof of said plant with a C-terminal encoded peptide (CEP), an analogue thereof or a CEP signaling agonist; or (b) contacting the leaves, shoots, stems or any combination thereof of said plant with a CEP signaling antagonist; or (c) introducing at least one mutation or exogenous nucleic acid into one or more plant cells which results in modulated CEP expression by cells of a plant regenerated from or comprising said one or more plant cells; or (d) introducing at least one mutation or exogenous nucleic acid into one or more plant cells which results in modulated CEP receptor expression by cells of a plant regenerated from or comprising said one or more plant cells; or (e) introducing at least one mutation or exogenous nucleic acid into one or more plant cells which results in modulated affinity of one or more CEPs for their respective CEP receptors, which modulated affinity arises through modifications in the CEP(s), CEP receptor(s) or in both expressed CEP(s) and CEP receptor(s).

According to another embodiment of this aspect, the present invention provides a method for increasing shoot growth or accelerating shoot development of a plant relative to an untreated or wild-type plant, comprising contacting the leaves, shoots, stems or any combination thereof of said plant with a CEP antagonist or introducing at least one mutation or at least one exogenous nucleic acid into one or more plant cells which at least one mutation or nucleic acid results in:

(i) decreased expression of one or more CEPs, decreased expression of one or more CEP receptors, or decreased expression of one or more CEPs and one or more CEP receptors by cells of a plant regenerated from or comprising said one or more plant cells, wherein said decreased expression of said CEP(s) or CEP receptor(s) occurs under conditions which would otherwise promote expression of said CEP(s) or CEP receptor(s); or (ii) reduced affinity of one or more CEPs for their respective CEP receptors, which reduced affinity arises through modifications in the CEP(s), CEP receptor(s) or in both expressed CEP(s) and CEP receptor(s) expressed by cells of a plant regenerated from or comprising said one or more plant cells.

According to an embodiment, the CEP comprises an amino acid sequence selected from SEQ ID NOs 2, 4, 6, 8, 10, 12, 14, 16, 18, 20, 22, 24, 26, 28, 30, 32, 34, 36 to 147, 338-350, 365, 367, 369, 371, 373, 375, 377, 379, 381, 383, 385, 387 to 395, 468, 470, 472, 474, 476, 478, 480, 482, 484, 486, 488, 491, 493, 499 or 501, or comprises a CEP domain having an amino acid sequence selected from SEQ ID Nos: 148 to 336, 351-363, 396-415, 451-453, 455-466 or 502-504, or is encoded by a nucleic acid comprising a nucleotide sequence selected from SEQ ID NOs 1, 3, 5, 7, 9, 11, 13, 15, 17, 19, 21, 23, 25, 27, 29, 31, 33, 35, 337, 364, 366, 368, 370, 372, 374, 376, 378, 380, 382, 384, 386, 467, 469, 471, 473, 475, 477, 479, 481, 483, 485, 487, 489, 490, 492, 494-498 or 500.

According to another embodiment, the CEP comprises an amino acid sequence selected from SEQ ID NOs 2, 4, 6, 8, 10, 12, 14, 16, 18, 20, 22, 24, 26, 28, 30, 32, 34, 36 to 147, 338-350, 468, 470, 472, 474, 476, 478, 480, 482, 484, 486, 488, 491, 493, 499 or 501, or comprises a CEP domain having an amino acid sequence selected from SEQ ID Nos: 148-336, 351-363, 451, 452, 455-466 or 502-504, or is encoded by a nucleic acid comprising a nucleotide sequence selected from SEQ ID NOs 1, 3, 5, 7, 9, 11, 13, 15, 17, 19, 21, 23, 25, 27, 29, 31, 33, 35, 337, 467, 469, 471, 473, 475, 477, 479, 481, 483, 485, 487, 489, 490, 492, 494-498 or 500.

According to another embodiment, the CEP comprises a CEP domain comprising an amino acid sequence $(X_1)_nX_2X_3X_4X_5X_6PGX_9SPGX_{13}GX_{15}$ (SEQ ID NO: 454), wherein:

n may be 0 or 1
$X_1$ is selected from D, G, P, A, S, L, E and V;
$X_2$ is selected from F, V, R, T, S, A, K and Y;
$X_3$ is selected from R, K, E, H, Q, S, P, D, V, G, and A;
$X_4$ is selected from P, S and G;
$X_5$ is selected from T, S and G;
$X_6$ is selected from N, A, T, G, P, D, K and S;
$X_9$ is selected from N, H, Y and S;
$X_{13}$ is selected from I, A and V; and
$X_{15}$ is selected from N and H;

wherein the amino acid at position 6, if threonine or serine, may be phosphorylated; the P at position 11, a P at position 7, a P at position 4, or any combination of such prolines may be hydroxylated; and tyrosine residues may be sulphonated. Any hydroxylated proline may be arabinosylated, such as mono-, di- or tri-arabinosylated. According to an embodiment a hydroxylated proline at position 11 is arabinosylated, optionally mono-, di- or tri-arabinosylated.

According to certain methods of the invention, the plants yield a greater amount of above-ground plant matter than an untreated or wild-type plant grown under the same conditions. According to other embodiments, the plants grow faster than an untreated or wild-type plant grown under the same conditions. According to other embodiments, the plants develop faster than an untreated or wild-type plant grown under the same conditions. In these embodiments, the conditions may comprise stress conditions and, according to a further embodiment, the stress conditions are abiotic and may further comprise stresses selected from the group comprising increased salinity, drought, nitrogen limitation and pH stress.

Plants obtained by the methods outlined above, and plant parts (including leaves, stems, roots, tubers, flowers, fruit, seeds and parts thereof) are also provided. According to an embodiment, the plants yield a greater amount of above-ground plant matter than an untreated or wild-type plant grown under the same conditions. According to another embodiment, the plants grow faster than an untreated or wild-type plant grown under the same conditions. According to another embodiment, the plants develop faster than an untreated or wild-type plant grown under the same conditions. In these embodiments, the conditions may comprise stress conditions and, according to a further embodiment, the stress conditions are abiotic and may further comprise stresses selected from the group comprising increased salinity, drought, nitrogen limitation and pH stress.

BRIEF DESCRIPTION OF THE DRAWINGS

FIG. 3—Amino acid sequence alignment of 11 putative CEP-coding genes in *M. truncatula*. All 11 sequences (again, labelled as RARs due to previous nomenclature) have predicted signal peptides at the N-terminus (boxed in blue), an intervening variable region of little or no sequence conservation and 15 amino acid long conserved region(s) close to the C-terminus end. CEP domains are boxed in red. Note some CEPs have more than one CEP domain (e.g. MtCEP10 has four CEP peptide motifs whereas MtCEP7, 9 and 1 each have two).

FIG. 4—Alignment of selected group I CEP domains from plants with root knot nematode CEPs. Amino acid sequences of (A) *M. incognita* CEP3, *Ricinus communis* CEP3, RcCEP11 and *Jatropha curcas* CEP1 and (B) *Meloidogyne hapla* CEP2, MhCEP11 and *Euphorbia esula* CEP2 domains, aligned using Geneious.

FIG. 5—Alignments of CEP domains and full length CEP preproproteins. Amino acid sequences of selected (A) CEP domains and (B-C) CEP preproproteins were aligned using Geneious.

DEFINITIONS

Figure 1:
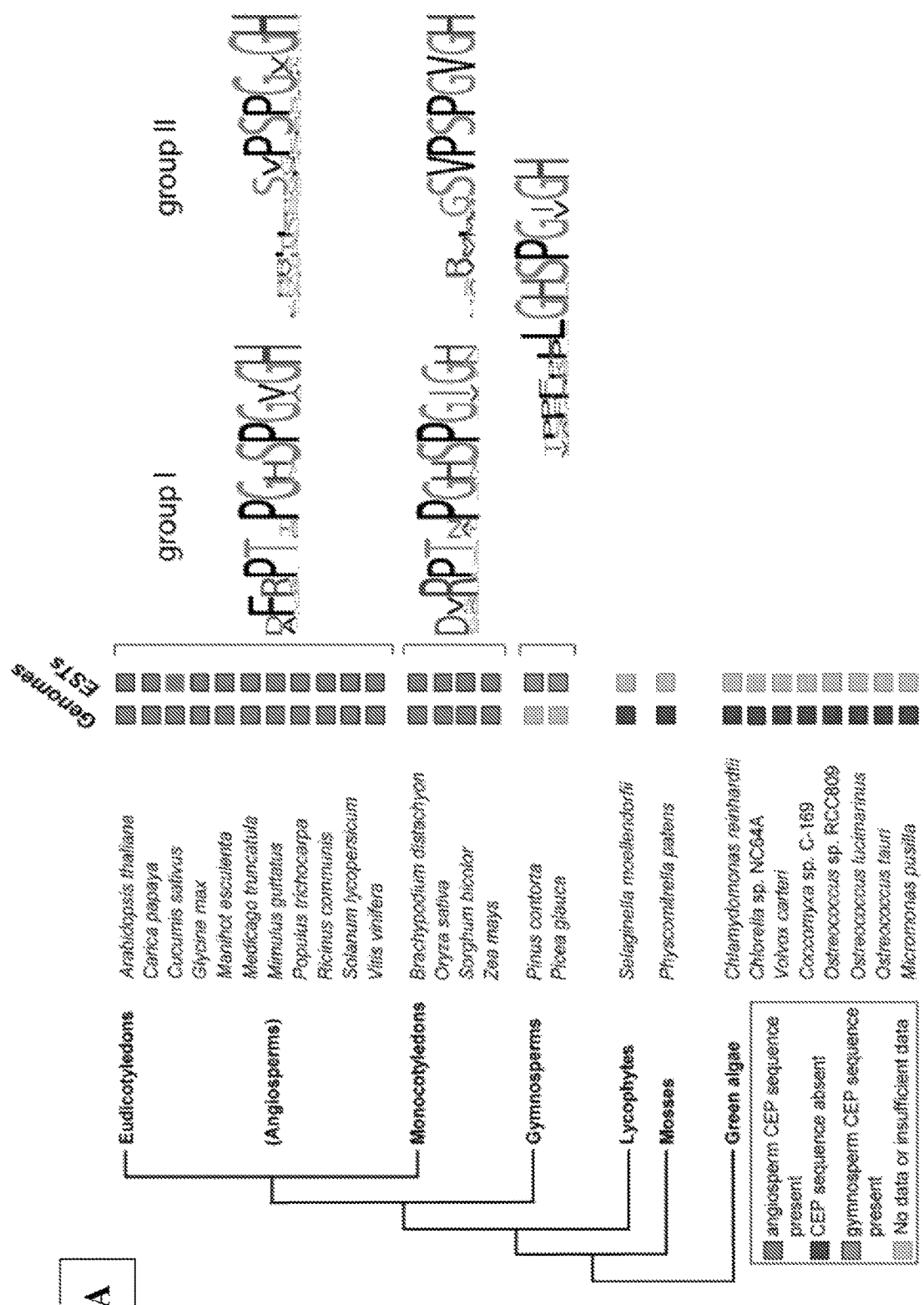
FIG. 1—CEP peptide ligands (identified as RARs due to previous nomenclature) occur in higher plants and RKNs. (A) Weblogo plots (graphical representations of an amino acid multiple sequence alignments. ach logo consists of stacks of symbols, one stack for each position in the sequence. The overall height of the stack indicates the sequence conservation at that position, while the height of symbols within the stack indicates the relative frequency of each amino or nucleic acid at that position) show the 15 AA CEP peptides each with particularly strong C-terminal conservation. Angiosperm (Weblogo plots generated from sequence alignments for SEQ ID NOs: 148-336, 455-466, 502-506 and 508) and RKN CEP peptides (the latter not shown) show strong similarity. Gymnosperm CEP-like peptides (SEQ ID NOs: 351-363) exhibit divergence at the amino-terminus with a highly conserved leucine instead of proline at position 7. Unlike dicot CEPs (SEQ ID NOs: 148-300, 455-466, 505 and 506), monocot CEPs (SEQ ID NOs: 301-336, 502-504 and 508), with few exceptions, do not contain F at position 2. (B) Putative MtCEP1 protein sequence. The amino-terminal signal sequence is blue and the conserved CEP (ligand A—SEQ ID NO: 166; ligand B—SEQ ID NO: 167) peptides are red. Non-conserved sequences are green. (C, D) Putative MhCEP1 and MiCEP1 proteins. Two forms of CEPs exist: the first has sequences flanking the CEP peptide (e.g. MhCEP1—SEQ ID NO: 507, C) and the second has no flanking sequences (e.g. MiCEP1—SEQ ID NO: 410; D).
Figure 1:
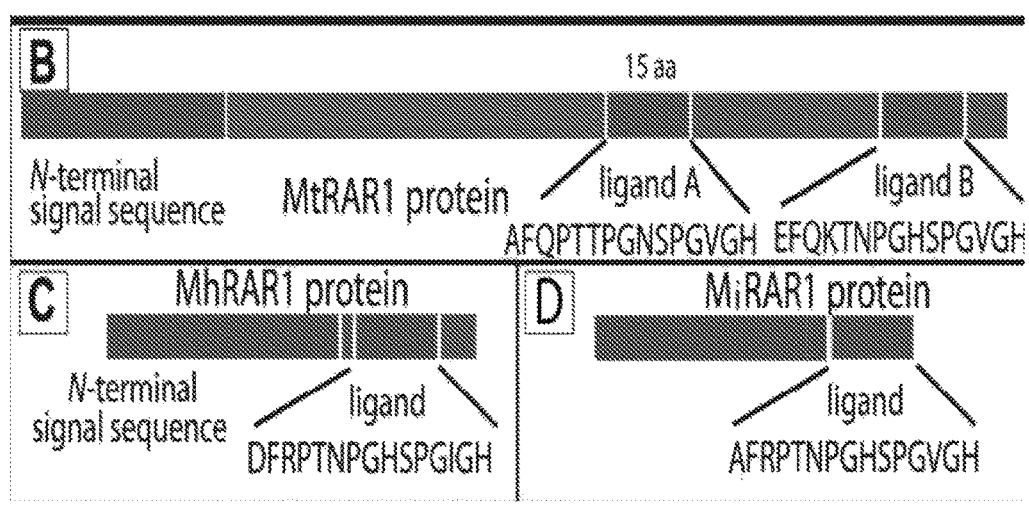

As used herein, the term "comprising" means "including principally, but not necessarily solely". Variations of the word "comprising", such as "comprise" and "comprises", have correspondingly similar meanings.

As used herein the term "gene", refers to a defined region that is located within a genome and that may comprise regulatory, nucleic acid sequences responsible for the control of expression, i.e., transcription and translation of the coding portion. A gene may also comprise other 5' and 3' untranslated sequences and termination sequences. Further elements that may be present are, for example, introns and coding sequences.

As used herein, the term "analogue" in the context of a peptide or protein means an artificial or natural substance that resembles the peptide or protein in function. For example, a CEP analogue will bind a CEP receptor and thereby bring about the same or similar result as if a natural CEP had bound to the receptor. In an embodiment such analogues may also resemble the CEP peptide in structure. Analogues contemplated in an embodiment of the present invention include fully or partially peptidomimetic compounds as well as peptides or proteins resembling a subject peptide in activity but comprising addition, deletion, or substitution of one or more amino acids compared to the subject peptide or protein. The term "analogue" as used herein with reference to nucleotide sequences encompasses sequences comprising addition, deletion, or substitution (including conservative amino acid substitutions) of one or more bases relative to a subject nucleotide sequence, wherein the encoded polypeptide resembles the polypeptide encoded by the subject nucleic acid molecule in function.

As used herein, the term "homologue" in the context of proteins means proteins having substantially the same functions and similar properties in different species, and which, within at least regions, share at least 50% amino acid identity. Such homologous proteins may share, over their entire amino acid sequences, at least about 30% amino acid identity, at least about 40% amino acid identity, at least about 50% amino acid identity, at least about 60% amino acid identity, at least about 70% amino acid identity, at least about 80% amino acid identity, at least about 90% amino acid identity or at least about 95% identity. Similarly, homologues of nucleic acid molecules are nucleic acid molecules that encode proteins having substantially the same functions and similar properties in different species, wherein the encoded proteins share, within at least regions, at least 50% amino acid identity (such nucleic acid homologues may share significantly less than 50% identity due to degeneracy in the genetic code, and differences in preferred codon usage amongst different genuses and species), and may share at least about 30%/o amino acid identity, at least about 40% amino acid identity, at least about 50% S amino acid identity, at least about 60% amino acid identity, at least about 70% amino acid identity, at least about 80% amino acid identity, at least about 90% amino acid identity or at least about 95% identity over the whole encoded amino acid sequences.

"Conservative amino acid substitutions" refer to the interchangeability of residues having similar side chains. For example, a group of amino acids having aliphatic side chains includes glycine, alanine, valine, leucine, and isoleucine; a group of amino acids having aliphatic-hydroxyl side chains includes serine and threonine; a group of amino acids having amide-containing side chains includes asparagine and glutamine; a group of amino acids having aromatic side chains includes phenylalanine, tyrosine, and tryptophan; a group of amino acids having basic side chains includes lysine, arginine, and histidine; and a group of amino acids having sulfur-containing side chains includes cysteine and methionine. Typically, conservative amino acids substitution groups are: valine-leucine-isoleucine, phenylalanine-tyrosine, lysine-arginine, alanine-valine, and asparagine-glutamine. Typically, conservative amino acid substitution(s) will result in a protein or polypeptide retaining at least some of the biological activity of the protein or polypeptide without such a conservative amino acid substitution. More typically, conservative amino acid substitution(s) will result in a protein or polypeptide having substantially the same, or at least comparable biological activity as the protein or polypeptide without such a conservative amino acid substitution. Conservative amino acid substitution(s) may result in proteins or polypeptides having greater biological activity than the protein or polypeptide without such a conservative amino acid substitution.

The term "isolated" indicates that the material in question has been removed from its naturally existing environment, and associated impurities reduced or eliminated. Essentially, the 'isolated' material is enriched with respect to other materials extracted from the same source (ie., on a molar basis it is more abundant than any other of the individual species extracted from a given source), and preferably a substantially purified fraction is a composition wherein the 'isolated' material comprises at least about 30 percent (on a molar basis) of all macromolecular species present. Generally, a substantially pure composition of the material will comprise more than about 80 to 90 percent of the total of macromolecular species present in the composition. Most preferably, the 'isolated' material is purified to essential homogeneity (contaminant species cannot be detected in the composition by conventional detection methods) wherein the composition consists essentially of the subject macromolecular species.

As used herein, the term "agonist" in the context of a peptide, polypeptide or protein refers to a molecule that binds with a receptor for that peptide, polypeptide or protein to trigger a physiological response usually triggered by the peptide, polypeptide or protein when it binds to said receptor. For example, a CEP agonist is a molecule that binds to a CEP receptor to trigger a shoot growth modulation or root architectural response.

As used herein, the term "antagonist" in the context of a peptide, polypeptide or protein refers to a substance that interferes with the physiological response usually triggered by the peptide, polypeptide or protein when it binds to said receptor, or which interferes with binding of said peptide, polypeptide or protein to its receptor. For example, a CEP antagonist may be a substance that binds to a CEP or a CEP receptor to inhibit interaction between the CEP and the CEP receptor, which interaction would trigger a shoot growth modulation or root architectural response. CEP antagonists may include antibodies to CEPs or CEP receptors.

As used herein, the term "mutation" means any change in a polypeptide or nucleic acid molecule relative to a wild-type polypeptide or nucleic acid molecule from which the 'mutant' is derived and may, for example, comprise single or multiple amino acid or nucleotide changes, or both nucleotide and amino acid changes, including point mutations, null mutations, frame-shift mutations, and may comprise deletions, or insertions, or substitutions of one or more nucleic acids or amino acids, which may comprise naturally or non-naturally occurring nucleotides or amino acids or analogues thereof.

A "nucleic acid", as referred to herein, refers to deoxyribonucleotides or ribonucleotides and polymers thereof in either single-, double-stranded or triplexed form. The term may encompass nucleic acids containing known analogues of natural nucleotides having similar binding properties as the reference nucleic acid. A particular nucleic acid sequence may also implicitly encompass conservatively modified variants thereof (e.g. degenerate codon substitutions) and complementary sequences. The terms "nucleic acid", "nucleic acid sequence" or "polynucleotide" may also be used interchangeably with gene, cDNA, and mRNA encoded by a gene.

The terms "polypeptide", "peptide" and "protein" may be used interchangeably herein to refer to a polymer of amino acid residues. Included within the scope of these terms are polymers in which one or more amino acid residues may comprise artificial chemical analogue(s) of corresponding naturally occurring amino acid(s), as well as, or instead of naturally occurring amino acid polymers. The terms "polypeptide", "peptide" and "protein" may also include polymers including modifications, including post-translational modifications, such as, but not limited to, glycosylation (including arabinosylation), lipid attachment, sulfation, phosphorylation, gamma-carboxylation of glutamic acid residues, hydroxylation and ADP-ribosylation. Modified amino-acids may include further modifications. For example, hydroxylated residues may be glycosylated, such as arabinosylated hydroxyproline residues.

The term "primer" as used herein means a single-stranded oligonucleotide capable of acting as a point of initiation of template-directed DNA synthesis. An "oligonucleotide" is a short nucleic acid, typically ranging in length from 2 to about 500 bases. The precise length of a primer will vary according to the particular application, but typically ranges from 15 to 30 nucleotides. A primer need not reflect the exact sequence of the template but must be sufficiently complementary to hybridize to the template.

Within the scope of the terms "protein", "polypeptide", "polynucleotide" and "nucleic acid" as used herein are fragments and variants thereof, including but not limited to reverse compliment and antisense forms of polynucleotides and nucleic acids.

DETAILED DESCRIPTION OF THE INVENTION

Cell-to-cell communication mechanisms coordinate cellular proliferation and differentiation in plants. Recently, new signal molecules have emerged that preside over the positional information required to co-ordinate plant growth. Amongst these are growth regulating peptides that act primarily as extracellular signals. Growth regulating plant peptides regulate all aspects of plant growth and development. The CLE (CLAVATA3/EMBRYO SURROUNDING REGION-related) peptides are well understood: different classes of plant CLEs regulate the differentiation and renewal of stem cell and control the developmental competency of legume roots for root nodule formation. Similarly, root growth factors (RGFs) are regulatory peptides that maintain the stem cell niche and transit cell proliferation.

The CEP (C-TERMINALLY ENCODED PEPTIDE) family was discovered using an in silico approach (Ohyama K, Ogawa M, and Matsubayashi Y (2008), "Identification of a biologically active, small, secreted peptide in *Arabidopsis* by in silico gene screening, followed by LC-MS-based structure analysis", *The Plant Journal* 55(1):152-160). The founding five members of this family in *Arabidopsis* were characterized by a conserved 15 amino acid peptide domain at or near the C-terminus. The mature product was shown to be a 14 or 15 amino acid peptide containing one or two hyroxylated proline residues and the 15 amino acid peptide was reported to be biologically active on roots. Overexpression of AtCEP1, which was mainly expressed in the shoot apical meristem and lateral root primordia during development, resulted in reduced primary and lateral root elongation as well as a smaller shoot system. Confocal imaging showed that CEP1 over-expression roots had a reduced number of meristem cells (Ohyama et al., 2008). AtCEP1 corresponds to CEP1 according to the nomenclature used herein.

Aside from the above study on CEP1, little is known about the CEP family. This includes their distribution beyond *Arabidopsis*, what controls CEP expression, the roles of different CEP family members in *Arabidopsis*, their molecular mode-of-action and mutant studies.

In the present studies, a number of CEP peptides have been identified across a broad range of plant families (angiosperms and gymnosperms), and some of these characterised. Phylogenetic and genetic tools were used to examine the distribution and function of this multigene family, and analyses indicate that this family of genes is unique to higher plants and, surprisingly, occur in root knot nematode (RKN) genomes as well. Generally, these genes encode secreted peptides that contain 14-15 amino acid long conserved domains. It has been found that CEP expression is regulated by environmental cues such as nitrogen limitation, increased salt levels, increased osmotic strength and increased $CO_2$ levels in both roots and shoots. Analysis of synthetic CEP variants showed that both peptide sequence and modifications of key amino acids affect CEP biological activity. Over-expression of several CEP genes gave differing root and shoot phenotypes. A cep3 knockout mutant showed enhanced root growth under a range of environmental conditions and enhanced shoot growth when grown hydroponically. We show that CEPs decrease lateral root formation and slow primary root growth. Collectively, the results indicate CEPs mediate developmental pathways, both in roots and above-ground (or 'non-root') plant parts, in response to environmental cues.

The present invention relates to methods for modulating plant growth, to create plants which, compared to untreated or unmodified plants, have modulated above-ground biomass yield and/or modulated development timelines. In embodiments, such changes occur under sub-optimal growth conditions. Thus, in embodiments, the plants yield a greater amount of above-ground plant matter than an untreated or wild-type plant grown under the same conditions. According to another embodiment, the plants grow faster than an untreated or wild-type plant grown under the same conditions. According to another embodiment, the plants develop faster than an untreated or wild-type plant grown under the same conditions. In these embodiments, the conditions may comprise stress conditions and, according to a further embodiment, the stress conditions are abiotic and may further comprise stresses selected from the group comprising increased salinity, drought, nitrogen limitation and pH stress.

CEPs and Encoding Nucleic Acids and Genes

Herein described are CEPs from a wide range of plants, including gymnosperms and angiosperms, as well as root knot nematodes (RKNs), as well as their encoding nucleotides. Previously described *Arabidopsis thaliana* CEP1 and its encoding nucleotide sequence is excluded from CEP peptides and encoding nucleotides according to the invention per se, but may be used in methods of the invention for modulation of non-root plant growth.

The CEPs may broadly have features as shown in FIG. 1A and/or comprise an amino acid sequence as set forth in SEQ ID NO:454. According to an embodiment, the CEP may comprise an amino acid sequence selected from SEQ ID NOs: 2, 4, 6, 8, 10, 12, 14, 16, 18, 20, 22, 24, 26, 28, 30, 32, 34, 36 to 147, 338-350, 365, 367, 369, 371, 373, 375, 377, 379, 381, 383, 385, 387-395, 468, 470, 472, 474, 476, 478, 480 482, 484, 486, 488, 491, 493, 499 or 501, or a CEP domain having an amino acid sequence selected from SEQ ID Nos: 148-336, 351-363, 396-415, 451-453, 455-466 or 502 to 504, or may comprise an amino acid sequence sharing at least 60% identity, at least 70% identity, at least 80% identity, at least 85% identity, at least 90% identity, at least 95% identity, or at least 99% identity with said amino acid sequences.

According to another embodiment, the CEP may comprise an amino acid sequence selected from any one of SEQ ID Nos: 2, 4, 6, 8, 10, 12, 14, 16, 18, 20, 22, 24, 26, 28, 30, 32, 34, 36 to 124, 126 to 147, 338-350, 365, 367, 369, 371, 373, 375, 377, 379, 381, 383, 385, 387-395, 468, 470, 472, 474, 476, 478, 480 or 482, or a CEP domain having an amino acid sequence selected from SEQ ID Nos: 148 to 336, 351 to 363, 396 to 415, 451 to 453 or 455 to 466, or a sequence sharing at least about 60% identity, at least 70% identity, at least 80% identity, at least 85% identity, at least 90% identity, at least 95% identity, or at least 99% identity with said amino acid sequences.

According to another embodiment, the CEP may comprise an amino acid sequence selected from any one of SEQ ID Nos: 10, 14, 16, 18, 20, 22, 24, 26, 28, 30, 32, 34, 36 to 124, 126 to 147, 338 to 350, 365, 367, 369, 371, 373, 375, 377, 379, 381, 383, 385, 387 to 395, 468, 470, 472, 474, 476, 478, 480 or 482, or a CEP domain having an amino acid sequence selected from SEQ ID Nos: 152 to 155, 157 to 336, 351 to 363, 396 to 415, 451 to 453 or 455 to 466, or a sequence sharing at least about 60% identity, at least 70% identity, at least 80% identity, at least 85% identity, at least 90% identity, at least 95% identity, or at least 99% identity with said amino acid sequences.

According to another embodiment, the CEP may comprise an amino acid sequence selected from any one of SEQ ID Nos: 16, 18, 20, 22, 24, 26, 28, 30, 32, 34, 36 to 124, 126 to 147, or 338 to 350, 365, 367, 369, 371, 373, 375, 377, 379, 381, 383, 385, 387 to 395, or a CEP domain having an amino acid sequence selected from SEQ ID Nos: 152 to 155, 157 to 336, 351 to 363, 396 to 415 or 451 to 453, or a sequence sharing at least about 60% identity, at least 70% identity, at least 80% identity, at least 85% identity, at least 90% identity, at least 95% identity, or at least 99/o identity with said amino acid sequences.

According to another embodiment, the CEP may comprise an amino acid sequence selected from any one of SEQ ID Nos: 16, 18, 20, 22, 24, 26, 28, 30, 32, 34, 36 to 124, 126 to 147, 365, 367, 369, 371, 373, 375, 377, 379, 381, 383, 385, 387 to 395, or a CEP domain having an amino acid sequence selected from SEQ ID Nos: 159 to 336, 396 to 415 or 451 to 453, or a sequence sharing at least about 60% identity, at least 70% identity, at least 80% identity, at least 85% identity, at least 90% identity, at least 95% identity, or at least 99% identity with said amino acid sequences.

CEP peptides according to the invention may include modifications to one or more of the amino acids. Such modifications may include natural modifications, such as post-translational modifications, including, for example, phosphorylation, hydroxylation, sulphonation and glycosylation. Such modifications may also be artificially created or instigated. According to an embodiment, a CEP peptide may comprise such modifications. For example, a CEP peptide as discussed herein may comprise phosphorylation of one or more threonine or serine residues, where present, hydroxylation of one or more proline residues, such as at positions 4, 7, 11 of SEQ ID NO: 454, or any combination thereof, where present, and sulphonation of the tyrosine at position 2, or at any other position when present, especially when preceded by aspartic acid. According to an embodiment, hydroxylated residues may be further modified. For example, hydroxylated prolines may be glycosylated. According to an embodiment, hydroxylated proline residues may be arabinosylated. According to a further embodiment, a hydroxylated proline at position 11 may be mono-, di- or tri-arabinosylated.

According to another embodiment, the CEP-encoding nucleic acid may comprise a nucleotide sequence selected from SEQ ID NOs 1, 3, 5, 7, 9, 11, 13, 15, 17, 19, 21, 23, 25, 27, 29, 31, 33, 35, 364, 366, 368, 370, 372, 374, 376, 378, 380, 382, 384, 386, 467, 469, 471, 473, 475, 477, 479 481, 483, 485, 487, 489, 490, 492, 494 to 498 or 500, or may comprise a nucleotide sequence sharing at least 60% identity, at least 70% identity, at least 80% identity, at least 85% identity, at least 90% identity, at least 95% identity, or at least 99% identity with a nucleotide sequence selected from SEQ ID NOs 1, 3, 5, 7, 9, 11, 13, 15, 17, 19, 21, 23, 25, 27, 29, 31, 33, 35, 364, 366, 368, 370, 372, 374, 376, 378, 380, 382, 384, 386, 467, 469, 471, 473, 475, 477, 479, 481, 483, 485, 487, 489, 490, 492, 494 to 498 or 500.

According to another embodiment, the CEP-encoding nucleic acid may comprise a nucleotide sequence selected from SEQ ID NOs 1, 3, 5, 7, 9, 11, 13, 15, 17, 19, 21, 23, 25, 27, 29, 31, 33, 35, 364, 366, 368, 370, 372, 374, 376, 378, 380, 382, 384, 386, 467, 469, 471, 473, 475, 477, 479 or 481, or may comprise a nucleotide sequence sharing at least 60% identity, at least 70% identity, at least 80% identity, at least 85% identity, at least 90% identity, at least 95% identity, or at least 99% identity with said nucleotide sequences.

According to another embodiment, the CEP-encoding nucleic acid may comprise a nucleotide sequence selected from SEQ ID NOs 9, 13, 15, 17, 19, 21, 23, 25, 27, 29, 31, 33, 35, 364, 366, 368, 370, 372, 374, 376, 378, 380, 382, 384, 386, 467, 469, 471, 473, 475, 477, 479 or 481, or may comprise a nucleotide sequence sharing at least 60% identity, at least 70% identity, at least 80% identity, at least 85% identity, at least 90% identity, at least 95% identity, or at least 99% identity with said nucleotide sequences.

According to another embodiment, the CEP-encoding nucleic acid may comprise a nucleotide sequence selected from SEQ ID NOs 15, 17, 19, 21, 23, 25, 27, 29, 31, 33, 35, 364, 366, 368, 370, 372, 374, 376, 378, 380, 382, 384, and 386, or may comprise a nucleotide sequence sharing at least 60% identity, at least 70% identity, at least 80% identity, at least 85% identity, at least 90% identity, at least 95% identity, or at least 99% identity with said nucleotide sequences.

According to another embodiment, the CEP is a plant CEP. According to a further embodiment, the plant CEP may comprise an amino acid sequence selected from SEQ ID NOs 2, 4, 6, 8, 10, 12, 14, 16, 18, 20, 22, 24, 26, 28, 30, 32, 34, 36 to 147, 338-350, 468, 470, 472, 474, 476, 478, 480, 482, 484, 486, 488, 491, 493, 499 or 501, or comprise a CEP domain having an amino acid sequence selected from SEQ ID Nos: 148-336, 351-363, 451, 452, 455 to 466 or 502 to 504, or may comprise an amino acid sequence sharing at least 60% identity, at least 70% identity, at least 80% identity, at least 85% identity, at least 90% identity, at least 95% identity, or at least 99% identity with said amino acid sequences.

According to another embodiment, the CEP may comprise an amino acid sequence selected from any one of SEQ ID Nos: 2, 4, 6, 8, 10, 12, 14, 16, 18, 20, 22, 24, 26, 28, 30, 32, 34, 36 to 124, 126 to 147, 338 to 350, 468, 470, 472, 474, 476, 478, 480 or 482, or a CEP domain having an amino acid sequence selected from SEQ ID Nos: 148-336, 351 to 363, 396 to 415, 451, 452 or 455 to 466, or a sequence sharing at least about 60% identity, at least 70% identity, at least 80% identity, at least 85% identity, at least 90% identity, at least 95% identity, or at least 99% identity with said amino acid sequences.

According to another embodiment, the CEP may comprise an amino acid sequence selected from any one of SEQ ID Nos: 10, 14, 16, 18, 20, 22, 24, 26, 28, 30, 32, 34, 36 to 124, 126 to 147, 338 to 350, 468, 470, 472, 474, 476, 478, 480 or 482, or a CEP domain having an amino acid sequence selected from SEQ ID Nos: 152 to 155, 157 to 336, 351 to 363, 451, 452 or 455 to 466, or a sequence sharing at least about 60% identity, at least 70% identity, at least 80% identity, at least 85% identity, at least 90% identity, at least 95% identity, or at least 99% identity with said amino acid sequences.

According to another embodiment, the CEP may comprise an amino acid sequence selected from any one of SEQ ID Nos: 16, 18, 20, 22, 24, 26, 28, 30, 32, 34, 36 to 124, 126 to 147, or 338-350, or a CEP domain having an amino acid sequence selected from SEQ ID Nos: 152 to 155, 157 to 336, 351 to 363, 451 or 452, or a sequence sharing at least about 60% identity, at least 70% identity, at least 80% identity, at least 85% identity, at least 90% identity, at least 95% identity, or at least 99% identity with said amino acid sequences.

According to another embodiment, the CEP may comprise an amino acid sequence selected from any one of SEQ ID Nos: 16, 18, 20, 22, 24, 26, 28, 30, 32, 34, 36 to 124, 126 to 147, or a CEP domain having an amino acid sequence selected from SEQ ID Nos: 159 to 336, 451 or 452, or a sequence sharing at least about 60% identity, at least 70% identity, at least 80% identity, at least 85% identity, at least 90% identity, at least 95% identity, or at least 99% identity with said amino acid sequences.

According to another embodiment, the CEP may comprise an amino acid sequence selected from any one of SEQ ID NOs: 150, 151, 156 and 310, or a sequence sharing at least at least 60% identity, at least 70% identity, at least 80% identity, at least 85% identity, at least 90% identity, at least 95% identity, or at least 99% identity with said amino acid sequences.

According to another embodiment, the plant CEP-encoding nucleic acid may comprise a nucleotide sequence selected from SEQ ID NOs 1, 3, 5, 7, 9, 11, 13, 15, 17, 19, 21, 23, 25, 27, 29, 31, 33, 35, 467, 469, 471, 473, 475, 477, 479, 481, 483, 485, 487, 489, 490, 492, 494 to 498 or 500, or may comprise a nucleotide sequence sharing at least 60% identity, at least 70% identity, at least 80% identity, at least 85% identity, at least 90% identity, at least 95% identity, or at least 99% identity with a nucleotide sequence selected from SEQ ID NOs 1, 3, 5, 7, 9, 11, 13, 15, 17, 19, 21, 23, 25, 27, 29, 31, 33, 35, 467, 469, 471, 473, 475, 477, 479, 481, 483, 485, 487, 489, 490, 492, 494 to 498 or 500.

According to another embodiment, the plant CEP-encoding nucleic acid may comprise a nucleotide sequence selected from SEQ ID NOs 1, 3, 5, 7, 9, 11, 13, 15, 17, 19, 21, 23, 25, 27, 29, 31, 33, 35, 467, 469, 471, 473, 475, 477, 479 or 481, or may comprise a nucleotide sequence sharing at least 60% identity, at least 70% identity, at least 80% identity, at least 85% identity, at least 90% identity, at least 95% identity, or at least 99% identity with said nucleotide sequences.

According to another embodiment, the plant CEP-encoding nucleic acid may comprise a nucleotide sequence selected from SEQ ID NOs 9, 13, 15, 17, 19, 21, 23, 25, 27, 29, 31, 33, 35, 467, 469, 471, 473, 475, 477, 479 or 481, or may comprise a nucleotide sequence sharing at least 60% identity, at least 70% identity, at least 80% identity, at least 85% identity, at least 90% identity, at least 95% identity, or at least 99% identity with said nucleotide sequences.

According to another embodiment, the plant CEP-encoding nucleic acid may comprise a nucleotide sequence selected from SEQ ID NOs 15, 17, 19, 21, 23, 25, 27, 29, 31, 33, and 35, or may comprise a nucleotide sequence sharing at least 60% identity, at least 70% identity, at least 80% identity, at least 85% identity, at least 90% identity, at least 95% identity, or at least 99% identity with said nucleotide sequences.

According to another embodiment, the CEP-encoding nucleotide sequence may comprise a nucleotide sequence encoding an amino acid sequence selected from any one of SEQ ID NOs: 150, 151, 156 and 310, or a sequence sharing at least at least 60% identity, at least 70% identity, at least 80% identity, at least 85% identity, at least 90% identity, at least 95% identity, or at least 99% identity with said amino acid sequences.

During the course of the studies leading to the present invention, the whole gene coding for the *Medicago truncatula* CEP (MtCEP1) was identified, and the promoter (SEQ ID NO: 337) found to be regulated by nutrient levels, especially available nitrogen. It is contemplated that such a promoter may be beneficial for expressing CEP peptides during periods of nitrogen limitation. Thus, according to a further embodiment, the CEP-encoding nucleic acid may be under the control of a promoter comprising the nucleotide sequence as shown in SEQ ID NO. 337, or comprising a nucleotide sequence sharing at least 60% identity, at least 70% identity, at least 80% identity, at least 85% identity, at least 90% identity, at least 95% identity, or at least 99% identity with the nucleotide sequence as shown in SEQ ID NO. 337.

Nucleic acid molecules for identifying other CEP-encoding sequences (and thereby the encoded peptides), or for suppressing the expression of CEP-encoding sequences (plant or RKN) are also contemplated by the present invention. Suitable nucleic acid molecules may be any appropriate sequence which is designed based on any one of the CEP-encoding sequences as disclosed herein.

The nucleotide sequence of said nucleic acid molecule may be identical to, or be complementary to at least a portion of any one of the CEP-encoding sequences as disclosed herein, and may comprise the full sequence, or complement thereof or, may comprise an oligonucleotide from about 10 nucleotides in length to about 100 nucleotides in length, such as from about 10 to about 50 nucleotides in length, about 15 to about 100 nucleotides in length, about 15 to about 50 nucleotides in length, about 10 to about 30 nucleotides in length, or about 15 to about 30 nucleotides in length.

Alternatively, a nucleic acid molecule of the invention may comprise a nucleotide sequence designed based on the amino acid sequence of one of the CEPs disclosed herein, or any one of the CEP domains disclosed herein, or having a domain complying with an amino acid consensus sequence as set forth in SEQ ID NO: 454, using degeneracy of the genetic code, and optionally preferred codon usage information. Suitable nucleic acid molecule sizes are as already discussed immediately above.

Nucleotide sequences as described above which may be employed as, or which may be comprised in primers, probes, antisense molecules, microRNA molecules or strands in double-stranded RNAi molecules may comprise one or more modifications as known in the art for stabilising the molecule(s) (for example, against enzymic degradation by ribonucleases), or for increasing the strength of hybridization with complementary molecule(s).

CEP Receptors and Encoding Sequences

Receptors for CEPs and their encoding sequences may be identified, isolated and sequenced by methods well known and understood in the art using CEP sequences as disclosed herein. Methods for identifying and characterising plant receptors through knowledge of their ligands are well established and have been described in, for example, Shinya T et al (2010), *Plant Cell Physiol* 51(2): 262-270, which describes a use of affinity cross-linking with biotinylated ligands to isolate receptors.

Methods for Modulating Plant Growth

In agriculture it would be desirable to be able to create plants which are capable of growing quicker, which yield greater amounts of biomass, which continue to grow notwithstanding at least short term stress conditions, which have shorter life cycles, especially shorter life-cycles while still delivering substantially the same yield, or any combination thereof. For example, a faster growing plant may use fertilizers (both soil and foliar applied) more efficiently, may use soil moisture more efficiently (losing less to evaporation over time), and may establish earlier and control weeds better. In addition, many plants respond to stresses, such as abiotic stresses like drought, salinity, temperature extremes, nutrient (and especially nitrogen) limitation, by slowing their growth rate or even stopping growth—it would be desirable to develop plants, or be able to treat plants such that they do not slow or stop growth with the onset of stress conditions (especially temporary or mild stress conditions).

Alternatively, it may be desirable to be able to slow plant growth, for example, to ready plants for impending stress conditions (as discussed above) or to allow greater content of particular components in the plants (which may accumulate to greater levels in plant part(s) over time), or to delay, for example, flowering.

One manner of achieving such adaptation(s) may be through increased or decreased expression of CEP genes, use of the expressed peptides, binding agents, their receptors and modulation of CEP signaling.

According to an aspect, methods of the present invention for modulating non-root plant growth may include:
(a) contacting the leaves, shoots, stems or any combination thereof of said plant with a C-terminal encoded peptide (CEP), an analogue thereof or a CEP signaling agonist; or
(b) contacting the leaves, shoots, stems or any combination thereof of said plant with a CEP signaling antagonist; or
(c) introducing at least one mutation or exogenous nucleic acid into one or more plant cells which results in modulated CEP expression by cells of a plant regenerated from or comprising said one or more plant cells; or
(d) introducing at least one mutation or exogenous nucleic acid into one or more plant cells which results in modulated CEP receptor expression by cells of a plant regenerated from or comprising said one or more plant cells; or
(e) introducing at least one mutation or exogenous nucleic acid into one or more plant cells which results in modulated affinity of one or more CEPs for their respective CEP receptors, which modulated affinity arises through modifications in the CEP(s), CEP receptor(s) or in both expressed CEP(s) and CEP receptor(s).

Of great interest to agriculture is the prospect of maintaining growth during periods of plant stress and/or the prospect of plants which grow quicker, with shorter lifecycles while still yielding substantially the same amount of biomass/seed/fruit. The present studies indicate that CEPs are general negative regulators of both root and shoot plant growth, indicating that regulation of expression of these regulatory peptides may allow for quicker or greater growth and/or accelerated plant development.

Methods for modulating non-root plant growth by a plant relative to an untreated or wild-type plant, may comprise contacting the leaves, shoots, stems or any combination thereof of said plant with at least one CEP, a CEP analogue, or a CEP signaling agonist. Methods for modulating non-root plant growth by a plant relative to an untreated or wild-type plant, may also comprise treating seeds of plants with at least one CEP, a CEP analogue, or a CEP signaling agonist prior to sowing. The CEP, CEP analogue, or CEP signaling agonist may be applied directly to the plant part(s), optionally in combination with a permeation/transferring agent, such as a surfactant, optionally in combination with one or more salts (optionally selected from divalent cations).

CEPs for use in such methods may be any CEP as described above. According to an embodiment, the CEP is not an *Arabidopsis thaliana* CEP1 peptide. According to another embodiment, the CEP is not an *Arabidopsis thaliana* CEP. According to another embodiment, the CEP is a plant CEP as described above.

According to another embodiment, the CEP may comprise an amino acid sequence selected from any one of SEQ ID NOs: 150, 151, 156 or 310, or a sequence sharing at least at least 60% identity, at least 70% identity, at least 80% identity, at least 85% identity, at least 90% identity, at least 95% identity, or at least 99% identity with said amino acid sequences.

According to another embodiment, the CEP-encoding nucleotide sequence may comprise a nucleotide sequence encoding an amino acid sequence selected from any one of SEQ ID NOs: 150, 151, 156 or 310, or a sequence sharing at least at least 60% identity, at least 70% identity, at least 80% identity, at least 85% identity, at least 90% identity, at least 95% identity, or at least 99% identity with said amino acid sequences.

A CEP analogue for use in a method of the present invention may be any artificial or natural substance that resembles the protein in function. For example, a CEP analogue may bind a CEP receptor and thereby bring about the same or similar result as if a natural CEP had bound to the receptor. In an embodiment such analogues may also resemble the protein in structure. Analogues contemplated in an embodiment of the present invention include fully or partially peptidomimetic compounds based on the structures of the CEPs disclosed herein. Peptidomimetic compounds (compounds designed to mimic biologically active peptides, but comprising structural differences—to provide advantages, especially in terms of stability, but also interaction with ligands/binding partners or substrates—and comprising unnatural amino acids or other unusual compounds) and their design is well-studied and is described in, for example, Floris M. et al (2011), *Nucleic Acids Research* 39(18): W261-269. Alternatively, an CEP analogue may be a peptide that resembles an CEP in function and activity, but comprise one or more amino acid substitutions, deletions or insertions compared to the subject CEP, and may share at least about 50% amino acid identity, at least about 60% identity, at least about 70% identity, at least about 80% identity, at least about 90% identity, at least about 95% identity, or at least about 99% identity with the amino acid sequence of the subject CEP.

A CEP signaling agonist for use in a method of the present invention may be any molecule that binds with a CEP receptor to trigger a physiological response usually triggered by a CEP peptide when it binds to the receptor. For example, a CEP agonist may be a molecule that binds to a CEP receptor to trigger a shoot growth modulation or root architectural response.

Methods for modulating non-plant growth by a plant relative to an untreated or wild-type plant, may also comprise introducing into one or more plant cells at least one exogenous CEP-encoding nucleic acid into one or more plant cells. Plants with increased or decreased CEP expression may be regenerated from, or comprise such transformed plant cells.

Transgenic plants with an introduced CEP-encoding sequence may be generated using standard plant transformation methods known to those skilled in the art including, for example, *Agrobacterium*-mediated transformation, cation or polyethylene glycol treatment of protoplasts, calcium phosphate precipitation, electroporation, microinjection, viral infection, protoplast fusion, microparticle bombardment, agitation of cell suspensions in solution with microbeads or microparticles coated with the transforming DNA, direct DNA uptake, liposome-mediated DNA uptake, and the like, as also described in a wide range of publicly available texts, such as: "Methods for Plant Molecular Biology" (Weissbach & Weissbach, eds., 1988); Clough, S. J. and Bent, A. F. (1998) "Floral dip: a simplified method for *Agrobacterium*-mediated transformation of *Arabidopsis thaliana*" Plant J. 16, 735-743; "Methods in Plant Molecular Biology" (Schuler & Zielinski, eds., 1989); "Plant Molecular Biology Manual" (Gelvin, Schilperoort, Verma, eds., 1993); and "Methods in Plant Molecular Biology-A Laboratory Manual" (Maliga, Klessig, Cashmore, Gruissem & Varner, eds., 1994). See also Sambrook, J. et al., Molecular Cloning, Cold Spring Harbor Laboratory (1989), Sambrook, J. and Russell, D. W. (2001), "*Molecular Cloning: A Laboratory Manual*", 3rd edition, Cold Spring Harbor Laboratory Press, and references cited therein and Ausubel et al. (eds) Current Protocols in Molecular Biology, John Wiley & Sons (2000), these references being incorporated herein by cross-reference.

The coding region may also be operably linked to an appropriate 3' regulatory sequence. For example, the nopaline synthetase (NOS) polyadenylation region or the octopine synthetase (OCS) polyadenylation region may be used.

The preferred method of transformation may depend upon the plant to be transformed. *Agrobacterium* vectors are often used to transform dicot species. For transformation of monocot species, biolistic bombardment with particles coated with transforming DNA and silicon fibers coated with transforming DNA are often useful for nuclear transformation. However, *Agrobacterium*-mediated transformation of monocotyledonous species, including wheat, are now known (see, for example, International patent publications WO 97/48814; see also Hiei, Y. et al (1994), Plant J. 6(2):271-282 and international patent publication WO 92/06205).

A CEP-encoding sequence can be comprised in a vector. Representative vectors include plasmids, cosmids, and viral vectors. Vectors can also comprise nucleic acids including expression control elements, such as transcription/translation control signals, origins of replication, polyadenylation signals, internal ribosome entry sites, promoters, enhancers, etc., wherein the control elements are operatively associated with a nucleic acid encoding a gene product. Selection of these and other common vector elements are conventional and many such sequences can be derived from commercially available vectors. See, for example. Sambrook, J. et al., Molecular Cloning, Cold Spring Harbor Laboratory (1989), Sambrook, J. and Russell, D. W. (2001), "*Molecular Cloning: A Laboratory Manual*", 3rd edition, Cold Spring Harbor Laboratory Press, and references cited therein and Ausubel et al. (eds) Current Protocols in Molecular Biology, John Wiley & Sons (2000).

According to an embodiment, the vector is an expression vector capable of directing the transcription of a CEP-encoding sequence into RNA.

DNA constructs for transforming a selected plant may comprise a coding sequence of interest operably linked to appropriate 5' regulatory sequences (e.g., promoters and translational regulatory sequences) and 3' regulatory sequences (e.g., terminators). In a preferred embodiment, the coding region is placed under a powerful constitutive promoter, such as the Cauliflower Mosaic Virus (CaMV) 35S promoter or the figwort mosaic virus 35S promoter. Other constitutive promoters contemplated for use in the present invention include, but are not limited to: T-DNA mannopine synthetase, nopaline synthase (NOS) and octopine synthase (OCS) promoters.

Using an *Agrobacterium* binary vector system for transformation, the selected coding region, under control of a constitutive or inducible promoter as described above, may be linked to a nuclear drug resistance marker, such as kanamycin resistance. Other useful selectable marker systems include, but are not limited to: other genes that confer antibiotic resistances (e.g., resistance to hygromycin or bialaphos) or herbicide resistance (e.g., resistance to sulfonylurea, phosphinothricin, or glyphosate).

According to an embodiment, the CEP-encoding sequence is operably linked to a promoter which is constitutive or inducible. An inducible promoter, for the purposes of the present invention, may be inducible by any appropriate stimulus. According to certain embodiments, an inducible promoter for use according to the present invention may be inducible by nutrient, drought, or other abiotic stress. According to an embodiment, an inducible promoter for use according to the present invention is inducible by nutrient status, such as by nitrogen starvation or by high carbon dioxide.

According to another embodiment, the CEP-encoding sequence is operably linked to a promoter which is shoot-specific, leaf-specific, or stem-specific.

According to another embodiment, the CEP-encoding sequence comprises a secretion signal sequence.

According to an embodiment, the CEP-encoding sequence is operably linked to a promoter comprising the nucleotide sequence as shown in SEQ ID NO: 337 or a homologue thereof sharing at least 60% identity with SEQ ID NO: 337. Alternatively, the promoter may be a root-specific glutamine synthetase gene promoter.

According to an embodiment, a method of the invention for modulating the root architecture of a plant, relative to a wild-type plant, comprises introducing into one or more plant cells the *Medicago truncatula* CEP1 gene, including the promoter sequence, disclosed herein as SEQ ID NO: 337, and the CEP-encoding sequence, disclosed herein as SEQ ID NO: 15.

The coding region may also be operably linked to an appropriate 3' regulatory sequence. For example, the nopaline synthetase (NOS) polyadenylation region or the octopine synthetase (OCS) polyadenylation region may be used.

Using an *Agrobacterium* binary vector system for transformation, the selected coding region, under control of a constitutive or inducible promoter as described above, may be linked to a nuclear drug resistance marker, such as kanamycin resistance. Other useful selectable marker systems include, but are not limited to: other genes that confer antibiotic resistances (e.g., resistance to hygromycin or bialaphos) or herbicide resistance (e.g., resistance to sulfonylurea, phosphinothricin, or glyphosate).

Any of the methods of the present invention, as discussed above or below, can be used to transform any plant cell. In this manner, genetically modified plants, plant cells, plant tissue, seed, and the like can be obtained. The plant cell(s) to be transformed may be a plant cell from any plant selected from angiosperms or gymnosperms. Non-exhaustive examples of angiosperms for treatment or transformation by a method of the invention may include any member of the Aceraceae, Anacardiaceae, Apiaceae, Asteraceae, Betulaceae, Brassicaceae, Buxaceae, Chenopodiaceae/Amaranthaceae, Compositae, Cucurbitaceae, Fabaceae, Fagaceae, Gramineae, Juglandaceae, Lamiaceae, Lauraceae, Leguminosae, Moraceae, Myrtaceae, Oleaceae, Platanaceae, Poaceae, Polygonaceae, Rosaceae, Rutaceae, Salicaceae, Solanaceae, Ulmaceae or Vitaceae. Examples of gymnosperms for treatment or transformation by a method of the invention may include any member of the Cuppressaceae, Pinaceae, Taxaceae or Taxodiaceae.

Cells which have been transformed may be grown into plants in accordance with conventional methods as are known in the art (See, for example, McCormick, S. et al (1986), *Plant Cell Reports* 5:81-84). The resulting plants may be self-pollinated, pollinated with the same transformed strain or different strains or hybridised, and the resulting plant(s) having modulated root architecture compared to wild-type plants identified. Two or more generations may be grown to ensure that this phenotypic characteristic is stably maintained. Alternatively, in vegetatively propagated crops, mature mutant/transgenic plants may be propagated by cutting or by tissue culture techniques to produce identical plants. Selection of mutant/transgenic plants can be carried out and new varieties may be obtained and propagated vegetatively for commercial use. For a general description of plant transformation and regeneration see, for example, Walbot et al. (1983) in "Genetic Engineering of Plants", Kosuge et al. (eds.) Plenum Publishing Corporation, 1983 and "Plant Cell, Tissue and Organ Culture: Fundamental Methods", Gamborg and Phillips (Eds.), Springer-Verlag, Berlin (1995). See also Sambrook, J. et al., Molecular Cloning, Cold Spring Harbor Laboratory (1989), Sambrook, J. and Russell, D. W. (2001), "*Molecular Cloning: A Laboratory Manual*", 3rd edition, Cold Spring Harbor Laboratory Press, and references cited therein and Ausubel et al. (eds) Current Protocols in Molecular Biology, John Wiley & Sons (2000).

Plants transformed/mutated by the methods of the invention may be screened based on expression of a marker gene, for example by detecting shoot growth modulation or root architecture modulation by the introduced nucleotide sequence, molecular analysis using specific oligonucleotide probes and/or amplification of the target gene.

Modulation of non-root plant growth may also be achieved through increasing or decreasing CEP signaling by modulation of the affinity of one or more CEPs for the corresponding CEP receptor(s) through mutation of the CEP(s) or CEP receptor(s), or introducing exogenous sequences coding for one or more CEP(s) or CEP receptor(s) with desirable signaling interaction attributes. Methods for introducing mutations into target nucleotide sequences, and screening thereof, are described further below.

Furthermore, it is also known that microRNAs (small post-transcriptional regulators that bind to complementary sequences on target mRNAs, resulting in translational repression or target degradation and gene silencing) are expressed by plants, and that these play a significant role in control of most, if not all, plant development regulatory mechanisms. See, for example, Voinnet O (2009) *Cell* 136(4): 669-687; Jones-Rhoades M W et al (2006) *Annual Review of Plant Biology* 57:19-53. It is therefore contemplated that CEPs and CEP receptor(s) would be subject to such regulation, the amount of mRNA encoding these species present in plant cells being regulated by expression of such microRNAs. Control or inhibition of expression of such microRNAs, or control of their interaction with targeted CEP or CEP receptor mRNAs or their inactivation (such as by use of microRNA decoys—see, for example, Ivashuta S et al (2011) *PLoS ONE* 6(6): e21330) is therefore contemplated as a further, or as a complementary means for modulating non-root plant growth. Identification of endogenous plant microRNAs which target CEP-encoding or CEP receptor-encoding mRNAs may be achieved using the nucleotide sequence encoding the subject CEP or CEP receptor, or homologues thereof by methods well known in the art. Alternatively an artificial microRNA approach could be adopted as disclosed in Schwab R et al. (2006), "Highly Specific Gene Silencing by Artificial MicroRNAs in *Arabidopsis*", *Plant Cell* 18:1121-1133, hereby incorporated in its entirety by cross-reference. RNAi gene silencing is another approach to silence plant or nematode genes in planta, as disclosed in Rosso M N et al. (2009) "RNAi and Functional Genomics in Plant Parasitic Nematodes" *Annual Review of Phytopathology* 47: 207-232, and *Plant Biotechnol J.* (2011) 10:1467-7652. "Biotechnological application of functional genomics towards plant-parasitic nematode control". miRNA-induced gene silencing is yet another approach to silence plant genes in planta, as disclosed in Felippes et al. (2012) "MIGS: miRNA-induced gene silencing" *Plant J* 70, 541-547".

Alternatively, avoidance of microRNA suppression of CEP or CEP receptor expression may be achieved by introducing into a subject plant, as described above, an exogenous CEP-encoding or CEP receptor-encoding sequence sufficiently different to any endogenous homologue sequences such that the microRNA is insufficiently homologous to the introduced sequence to achieve suppression. RKN CEP-encoding sequences may be advantageous in this regard.

Methods of the present invention for modulating non-root plant growth, based on the herein disclosed understanding of CEPs and their effects, may also include methods for promoting shoot growth, proliferation of shoots, or combinations thereof, in plants compared to wild-type plants. The studies leading to the present invention found that overexpression of CEPs generally leads to suppression of plant growth, although a couple of exceptions have been observed during early seedling growth. It is contemplated that suppression of CEP expression will, conversely, promote non-root plant growth and development. The present studies also indicate that suppression of CEP expression promotes growth of non-root plant material even under stress conditions, such as, but not limited to, nitrogen limitation, sodium or potassium-induced stresses, low pH stress, and low water activity stress.

Methods of the invention for promoting non-root plant growth and development, relative to an untreated or wild-type plant, may comprise contacting the leaves, shoots, stems or any combination thereof of said plant with a CEP antagonist or introducing at least one mutation or at least one exogenous nucleic acid into one or more plant cells which at least one mutation or nucleic acid results in:

(i) decreased expression of one or more CEPs, decreased expression of one or more CEP receptors, or decreased expression of one or more CEPs and one or more CEP receptors by root cells of a plant regenerated from or comprising said one or more plant cells, wherein said decreased expression of said CEP(s) or CEP receptor(s) occurs under conditions which would otherwise promote expression of said CEP(s) or CEP receptor(s); or (ii) reduced affinity of one or more CEPs for their respective CEP receptors, which reduced affinity arises through modifications in the CEP(s), CEP receptor(s) or in both expressed CEP(s) and CEP receptor(s) expressed by root cells of a plant regenerated from or comprising said one or more plant cells.

A CEP signaling antagonist for use in a method of the present invention may be any substance that interferes with the physiological response usually triggered by an CEP when it binds to its receptor, or which interferes with binding of the CEP to its receptor. For example, a CEP antagonist may be a substance that binds to a CEP or a CEP receptor to inhibit interaction between the CEP and the CEP receptor, which interaction would trigger a growth suppression response.

Decreased expression of one or more CEPs, one or more CEP receptors, or both, may be achieved by any suitable technique, many being known in the art, including, antisense technology, interfering RNA technology, ribozyme technology, mutation of the gene(s) to create null mutants, and replacement or mutation of regulatory regions to reduce or obviate gene expression.

For example, a method of the invention may comprise inserting into said one or more plant cells exogenous nucleic acid which inhibits expression of the activity of an endogenous CEP (for example, via regulatory regions controlling expression of a CEP, via the CEP-encoding sequence, or via mRNA translated from the CEP-encoding sequence), or which replaces expression of an endogenous CEP or homologue thereof with expression of an exogenous protein. The exogenous protein may be an exogenous mutant CEP or homologue thereof, or any other suitable protein, such as a protein providing a screenable phenotype.

According to an embodiment for carrying out a method of the invention, a plant with promoted lateral root growth or development, relative to a wild-type plant, may be created by inhibiting translation of a CEP mRNA by RNA interference (RNAi), antisense or post-transcriptional gene silencing techniques. The CEP gene targeted for down-regulation, or a fragment thereof, may be utilized to control the production of the encoded protein. Full-length antisense molecules can be used for this purpose. Alternatively, double stranded oligonucleotides, sense and/or antisense oligonucleotides, or a combination thereof targeted to specific regions of the CEP-encoded RNA may be utilized. The use of oligonucleotide molecules to decrease expression levels of a pre-determined gene is known in the art (see, for example, Hamilton, A. J. and Baulcombe, D. C. (1999), *Science* 286:950-952; Waterhouse P. M. et al (1998), *Proc. Natl. Acad. Sci. USA* 95:13959-13964; Fire et al. (1998) Nature 391: 806-811; Hammond, et al. (2001) Nature Rev, Genet. 2: 110-1119; Hammond et al. (2000) Nature 404: 293-296; Bernstein et al. (2001) Nature 409: 363-366; Elbashir et al (2001) Nature 411: 494-498; and International patent publications WO 99/53050, WO 99/49029, WO 99/32619, the disclosures of which are incorporated herein by reference). RNA interference (RNAi) refers to a means of selective post-transcriptional gene silencing by destruction of specific mRNA by small interfering RNA molecules (siRNA). The siRNA is typically generated in vivo by cleavage of double stranded RNA, where one strand is identical to the message to be inactivated. Double-stranded RNA molecules may be synthesised in which one strand is identical to a specific region of the mRNA transcript and introduced directly. Alternatively corresponding dsDNA can be employed, which, once presented intracellularly is converted into dsRNA. Methods for the synthesis of suitable single or double-stranded oligonucleotides, or constructs capable of expressing them in planta for use in antisense or RNAi and for achieving suppression of gene expression are known to those of skill in the art. The skilled addressee will appreciate that a range of suitable single- or double-stranded oligonucleotides capable of inhibiting the expression of the disclosed polynucleotides, or constructs capable of expressing them in planta can be identified and generated based on knowledge of the sequence of the gene in question using routine procedures known to those skilled in the art without undue experimentation. Oligonucleotide molecules may be provided in situ by transforming plant cells with a DNA construct which, upon transcription, produces double stranded and/or antisense RNA sequences, which may be full-length or partial sequences. The gene silencing effect may be enhanced by over-producing both sense and/or antisense sequences (which may be full-length or partial) so that a high amount of dsRNA is produced.

Suitable molecules can be manufactured by chemical synthesis, recombinant DNA procedures or by transcription in vitro or in vivo when linked to a promoter, by methods known to those skilled in the art, and may be modified by chemistries well known in the art for stabilising the molecules in vive and/or enhancing or stabilising their interaction with target complexes or molecules.

Those skilled in the art will appreciate that there need not necessarily be 100% nucleotide sequence match between the target sequence and the RNAi sequence. The capacity for mismatch is dependent largely on the location of the mismatch within the sequences. In some instances, mismatches of 2 or 3 nucleotides may be acceptable but in other instances a single nucleotide mismatch is enough to negate the effectiveness of the siRNA. The suitability of a particular siRNA molecule may be determined using routine procedures known to those skilled in the art without undue experimentation.

Sequences of/for antisense constructs may be derived from various regions of the target gene(s). Antisense constructs may be designed to target and bind to regulatory regions of the nucleotide sequence, such as the promoter, or to coding (exon) or non-coding (intron) sequences. Antisense constructs of the invention may be generated which are at least substantially complementary across their length to the region of the gene in question. Binding of an antisense construct to its complementary cellular sequence may interfere with transcription, RNA processing, transport, translation and/or mRNA stability.

In particular embodiments of the invention, suitable sequences encoding inhibitory nucleic acid molecules may be administered in a vector. The vector may be a plasmid vector, a viral vector, or any other suitable vehicle adapted for the insertion of foreign sequences and introduction into eukaryotic cells. Preferably the vector is an expression vector capable of directing the transcription of the DNA sequence of an inhibitory nucleic acid molecule of the invention into RNA.

Transgenic plants expressing a sense and/or antisense CEP-encoding sequence, or a portion thereof under an inducible promoter are also contemplated to be within the scope of the present invention. Promoters inducible by nutrient conditions, such as low nitrogen are especially contemplated by the present invention. Promoters which may be used according to the invention may include, for example, the Cauliflower mosaic virus (CMV) promoter, or the *M. truncatula* promoter disclosed herein as SEQ ID NO: 337, for expression in the transformed plant.

Suitable constructs and vectors and transformation techniques for introducing inhibitory nucleic acids or constructs encoding them into plants, as well as methods for regenerating plants from transformed cells have already been discussed above.

As mentioned above, a further means of inhibiting gene expression may be achieved by introducing catalytic antisense nucleic acid constructs, such as ribozymes, which are capable of cleaving RNA transcripts and thereby preventing the production of the native protein. Ribozymes are targeted to and anneal with a particular sequence by virtue of two regions of sequence complementarity to the target flanking the ribozyme catalytic site. After binding, the ribozyme cleaves the target in a site-specific manner. The design and testing of ribozymes which specifically recognize and cleave sequences of interest, such as CEP-encoding sequences and CEP receptor-encoding sequences, can be achieved by techniques well known to those in the art (for example Lieber and Strauss, (1995) *Mol. Cell. Biol.* 15:540-551, and de Feyter R and Gaudron J (1998) "Expressing Ribozymes in Plants", *Methods in Molecular Biology* 74: 403-415, the disclosures of which are incorporated herein by reference).

Suitable constructs and vectors and transformation techniques for introducing ribozymes or constructs encoding them into plants, as well as methods for regenerating plants from transformed cells have already been discussed above.

Similar to the situation described above, where CEP or CEP receptor expression or overexpression is promoted to modulate non-root plant growth, microRNA manipulation may also be employed to suppress CEP or CEP receptor expression. It is contemplated that overexpression, or constitutive expression of microRNAs specifically targeting subject CEP-encoding or CEP receptor-encoding sequences may be employed to suppress expression of those sequences to promote non-root plant growth or development. Alternatively, exogenous nucleotide construct(s) encoding microRNAs specific for subject CEP-encoding or CEP receptor-encoding sequences, under the control of desired regulatory sequences may be introduced into plant cells, as disclosed in Schwab R et al. (2006), "Highly Specific Gene Silencing by Artificial MicroRNAs in *Arabidopsis*", *Plant Cell* 18:1121-1133. Modulation of non-root plant growth by a method of the present invention may also be achieved by modulating the affinity of CEP(s) for respective CEP receptor(s). Reduced affinity or reduced expression of one or more CEPs for their respective CEP receptors, or vice versa, so as to promote non-root growth in plants, may be effected by a number of means, such as through modifications in endogenous sequences coding for the CEP(s) or CEP receptor(s), or by replacing the CEP-encoding sequence(s) or CEP receptor-encoding sequence(s) with sequences coding for a CEP or CEP receptor having less binding affinity for the corresponding molecule.

Modifications in endogenous sequences coding for CEP(s) or CEP receptor(s) may be achieved by in situ mutation, either by physical or chemical mutagenesis or by introduction of exogenous nucleic acid which introduces mutations into the target nucleotide sequence(s).

In one embodiment the exogenous nucleic acid may comprise an oligonucleotide or polynucleotide which introduces a mutation comprising single or multiple nucleotide insertions, deletions or substitutions into the endogenous nucleotide sequence encoding an CEP or an CEP receptor, or a homologue(s) thereof via homologous recombination.

Single or multiple nucleotide insertions, deletions or substitutions may be introduced via recombination of the target mutation site with an introduced targeting nucleotide sequence. Such an introduced nucleotide sequence may, for example, comprise a nucleotide sequence to be introduced into the genome flanked either side by nucleotide sequences homologous to target sequences contiguous in or located either side of a desired mutation insertion point. In accordance with the methods of the present invention, a nucleotide sequence to be introduced into the genome may also include a selectable marker operably linked to desired regulatory regions (which may include, for example, a root-specific promoter).

The nucleotide sequences homologous to the target sequences may be isogenic with the target sequences to thereby promote the frequency of homologous recombination.

Homologous nucleotide sequences that are not strictly isogenic to the target sequences can also be used. Although mismatches between the homologous nucleotide sequences and the target sequences can adversely affect the frequency of homologous recombination, isogenicity is not strictly required and substantial homology may be sufficient. For the purposes of the present invention, the level of homology between the homologous sequences and the target sequences may be at least about 90% identity, at least about 95% identity, at least about 99% identity or 100% identity.

A targeting nucleotide sequence can be comprised in a vector. Representative vectors include plasmids, cosmids, and viral vectors. Vectors can also comprise nucleic acids including expression control elements, such as transcription/translation control signals, origins of replication, polyadenylation signals, internal ribosome entry sites, promoters, enhancers, etc., wherein the control elements are operatively associated with a nucleic acid encoding a gene product. Selection of these and other common vector elements are conventional and many such sequences can be derived from commercially available vectors. See, for example, Sambrook, J. et al., Molecular Cloning, Cold Spring Harbor Laboratory (1989), Sambrook, J. and Russell, D. W. (2001), "*Molecular Cloning: A Laboratory Manual*", 3rd edition, Cold Spring Harbor Laboratory Press, and references cited therein and Ausubel et al. (eds) Current Protocols in Molecular Biology, John Wiley & Sons (2000).

A targeting vector can be introduced into targeted cells using any suitable method known in the art for introducing DNA into cells, including but not limited to microinjection, electroporation, calcium phosphate precipitation, liposome-mediated delivery, viral infection, protoplast fusion, direct transfection (optionally assisted by permeation enhancing or transferring agents—for example, surfactants, optionally in combination with one or more salts. See, for example, United States patent publication no. 20110296556, incorporated herein by cross reference), and particle-mediated uptake.

Optionally, a targeting DNA is co-administered with a recombinase, for example recA, to a target cell to thereby enhance the rate of homologous recombination. The target cell(s) may already comprise, or have been transformed to comprise suitable recombinase target sequences, if required. For example, a recombinase protein(s) can be loaded onto a targeting DNA as described in U.S. Pat. No. 6,255,113. To enhance the loading process, a targeting DNA can contain one or more recombinogenic nucleation sequences. A targeting DNA can also be coated with a recombinase protein by pre-incubating the targeting polynucleotide with a recombinase, whereby the recombinase is non-covalently bound to the polynucleotide. See, for example, A. Vergunst et al (1998), *Nucleic Acids Res.* 26:2729 and A. Vergunst and P. Hooykaas (1998), *Plant Molec. Biol.* 38:393 406, International patent publications WO 99/25821, WO 99/25840, WO 99/25855, and WO 99/25854 and U.S. Pat. Nos. 5,780, 296, 6,255,113, and 6,686.515.

Suitable constructs and vectors and transformation techniques for introducing targeting sequences as discussed above, as well as methods for regenerating plants from transformed cells have already been discussed above.

Mutations may also be introduced into plants using zinc finger nucleases (ZFNs), transcription activator-like effector nucleases (TALENs), clustered regulatory interspaced short palindromic repeat (CRISPR)/Cas-based RNA-guided DNA endonucleases, and homing endonucleases (HEs) as discussed in, for example, Gaj T. et al (2013; *Trends Biotechnol.* 31(7): 397-405), Carroll D. (2012; *Molecular therapy* 20(9): 1659-1660), Xiao A. et al (6 Jun. 2013; *Nucleic Acids Research* 2013, 1-11, doi: 10.1093/nar/gkt464, the disclosures of these references being hereby incorporated by cross-reference.

Plants transformed/mutated by the methods of the invention may be screened based on the lack of or reduced expression, or of overexpression of a CEP or CEP receptor protein, or homologues thereof, or of their activity or by observation of modulated root growth compared to wild-type plants, molecular analysis using specific oligonucleotide probes and/or amplification of the target gene.

A mutation which results in reduced expression of CEP(s) or CEP receptor(s), or homologues thereof in plant cells may be introduced into the one or more plant cells by any appropriate methods as are known in the art. For example, suitable methods may comprise exposing the one or more plant cells (which may be plant seed cells, or cells of a part of a plant, as well as isolated plant cells) to chemical or physical mutagenic means, or insertional mutagenic means such as transposons, retrotransposons, retroviruses, or T-DNA. Suitable materials and methods for introducing mutations into a plant genome are also described in, for example, International patent publication WO 98/26082, "*Arabidopsis* Protocols" (2$^{nd}$ Edition, Salinas, J. and Sanchez-Serrano, J., eds, Methods in Molecular Biology 323 (2006), Humana Press), and "Current Protocols in Molecular Biology" (Ausubel et al. (eds), John Wiley & Sons (2000)), herein incorporated by reference.

The mutation may also be introduced into the one or more plant cells by crossing a wild-type plant with a plant comprising a desirable mutation (as determined previously by genetic screening and/or analysis—plants comprising a desired mutation may already exist in available plant germplasm/culture/seed collections/varieties), and plants may be generated from the resulting seed and then screened for inheritance of the mutation.

The mutation(s) may be introduced into one or more sequence(s) encoding CEP(s) or CEP receptor(s), or may be introduced into other sequences affecting expression of those proteins (such as upstream sequences, including promoters).

According to an embodiment of the invention, a mutation is introduced into a nucleotide sequence encoding a CEP or CEP receptor or a homologue thereof in one or more plant cells, and may comprise an insertion, deletion or substitution of one or more nucleotides in the nucleotide sequence encoding the CEP or CEP receptor or homologue thereof. In one embodiment the mutation is a CEP or CEP receptor null mutation. Alternatively, the mutation may result in an expressed product which, however, has at least reduced affinity for its binding partner.

The methods of the present invention can employ any mutagenic agent known in the art (employing methods also known in the art) including, but not limited to ultraviolet light, X-ray radiation, gamma radiation or fast neutron mutagenesis, N-ethyl-N-nitrosourea (ENU), methylnitrosourea (MNU), procarbazine (PRC), triethylene melamine (TEM), acrylamide monomer (AA), chlorambucil (CHL), melphalan (MLP), cyclophosphamide (CPP), diethyl sulfate (DES), ethyl methane sulfonate (EMS), methyl methane sulfonate (MMS), 6-mercaptopurine (6-MP), mitomycin-C (MMC), N-methyl-N'-nitro-N-nitrosoguanidine (MNNG), $^3H_2O$, and urethane (UR).

The frequency of genetic modification upon exposure to one or more mutagenic agents can be modulated by varying dose and/or repetition of treatment, and can be tailored for a particular application. In one embodiment, the treatment dose and regimen does not induce substantial cytotoxicity to the one or more cells.

Mutations in CEP(s) or CEP receptor(s) or homologues thereof can be detected and followed (through generations) by probing with known CEP-encoding sequence(s), such as are disclosed herein (see SEQ ID NOs: 3, 5, 7, 9, 11, 13, 15, 17, 19, 21, 23, 25, 27, 29, 31, 33, 35, 364, 366, 368, 370, 372, 374, 376, 378, 380, 382, 384 or 386) or CEP receptor-encoding sequence(s), which may be identified as described above, using techniques well known in the art and suitable probes or primers based on the gene(s) or nucleotide sequence(s) encoding CEP(s). CEP receptor(s) or homologues thereof.

If the mutation is in a sequence other than CEP-encoding sequence(s) or CEP receptor-encoding sequence(s), the mutation may need to be identified, located and/or characterised before it can be traced/followed through plant generations. Suitable methods for identifying, locating and characterising unknown mutations are known to those in the art and are described in a number of well-known standard texts, such as Sambrook, J. et al., Molecular Cloning, Cold Spring Harbor Laboratory (1989), Sambrook, J. and Russell, D. W. (2001), "*Molecular Cloning: A Laboratory Manual*", 3rd edition, Cold Spring Harbor Laboratory Press, and references cited therein and Ausubel et al. (eds) Current Protocols in Molecular Biology, John Wiley & Sons (2000). See also Rossel, J. B., Cuttriss, A. and Pogson, B. J. "Identifying Photoprotection Mutants in *Arabidopsis thaliana*" in Methods in Molecular Biology 274: 287-299 (Carpentier, R. ed, Humana Press). More recent methods for identifying mutant alleles include 'Tilling' and high resolution melts (HRMs).

TILLING (Targeting Induced Local Lesions in Genomes) is a method in molecular biology that allows directed identification of mutations in a specific gene. The method combines a standard technique (for example, mutagenesis with a chemical mutagen such as Ethyl methanesulfonate (EMS)) with a sensitive DNA screening-technique that identifies single base mutations (also called point mutations) in a target gene. The first paper describing TILLING in *Arabidopsis* (McCallum C M, Comai L, Greene E A, Henikoff S, "Targeted screening for induced mutations", *Nat Biotechnol*. (2000) April; 18(4):455-7, hereby incorporated by cross-reference) used dHPLC HPLC to identify mutations. The method was made more high throughput by using the restriction enzyme Cel-I combined with a gel based system to identify mutations (Colbert T, Till B J, Tompa R, Reynolds S, Steine M N, Yeung A T, McCallum C M, Comai L, Henikoff S, "High-throughput screening for induced point mutations", *Plant Physiol*. (2001) June; 126(2):480-4, also hereby incorporated by cross-reference). Other methods of mutation detection, such as resequencing DNA, have been combined for TILLING. TILLING has since been used as a reverse genetics method in other organisms such as zebrafish, corn, wheat, rice, soybean, tomato and lettuce. See also: McCallum C M, Comai L, Greene E A, Henikoff S. "Targeting induced local lesions in genomes (TILLING) for plant functional genomics" *Plant Physiol*. (2000) June; 123(2):439-42; Colbert T, Till B J, Tompa R, Reynolds S, Steine M N, Yeung A T, McCallum C M, Comai L, Henikoff S. High-throughput screening for induced point mutations", *Plant Physiol*. (2001) June; 126(2):480-4; Draper B W, McCallum C M, Stout J L, Slade A J, Moens C B, "A high-throughput method for identifying N-ethyl-N-nitrosourea (ENU)-induced point mutations in zebrafish", *Methods Cell Biol.* (2004); 77:91-112; and Slade A J, Fuerstenberg S I, Loeffler D, Steine M N, Facciotti D, "A reverse genetic, nontransgenic approach to wheat crop improvement by TILLING", *Nat Biotechnol.* (2005) January; 23(1):75-81, also hereby incorporated by cross-reference.

HRM (High Resolution Melt) is a recent development that can greatly extend the utility of traditional DNA melting analysis by taking advantage of recent improvements in high resolution melt instrumentation and the development of double strand specific DNA (dsDNA) binding dyes that can be used at high enough concentrations to saturate all double stranded sites produced during PCR amplifications (see http://www.corbettlifescience.com/control.cfm?page=Introduction_4&bhcp=1), as well as: Dufresne S D, Belloni D R, Wells W A, Tsongalis G J, "BRCA1 and BRCA2 Mutation Screening using SmartCyclerII high-resolution melt curve analysis", *Arch Pathol Lab Med* (2006) 130: 185-187; Graham R, Liew M, Meadows C, Lyon E, Wittwer C T, "Distinguishing different DNA heterozygotes by high resolution melting", *Clinical Chemistry* (2005) 51: 1295-1298; Hermann M G, Durtschl J D, Bromley K, Wittwer C T, Voelkerding K V, "Amplicon DNA melting analysis for mutation scanning and genotyping: cross-platform comparison of instruments and dyes", *Clinical Chemistry* (2006) 52: 494-503; Liew M, Pryor R, Palais R, Meadows C, Erali M, Lyon E, Wittwer C, "Genotyping of single nucleotide polymorphisms by high resolution melting of small amplicons", *Clinical Chemistry* (2004) 50: 1156-1164; Margraf R L, Mao R, Highsmith W E, Holtegaard L M, Wittwer C T, "Mutation Scanning of the RET protooncogene using high resolution melting analysis", *Clinical Chemistry* (2006) 52: 138-141; NGRL (Wessex) Reference Reagent Report January 2006, "Plasmid based generic mutation detection reference reagents; production and performance indicator field trial" (www.ngrl.org.uk/Wessex/downloads.htm); NGRL (Wessex) Reference Reagent Report January 2006. "Production and field trial evaluation of reference reagents for mutation screening of BRCA1, BRCA2, hMLH1 and MHS2" (www.ngrl.org.uk/Wessex/downloads.htm); NGRL (Wessex) Reference Reagent Report June 2006, "Mutation Scanning by High Resolution Melts: Evaluation of Rotor-Gene™ 6000 (Corbett Life Science), HR-1 ™ and 384 well LightScanner™ (Idaho Technology)" (www.ngrl.org.uk/Wessex/downloads.htm); Reed G H, Wittwer C T, "Sensitivity and specificity of single-nucleotide polymorphism scanning by high resolution melting analysis", *Clinical Chemistry* (2004) 50: 1748-1754; Willmore-Payne C, Holden J A, Tripp S, Layfield L J, "Human malignant melanoma: detection of BRAF- and c-kit-activating mutations by high-resolution amplicon melting analysis", *Human Pathology* (2005) 36: 486-493; Wittwer C T, Reed G H, Gundry C N, Vandersteen J G, Pryor R J, "High-resolution genotyping by amplicon melting analysis using LCGreen" *Clinical Chemistry* (2003) 49: 853-860; Worm J, Aggerholm A, Guldberg P, "In-tube DNA methylation profiling by fluorescence melting curve analysis" *Clinical Chemistry* (2001) 47: 1183-1189; Zhou L, Myers A N, Vandersteen J G, Wang L, Wittwer C T, "Closed-tube genotyping with unlabeled oligonucleotide probes and a saturating DNA dye", *Clinical Chemistry* (2004) 50: 1328-1335; and Zhou L, Wang L, Palais R, Pryor R, Wittwer C T, "High-resolution DNA melting analysis for simultaneous mutation scanning and genotyping in solution", *Clinical Chemistry* (2005) 51: 1770-1777.

Oligonucleotide primers can be designed or other techniques can be applied to screen lines for mutations/insertions in CEP-encoding sequence(s) or CEP receptor-encoding sequence(s). Through breeding, a plant line may then be developed that is homozygous for the mutated copy of the CEP-encoding sequence(s) or CEP receptor-encoding sequence(s). PCR primers for this purpose may be designed so that a large portion of the coding sequence of the desired sequence is specifically amplified using the sequence of the sequence from the species to be probed (see, for example, Baumann, E. et al. (1998), "Successful PCR-based reverse genetic screens using an En-1-mutagenised *Arabidopsis thaliana* population generated via single-seed descent", *Theor. Appl. Genet.* 97:729 734).

Other CEP or CEP receptor mutants may be isolated from mutant populations or existing germplasm using the distinctive phenotypes characterized as described herein (including modulated root architecture and modulated non-root plant growth and/or development, compared to the wild-type plants). That the phenotype is caused by a mutation in CEP-encoding sequence(s) or CEP receptor-encoding sequence(s) or a homologue thereof may then be established by molecular means well known in the art.

CEP or CEP receptor mutants, including mutants heterozygous for the allele, and which may not express the modulated phenotype, may also be screened for, as described herein, and the mutants used for breeding programs to introgress the mutation into homozygous line, or the mutant gene isolated and used in recombinant techniques for generating mutant plants.

While mutants of the present invention may be generated by random mutagenesis (or may already exist), any plant may be recombinantly engineered to display a similar phenotype, for example once the genetic basis of the mutation, such as a mutated CEP-encoding gene, has been determined. For a general description of plant transformation and regeneration see, for example, Walbot et al. (1983) in "Genetic Engineering of Plants", Kosuge et al. (eds.) Plenum Publishing Corporation, 1983 and "Plant Cell, Tissue and Organ Culture: Fundamental Methods", Gamborg and Phillips (Eds.), Springer-Verlag, Berlin (1995). See also Sambrook, J. et al., Molecular Cloning, Cold Spring Harbor Laboratory (1989), Sambrook, J. and Russell, D. W. (2001), "*Molecular Cloning: A Laboratory Manual*", 3rd edition, Cold Spring Harbor Laboratory Press, and references cited therein and Ausubel et al. (eds) Current Protocols in Molecular Biology, John Wiley & Sons (2000).

Screening a plant for the presence of at least one mutant allele of a nucleotide sequence encoding a CEP, CEP receptor, or homologue thereof, may comprise analysing DNA of the plant using at least one nucleic acid molecule suitable as a probe or primer which is capable of hybridising to a CEP gene, CEP receptor gene, or homologue thereof under stringent conditions. In a more specific method, the screening method may comprise the use of at least one oligonucleotide primer pair suitable for amplification of a region of the CEP gene, CEP receptor gene, or homologue thereof, comprising a forward primer and a reverse primer to detect the presence or absence of a mutation in said region. The region may comprise the whole CEP gene, CEP receptor gene, or homologue thereof, or may comprise only a portion thereof.

DNA from the plant to be assessed may be extracted by a number of suitable methods known to those skilled in the art, such as are described in a wide range of well known texts, including (but not limited to) Sambrook, J. et al., Molecular Cloning, Cold Spring Harbor Laboratory (1989), Sambrook, J. and Russell, D. W. (2001), "*Molecular Clon-* ing: *A Laboratory Manual*", 3rd edition, Cold Spring Harbor Laboratory Press, and references cited therein and Ausubel et al. (eds) Current Protocols in Molecular Biology, John Wiley & Sons (2000), incorporated herein by cross-reference. See also the methods described in Lukowitz, W., Gillmor, C. S. and Scheble, W-R. (2000) "Positional Cloning in *Arabidopsis*: Why It Feels Good to Have a Genome Initiative Working for You" *Plant Physiology* 123, 795-805, and references cited therein.

Once suitable DNA has been isolated, this may be analysed for the presence or absence of a mutation by any suitable method as known in the art, and which method/strategy is employed may depend on the specificity desired, and the availability of suitable sequences and/or enzymes for restriction fragment length polymorphism (RFLP) analysis. Suitable methods may involve detection of labelled hybridisation product(s) between a mutation-specific probe and at least a portion of the CEP gene, CEP receptor gene, or homologue thereof or, more typically, by amplification of at least a portion of the CEP gene, CEP receptor gene, or homologue thereof using either a primer and suitable probe, or using a pair of primers (forward and reverse primers) for amplification of a specific portion of the CEP gene, CEP receptor gene, or homologue thereof, followed by either direct partial and/or complete sequencing of the amplified DNA, or RFLP analysis thereof. Suitable primer pairs for amplifying portions of CEP genes from *Medicago truncatula* are provided in Table 1—other suitable primers or primer pairs for analysing CEP genes or homologues thereof may be designed based on any one of SEQ ID NOs: 3, 5, 7, 9, 11, 13, 15, 17, 19, 21, 23, 25, 27, 29, 31, 33, 35, 364, 366, 368, 370, 372, 374, 376, 378, 380, 382, 384 or 386.

The methods and reagents for use in a PCR amplification reaction are well known to those skilled in the art. Suitable protocols and reagents will largely depend on individual circumstances. Guidance may be obtained from a variety of sources, such as for example Sambrook, J. et al., Molecular Cloning, Cold Spring Harbor Laboratory (1989), Sambrook, J. and Russell, D. W. (2001), "*Molecular Cloning: A Laboratory Manual*", 3rd edition, Cold Spring Harbor Laboratory Press, and references cited therein and Ausubel et al. (eds) Current Protocols in Molecular Biology, John Wiley & Sons (2000), incorporated herein by cross-reference.

A person skilled in the art would readily appreciate that various parameters of the PCR reaction may be altered without affecting the ability to amplify the desired product. For example the $Mg^{2+}$ concentration and temperatures employed may be varied. Similarly, the amount of genomic DNA used as a template may also be varied depending on the amount of DNA available.

Other methods of analysis of the amplified DNA to determine the presence or absence of a mutation are well known to those skilled in the art. For instance, following digestion of the amplified DNA with a suitable restriction enzyme to detect a mutation in a CEP gene, CEP receptor gene, or homologue thereof, the DNA may be analysed by a range of suitable methods, including electrophoresis. Of particular use is agarose or polyacrylamide gel electrophoresis, a technique commonly used by those skilled in the art for separation of DNA fragments on the basis of size. The concentration of agarose or polyacrylamide in the gel in large part determines the resolution ability of the gel and the appropriate concentration of agarose or polyacrylamide will therefore depend on the size of the DNA fragments to be distinguished.

Detection and/or determination of the existence of a mutation in a CEP gene, CEP receptor gene, or homologue thereof may be aided by computer analysis using any appropriate software. Suitable software packages for comparison of determined nucleotide sequences are well known in the art and are readily available.

Plants with Modulated Growth

Plants having modulated growth, compared to the plant(s) from which they are derived, obtained by any of the methods described above, are also encompassed within the ambit of the present invention. Such plants may include, for example, plants with increased or decreased growth (ie. increased or decreased biomass and/or increased or decreased seed or fruit yield), accelerated or delayed growth, shorter or longer life-cycles, earlier or delayed maturation. According to an embodiment, the present invention provides plants which are at least partially insensitive to environmental stresses (especially nutrient limitation, sodium or salt stress, drought, etc.) and therefore grow faster under those conditions compared to the plant(s) from which plants according to the invention are derived.

Also encompassed are plant parts, including but not restricted to leaves, stems, roots, tubers, flowers, fruits and seeds obtained from such plants.

Preferred forms of the present invention will now be described, by way of example only, with reference to the following examples (with relevant portions of Examples 1 to 3 having been previously presented in WO 2013/104026, but reproduced herein by way of complete description), including comparative data, and which are not to be taken to be limiting to the scope or spirit of the invention in any way.

EXAMPLES

Example 1

Materials and Methods

Plant Materials and Growth Conditions

Seeds of *M. truncatula* cv Jemalong genotype A17 wild-type and *M. truncatula* 2HA line carrying either GH3 promoter-GUS reporter fusion gene (GH3:GUS) were grown under standard conditions (Holmes P, Goffard N, Weiller G F, Rolfe B G, & Imin N (2008), "Transcriptional profiling of *Medicago truncatula* meristematic root cells", *BMC Plant Biol* 8:21).

For root assays, seeds of *Arabidopsis thaliana* (accession Col-0) were surface sterilized with 6.25% bleach, stratified for 3-4 days and sown onto plates. Standard growth medium was ½ MS medium with Gamborg's vitamins (M0404; Sigma Aldrich) adjusted to pH 5.7 and solidified with 1% phytagel (P8169; Sigma Aldrich). Modified ½ MS medium consisted of basal micronutrient solution (M0529; Sigma Aldrich) with macronutrients added to the concentrations described (Murashige and Skoog, 1962) as indicated in the text. Plates were placed vertically in a growth chamber at 22° C. with a 16 hour photoperiod and photosynthetically active radiation of 100 $\mu mol/m^{-2}/s^{-1}$. Plates were imaged using an Epson scanner and images were analysed using the SmartRoot plugin (Lobet et al., 2011) in ImageJ. Statistically significant differences were determined using a two-sample t-test (Genstat $14^{th}$ edition) where appropriate.

For hydroponic growth assays, the lids of Eppendorf tubes were separated and a hole was punched in the top. The lids were filled with 0.5% agar and a single stratified seed was placed in the hole. Lids were placed in floating holders in tubs containing ¼ MS medium (M0404; Sigma Aldrich). Tubs were aerated for 15 mins every two hours.

Figure 6:
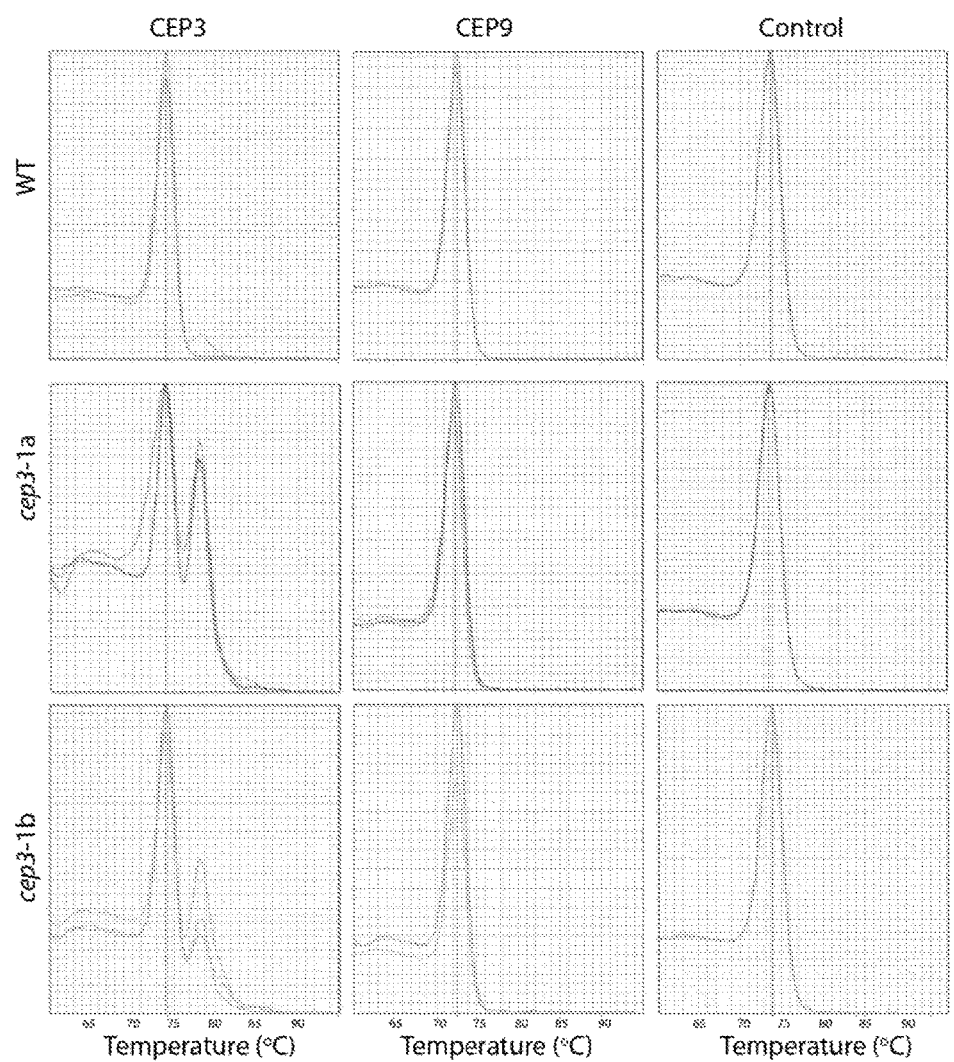
FIG. 6—Melt curves from qRT-PCR of cep3 knockout mutants and Col-0. Melt curves for cep3-1a and cep3-1b both show non-specific binding for CEP3 primers compared to Col-O, indicating a lack of CEP3 transcript in these samples. CEP9 and control (At1g13320) melt curves show consistent binding.

SALK_15856C, which has a T-DNA insertion in the CEP3 gene (Alonso J M, Stepanova A N, Leisse T J. et al. (2003), "Genome-wide insertional mutagenesis of *Arabidopsis thaliana*", Science 301, 653-657), was obtained from ABRC. As it was initially expected that redundancy would occur in the CEP family, this mutant was crossed with SALK_075885, which has a T-DNA insertion in the CEP9 gene. In this line, cep3-1a was confirmed to be homozygous for the T-DNA in CEP3 and hemizygous for the T-DNA insertion in CEP9. qRT-PCR was used to confirm that CEP3 expression was absent and CEP9 expression was not reduced in this line (FIG. 6). Additionally, phenotypes were extremely consistent within treatments, indicating that the hemizygous insertion in CEP9 was not affecting the phenotype. cep3-1a was used in the majority of phenotyping assays. From the progeny of cep3-1a, a line with a single homozygous T-DNA insertion in the CEP3 gene and no insertion in the CEP9 gene, cep3-1b, was obtained. This line showed phenotypes consistent with cep3-1a in selected assays (FIG. 7A). qRT-PCR was used to confirm that CEP3 expression was absent and CEP9 expression was not reduced in this line (FIG. 6).

Identification of CEPs in Nematodes

All available genome sequence for the plant parasitic nematodes *Meloidogyne hapla*, *M. incognita*, and *M. chitwoodi*, *Globodera rostochiensis*, *Heterodera glycines*, *Pratylenchus coffeae*, *Radopholus similis* as well as the free-living nematode *C. elegans* were processed to discover open reading frames between 30 and 150 amino acids long, from ATG to stop, using the program getorf. SignalP was used to search for signal sequences in all resulting ORFs, using both neural network (NN) and Hidden Markov Model (HMM) modes. A custom-made database of ORFs with an identifiable signal sequence was created and searched for the pattern "xfrPTxpGxSPGxGx" (SEQ ID NO: 416) using a double-affine Smith-Waterman algorithm from TimeLogic (TimeLogic DeCypher systems). Resulting matches were hand-curated for conservation of CEP domains as compared to CEP domains found in *A. thaliana* and *M. truncatula*.

Identification of CEPs in Plants

The pervasiveness of genes with CEP domains in plant genomes was examined using the conserved 15-amino-acid *M. truncatula* CEP sequences as queries for BLAST searches (http://blast.ncbi.nlm.nih.gov/Blast.cgi).

RNA Extraction, cDNA Synthesis and qRT-PCR Analysis.

RNA extraction, cDNA synthesis and qRT-PCR analysis was performed as described in L. Kusumawati, N. Imin, M. A. Djordjevic, (2008), "Characterization of the secretome of suspension cultures of *Medicago* species reveals proteins important for defense and development" *J. Proteome Res.* 7: 4508. The primers used are listed in Table 1 (see below). Normalization was conducted by calculating the differences between the $C_T$ of the target gene and the $C_T$ of MtUBQ10 (MtG1 accession number TC161574). Normalization for relative quantification for the transcript level of each gene was carried out according to 'delta-delta method (2). According to the method, the average $C_T$ values

TABLE 1

Primers used for cloning of *M. truncatula* CEP gene and the real-time qRT-PCR analysis.

| Name | Accession number | Forward primer (5'-3') | Reverse primer (5'-3') |
|---|---|---|---|
| | | Gateway cloning | |
| MtCEP1 | Mtr.7265.1.S1_at | CACCATGGCTT ATAAATTTCAA TACACAATGA (SEQ ID NO: 417) | TCAATTTCCAAT TTTGTTTTGGT (SEQ ID NO: 418) |
| | | qRT-PCR analysis | |
| MtCEP1 | Mtr.7265.1.S1_at | CCGATGAAGAT ATCGACGTGAA (SEQ ID NO: 419) | GAACTCATTTG TAGTATCCTCA GTCACAT (SEQ ID NO: 420) |
| MtCEP2 | META519TF | TAGCTCGCATT TGCTTGTTC (SEQ ID NO: 421) | GGCTGAATGCT TTGTCTCAA (SEQ ID NO: 422) |
| MtCEP3 | TC125059 | ACGTTGAGCTC CACCATTTT (SEQ ID NO: 423) | GAGCGCTCCAC CTCCTATTA (SEQ ID NO: 424) |
| MtCEP4 | Medtr5g025790.1 | CATGGAGGTGG TGTTTGATG (SEQ ID NO: 425) | TTTTCGCCCTA CAAGTCCAG (SEQ ID NO: 426) |
| MtCEP5 | Medtr5g017710.1 | GTGTTGTTTTG AGCCCAAGG (SEQ ID NO: 427) | TGTTGGTCGAA AAGCTTCAA (SEQ ID NO: 428) |
| MtCEP6 | AC233112_1004.1 | GCTCATCATGG AGGGAAGTC (SEQ ID NO: 429) | TATGCCCTGGA GATGTAGGC (SEQ ID NO: 430) |

TABLE 1-continued

Primers used for cloning of M. truncatula CEP gene and the real-time qRT-PCR analysis.

| Name | Accession number | Forward primer (5'-3') | Reverse primer (5'-3') |
|---|---|---|---|
| MtCEP7 | AC233112_1013.1 | CCGGATGTTGAGGTTTTTGT (SEQ ID NO: 431) | GGCCAACTCCAGGACTATGA (SEQ ID NO: 432) |
| MtCEP8 | AC233112_1014.1 | TCCAACAATATTGCCACCAA (SEQ ID NO: 433) | GGGTTGTGGGTCTAAAAGCA (SEQ ID NO: 434) |
| MtCEP9 | AC233112_1014.1 | TGATGCCAAATCATGGTGTC (SEQ ID NO: 435) | GGACTGCTTCCTGGTGTTGT (SEQ ID NO: 436) |
| MtCEP10 | Medtr5g030490.1 | TCAATGGAAGCATCAAGGTTT (SEQ ID NO: 437) | TATATGTCCCACCCCAAGAC (SEQ ID NO: 438) |
| MtCEP11 | Medtr8g086600.1 | AGCTCCTTCCATTGGCTTTT (SEQ ID NO: 439) | CCCCACCAGGACTATGACC (SEQ ID NO: 440) |
| MtNRT2.5 | Mtr.35456.1.S1_at | GGAGAAGGAGAAAGGGTCTCA (SEQ ID NO: 441) | TCAGAAGGCCTAGTTGAAATG (SEQ ID NO: 442) |
| MtAGL1 | Mtr.15656.1.S1_at | GAACCGAAGGGAAGCATAA (SEQ ID NO: 443) | TGTCGTGCCATACACCTTTT (SEQ ID NO: 444) |
| MtLBD38* | Mtr.22734.1.S1_at | GCCACGCTACTGTTTTCGTA (SEQ ID NO: 445) | GAGCTGGTCTCTGTGGTTCA (SEQ ID NO: 446) |
| MhCEP10 | Mh_Contig368 | GCACCTCAACCTCCTTTCTGCA (SEQ ID NO: 447) | TGTCCATTTACTGGTGGCTTACATGG (SEQ ID NO: 448) |
| MtUBQ10 | TC100142 | AACTTGTTGCATGGGTCTTGA (SEQ ID NO: 449) | CATTAAGTTTGACAAAGAGAAAGAGACAGA (SEQ ID NO: 450) |

Accession numbers are from either Affymetrix probe IDs or M. truncatula gene index IDs (compbio.dfci.harvard.edu) or from International Medicago Genome Annotation (www.medicago.org/genome/IMGAG/) IDs. MtCEP6-9 sequences are from unannotated sequences.
*Annotated as LOB domain-containing protein 38 (ID, Medtr4g095600.1) by IMGAG.

of the gene of interest from the technical triplicate of a sample is subtracted with the average $C_T$ values of the housekeeper gene (MtUBQ10) from the same sample as shown in the formula below: $\Delta Ct = C_T^{gene\ of\ interest} - C_T^{housekeeper\ gene\ (MtUBQ10)}$. The same calculation was carried out for both the control sample and the sample of study. The $\Delta C_T$ value obtained from the above calculation was then used to calculate the 'delta-delta' Ct value according to the formula below: $\Delta\Delta C_T = \Delta C_T^{sample\ of\ study} - \Delta C_T^{control}$. These values were then used to calculate for the fold differences of each sample by using the following formula: Fold difference=$2^{-\Delta\Delta C_T}$. From the calculation, the control samples were valued close to 1 and all the other samples had a relative value to the controls. These values were then calculated in Excel for their standard error and their P-values using Student's t-test. Three biological (independent root samples), two experimental (independent cDNA synthesis) and three technical repeats (independent real-time PCR) were done for each sample.

Alternatively, RNA was extracted using the Trizol reagent (Life Technologies) and purified using spin columns (RNeasy plant mini kit; QIAGEN). cDNA was synthesized using the Superscript III Kit (Invitrogen). Taqman reactions were set up and run according to manufacturer's specifications (Life Technologies) using gene specific probes and a control probes (PP2AA3; At1g13320) designed by the manufacturer. Three biological replicates and three technical replicates were used.

Outliers were omitted from analysis. Data was analysed using the $\Delta\Delta C_T$ method (Livak K J, Schmittgen T D (2001), "Analysis of relative gene expression data using real-time quantitative PCR and the $2^{-\Delta\Delta CT}$ method", Methods 25, 402-408) and statistical analysis was performed as described using a t-test (Yuan J, Reed A, Chen F, et al. (2006), "Statistical analysis of real-time PCR data", BMC Bioinformatics 7, 85). For CEP3 and CEP9 expression assays in the cep3-1 mutants and for confirmation of CEP over-expression lines, primers were used together with Fast Sybr Green Mastermix (Invitrogen) according to manufacturer's instructions. Melt curves were analysed for to ensure specific primer binding. Data was analysed as described above.

*Agrobacterium Rhizogenes*—Mediated Hairy Root Transformation

A PCR fragment corresponding to the full-length open reading frames of MtCEP1 was amplified from *M. truncatula* cDNA and cloned into the pK7WG2D vector by methods as described in Karimi M, Inze D, & Depicker A (2002) "GATEWAY vectors for *Agrobacterium*-mediated plant transformation", *Trends Plant Sci* 7(5):193-195. The respective constructs were transformed into *A. rhizogenes* strain Arqual as described in Saur I M, Oakes M, Djordjevic M A, & Imin N (2011), "Crosstalk between the nodulation signaling pathway and the autoregulation of nodulation in *Medicago truncatula*", *New Phytol*, 190(4):865-874. Transgenic roots were identified by the presence of green fluorescent protein (GFP) with an Olympus SZX16 stereomicroscope equipped with a GFP filter unit (Model SZX2-FGFPA, Shinjuku-ku, Tokyo, Japan).

Nodulation with *Sinorhizobium meliloti* and Assessment of Nodule Numbers

The 3-weeks old transformed hairy-roots plants were first transferred to a modified Fahraeus media without $NH_3NO_4$ and kanamycin to starve the plants of nitrogen for 4 days. Inoculation with *Sinorhizobium meliloti* was done as described in Saur I M, Oakes M, Djordjevic M A, & Imin N (2011), "Crosstalk between the nodulation signaling pathway and the autoregulation of nodulation in *Medicago truncatula*", *New Phytol* 190(4):865-874.

Exogenous Application of Synthetic Peptides

The CEP peptides were synthesized at the Biomolecular Resource Facility, The Australian National University. The 15 amino acid (aa) peptides corresponding to the conserved domains of MtCEP1 (AFQHypTTPGNSHypGVGH and EFQKTNPGHSHypGVGH—SEQ ID Nos: 451 and 452 respectively—where Hyp indicates hydroxy proline residue) and *M. hapla* MhCEP2 (AFRHypTAPGHSHypGVGH; SEQ ID NO: 453) were synthesized and validated as previously described in Djordjevic M A, et al. (2011), "Border sequences of *Medicago truncatula* CLE36 are specifically cleaved by endoproteases common to the extracellular fluids of *Medicago* and soybean", *J Exp Bot* 62(13):4649-4659. The root length of wild-type plants was measured four days after transfer to Fåhraeus-medium containing the synthetic peptide. For the hormone assays, A17 plants were grown on Fåhraeus-medium for 10 days before transferring to Fåhraeus-medium containing $10^{-6}$ M of the respective phytohormones; 1-aminocyclopropane-1-carboxylic acid (ACC), 6-benzylaminopurine (BAP), gibberellic acid (GA), synthetic analog of strigolactone (GR24), methyl jasmonate (MeJA) and 1-naphthaleneacetic acid (NAA).

β-glucuronidase (GUS) Staining and Sectioning

GUS activity was localized in transgenic hairy roots carrying GH3:GUS or MtCEP1:GUS constructs. For the promoter analysis of MtCEP1, the upstream 2.2-kb promoter region of MtCEP1 was amplified by genomic PCR, then cloned into the binary vector pKGWFS7. *M. truncatula* (A17) roots was transformed with these constructs via *Agrobacterium rhiogenes* by hairy root transformation method as described in Saur I M, Oakes M, Djordjevic M A. & Imin N (2011), "Crosstalk between the nodulation signaling pathway and the autoregulation of nodulation in *Medicago truncatula*", *New Phytol* 190(4):865-874. Histochemical analysis of GUS gene expression in the transformed plant roots was performed as described in Vitha S, Benes K, Phillips J P, & Gartland K M (1995), "Histochemical GUS analysis", *Methods Mol Biol* 44:185-193. Staining and sectioning was performed three times, each time taking roots of four plants, and similar results were obtained each time. Staining was examined with a Nikon SMZ1500 stereomicroscope and photographed with a mounted Digital Sight DS-Ri1 camera (Nikon Inc., Melville, N.Y., USA). Sectioning of the roots was done as described in Saur I M, Oakes M, Djordjevic M A, & Imin N (2011), "Crosstalk between the nodulation signaling pathway and the autoregulation of nodulation in *Medicago truncatula*", *New Phytol* 190(4):865-874.

Confocal Microscopy

Root samples were fixed in fixative (50% methanol and 10% acetic acid) at 4° C. for overnight, rinsed with water and stained with 10 µg/ml propidium iodide in water at room temperature (avoiding light) until plants were visibly stained (less than 3 h). Then the roots were examined by multiphoton imaging using a LSM 780 confocal microscopy (Carl Zeiss, Jena, Germany).

Other Microscopy and Imaging

To define the stages of lateral root development, Differential Interference Contrast microscopy was performed on cleared roots as described (Malamy J E, Benfey P N (1997), "Organization and cell differentiation in lateral roots of *Arabidopsis thaliana*", *Development* 124, 33-44).

Over-Expression Constructs and Plant Transformation

To make over-expression constructs, CEP2, CEP3, CEP4, CEP5, CEP6 and CEP9 coding sequences were PCR amplified from genomic DNA and cloned into pENTR D-TOPO. An LR recombination reaction was performed with the pK7WG2D destination vector (Karimi et al., 2002). Constructs were transformed into *Agrobacterium tumefaciens* strain LBA4404 (Invitrogen), which was used to transformed the vector into Col-0 plants using the floral dip method (Clough and Bent, 1998). Over-expression was confirmed by qRT-PCR in selected independent lines (independent lines are identified by different numbers). All lines were at least generation $T_3$.

RNA Extraction, cDNA Synthesis and qRT-PCR Analysis

RNA was extracted using the Trizol reagent (Life Technologies) and purified using spin columns (RNeasy plant mini kit; QIAGEN). cDNA was synthesized using the Superscript III Kit (Invitrogen). Taqman reactions were set up and run according to manufacturer's specifications (Life Technologies) using gene specific probes and a control probes (PP2AA3; At1g13320) designed by the manufacturer. Three biological replicates and three technical replicates were used. Outliers were omitted from analysis. Data was analysed using the $\Delta\Delta C_T$ method (Livak and Schmittgen, 2001) and statistical analysis was performed as described using a t-test (Yuan et al., 2006). For CEP3 and CEP9 expression assays in the cep3-1 mutants and for confirmation of CEP over-expression lines, primers were used together with Fast Sybr Green Mastermix (Invitrogen) according to manufacturer's instructions. Melt curves were analysed for to ensure specific primer binding. Data was analysed as described above.

Data Mining Analyses

To instigate our analysis of CEP expression profiles in *Arabidopsis*, we used Genevestigator (Hruz et al., 2008). Data were filtered to show only results with a fold change greater than 1.5 and a P value of <0.05.

Example 2

Plant CEPs

We examined the distribution and function of a multigene family we call CEPs (Root Architecture Regulators). Phylogenetic analyses indicate that CEP genes are unique to the genomes of higher plants and RKN, and encode a conserved 15 amino acid CEP domain that is predicted to be secreted. Using expression analysis we show that in the model legume *Medicago truncatula*, CEPs are regulated by lowered N-status and elevated $CO_2$ and they play an important role in controlling root development and the expression of genes integral to the control of N-status and uptake including ANR1, NRT2.1, NRT2.5 and LBD38. Due to the technological difficulties experienced with knockdown strategies for large multigene families we used over-expression studies to demonstrate that the CEP domain encoding gene, MtCEP1, profoundly affect multiple aspects of root architecture and development including lateral root and nodule formation and root hair development. Superficially, the periodic bumps induced resemble galls produced by root knot nematodes, and this is corroborated by confocal imaging.

Figure 3:
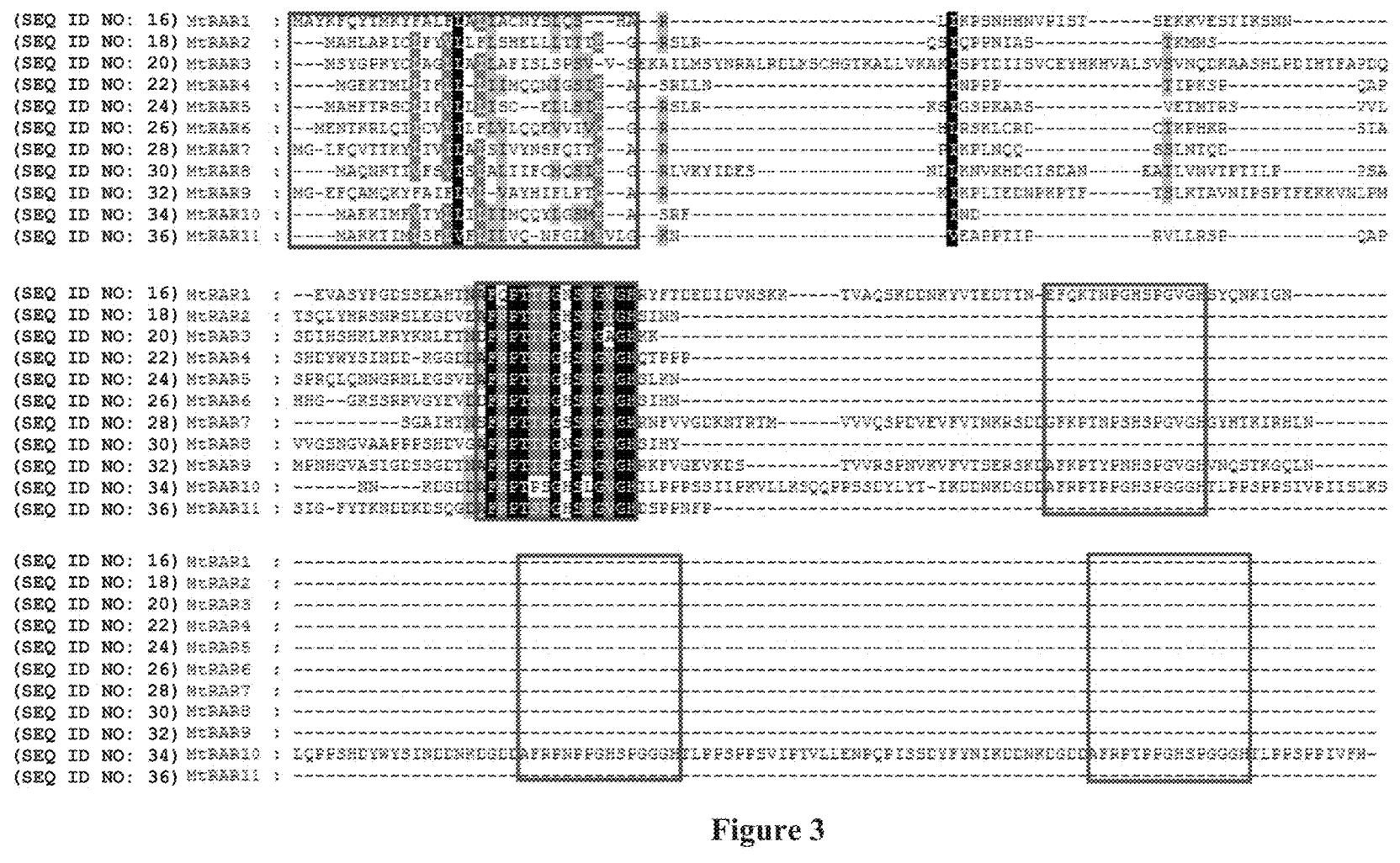

Ohyama et al (2008) had previously shown that an *Arabidopsis* gene AtCEP1 (C-terminal encoded peptide) produces a 14 or 15 amino acid secreted ligand that affects primary root growth only (Ohyama K, Ogawa M, & Matsubayashi Y (2008), "Identification of a biologically active, small, secreted peptide in *Arabidopsis* by in silico gene screening, followed by LC-MS-based structure analysis", *Plant J* 55:152-160). AtCEP1 corresponds to AtCEP1, and is thus the historical canonical member of this family. However, since our results place *M. truncatula* CEPs at the crossroads of root development and responses to nutritional cues, we temporarily renamed the CEPs as RARs (as reflected in FIGS. 1 to 3) to reflect this key function. In addition, our results also point to CEP ligand mimicry by RKNs suggesting a role for these nematode peptides in gall formation.

Conserved CEP domains are widely dispersed in angiosperms as multigene families (FIG. 1A, FIG. 2A and SEQ ID NOs: 2, 4, 6, 8, 10, 12, 14, 16, 18, 20, 22, 24, 26, 28, 30, 32, 34 and 36-147, 451 and 452 for peptide sequences, and SEQ ID NOs: 1, 3, 5, 7, 9, 11, and 13 for *Arabidopsis thaliana* CEP-encoding sequences, and SEQ ID NOs: 15, 17, 19, 21, 23, 25, 27, 29, 31, 33 and 35 for *Medicago truncatula* CEP-encoding sequences).

*M. truncatula* was found to encode eleven CEP loci (see SEQ ID NOs: 15, 17, 19, 21, 23, 25, 27, 29, 31, 33 and 35 for *Medicago truncatula* CEP-encoding sequences and SEQ ID NOs: 16, 18, 20, 22, 24, 26, 28, 30, 32, 34 and 36 for *Medicago truncatula* CEP translated peptide sequences). Except for the peptide domains, little sequence conservation exits amongst CEP genes (see FIGS. 1A and 3). However, CEP genes encode an amino-terminal signal peptide or a non-classical secretion signal (see, for example, FIGS. 1B to 1D, 2D and 3), which is a feature of secreted regulatory plant peptide families. A strongly conserved functional CEP subdomain occurs at the C-terminus of the CEP domain (FIG. 1A).

CEP genes can encode single or multiple CEP peptides. For example, MtCEP1 (SEQ ID NO: 15) encodes two peptides (see FIG. 1B and SEQ ID NOs: 166 and 167; see also SEQ ID NO: 16 for fully translated sequence), MtCEP10 (SEQ ID NO: 33) encodes four peptides (see SEQ ID NOs: 178 to 181; see also SEQ ID NO: 34 for fully translated sequence) and the poplar gene, PtCEP2, encodes seven (see SEQ ID NOs: 231-237 and SEQ ID NO: 72 for fully translated sequence).

CEP domains in monocots are distinctive to those in dicots (FIG. 1A and FIG. 2A, and see also SEQ ID NOs: 301to 336- monocot CEP peptide domain sequences—vs SEQ ID NOs: 148 to 300—dicot CEP peptide domain sequences). Monocot CEP peptides, with few exceptions, universally lack the conserved phenylalanine residue (at position 2) common to dicot CEP peptides, and all dicot CEP domains terminated with histidine whereas monocot CEP domains terminated with histidine or asparagine (Figs. 1A and 2A). We also found genes encoding CEP-like domains in gymnosperms (white spruce and lodgepole pine—peptide sequences: SEQ ID NOs: 338-350; domain sequences: SEQ ID NOs: 351-363) but not in the evolutionary more primitive plants, *Selaginella* or mosses (FIG. 1A, Table 2), unlike CLEs (found in *Selaginella* and moss) or RGFs (found in *Selaginella*). Angiosperm CEP genes encoded an amino-terminal secretion signal, lacked introns, and consisted of one to seven, 15 amino acid, CEP encoding domains. Apart from the secretion signals and the CEP-encoding domains themselves, and a lack of introns, plant CEP genes had little other sequence conservation (See, for example, FIG. 1A). The gymnosperm CEP-like domains are different from angiosperm CEP in that they exhibit divergence at the first 6 amino acids and have a highly conserved leucine, instead of proline, at position 7. However, the remaining eight carboxyl amino acids of gymnosperm CEP-like domains are strongly conserved with those of angiosperm CEP domains (FIG. 1A).

Figure 2:
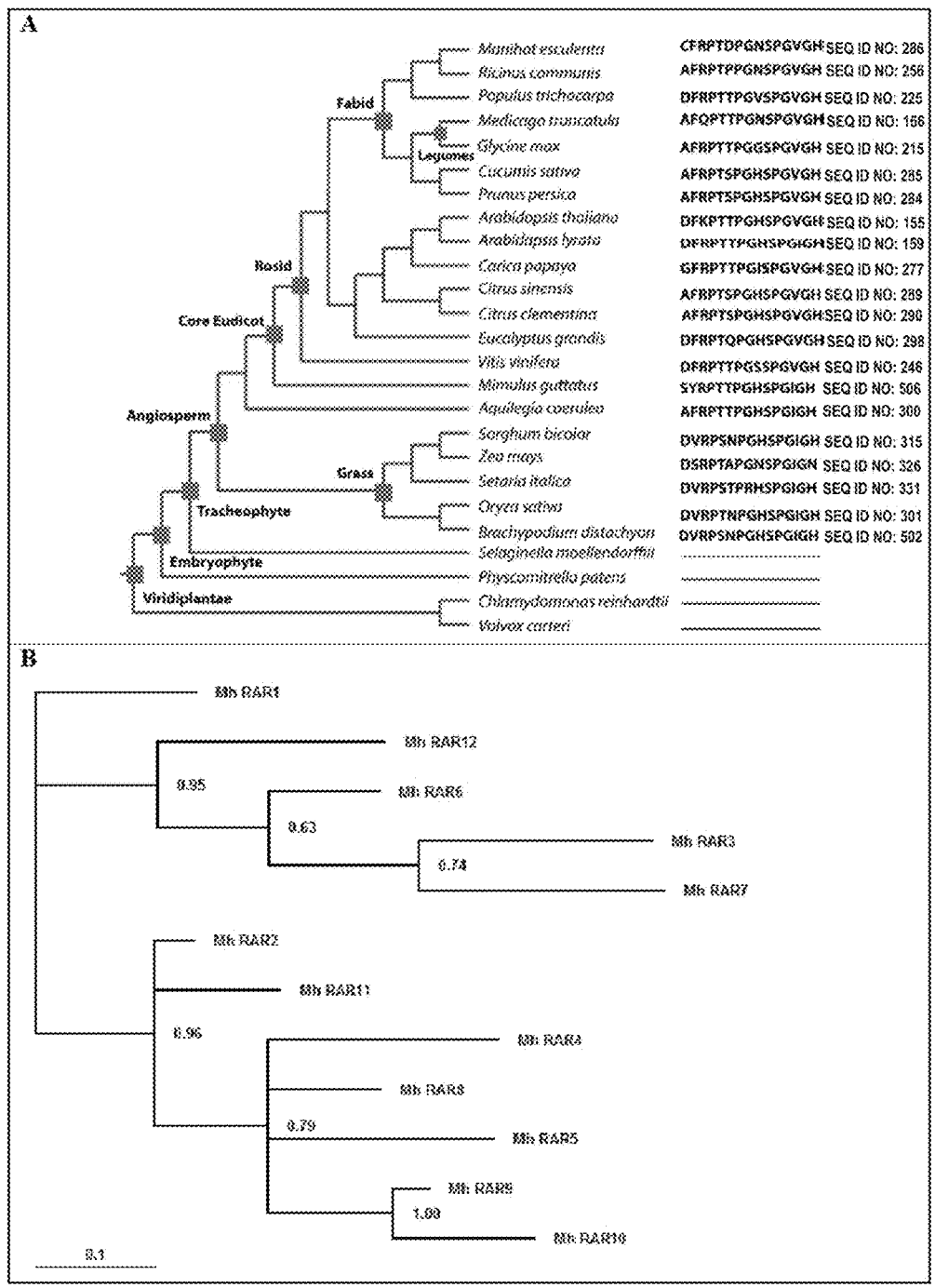
FIG. 2—Shows a sequence analysis of CEP domains (again, shown as RARs due to previous nomenclature) in higher plants and the RKNs. (A) Cladistic representation of CEP genes in plants. The CEP domains are shown for each evolutionarily significant Glade only. (B) Phylogenetic analysis of CEP domains in *Meloidogyne hapla*. (C) Phylogenetic analysis of CEP domains in higher plants and RKNs. (D) Alignment of RKN CEPs (*Meloidogyne hapla* RARs 1-12 —SEQ ID NOs: 365, 367, 369, 371, 373, 375, 377, 379, 381, 383, 385, 387 respectively; and *Meloidogyne incognita* RARs 1-8—SEQ ID NOs: 388-395 respectively). Blue box indicates signal sequence. Red box indicates CEP domain. For (B) and (C) sequence alignment of pro- CEP and C-terminal domains was done by a combination of ClustalW and manual adjustment. Phylogenic tree construction was done by MrBayes. Numbers report the posterior probabilities of the 50% majority consensus tree.

We also found a distinctive group of CEP genes in angiosperms, in which the CEP domain contains a strongly conserved nine amino acid C-terminal region and exhibits divergence in the first six N-terminal amino acids (FIG. 1).

Example 3

CEP Genes are Found Exclusively in Higher Plants and Root-Knot Nematodes

Apart from higher plants (angiosperms and gymnosperms) only the obligate plant parasitic animals, root knot nematodes (RKNs), were found to encode CEP genes.

Eight and twelve CEP genes occur in the genomes of *Meloidogyne incognita* and *M. hapla*, respectively (FIG. 2D, Table 2 and SEQ ID NOs: 364, 366, 368, 370, 372, 374, 376, 378, 380, 382, 384 and 386 for *M. hapla* CEP-encoding sequences, SEQ ID NOs: 365, 367, 369, 371, 373, 375, 377, 379, 381, 383, 385 and 387 for *M. hapla* CEP peptide sequences, and SEQ ID NOs: 388-395 for *M. incognita* CEP peptides), but none are found in non-root-knot nematodes including *C. elegans* or the plant parasitic cyst nematodes (see Table 2).

TABLE 2

Existence of growth regulatory peptide coding genes in plants and nematodes. A representative domain sequence is given for species in each clade.

| | CEP (or CEP-like*) |
|---|---|
| Moss (*Physcomitrella patens*) | X |
| Pteridophyte (*Selaginella moellendorffii*) | X |
| Gymnosperms (*Pinus contorta* & *Picea sitchensis*) | ISPFKPLGHSPGIGH* (SEQ ID NO: 359) |
| Angiosperms (*Arabidopsis*) | DFRPTNPGNSPGVGH (SEQ ID NO: 148) |

TABLE 2-continued

Existence of growth regulatory peptide coding genes in plants and nematodes. A representative domain sequence is given for species in each clade.

| | CEP (or CEP-like*) |
|---|---|
| Root-Knot Nematodes (M. hapla) | DFRPTNPGHSPGIGH (SEQ ID NO: 396) |
| Cyst Nematodes (Heterodera glycines) | X |

Like plant (CEP genes, each RKN CEP identified encoded a putative amino terminal secretion signal but only a single CEP domain peptide, and some RKN CEP genes (e.g. MiCEP1, 3 and 4) encode only an amino terminal signal sequence and a CEP domain (FIG. 2D).

There are two types of RKN CEPs: type one has flanking sequences between the signal sequence and CEP domain and at the C-terminus end of the CEP domain; type two has no flanking sequences between the signal sequence and CEP domain or at the C-terminus end of the CEP domain (FIGS. 1C&D). The juxtaposition of a signal sequence to a RKN CEP domain would obviate the need for processing of several of the CEP domains by additional protease cleavage. Conservation exists between RKN CEP domains and the CEP domains of plant hosts (FIG. 1A; FIG. 2C to 2D and SEQ ID NOs: 148-336, 351-363, 396-415, 451-453 and 502-504).

Because the precise evolutionary history of the CEP genes is not known, it is not possible to ascribe orthology, either within the genus, or with plant CEPs. Thus, we named the RKN CEPs according to their genome assembly coordinates.

CEP loci are absent from the available non-RKN plant parasitic nematode genomes including those of the soybean cyst nematode (Heterodera glycines), potato cyst nematode (Globodera rostochiensis) and the migratory plant parasitic nematodes (Radopholus similis and Pratylenchus coffeae) as well as C. elegans.

Phylogenetic analysis has shown that different MhCEP are more similar to dicot CEP than to each other (FIG. 2C). For instance, the CEP domain sequence (AFRPTAPGH-SPGVGH) of M. hapla MhCEP2 and MhCEP11 (SEQ ID NOs: 397 and 406) was identical to CEP domains of Euphorbia esula (Green spurge; EeCEP2.1, 2.2, 2.3 and 2.5; SEQ ID Nos: 194-196 and 198), and the CEP domain sequence (AFRPTNPGHSPGVGH) of M. incognita MiCEP3 (SEQ ID NO: 410) was identical to the CEP domains in Ricinus communis (castor oil plant; RcCEP3 and RcCEP7; SEQ ID Nos: 261 and 265) and Jatropha curcas (physic nut; JcCEP1; SEQ ID NO: 267). This result may point to RKN and plant CEPs sharing an overlapping functional space.

Figures 4, 5:
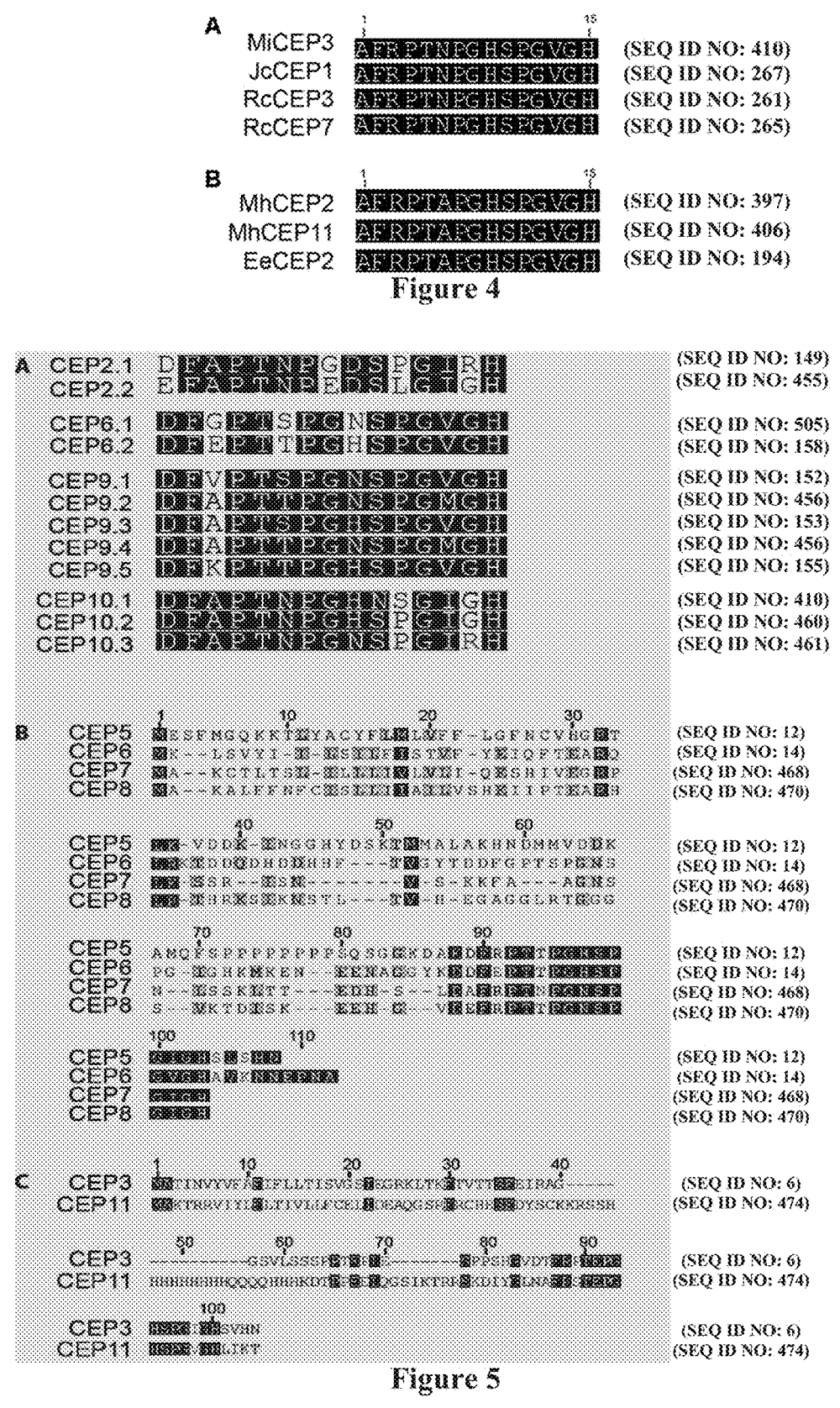

Recently, it was reported that CEP genes are present outside plants only in root knot nematodes (RKN) but not in other plant parasitic or free living nematodes. A comparison of plant and RKN CEP domains showed that RKN domains were more similar to group I CEP domains than to other RKN domains (FIG. 4). In some instances, the RKN CEP domains were identical to the CEP domains of angiosperm group I CEPs (FIG. 4). This result may point to RKN and plant CEPs sharing an overlapping functional space and the possibility of RKN utilising CEP mimics for parasitism. It also raises the question of whether CEP genes were acquired by RKN through horizontal gene transfer.

RKN CEP peptides exhibit remarkable similarity to plant CEP peptides (FIGS. 1A and 2), and an overall consensus sequence based on the CEP domains (plant and RKN) may be represented as a 14 to 15 amino acid peptide represented as $(X_1)X_2X_3X_4X_5X_6PGX_9SPGX_{13}GX_{15}$ (SEQ ID NO:454). Typically, the peptide will comprise 15 amino acids. Aspartic acid, glycine, proline and alanine are typically present at position $X_1$, although serine and valine, and to a lesser extent other amino acids may be present at this position. Phenylalanine or valine are typically present at position $X_2$, although threonine, serine, alanine, lysine and tyrosine are often also found at this position, with other amino acids occasionally being observed. Arginine is the predominant amino acid found at position $X_3$, especially in monocots and RKNs, proline is the predominant amino acid found at position $X_4$, threonine, serine or glycine predominantly at position $X_5$, threonine, alanine or asparagine at position $X_6$, asparagine or histidine is predominant at position $X_9$, isoleucine, alanine or valine predominant at position $X_{13}$ and asparagine or histidine is predominant at position $X_{15}$. While amino acid substitutions have been observed at positions 7, 8, these are infrequent (and only proline observed at position 7 in monocots, and isoleucine, serine, asparagine and glutamine observed at position 8 in dicots and RKNs). The SPG motif at positions 10-12 is particularly strongly conserved, especially in monocots and RKNs, with very few substitutions being observed in dicots, and only rare substitutions (arginine or threonine) have been observed at position 14, in monocots and dicots.

Our studies show that CEP or CEP-like genes occur only in higher plants (angiosperms and gymnosperms) and RKNs. Central to the obligate parasitism of diverse higher plants by RKNs is their ability to subvert intrinsic developmental pathways to enable gall formation. The periodic bumps induced by over-expressing MtCEP1 or the ligands of MtCEP1 or M. hapla MhCEP2, outwardly resemble galls and this supports CEP peptides being bioactive. RKN CEP ligands most likely mimic plant CEPs and co-opt plant CEP-dependent pathways during infection and gall formation. RKN CEP expression during gall formation and the tight distribution of CEP loci in the RKN genomes supports this.

CEP Genes in *Arabidopsis*

Five CEP genes were found previously in the *Arabidopsis* genome (Ohyama et al., 2008). Using a bioinformatic approach, we identified an additional ten CEP genes in *Arabidopsis* (Table 3, below). The CEP genes are provided herein as: CEP1—SEQ ID NO: 1; CEP2—SEQ ID NO: 3; CEP3—SEQ ID NO: 5: CEP4—SEQ ID NO: 7; CEP5—SEQ ID NO: 11; CEP6—SEQ ID NO: 13; CEP7—SEQ ID NO: 467; CEP8—SEQ ID NO: 469; CEP9—SEQ ID NO: 9; CEP10—SEQ ID NO: 471; CEP11—SEQ ID NO: 473; CEP12—SEQ ID NO: 475; CEP13—SEQ ID NO: 477; CEP14—SEQ ID NO: 479; CEP15—SEQ ID NO: 481. The proteins encoded by these genes are provided herein as: CEP1—SEQ ID NO:2; CEP2—SEQ ID NO: 4; CEP3—SEQ ID NO: 6; CEP4—SEQ ID NO: 8; CEP5—SEQ ID NO: 12: CEP6—SEQ ID NO: 14; CEP7—SEQ ID NO: 468; CEP8—SEQ ID NO: 470; CEP9—SEQ ID NO: 10; CEP10—SEQ ID NO: 472; CEP11—SEQ ID NO: 474; CEP12—SEQ ID NO: 476; CEP13—SEQ ID NO: 478; CEP14—SEQ ID NO: 480; CEP15—SEQ ID NO: 482. Four of the novel CEP genes were un-annotated (CEP7, CEP8, CEP10 and CEP11) and one (CEP6) was annotated as the first exon of an unrelated gene (TAIR10). Each AtCEP encodes a small protein (77-133 amino acids) with a predicted signal peptide and one or more CEP domains except

TABLE 3

CEP genes in Arabidopsis.

| Gene name | Locus | AGI Coordinates | Signal P Score | Peptide domain name | Peptide domain sequence |
|---|---|---|---|---|---|
| CEP1 | At1g47485 | 17422448-17423066 | 0.84 | CEP1 | DFRPTNPGNSPGVGH (SEQ ID NO: 148) |
| CEP2 | At1g59835 | 22025041-22025421 | 0.68 | CEP2.1 | DFAPTNPGDSPGIRH (SEQ ID NO: 149) |
| | | | | CEP2.2 | EFAPTNPEDSLGIGH (SEQ ID NO: 455) |
| CEP3 | At2g23440 | 9979405-9979819 | 0.96 | CEP3 | TFRPTEPGHSPGIGH (SEQ ID NO: 150) |
| CEP4 | At2g35612 | 14955241-14955501 | 0.83 | CEP4 | AFRPTHQGPSQGIGH (SEQ ID NO: 151) |
| CEP5 | At5g66815 | 26677365-26677865 | 0.81 | CEP5 | DFRPTTPGHSPGIGH (SEQ ID NO: 156) |
| CEP6 | At5g66816 | 26681495-26681800 | 0.82 | CEP6.1 | DFGPTSPGNSPGVGH (SEQ ID NO: 157) |
| | | | | CEP6.2 | DFEPTTPGHSPGVGH (SEQ ID NO: 158) |
| CEP7 | Between At5g66816 and At5g66820 | 26683388-26683615 | 0.99 | CEP7 | AFRPTNPGNSPGIGH (SEQ ID NO: 457) |
| CEP8 | Between At5g66816 and At5g66820 | 26686261-26686521 | 0.97 | CEP8 | EFRPTTPGNSPGIGH (SEQ ID NO: 458) |
| CEP9 | At3g50610 | 18779723-18780412 | 0.77 | CEP9.1 | DFVPTSPGNSPGVGH (SEQ ID NO: 152) |
| | | | | CEP9.2 | DFAPTSPGHSPGVGH (SEQ ID NO: 153) |
| | | | | CEP9.3 | DFAPTSPGNSPGIGH (SEQ ID NO: 154) |
| | | | | CEP9.4 | DFAPTTPGNSPGMGH (SEQ ID NO: 456) |
| | | | | CEP9.5 | DFKPTTPGHSPGVGH (SEQ ID NO: 155) |
| CEP10 | Between At1g36040 and At1g36050 | 13448921-13449316 | 0.90 | CEP10.1 | DFAPTNPGHNSGIGH (SEQ ID NO: 459) |
| | | | | CEP10.2 | DFAPTNPGHSPGIGH (SEQ ID NO: 460) |
| | | | | CEP10.3 | DFAPTNPGNSPGIRH (SEQ ID NO: 461) |
| CEP11 | Between At2g23440 and At2g23450 | 9986193-9986504 | 0.84 | CEP11 | AFRSTEPGHSPGVGH (SEQ ID NO: 462) |
| CEP12 | Exon 1 of At1g31670 | 11337558-11337836 | 0.94 | CEP12 | AFRPTGQGPSQGIGH (SEQ ID NO: 463) |
| CEP13 | At1g16950 | 5796009-5796559 | 0.90 | CEP13 | IYRRLESVPSPGVGH (SEQ ID NO: 464) |
| CEP14 | At1g29290 | 10244966-10245572 | 0.57 | CEP14 | VDRYLRSVPSPGVGH (SEQ ID NO: 465) |
| CEP15 | At2g40530 | 16927502-16928208 | 0.45 | CEP15 | IYRRQGDVPSPGIGH (SEQ ID NO: 466) |

The CEP genes identified in previous study (Ohyama et al. 2008) are indicated with underscores.

TABLE 4

CEPs are induced by environmental cues. Plants were grown on standard medium for 6 days before being transferred to specified treatments. Root and shoot tissue was harvest 24 h after transfer. qRT-PCR was performed using Taqman probes and data was analysed using the $\Delta\Delta C_T$ method. Expression shown is relative to a control treatment (transfer to standard medium for 24 hours). n.d. indicates no reproducible data could be obtained, suggesting genes are not expressed. n.t indicates not tested. Fold change ± standard error is shown. *$P \leq 0.05$; $P \leq 0.01$; *$P \leq 0.001$.

| Tissue | Treatment | CEP1 | CEP2 | CEP3 | CEP4 | CEP5 |
|---|---|---|---|---|---|---|
| root | 0 mM nitrogen | n.e. | n.e. | 10.15 ± 0.58*** | 1.60 ± 0.23* | 2.13 ± 0.21** |
|  | 0.25 mM nitrate | n.e. | n.e. | 1.31 ± 0.08 | 1.17 ± 0.12 | 1.79 ± 0.08*** |
|  | 0.25 mM NH$_4$Cl | n.e. | n.e. | 1.36 ± 0.03 | 1.26 ± 0.05* | 0.71 ± 0.02*** |
|  | 100 mM mannitol | n.e. | n.e. | 0.57 ± 0.13 | 2.35 ± 0.49* | 1.08 ± 0.21 |
|  | 100 mM NaCl | n.e. | n.e. | 2.00 ± 0.13* | 1.68 ± 0.17** | 1.08 ± 0.08 |
|  | 1000 ppm CO$_2$ | n.e. | n.e. | 0.18 ± 0.03*** | 1.02 ± 0.1 | 1.11 ± 0.13 |
| shoot | 0 mM nitrogen | 4.40 ± 0.97** | 0.46 ± 0.06** | 1.16 ± 0.16 | 0.70 ± 0.09 | 0.65 ± 0.10 |
|  | 0.25 mM nitrate | 3.72 ± 0.11** | 4.94 ± 3.18* | 5.89 ± 0.37*** | 4.34 ± 4.91 | 3.62 ± 2.08 |
|  | 0.25 mM NH$_4$Cl | 0.80 ± 0.03 | 0.63 ± 0.08* | 1.14 ± 0.11 | 1.01 ± 0.91 | 1.7 ± 0.51 |
|  | 100 mM mannitol | 4.79 ± 0.56*** | 1.28 ± 0.08* | 2.49 ± 0.34** | 1.86 ± 0.16* | 1.83 ± 0.16* |
|  | 100 mM NaCl | 2.85 ± 0.26** | 0.77 ± 0.26 | 1.75 ± 0.98 | 1.53 ± 0.93 | 1.05 ± 0.65 |
|  | 1000 ppm CO$_2$ | 1.29 ± 0.09 | 0.94 ± 0.14 | 1.45 ± 0.12 | 1.65 ± 0.46 | 1.04 ± 0.19 |

| Tissue | Treatment | CEP9 | CEP13 | CEP14 | CEP15 |
|---|---|---|---|---|---|
| root | 0 mM nitrogen | 1.30 ± 0.14 | 1.61 ± 0.80 | 1.04 ± 0.14 | 1.05 ± 0.08 |
|  | 0.25 mM nitrate | 1.29 ± 0.35 | 2.29 ± 0.08 | 1.09 ± 0.02 | 0.82 ± 0.06 |
|  | 0.25 mM NH$_4$Cl | 0.48 ± 0.02*** | 2.31 ± 0.26 | 1.21 ± 0.03 | 0.84 ± 0.03 |
|  | 100 mM mannitol | 0.34 ± 0.03** | 2.67 ± 0.66 | 0.87 ± 0.06 | 1.25 ± 0.16 |
|  | 100 mM NaCl | 1.70 ± 0.41 | 1.00 ± 0.15 | 1.48 ± 0.29 | 1.04 ± 0.04 |
|  | 1000 ppm CO$_2$ | 0.90 ± 0.41 | 0.58 ± 0.44 | 1.15 ± 0.04* | 1.23 ± 0.06 |
| shoot | 0 mM nitrogen | 1.39 ± 0.18 | 0.62 ± 0.01* | 0.96 ± 0.07 | 0.89 ± 0.04 |
|  | 0.25 mM nitrate | n.t. | n.t. | n.t. | n.t. |
|  | 0.25 mM NH$_4$Cl | n.t. | n.t. | n.t. | n.t. |
|  | 100 mM mannitol | 1.50 ± 0.04 | 1.63 ± 0.23 | 3.82 ± 0.46** | 1.04 ± 0.08 |
|  | 100 mM NaCl | 1.75 ± 0.63 | 0.77 ± 0.41 | 1.26 ± 0.01 | 0.85 ± 0.15 |
|  | 1000 ppm CO$_2$ | 1.06 ± 0.06 | 1.06 ± 0.06 | 1.06 ± 0.06 | 1.06 ± 0.06 |

AtCEP9, which possesses six CEP domains and encodes for a larger protein of 230 amino acids. The internal expansion of the CEP domain in CEP2, CEP6, CEP9 and CEP10 is intriguing as the domain sequences are not always identical to each other (FIG. 5A). Furthermore, CEP genes were often located in close proximity to each other. For example, CEP3 and CEP11 are located in tandem on chromosome 2 and CEP5, CEP6, CEP7 and CEP8 are also arranged sequentially on chromosome 5. Analysis of the amino acid sequences of these preproproteins shows no significant similarity in the N-terminal signal peptide or variable region and the domain sequences are not identical (FIG. 5B-C), indicating these genes did not arise through a recent duplication event. These data indicate that evolution may be favouring diversity in CEP domain sequence as opposed to an increase in domain dosage.

Example 4

AtCEPs are Induced by Environmental Cues and Show Tissue Specific Expression

AtCEP3, CEP5 and CEP9 were found to be significantly induced by environmental conditions, particularly nutrient and biotic stress. For these three genes, nitrate starvation was one of the top three conditions under which a significant perturbation in gene expression occurred. CEP1, CEP13 and CEP14 were significantly induced under a range of different stimuli (data not shown).

To deepen our understanding of CEPs, we explored the expression of nine CEP genes under various growth conditions. Plants were grown for six days on standard medium before being transferred to various treatments for 24 hours (Table 4, above). We found that the expression of all the CEP genes were perturbed by the environmental stimuli tested in the root, shoot or both, except for CEP15. As the environmental stimuli tested were by no means comprehensive, it is possible that CEP15 expression is responsive to other environmental factors. Our results suggest that CEP1 and CEP2 are not expressed in the root under the conditions tested, but this may be due to the fact that 7-day-old plants do not have many lateral root primordia and as we were taking whole root samples the expression may have been diluted. Additionally, the expression of CEP1 and CEP2 in the roots may be induced by other factors not tested in this assay.

The most notable perturbation was a ten-fold increase in CEP3 expression in the roots under nitrogen depletion. This strong induction was not seen in the shoots, or under nitrogen limiting conditions in the roots. However, significant induction in the shoots was seen under nitrate, but not ammonium limitation. These data indicate that the response of CEP3 to low nitrogen is both tissue and nitrogen source specific. CEP3 was up-regulated two fold in response to increased salt in the roots and increased osmotic strength in the shoots. CEP3 was severely down-regulated in response to increased CO$_2$ levels in the roots only.

The expression of other CEP genes was also perturbed under the conditions tested. CEP1 was up-regulated in the shoots under nitrogen depletion and nitrate limitation, but not ammonium limitation. Increased osmotic strength and increased salt levels also induced CEP1 in the shoots. CEP2 expression was down-regulated in the shoots under nitrogen depletion and ammonium limitation, but was induced by nitrate limitation. CEP4 expression was induced slightly in the roots by nitrogen depletion and ammonium limitation, but not by nitrate limitation. The strongest induction in CEP4 expression was seen under increased osmotic strength in both the roots and shoots. CEP5 was induced in the roots under nitrogen depletion and nitrate limitation, and repressed under ammonium limitation. The only change in CEP13 expression was repression seen in the shoots under nitrogen depletion. CEP14 expression was increased slightly in the roots under increased $CO_2$ levels and more strongly in the shoots under increased osmotic pressure.

CEP9 expression was repressed under ammonium limitation as well as increased osmotic strength in the roots. The expression of CEP9 was not significantly induced in either roots or shoots.

Our data indicated that CEP expression is perturbed by different environmental stimuli. This implicates CEPs as regulators of plant development in response to environmental stress. Expression changes were specific to roots and shoots and each CEP gene tested had a different expression profile.

Example 5

Activity of Synthetic CEP Variants in *Arabidopsis*

A previous report described the mature product of CEP1 as a 14 or 15 amino acid peptide with either one or two hydroxylated proline residues (Ohyama et al., 2008). Treating plants with a synthetic 15 amino acid CEP1 peptide at $10^{-6}$ M to $10^{-7}$ M inhibited root growth and generated a phenotype similar to CEP1 over-expression (Ohyama et al., 2008). We explored the phenotypic activity of variants of CEP3, CEP5 and CEP9 as well as a scrambled peptide based on the amino acid sequence of CEP5 H (FIG. 8A-B; FIG. 9).

Figure 8:
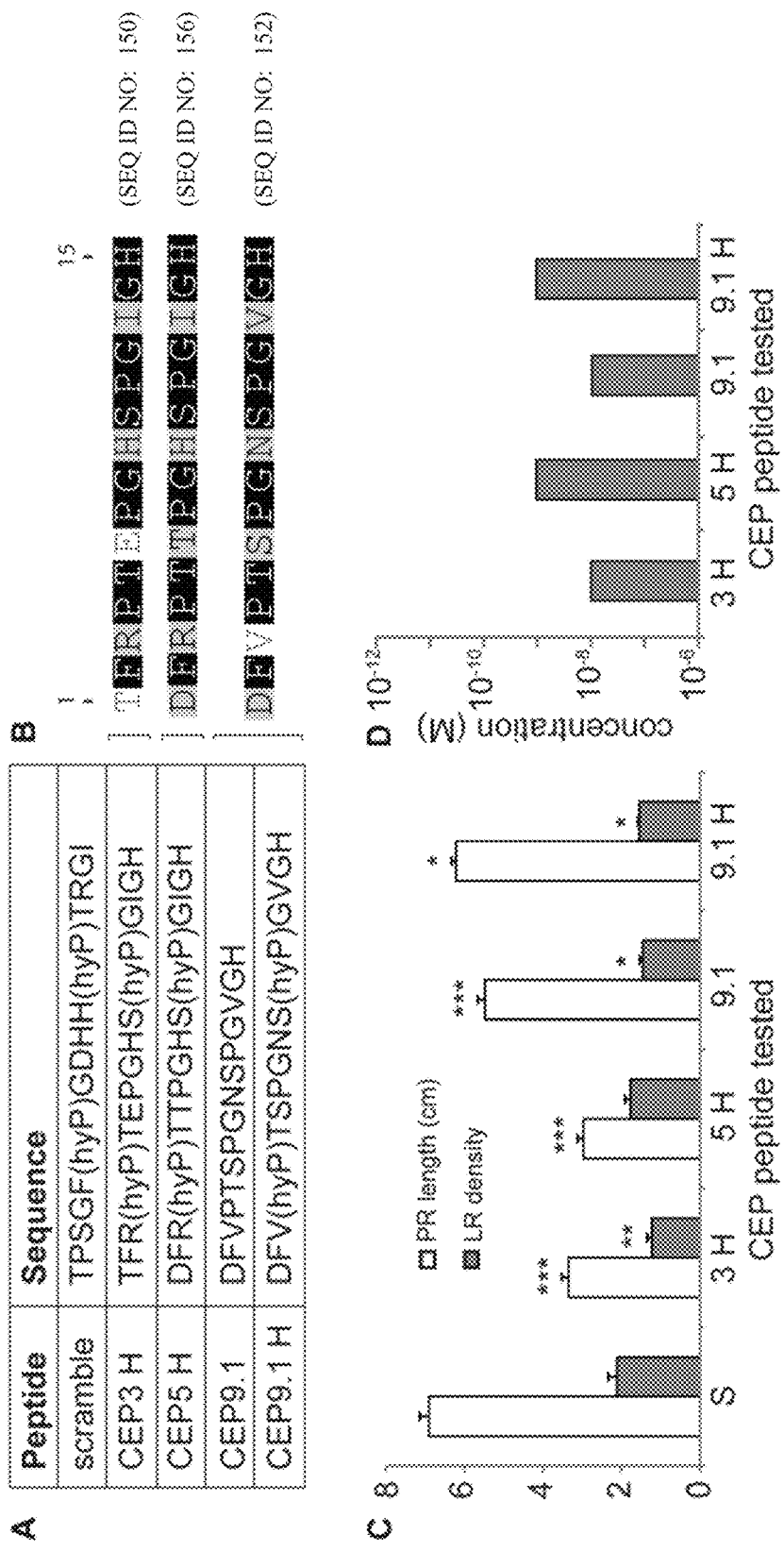
FIG. 8—CEP synthetic peptides decrease primary root length and lateral root density. (A) CEP peptides used in growth assays. (hyP) indicates hydroxyproline residues. (B) Alignment of CEP3, CEP5 and CEP9.1 peptide domains. (C) Primary root length and lateral root density of 12-day-old Col-0 plants grown on standard medium supplemented with 1 µM of the specified peptide. n≥7 plants. (D) Differential biological activity of CEP3, CEP5 and CEP9 peptide variants. The histogram indicates the lowest concentration at which a peptide elicited a significant reduction in primary root length compared to untreated plants (P<0.05). Col-0 plants were grown vertically for 12 days on standard medium supplemented with peptide concentrations ranging from $10^{-6}$ M to $10^{-12}$ M. n=7-16 plants. Error bars show standard error. *P≤0.05; P≤0.01; * P≤0.001 (two-sample t-test, Genstat).
Figure 9:
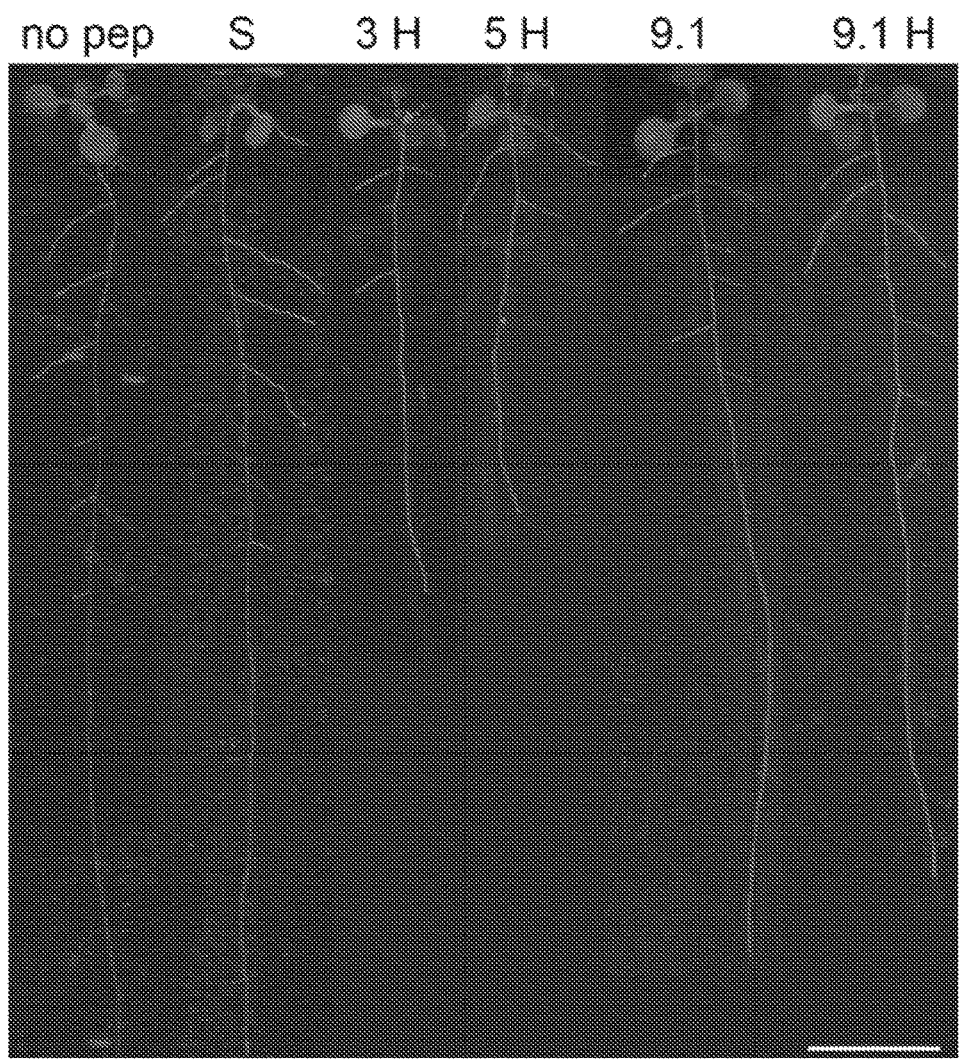
FIG. 9—Phenotypes of 12-day-old Col-0 plants grown on standard medium supplemented with 1 µM of the specified peptide. See FIG. 2 for peptide sequences. Scale bar=1 cm.

All of the CEP variants, applied to plants at 10–6 M, not only decreased primary root length, but also significantly decreased lateral root density, except for CEP 5H (FIG. 8C). As expected, the scrambled peptide showed no effect on root growth. The severity of the effect of CEP variants was dependent on the peptide sequence as well as the modification. CEP3 H and CEP5 H both severely affected primary root length, reducing it to about half that of untreated plants. However only CEP3 H significantly decreased lateral root density. These two peptide variants are very similar in amino acid sequence, with only three residues differing and the last nine residues being identical (FIG. 8B). CEP9.1 and CEP9 H had a much weaker effect on primary root length, but also reduced lateral root density. Two of the terminal nine residues of CEP9.1 are different (but synonymous) to CEP3 H and CEP5 H. Thus, the terminal residues play a crucial role in peptide activity, potentially as they are required for interaction with receptors. In particular, the terminal residues of CEP peptide domains are highly conserved.

To determine the differential biological activity of each peptide, a titration was performed using primary root length as an indicator of biological activity (FIG. 8D). CEP3 H, which had the most severe effect on overall root architecture (FIG. 8B), was active at 10–8 M. Biological activity was seen with CEP5 H at 10–9 M. CEP9.1 H was active at a lower concentration than the non-hydroxylated CEP9.1, even though the effect of CEP9.1 H on primary root length at $10^{-6}$ M was less severe. These data suggest both domain sequence and modifications determine functional activity and may present an avenue for regulation of peptide activity through post-translational modification. It is possible that the difference in potency of our CEP peptide variants is due to changes in the affinity of the peptide for its receptor. Our data further highlight the dynamics of peptide-mediated regulation and the importance of the peptide sequence and structure.

Example 6

Over-Expression Reveals a Role for CEPs in Root and Shoot Development

Figure 10:
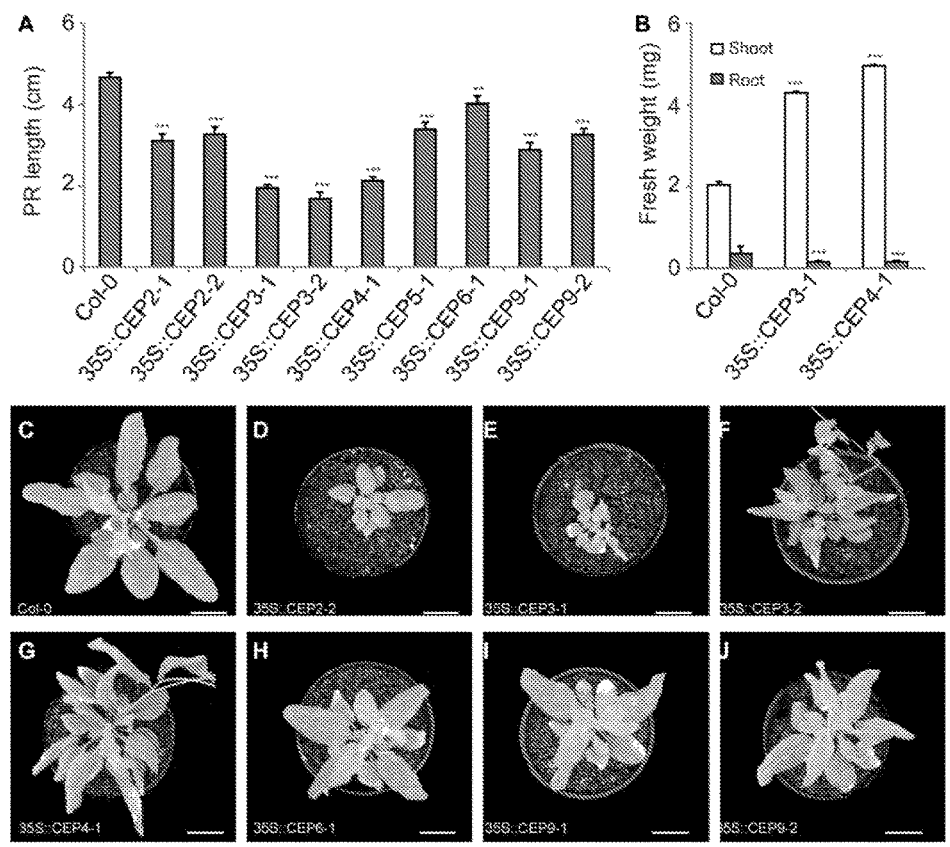
FIG. 10—CEP over-expression (pro35S::CEP) affects root and shoot architecture. (A) Primary root length of CEP over-expression lines. Plants were grown on standard ½ MS medium for 12 days. n=9-27 plants. (B) Root and shoot fresh weight of (CEP3 or CEP4 over-expression lines. Plants were grown on standard ½ MS medium for 12 days. n≥13 plants. (C-J) Phenotypes of 5-week-old Col-0 and CEP over-expression lines grown in soil. Scale bar=1.25 cm. Error bars show standard error. *p≤0.05; p≤0.01; *p≤0.001 (two-sample t-test, Genstat). (K) Phenotypes of 5-week-old Col-0 and CEP3 over-expression lines grown in soil.
Figure 11:
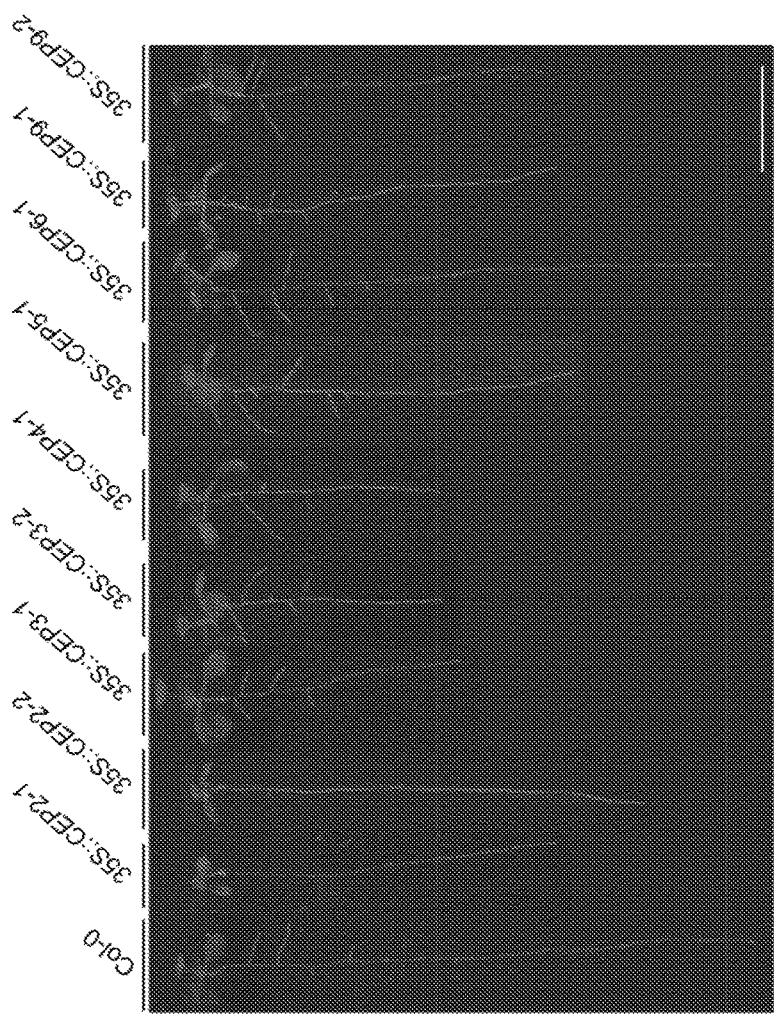
FIG. 11—Phenotypes of CEP over-expression lines. Plants were grown on standard ½ MS medium for 12 days. Scale bar=1 cm.

To investigate the roles of CEPs in plant development, we over-expressed six CEP genes under the control of a constitutive 35S promoter. When grown on standard medium for 12 days, we observed a significant decrease in primary root length in all CEP over-expression lines (FIG. 10A; FIG. 11). The most severe decrease was seen in the p35S::CEP3 and p35S::CEP4 lines. While the primary root length of all lines tested was reduced, some unique phenotypes were observed on plates. The shoots of the p35S::CEP3 and p35S::CEP4 lines were significantly larger than in the WT lines, even though the roots were severely impaired. Fresh weight measurements showed the shoots of these lines were double the weight of the WT (FIG. 10B). This increase in shoot size was not observed in the other over-expression lines (FIG. 11).

To further investigate the shoot phenotypes the over-expression lines were grown in pots (FIG. 10C-J). The phenotypes seen were diverse and unique to each over-expression line. Five-week old p35S::CEP2 plants had fewer rosette leaves, delayed flowering and altered leaf morphology, showing flat, round leaves (FIG. 10D). p35S::CEP3 lines displayed leaf morphology defects including epinasty, leaf yellowing and reduced rosette size (FIG. 10E-F). p35S::CEP4 plants showed a similar phenotype to p35S::CEP3, although plants appeared to be larger overall (FIG. 10G). p35S::CEP6 and p35S::CEP9 plants were not as severely affected, but showed epinasty and yellowing (FIG. 10H-J). p35S::CEP9 lines also show reduced rosette size.

Combining the results from plate and pot assays, it appears that those peptides that elicit a more severe root phenotype also display a much more severe shoot phenotype.

Example 7

Figure 7:
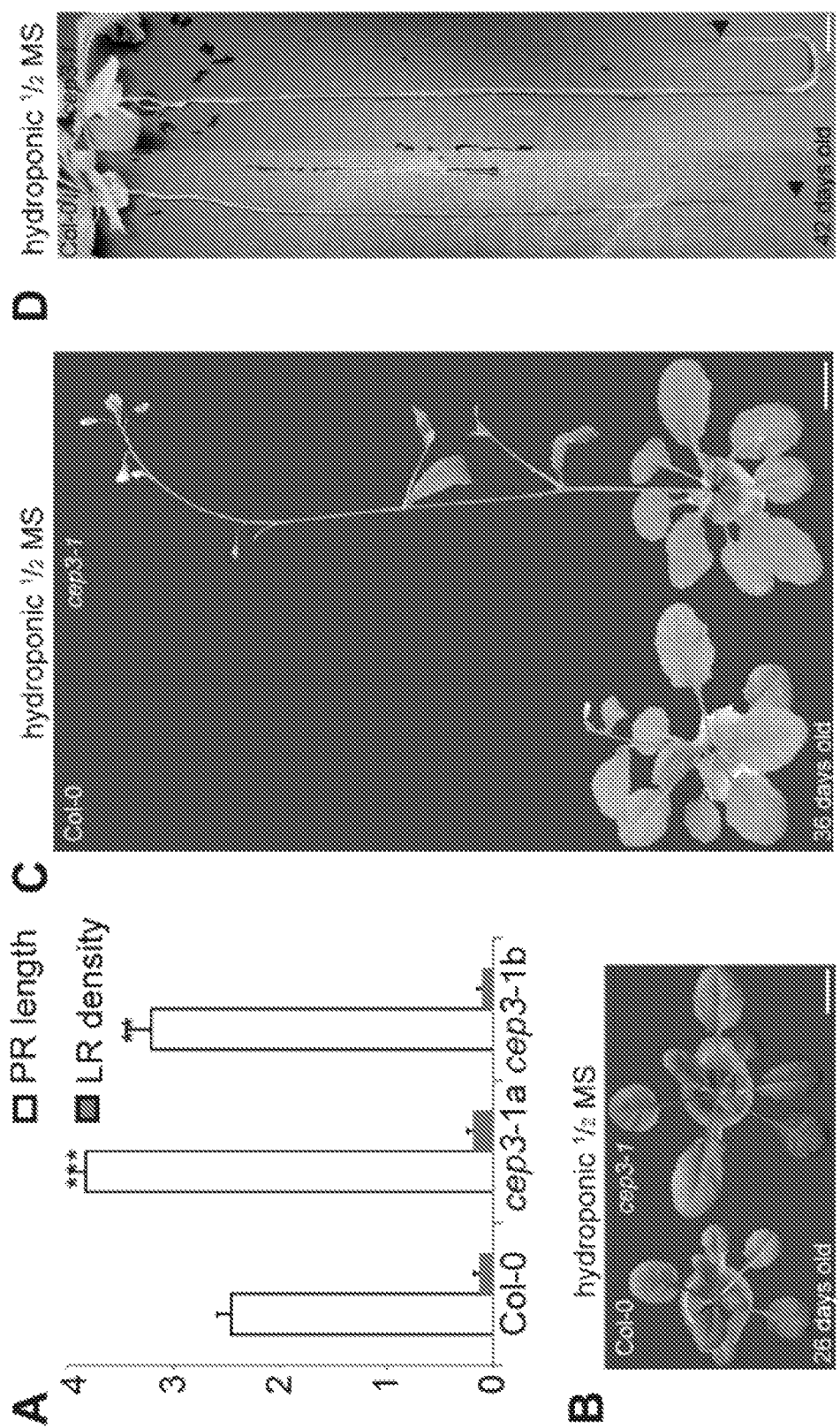
FIG. 7—Phenotypes of cep knockout mutants. (A) Primary root length and lateral root density of 12-day-old Col-0, cep3-1a and cep3-1b mutants. Plants were grown modified ½ MS medium containing 0.25 mM $KNO_3$ as the only source of nitrogen. n≥12 plants. Error bars show standard error. *P≤0.05; P≤0.01; *P≤0.001 (two-sample t-test, Genstat). (B-D) Representative 26-day-old plants (B), 36-day-old plants (C) and 42-day-old root systems (D) of Col-0 and cep3-1a plants grown hydroponically in ¼ MS medium. Scale bar=0.9 mm. Arrowhead indicates root tip.
Figure 12:
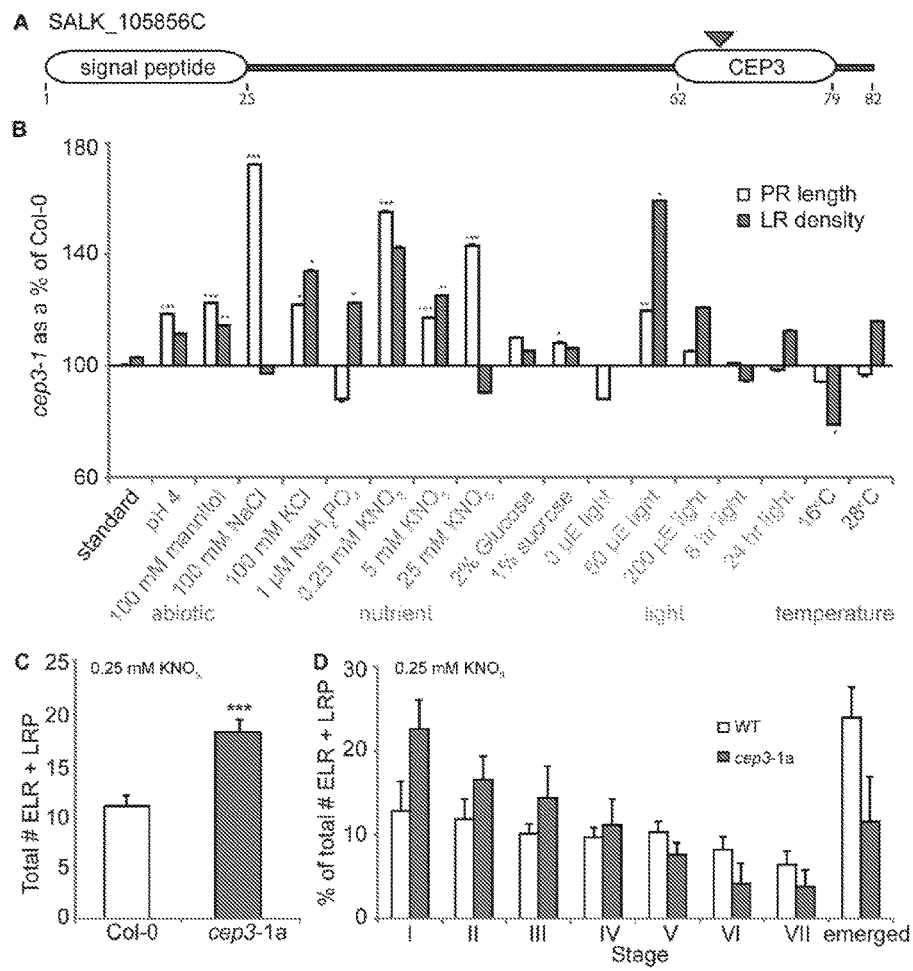
FIG. 12—A cep3 knockout mutant has a larger root system under a range of environmental conditions. (A) Representation of T-DNA insertion site in cep3 knockdown line SALK_105856. Amino acid number is shown. (B) Histogram shows cep3-1a primary root length and lateral root density as a proportion of Col-0. Plants were grown on standard medium modified as indicated. For nitrate treatments, modified medium containing the indicated $KNO_3$ levels as the only source of nitrogen was used. For the phosphate limitation treatment, modified medium containing 1 µM $NaH_2PO_4$ as the only source of phosphorus was used. For light and temperature treatments, standard medium was used. n≥8 individual plants. (C-D) Total number of emerged LRs (ELR) plus lateral root primordia (LRP) (C) and proportion of LRP at each stage of development divided by total number of LRs (D). 12-day-old Col-0 and cep3-1a plants were grown on modified ½ MS medium containing 0.25 mM $KNO_3$ as the only nitrogen source. n=10. Error bars show standard error. *P≤0.05; P≤0.01; *P≤0.001 (two-sample t-test, Genstat).
Figure 13:
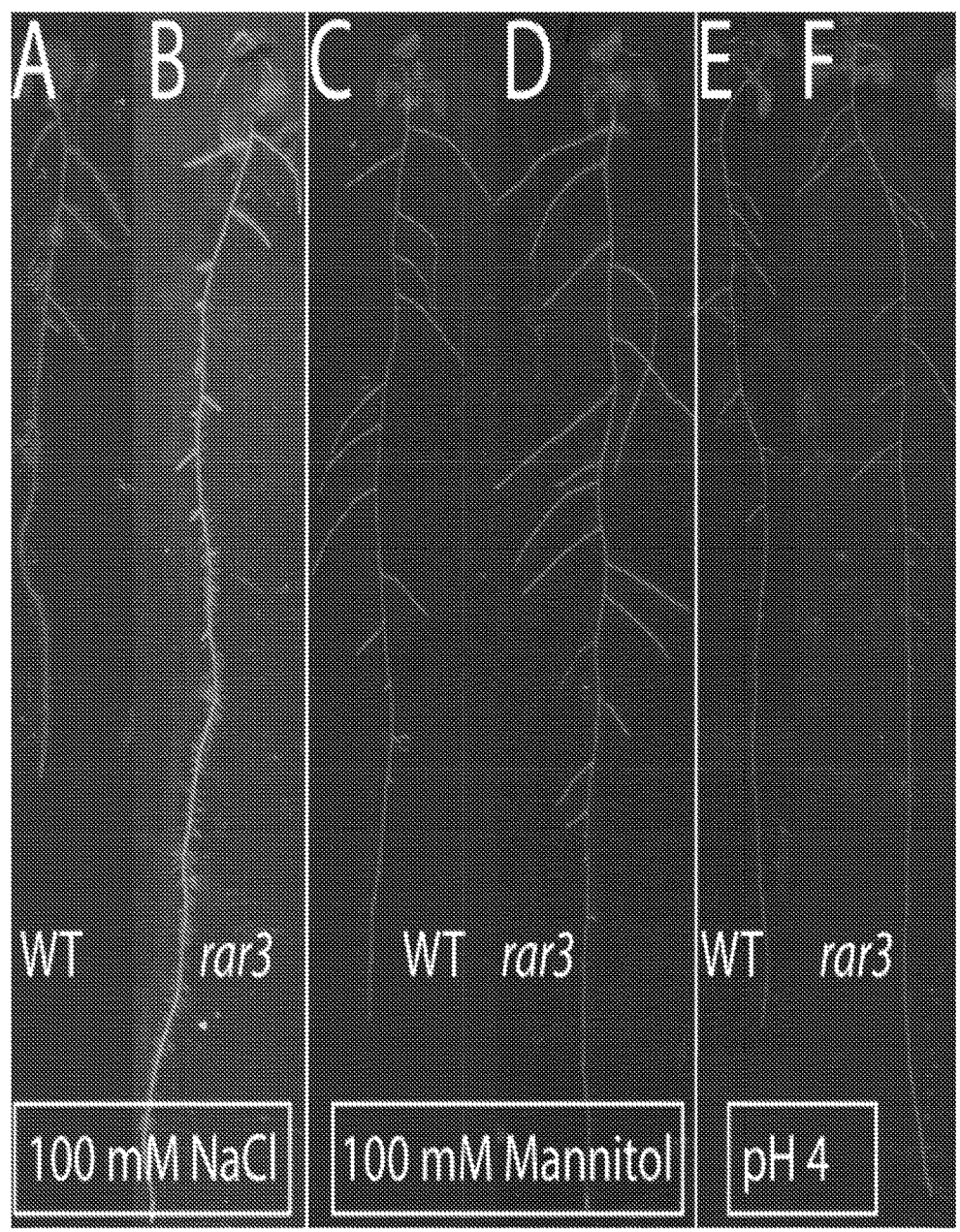
FIG. 13—Shows the effect of certain environmental conditions on hydroponic growth of knockout mutant cep3-1a (identified as rar3 in the figure) compared to the Col-o wild type (WT), including increased salt, non-salt hyperosmotic conditions (mannitol), or acidic conditions.

A Knockout Mutant Confirms the Role of CEPs in Plant Development in Response to Environmental Cues The role of CEPs as negative regulators of root development was confirmed by CEP3 T-DNA insertion knockout lines (FIG. 12A). When grown on standard medium, cep3-1a and cep3-1b showed no significant difference in root architecture compared to Col-0 (FIG. 12B). However, when grown under nitrogen limiting conditions, these lines had significantly larger root systems (FIG. 7A). We also observed increased root and shoot growth rates when cep3-1a was grown hydroponically (FIGS. 7B-D and FIG. 15).

To further investigate the role of environmental conditions on cep3-1a growth, several abiotic stress, nutrient, light and temperature regimes were assayed (FIG. 12B). The largest increase in root system size was found when cep3-1a was grown under increased salt and nitrogen limiting conditions (FIG. 13A to D; cep3 represented as rar3). This coincides well with our finding that CEP3 is significantly induced under these two conditions in the roots. cep3-1a root systems were also significantly larger than Col-0 (WT in FIG. 13) when grown in acidic or high salt conditions, under increased osmotic strength (mannitol), in the presence of sucrose and under decreased or increased irradiance, but not when grown with different day lengths. Elevated temperature did not affect the size of the root system significantly whereas decreased temperature reduced the lateral root density but not primary root length. These data, together with gene expression analysis, suggest CEPs may act as intermediates between environmental conditions and root development.

To explore the effect of cep3 knockout on lateral root formation, we examined lateral root primordia of plants grown under nitrogen limiting conditions. The total number of emerged lateral roots plus lateral root primordia was significantly increased in the cep3-1a mutant compared to Col-0 (FIG. 12C). When lateral root stages were audited, we observed no significant difference in the number of lateral root primordia at any developmental stage (as a percentage of total lateral roots; FIG. 12D). This lateral root phenotype may be the product of increased root growth.

Example 8

Figure 14:
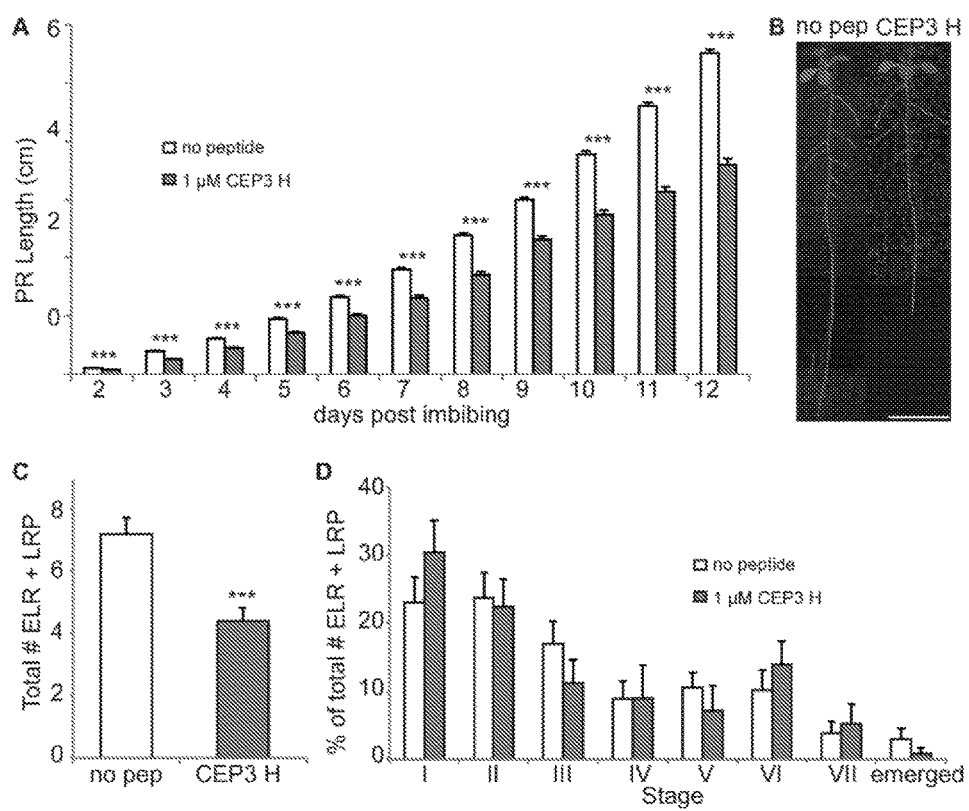
FIG. 14—Shows CEP3 peptide slows primary root growth and affects lateral root formation. (A) Effect of CEP3 H on primary root growth over time. Col-0 plants were grown vertically on standard medium supplemented with 1 µM of CEP3 H or no peptide and imaged every day for 12 days. n≥36 plants. (B) Representative phenotypes of 12-day-old Col-0 plants treated with no peptide or 1 µM of CEP3 H. Scale bar=1 cm. (C-D) Total number of emerged LRs (ELR) plus lateral root primordia (LRP) (C) and proportion of LRP at each stage of development divided by total number of LRs (D). 12-day-old Col-0 plants grown on standard MS medium with or without 1 µM of CEP3 H peptide. n=15. Error bars show standard error. *P≤0.05; P≤0.01; *P≤0.001 (two-sample t-test, Genstat).
Figure 15:
FIG. 15—Shows further phenotypes of cep knockout mutants (identified as rar3 mutant) compared to Col-0 wild type. Plants were grown on modified ½ MS medium containing 0.25 mM $KNO_3$ as the only source of nitrogen.

CEPs are Negative Regulators that Slow Root Growth and Reduce Lateral Root Formation Our synthetic peptide assays and over-expression results indicated that CEPs decrease both primary root length and emerged lateral root density. To determine whether the peptide arrested or slowed root growth, we performed a time course over 12 days using CEP3 H (FIG. 14A-B). We found that the primary roots of plants treated with CEP continued growing, albeit it at a significantly slower rate than untreated plants. The results indicate that CEPs do not arrest cell division potential, rather they just slow the process.

To investigate the lateral root phenotype further, we examined the number (FIG. 14C) and developmental stages (FIG. 14D) of lateral root primordia in CEP3 H treated and untreated plants. The total number of emerged lateral roots plus lateral root primordia was significantly reduced in CEP treated plants. When lateral root stages were audited, we observed no significant difference in the number of lateral root primordia at any developmental stage (as a percentage of total lateral roots). This indicated that once lateral roots were successfully initiated, CEP was not specifically inhibiting lateral root development at any particular stage. Therefore, the significant reduction in total lateral roots induced by CEP suggests that it may be acting to stop lateral root formation prior to the first asymmetric cell division.

We have demonstrated that CEPs are negative regulators of plant development. Together, our data indicate that CEPs are able to elicit developmental phenotypes in both roots and shoots and are induced in these two tissues under different conditions, reflecting plasticity in the plants ability to respond to environmental stress.

Example 9

CEPs Affect Shoot Growth in *B. distachyon*

*Brachypodium. distachyon* BD21 seeds were sterilised by washing in 80% ethanol for 1 minute, followed by shaking in 50 ml of 10% stock sodium hypochlorite (Northfork) with 200 μl of Triton X-100 (per 50 mL) for 5 minutes, before rinsing three times in sterile water. Seeds were then stratified for 3 days in the dark at 4° C. to induce synchronized germination. Plants were grown at 21° C. on a 16/8 h light/dark cycle in a constant environment walk-in cabinet (100 μmol/m$^{-2}$/s$^{-2}$).

Murashige and Skoog basal medium (Sigma-Aldrich Corporation, St. Louis, USA) was prepared (2.2 g/L, sterile RO water), 10% MES buffer added, and the pH adjusted to 5.7 using 1 M KOH. Falcon tubes (BD Biosciences, Australia; 50 mL max volume) containing two agar layers were prepared using the following ranges of agar concentrations: 0.2%, 0.4%, 0.5%, 0.8%, 1.0% for soft top layer and 0.5%, 1.0%, 1.5%, 2.0%, 2.5%, 3.0% and 4.0% for hard bottom layer. Type-M agar (Sigma-Aldrich Corporation) was used in all experiments. The hard layers contained 15 mL of agar and the (upper) soft layers contained 10 mL of agar. Seeds were placed one per falcon tube for root assays, with embryos facing away from the media.

Figure 16:
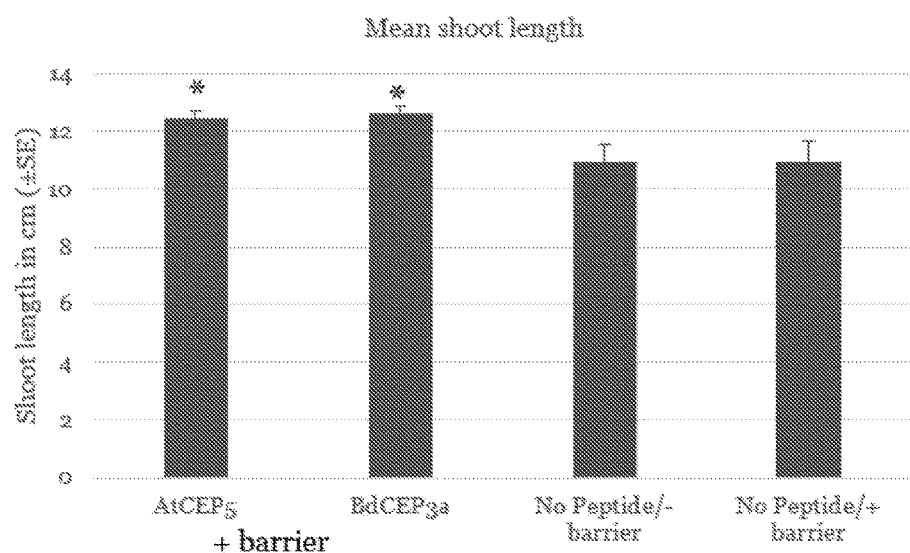
FIG. 16—Shows the effect of CEP peptides on shoot length of 16 day old plants. Shoot length was measured from the base of the upper stem sheath and compared using ANOVA. Peptide treated plants had significantly longer shoots in both treatments (*; AtCEP5 p<0.026, BdCEP1, represented as BdCEP3a in the figure, p<0.020) compared to the no peptide controls. There was no significant difference in shoot length between the controls attributable to the mechanical barrier (p=0.665), suggesting that the difference in shoot length is linked to the activity of the added peptide.
Figure 17:
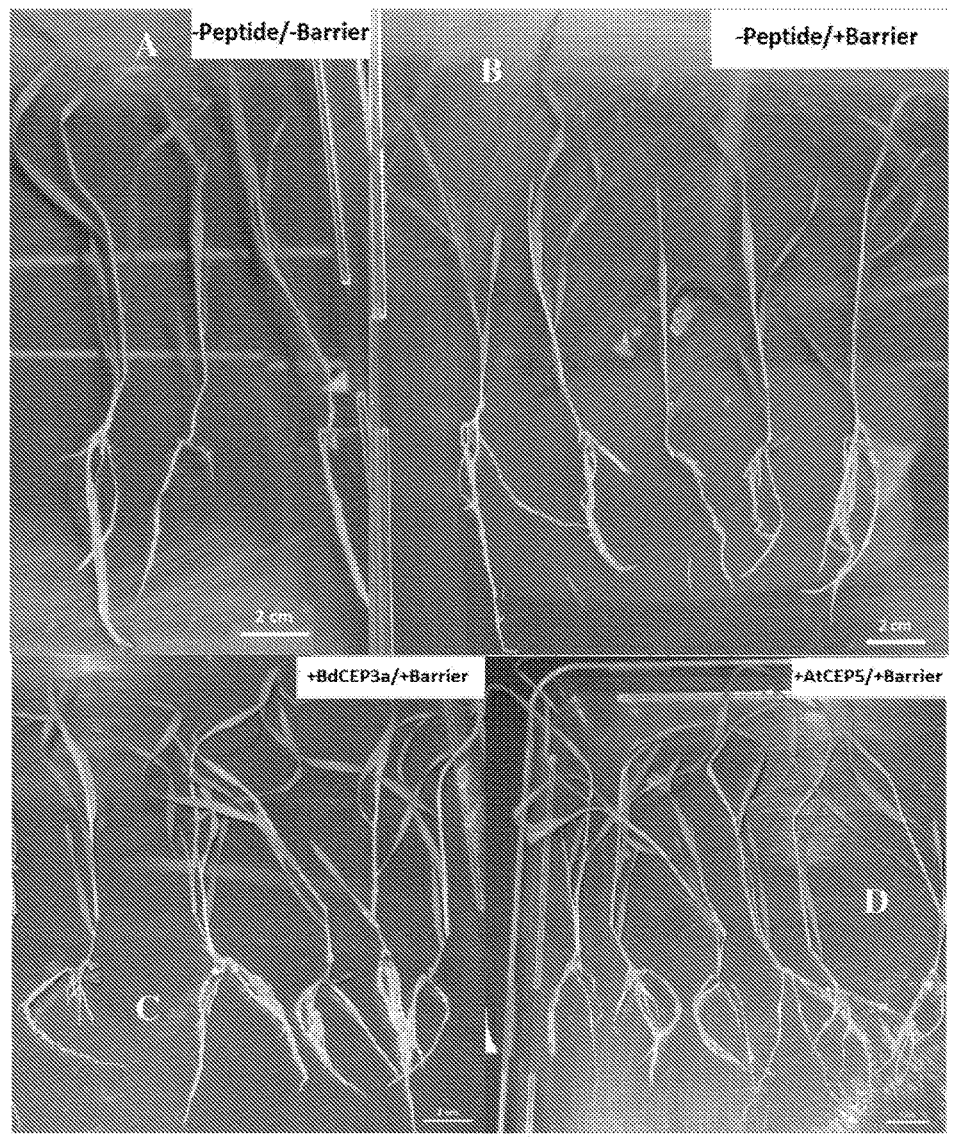
FIG. 17—Shows the effect of CEP peptides on shoot morphology of 16 day old plants. Plants were grown in medium containing peptide (AtCEP5 with barrier, BdCEP1, represented as BdCEP3a in the figure, with barrier) or no peptide (+/− barrier). In both peptide treatments, shoots were significantly longer (ANOVA p<0.05, FIG. 12) with more consistent growth. Peptide treated plants had a higher number of leaves per plant on average (AtCEP5: 4.9 leaves, p=0.007; BdCEP1: 4.7 leaves p=0.033), compared to the no peptide treatments (−barrier 3.7 leaves; +barrier 3.9 leaves).

Synthetic CEP peptides corresponding to those predicted to be the final products of the BdCEP1 and AtCEP5 coding sequences (SEQ ID NOs: 483 and 11, respectively) were prepared (but the BdCEP1 peptide was synthesized missing the first two amino acids, and designated as BdCEP3a in FIGS. 16 and 17) and added to molten media (60° C.) to a final concentration of 1μM.

```
AtCEP5
                                       (SEQ ID NO: 156)
DFRPTTPGHSPGIGH

BdCEP3a
                                       (SEQ ID NO: 508)
DSTTPGHSPSIGH
```

Final predicted peptides, AtCEP5 and BdCEP3a, with post-translational modifications (hydroxyprolination, shown in bold). Both peptides are predicted to be of approximately the same size (15 and 13 aa, respectively). AtCEP5 is hydroxylated at prolines 4 and 11 , and BdCEP3a is hydroxylated at the equivalent of prolines 7 and 11.

Tubes were set up with optimal agar concentrations of 0.5% for soft top layer and 2.5% for hard bottom layer which induced a strong mechanical response in untreated plants. A layered agar system with no peptide addition and an un-layered system (0.5%, uniform agar concentration; 25 ml) with no peptide addition were used as controls. Each tube was fitted into an 8 slot Falcon tube rack which was covered in aluminum foil to minimize light exposure to the root systems. This system allowed tubes to be periodically removed for easy visual inspection. The upper level of the soft layer was below the level of the rack.

Shoot length was measured at the end of the growth period. Data obtained from analyzing root system measurements were statistically analyzed.

Shoot growth was significantly affected, with longer shoots occurring in both peptide treatments (ANOVA p<0.05, FIG. 16). Peptide treated plants also had a significantly higher number of leaves per plant (ANOVA p<0.05, FIG. 17). There was no significant difference in shoot length or morphology between the no peptide controls (p=0.665), indicating that the difference in shoot length is most likely due to the activity of the added peptide. This indicates that CEPs have an effect on the overall development of *B. distachyon* plants.

As AtCEP5 and BdCEP1 (represented by BdCEP3a) peptides both affected the growth of *B. distachyon* to a similar degree in all treatments, *B. distachyon* appears to recognize both peptides. This suggests that CEP receptors are conserved in monocots and dicots.

Example 10

Post-Translational Modifications in CEPs

CEP1 overexpressing *Medicago truncatula* plants were generated by *Agrobacterium rhizogenes* hairy root transformation essentially as described in Example 1. Transgenic roots were then excised and grown on solid Fåhraeus medium containing 100 mg/L cefotaxime and 1% sucrose in the dark at 25° C. and sub-cultured every week until axenic. The transgenic roots were then transferred to liquid Fåhraeus medium and grown in the dark at 25° C. with continuous shaking at 100 rpm for 14 days prior to exudate collection.

Culture exudate (150 mL/flask) was filtered through 100 µm nylon mesh and concentrated 10 times by rotary evaporation prior to o-chlorophenol/acetone precipitation as described by Ohyama et al. (2008). Centrifugation was conducted at 9000 g for two hours instead of 10 mins at 10,000 g to improve peptide precipitation. The pellet was dissolved in 500 µL of water and the solution was run through a PD MidiTrap G-10 size exclusion gravity column (exclusion limit>700 Mr, GE Healthcare Life Sciences). The peptide fraction was eluted off the column with 1.2 mL of 100 mM ammonium acetate. The eluates were lyophilized overnight and resuspended in 40 µL 3% acetonitrile with 0.1% formic acid prior to analysis using QExactive PLUS nano LC ESI-MS/MS. For the analysis using nano-LC-Chip-ESI-MS/MS, the samples were resuspended in 20 µL of 10% acetonitrile/water with 0.1% formic acid.

A Thermo Scientific Easy-nLC 1000 HPLC system was used in a two column configuration for separation of the concentrated peptide-enriched extracts. The extracts were initially loaded onto a Thermo Acclaim PepMap C18 trap reversed-phase column (75 µm×2 cm nanoviper, 3 µm particle size) at a maximum pressure setting of 800 bar. Separation was achieved at 300 nL/minute using buffer A (0.1% formic acid in water) and buffer B (0.1% formic acid in acetonitrile) as mobile phases for gradient elution with a 75 µm×25 cm PepMap RSLC C18 (2 µm particle size) Easy-Spray Column at 350° C. Peptide elution employed a 3-10% acetonitrile gradient for 10 mins followed by 10-38% acetonitrile gradient for 47 mins. The total acquisition time, including a 95% acetonitrile wash and re-equilibration, was 70 mins. For each run, 7 µl of the pre-diluted samples from the over expressed and vector control root exudates were injected. Two blank runs were included between each sample to minimize carryover to negligible levels.

The eluted peptides from the C18 column were introduced to mass spectrometer via nano-ESI and analysed using the Q-Exactive Plus (Thermo Fisher Scientific, Waltham, Mass., USA). The electrospray voltage was 1.8 kV, and the ion transfer tube temperature was 275° C. Employing a top 10 ddMS2 acquisition method with preference for a specified target list of +1, +2 and +3 charged species, full MS scans were acquired in the Orbitrap mass analyzer over the range m/z 350-1800 with a mass resolution of 70,000 (at m/z 200). The target value was 1.00E+06. The 10 most intense peaks with a charge state≥1 were fragmented in the HCD collision cell with normalized collision energy of 27% and tandem mass spectra were acquired in the Orbitrap mass analyzer with a mass resolution of either 17,500 or 35,000 at m/z 200. The AGC target value in both instances was set to 5.0E+04. The ion selection threshold was 1.00E+04 counts at 17.5K and 4.50E+03 at 35K resolution. The maximum allowed ion accumulation times was 30 ms for full MS scans and 50 and 110 ms for tandem mass spectra at 17.5 and 35 k, respectively. For all the experiments, the dynamic exclusion time was set to 10 s.

Nine mature 15 amino acid bioactive peptides corresponding to both putative peptide domains of MtCEP1 were isolated and identified. Four proline-hydroxylated variants came from the D1 peptide (SEQ ID NOs: 167 and 451). Hydroxylation occurred at Pro11 (D1:HyP11), Pro4 and Pro11 (D1:HyP4,11), Pro7 and Pro11 (D1:HyP47,11) and, Pro4, Pro7 and Pro11 (D1:HyP4,7,11). Another four D1 peptide variants were identified as having triarabinosylation at Pro11. These peptides were arabinosylated counterparts of the four hydroxylated D1 peptides. The peptides were identified with triarabinosylation at Pro11 (D1:TaP11), hydroxylation at Pro4 and triarabinosylation at Pro11 (D1:HyP4, TaP11), hydroxylation at Pro7 and triarabinosylation at Pro11 (D1:HyP7,TaP11), and hydroxylation on both Pro4 and Pro7 with triarabinosylation on Pro11 (D1:HyP4,7, Tap11). For the D2 peptide (SEQ ID NOs: 168 and 452), only one species was identified with hydroxylation at Pro11. The hydroxylated peptides were found to constitute 93.5% of the total peptide isolated from MtCEP1 while the triarabinosylated peptide only constitutes 6.5%.

Greater biological activity (compared to unmodified CEPs) and differential location of effects, as determined for roots, was observed for the different species of hydroxylated CEPs. The difference in the degree and position of the hydroxylation moieties on the D1 peptides resulted in different effects on root development. Without wishing to be bound by theory, the contrasting biological activities of MtCEP1 peptide species could be due to differential perception and recognition of specific peptides by the root. NMR analysis of MtCEP1 (D1:HyP4,11) and a root-knot nematode CEP revealed that hydroxylation of Pro4 and Pro11 resulted in lower structural constraints on the peptide backbone. This may reflect the different biological effects imparted by MtCEP1 peptides with different proline hydroxylation patterns. Other modifications such as arabinosylation and sulfation alter biological activities of RGF and CLE peptides. These structural differences resulting from the post-translational modifications could provide binding specificity of the peptides to their respective receptor(s).

CONCLUSIONS

Regulatory peptides are being increasingly recognized for playing key roles in plant development. We have extended the analysis of the CEP family of regulatory peptides. Our in silico analysis indicates that CEP genes have a distribution restricted to seed plants. We report that the expression of eight of the nine CEP tested is perturbed by environmental cues such as decreased nitrogen levels, increased salt levels, increased osmotic strength and increased $CO_2$ levels. We demonstrate synthetic CEPs can act at concentrations ranging from µM to nM. Peptide sequence, particularly the last nine residues and modifications to key amino acids are both important for biological activity and the extent of activity. Our analyses indicate that CEPs act as negative growth regulators for both root and shoot systems. More specifically, CEPs reduce primary root length by slowing growth and reduce lateral root density prior to lateral root initiation. As recently evolved regulators, CEPs may serve to provide a fine-tuning of developmental processes in plants to enable a rapid adjustment to constantly changing environmental conditions.

It will be appreciated that, although specific embodiments of the invention have been described herein for the purpose of illustration, various modifications may be made without deviating from the spirit and scope of the invention as defined in the following claims.

The invention claimed is:

1. A method for increasing, accelerating or increasing and accelerating non-root plant growth in a plant relative to a wild-type plant grown under the same conditions, said method comprising introducing at least one mutation or at least one exogenous nucleic acid into one or more plant cells which at least one mutation or nucleic acid results in:

(i) decreased expression of one or more C-TERMINALLY ENCODED PEPTIDEs (CEPs), decreased expression of one or more CEP receptors, or decreased expression of one or more CEPs and one or more CEP receptors by cells of a plant regenerated from or comprising said one or more plant cells, wherein said at least one mutation is in a sequence encoding a CEP, a CEP receptor or an upstream sequence thereof or wherein said exogenous nucleic acid is either a CEP-encoding sequence or a CEP receptor-encoding sequence, or said exogenous nucleic acid modulates, or its product modulates expression of at least one endogenous CEP-encoding nucleic acid or CEP receptor-encoding nucleic acid, wherein said exogenous nucleic acid comprises a nucleic acid sequence homologous to, or complementary to at least a portion of the endogenous CEP-encoding or CEP receptor-encoding nucleic acid; or (ii) reduced affinity of one or more CEPs for their respective CEP receptors, which reduced affinity arises through modifications in the CEP(s), CEP receptor(s) or in both expressed CEP(s) and CEP receptor(s) expressed by cells of a plant regenerated from or comprising said one or more plant cells, wherein said at least one mutation is in a sequence encoding a CEP or a CEP receptor, or wherein said exogenous nucleic acid is either a CEP-encoding sequence or a CEP receptor-encoding sequence, wherein said CEP comprises a CEP domain comprising the amino acid sequence $(X_1)_n X_2 X_3 X_4 X_5 X_6 PGX_9 SPGX_{13} GX_{15}$ (SEQ ID NO:454), wherein n is 0 or 1, $X_1$ is selected from D, A, P, G, S, V, E, P, T, Q, I, N, K, and C;

$X_2$ is selected from F, V, T, S, A, K, Y, R, G, I, Q, H, D, G, and W;

$X_3$ is selected from R, A, Q, G, E, V, D, K, P, S, H, and Q;

$X_4$ is selected from P, G, S, T, A, N, C, H, V, E, Y, and K;

$X_5$ is selected from T, S, A, P, G, V, N, M, and I;

$X_6$ is selected from T, N, A, G, P, D, K, S, V, Y, Q, E, C, and H;

X₉ is selected from H, N, S, Y, P, R, T, G, V, F, Q, and D;

X₁₃ is selected from I, V, and A; and

X₁₅ is selected from H, and N.

2. The method of claim 1, which comprises introducing into said one or more plant cells exogenous nucleic acid which suppresses, or the product of which suppresses expression of at least one endogenous CEP-encoding nucleic acid.

3. The method of claim 2, wherein said exogenous nucleic acid comprises a nucleic acid sequence homologous to, or complementary to at least a portion of the endogenous CEP-encoding nucleic acid.

4. The method of claim 2, wherein said exogenous nucleic acid is, or encodes a microRNA or siRNA.

5. The method of claim 1, wherein said plant is selected from members of the angiosperm families Aceraceae, Anacardiaceae, Apiaceae, Asteraceae, Betulaceae, Brassicaceae, Buxaceae, Chenopodiaceae/Amaranthaceae, Compositae, Cucurbitaceae, Fabaceae, Fagaceae, Gramineae, Juglandaceae, Lamiaceae, Lauraceae, Leguminosae, Moraceae, Myrtaceae, Oleaceae, Platanaceae, Poaceae, Polygonaceae, Rosaceae, Rutaceae, Salicaceae, Solanaceae, Ulmaceae or Vitaceae or gymnosperm families Cuppressaceae, Pinaceae, Taxaceae or Taxodiaceae.

6. The method of claim 1, wherein said CEP comprises an amino acid sequence selected from SEQ ID NOs 2, 4, 6, 8, 10, 12, 14, 16, 18, 20, 22, 24, 26, 28, 30, 32, 34, 36 to 147, 338-350, 365, 367, 369, 371, 373, 375, 377, 379, 381, 383, 385, 387-395, 468, 470, 472, 474, 476, 478, 480, 482, 484, 486, 488, 491, 493, 499 or 501, or comprises an CEP domain having an amino acid sequence selected from SEQ ID Nos: 148-336, 351-363, 396-415, 451-453, 455-466 or 502-504, or is encoded by a nucleic acid comprising a nucleotide sequence selected from SEQ ID NOs 1, 3, 5, 7, 9, 11, 13, 15, 17, 19, 21, 23, 25, 27, 29, 31, 33, 35, 364, 366, 368, 370, 372, 374, 376, 378, 380, 382, 384, 386, 467, 469, 471, 473, 475, 477, 479, 481, 483, 485, 487, 489, 490, 492, 494-498 or 500.

7. The method of claim 6, wherein said CEP comprises an amino acid sequence selected from SEQ ID NOs 2, 4, 6, 8, 10, 12, 14, 16, 18, 20, 22, 24, 26, 28, 30, 32, 34, 36 to 147, 338-350, 468, 470, 472, 474, 476, 478, 480, 482, 484, 486, 488, 491, 493, 499 or 501, or comprises a CEP domain having an amino acid sequence selected from SEQ ID Nos: 148-336, 351-363, 451, 452, 455-466 or 502-504, or is encoded by a nucleic acid comprising a nucleotide sequence selected from SEQ ID NOs 1, 3, 5, 7, 9, 11, 13, 15, 17, 19, 21, 23, 25, 27, 29, 31, 33, 35, 467, 469, 471, 473, 475, 477, 479, 481, 483, 485, 487, 489, 490, 492, 494-498 or 500.

8. The method according to claim 1, wherein said CEP comprises a CEP domain comprising an amino acid sequence $(X_1)_n X_2 X_3 X_4 X_5 X_6 PGX_9 SPGX_{13} GX_{15}$ (SEQ ID NO:454), wherein:

n may be 0 or 1

X₁ is selected from D, G, P, A, S, L, E and V;

X₂ is selected from F, V, R, T, S, A, K and Y;

X₃ is selected from R, K, E, H, Q, S, P, D, V, G, and A;

X₄ is selected from P, S and G;

X₅ is selected from T, S and G;

X₆ is selected from N, A, T, G, P, D, K and S;

X₉ is selected from N, H, Y and S;

X₁₃ is selected from I, A and V; and

X₁₅ is selected from N and H;

wherein the amino acid at position 6, if threonine or serine, is phosphorylated; and/or the P at position 11, a P at position 7, a P at position 4, or any combination of such prolines are hydroxylated, or hydroxylated and arabinosylated; and/or any combination of tyrosine residues are sulphonated.

9. The method according to claim 1, wherein said plant yields a greater amount of above-ground plant matter than the wild-type plant grown under the same conditions.

10. The method according to claim 1, wherein said plant grows faster than the wild-type plant grown under the same conditions.

11. The method according to claim 1, wherein said plant develops faster than the wild-type plant grown under the same conditions.

12. The method according to claim 9, wherein said conditions comprise stress conditions.

13. The method according to claim 12, wherein said stress conditions are abiotic stress conditions.

14. The method according to claim 13, wherein said stress conditions are selected from the group comprising increased salinity, drought, nitrogen limitation and pH stress.

15. A plant with increased, accelerated or increased and accelerated plant growth relative to the wild-type plant, obtained by the method of claim 1, or a part thereof.

16. The plant of claim 15 that has increased shoot growth or accelerated shoot development relative to the wild-type plant.

17. The plant of claim 15, wherein said plant is selected from members of the angiosperm families Aceraceae, Anacardiaceae, Apiaceae, Asteraceae, Betulaceae, Brassicaceae, Buxaceae, Chenopodiaceae/Amaranthaceae, Compositae, Cucurbitaceae, Fabaceae, Fagaceae, Gramineae, Juglandaceae, Lamiaceae, Lauraceae, Leguminosae, Moraceae, Myrtaceae, Oleaceae, Platanaceae, Poaceae, Polygonaceae, Rosaceae, Rutaceae, Salicaceae, Solanaceae, Ulmaceae or Vitaceae or gymnosperm families Cuppressaceae, Pinaceae, Taxaceae or Taxodiaceae.

* * * * *